US008530168B2

(12) United States Patent
Chu et al.

(10) Patent No.: US 8,530,168 B2
(45) Date of Patent: Sep. 10, 2013

(54) FUSION PROTEIN COMPRISING A CASPASE DOMAIN AND A NUCLEAR HORMONE RECEPTOR BINDING DOMAIN AND METHODS AND USES THEREOF

(75) Inventors: Yuanyuan Chu, Munich (DE); Ralf Kuehn, Freising (DE); Wolfgang Wurst, Munich (DE)

(73) Assignee: Helmholtz Zentrum Munich Deutsches Forschungszentrum fuer Gesundheit und Umwelt (GmbH), Neuherberg (DE)

( * ) Notice: Subject to any disclaimer, the term of this patent is extended or adjusted under 35 U.S.C. 154(b) by 82 days.

(21) Appl. No.: 12/665,680

(22) PCT Filed: Jun. 20, 2008

(86) PCT No.: PCT/EP2008/005013

§ 371 (c)(1),
(2), (4) Date: Sep. 27, 2010

(87) PCT Pub. No.: WO2008/155133

PCT Pub. Date: Dec. 24, 2008

(65) Prior Publication Data

US 2011/0023137 A1 Jan. 27, 2011

(30) Foreign Application Priority Data

Jun. 21, 2007 (EP) ..................................... 07012138

(51) Int. Cl.

*G01N 33/53* (2006.01)
*C07H 21/04* (2006.01)
*C12P 21/06* (2006.01)
*C12N 15/00* (2006.01)
*C12N 5/00* (2006.01)
*C07K 1/00* (2006.01)

(52) U.S. Cl.

USPC ....... 435/7.1; 536/23.4; 435/69.1; 435/320.1; 435/325; 530/350

(58) Field of Classification Search

None
See application file for complete search history.

(56) References Cited

U.S. PATENT DOCUMENTS

| | | | |
|---|---|---|---|
| 4,736,866 A | 4/1988 | Leder et al. | |
| 5,583,278 A | 12/1996 | Alt et al. | |
| 5,625,122 A | 4/1997 | Mak | |
| 5,698,765 A | 12/1997 | Mak | |
| 5,750,825 A | 5/1998 | Yazaki et al. | |
| 6,399,327 B1 * | 6/2002 | Wallach et al. | 435/69.1 |
| 6,699,686 B1 | 3/2004 | Brocard et al. | |
| 7,754,209 B2 * | 7/2010 | Ledbetter et al. | 424/133.1 |
| 2009/0099826 A1 * | 4/2009 | Shi | 703/11 |

FOREIGN PATENT DOCUMENTS

| | | |
|---|---|---|
| DE | 196 25 049 | 1/1998 |
| WO | WO 98/36052 | 8/1998 |
| WO | WO 01/32855 | 5/2001 |

OTHER PUBLICATIONS

Bowie et al, 1990, Science 247:1306-1310.*
Wells, 1990, Biochemistry 29:8509-8517.*
Ngo et al., 1994, The Protein Folding Problem and Tertiary Structure Prediction, Merz et al., eds, Birkhauser, Boston, pp. 433-506.*
Wang et al(2001. J. Biol Chem. 276:49213-49220.*
Frantz Nature Reviews Drug Discovery 2003, 2, p. 501.*
Pettit et al 1998. Trends in Biotech. 16:343-349.*
Agger et al., "Conditional E2F1 Activation in Transgenic Mice Causes Testicular Atrophy and Dysplasia Mimicking Human CIS," *Oncogene* 24:780-789 (2005).
Altschul et al., "Basic Local Alignment Search Tool," *J. Mol. Biol.* 215:403-410 (1990).
Bao and Shi, "Apoptosome: A Platform for the Activation of Initiator Caspases," *Cell Death Differ*. 14:56-65 (2007).
Berger et al., "Pharmacologically Regulated Fas-Mediated Death of Adoptively Transferred T Cells in a Nonhuman Primate Model," *Blood* 103:1261-1269 (2004).
Bergman et al., "Up-Regulation of the Uterine Estrogen Receptor and Its Messenger Ribonucleic Acid During the Mouse Estrous Cycle: The Role of Estradiol," *Endocrinology* 130:1923-1930 (1992).
Bex et al., "Controlling Gene Expression in the Urothelium Using Transgenic Mice with Inducible Bladder Specific Cre-Lox Recombination," *J. Urol*. 168:2641-2644 (2002).
Bierer et al., "Cyclosporin A and FK506: Molecular Mechanisms of Immunosuppression and Probes for Transplantation Biology," *Curr. Opin. Immunol*. 5:763-773 (1993).
Bosenberg et al., "Characterization of Melanocyte-Specific Inducible Cre Recombinase Transgenic Mice," *Genesis* 44:262-267 (2006).
Breitman et al., "Genetic Ablation in Transgenic Mice with an Attenuated Diphtheria Toxin A Gene," *Mol. Cell. Biol*. 10:474-479 (1990).
Breitman et al., "Genetic Ablation: Targeted Expression of a Toxin Gene Causes Microphthalmia in Transgenic Mice," *Science* 238:1563-1565 (1987).
Bridgewater et al., "The Bystander Effect of the Nitroreductase/CB1954 Enzyme/Prodrug System is Due to a Cell-Permeable Metabolite," *Hum. Gene Ther*. 8:709-717 (1997).
Brocard et al., "A Chimeric Cre Recombinase Inducible by Synthetic, but Not by Natural Ligands of the Glucocorticoid Receptor," *Nucleic Acids Res*. 26:4086-4090 (1998).

(Continued)

*Primary Examiner* — Shulamith H Shafer
(74) *Attorney, Agent, or Firm* — Clark & Elbing LLP

(57) ABSTRACT

The present invention relates to a fusion protein comprising a Caspase domain or a functionally active variant thereof and a ligand binding domain of a nuclear hormone receptor, a nucleic acid coding for the fusion protein, a vector or cell comprising the nucleic acid, a method of producing the fusion protein, a non-human transgenic animal containing the nucleic acid, the use of the fusion protein for ligand-mediated induction of apoptosis of a cell, or for studying the function of a cell, tissue and/or organ or the use of a transgenic organism for studying the function of a cell at various developmental stages or as a disease model, a method for inducing apoptosis of a cell expressing a fusion protein or for identifying a ligand, or a medicament comprising a fusion protein, the nucleic acid, the vector or the cell, particularly for the treatment of cancer or for or after transplantation, particularly as safety mechanism.

20 Claims, 15 Drawing Sheets

(56) References Cited

OTHER PUBLICATIONS

Figure 1:
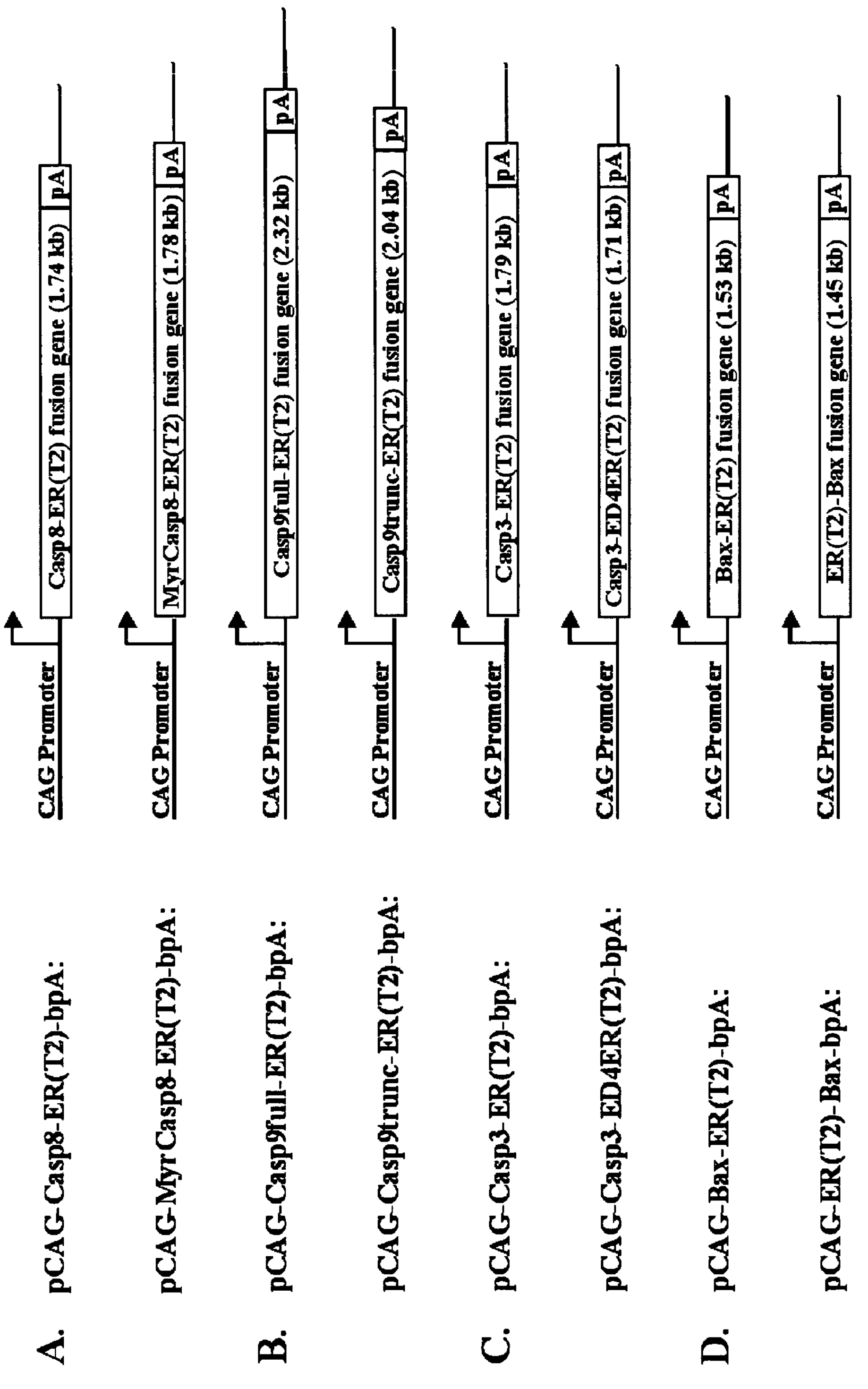
Figure 1:
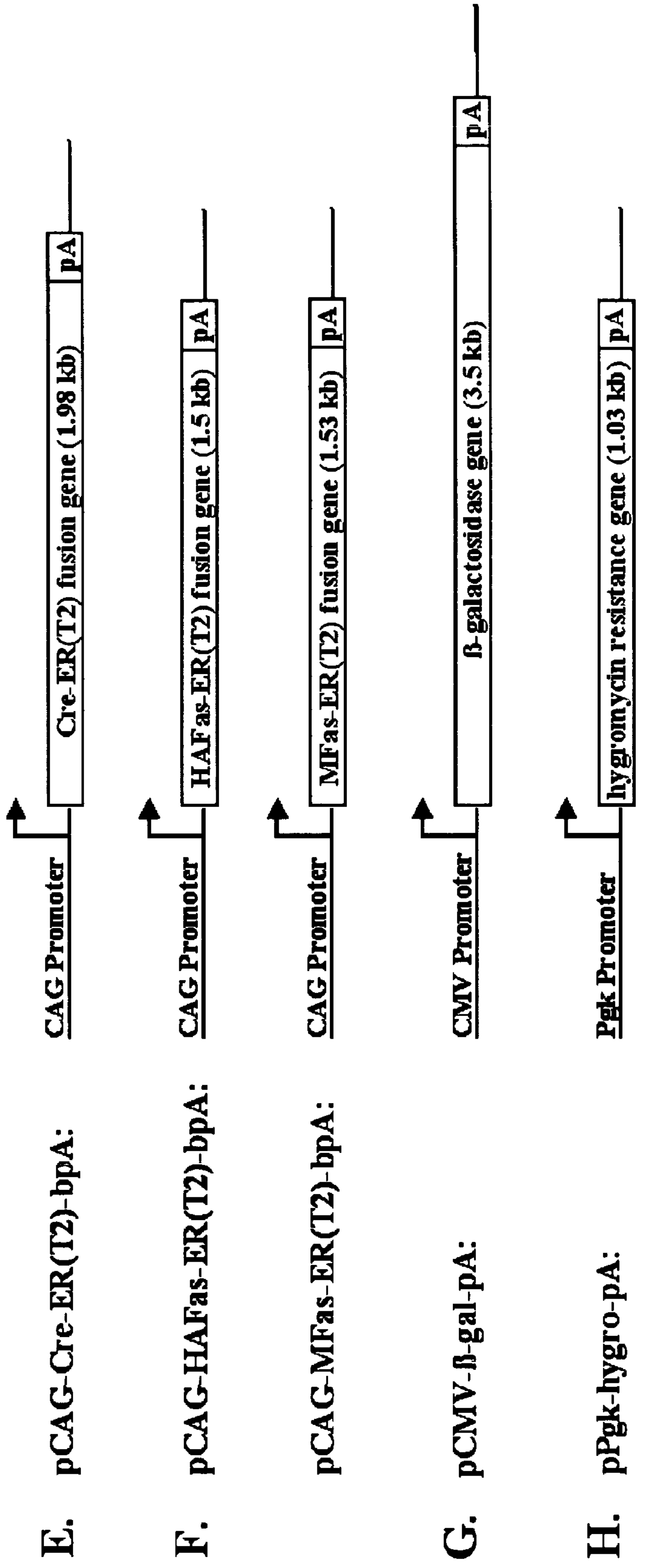

Brockschnieder et al., "An Improved Mouse Line for Cre-induced Cell Ablation Due to Diphtheria Toxin A, Expressed from the Rosa26 Locus," *Genesis* 44:322-327 (2006).

Brockschnieder et al., "Cell Depletion Due to Diphtheria Toxin Fragment A After Cre-Mediated Recombination," *Mol. Cell. Biol.* 24:7636-7642 (2004).

Buch et al., "A Cre-Inducible Diphtheria Toxin Receptor Mediates Cell Lineage Ablation After Toxin Administration," *Nat. Methods* 2:419-426 (2005).

Chang and Yang, "Activation of Procaspases by FK506 Binding Protein-Mediated Oligomerization," *Sci. STKE* 2003:PL1 (1-11) (2003).

Chang et al., "Oligomerization is a General Mechanism for the Activation of Apoptosis Initiator and Inflammatory Procaspases," *J. Biol. Chem.* 278:16466-16469 (2003).

Chen et al., "High-Throughput Selection of Retrovirus Producer Cell Lines Leads to Markedly Improved Efficiency of Germ Line-Transmissable Insertions in Zebra Fish," *J. Virol.* 76:2192-2198 (2002).

Clark et al., "Selctive Cell Ablation in Transgenic Mice Expressing *E. coli* Nitroreductase," *Gene Ther.* 4:101-110 (1997).

Cocco and Ucker, "Distinct Modes of Macrophage Recognition for Apoptotic and Necrotic Cells Are Not Specified Exclusively by Phosphatidylserine Exposure," *Mol. Biol. Cell* 12:919-930 (2001).

Cohen et al., "Immunological Defects After Suicide Gene Therapy of Experimental Graft-Versus-Host Disease," *Hum. Gene Ther.* 10:2701-2707 (1999).

Cohen et al., "Would Suicide Gene Therapy Solve the 'T-Cell Dilemma' of Allogenic Bone Marrow Transplantation?," *Immunol. Today* 20:172-176 (1999).

Cohen et al., "Suicide Gene-Mediated Modulation of Graft-Versus-Host Disease," *Leuk. Lymphoma* 34:473-480 (1999).

Cui et al., "Inducible Ablation of Astrocytes Shows that These Cells are Required for Neuronal Survival in the Adult Brain," *Glia* 34:272-282 (2001).

Dancer et al., "Expression of Thymidine Kinase Driven by an Endothelial-Specific Promoter Inhibits Tumor Growth of Lewis Lung Carcinoma Cells in Transgenic Mice," *Gene Ther.* 10:1170-1178 (2003).

Danielian et al., "Identification of Residues in the Estrogen Receptor that Confer Differential Sensitivity to Estrogen and Hydroxytamoxifen," *Mol. Endocrinol.* 7:232-240 (1993).

Doerflinger et al., "Inducible Site-Specific Recombination in Myelinating Cells," *Genesis* 35:63-72 (2003).

Doetschman, "Gene Transfer in Embryonic Stem Cells," in Pinkert, *Transgenic Animal Technology: A Laboratory Handbook*, Academic Press, San Diego, USA pp. 115-146 (1994).

Etgen, "Antiestrogens: Effects of Tamoxifen, Nafoxidine, and CI-628 on Sexual Behavior, Cytoplasmic Receptors, and Nuclear Binding of Estrogen," *Horm. Behav.* 13:97-112 (1979).

Fan et al., "Improved Artificial Death Switches Based on Caspases and FADD," *Hum. Gene Ther.* 10:2273-2285 (1999).

Fawell et al., "Characterization and Colocalization of Steroid Binding and Dimerization Activities in the Mouse Estrogen Receptor," *Cell* 60:953-962 (1990).

Fawell et al., "Inhibition of Estrogen Receptor-DNA Binding by the "Pure" Antiestrogen ICI 164,384 Appears to be Mediated by Impaired Receptor Dimerization," *Proc. Natl. Acad. Sci. USA* 87:6883-6887 (1990).

Feil et al., "Regulation of Cre Recombinase Activity by Mutated Estrogen Receptor Ligand-Binding Domains," *Biochem. Biophys. Res. Commun.* 237:752-757 (1997).

Friml et al., "A PINOID-Dependent Binary Switch in Apical-bAsal PIN Polar Targeting Directs Auxin Efflux," *Science* 306:862-865 (2004).

Fromson et al., "The Metabolism of Tamoxifen (I.C.I. 46,474) Part I: In Laboratory Animals," *Xenobiotica* 3:693-709 (1973).

Fromson et al., "The Metabolism of Tamoxifen (I.C.I. 46,474) Part II: In Female Patients," *Xenobiotica* 3:711-714 (1973).

Furr and Jordan, "The Pharmacology and Clinical Uses of Tamoxifen," *Pharmacol. Ther.* 25:127-205 (1984).

Gavrieli et al., "Identification of Programmed Cell Death In Situ Via Specific Labeling of Nuclear DNA Fragmentation," *J. Cell. Biol.* 119:493-501 (1992).

Grainger and Metcalfe, "Tamoxifen: Teaching an Old Drug New Tricks?," *Nat. Med.* 2:381-385 (1996).

Grove et al., "Generation of *Escherichia coli* Nitroreductase Mutants Conferring Improved Cell Sensitization to the Prodrug CB1954," *Cancer Res.* 63:5532-5537 (2003).

Guo et al., "A Cre Recombinase Transgene with Mosaic, Widespread Tamoxifen-Inducible Action," *Genesis* 32:8-18 (2002).

Gusterson et al., "Development of Novel Selective Cell Ablation in the Mammary Gland and Brain to Study Cell-Cell Interactions and Chemoprevention," *Recent Results Cancer Res.* 163:31-45 (2003).

Hanahan and Weinberg, "The Hallmarks of Cancer," *Cell* 100:57-70 (2000).

Hayashi and McMahon, "Efficient Recombination in Diverse Tissues by a Tamoxifen-Inducible Form of Cre: A Tool for Temporally Regulated Gene Activation/Inactivation in the Mouse," *Dev. Biol.* 244:305-318 (2002).

Hirrlinger et al., "Temporal Control of Gene Recombination in Astrocytes by Transgenic Expression of the Tamoxifen-Inducible DNA Recombinase Variant CreERT2," *Glia* 54:11-20 (2006).

Hitz et al., "Conditional Brain-Specific Knockdown of MAPK Using Cre/loxP Regulated RNA Interface," *Nucleic Acids Res.* 35:1-12 (2007).

Ho and Hawkins, "Mammalian Initiator Apoptotic Caspases," *FEBS J.* 272:5436-5453 (2005).

Hou and Hsu, "Bax Translocates from Cytosol to Mitochondria in Cardiac Cells During Apoptosis: Development of a GFP-Bax-Stable H9c2 Cell Line for Apoptosis Analysis," *Am. J. Physiol. Heart Circ. Physiol.* 289:H477-487 (2005).

Hunter et al., "Ligand-Activated Flpe for Temporally Regulated Gene Modifications," *Genesis* 41:99-109 (2005).

Hurwitz et al., "Suicide Gene Therapy for Treatment of Retinoblastoma in a Murine Model," *Hum. Gene Ther.* 10:441-448 (1999).

Imai et al., "Selective Ablation of Retinoid X Receptor $\alpha$ in Hepatocytes Impairs Their Lifespan and Regenerative Capacity," *Proc. Natl. Acad. Sci. USA 98*:4581-4586 (2001).

Indra et al., "Temporally-Controlled Site-Specific Mutagenesis in the Basal Layer of the Epidermis: Comparison of the Recombinase Activity of the Tamoxifen-Inducible Cre-$ER^T$ and Cre-$ER^{T2}$ Recombinases," *Nucleic Acids Res.* 27:4324-4327 (1999).

Isles et al., "Conditional Ablation of Neurones in Transgenic Mice," *J. Neurobiol.* 47:183-193 (2001).

Ito et al., "Stem Cells in the Hair Follicle Bulge Contribute to Wound Repair but Not to Homeostasis of the Epidermis," *Nat. Med.* 11:1351-1354 (2005).

Ivanova et al., "In Vivo Genetic Ablation by Cre-Mediated Expression of Diphtheria Toxin Fragment A," *Genesis* 43:129-135 (2005).

Jacobson et al., "Programmed Cell Death in Animal Development," *Cell* 88:347-354 (1997).

Kaczmarczyk and Green, "Induction of Cre Recombinase Activity Using Modified Androgen Receptor Ligand Binding Domains: A Sensitive Assay for Ligand-Receptor Interactions," *Nucleic Acids Res.* 31:e86 (8 pages) (2003).

Kametaka et al., "Reduction of CTLL-2 Cytotoxicity by Induction of Apoptosis with a Fas-Estrogen Receptor Chimera," *Cancer Sci.* 94:639-643 (2003).

Kamogawa et al., "Cutting Edge: A Conditionally Active Form of State can Mimic Certain Effects of IL-4," *J. Immunol.* 161:1074-1077 (1998).

Kaur et al. "Targeted Ablation of $\alpha$-Crystallin-Synthesizing Cells Produces Lens-Deficient Eyes in Transgenic Mice," *Development* 105:613-619 (1989).

Kawaguchi et al., "Expression of Fas-Estrogen Receptor Fusion Protein Induces Cell Death in Pancreatic Cancer Cell Lines," *Cancer Lett.* 116:53-59 (1997).

Kellendonk et al., "Inducible Site-Specific Recombination in the Brain," *J. Mol. Biol.* 185:175-182 (1999).

Kellendonk et al., "Regulation of Cre Recombinase Activity by the Synthetic Steroid RU 486," *Nucleic Acids Res.* 24:1404-1411 (1996).
Kodaira et al., "Fas and Mutant Estrogen Receptor Chimeric Gene: A Novel Suicide Vector for Tamoxifen-Inducible Apoptosis," *Jpn. J. Cancer Res.* 89:741-747 (1998).
Kohler et al., "Evaluation of Caspase Activity in Apoptotic Cells," *J. Immunol. Methods* 265:97-110 (2002).
Krammer, "CD95's Deadly Mission in the Immune System," *Nature* 407:789-795 (2000).
Krysko et al., "Clearance of Apoptotic and Necrotic Cells and its Immunological Consequences," *Apoptosis* 11:1709-1726 (2006).
Kuhbandner et al., "Temporally Controlled Somatic Mutagenesis in Smooth Muscle," *Genesis* 28:15-22 (2000).
Kumar and Chambon, "The Estrogen Receptor Binds Tightly to Its Responsive Element as a Ligand-Induced Homodimer," *Cell* 55:145-156 (1988).
Kumar and Thompson, "The Structure of the Nuclear Hormone Receptors," *Steroids* 64:310-319 (1999).
Lalancetter-Hebert et al., "Selective Ablation of Proliferating Microglial Cells Exacerbates Ischemic Injury in the Brain," *J. Neurosci.* 27:2596-2605 (2007).
Landel et al., "Lens-Specific Expression of Recombinant Ricin Induces Developmental Defects in the Eyes of Transgenic Mice," *Genes Dev.* 2:1168-1178 (1988).
Leone et al., "Tamoxifen-Inducible Glia-Specific Cre Mice for Somatic Mutagenesis in Oligodendrocytes and Schwann Cells," *Mol. Cell. Neurosci.* 22:430-440 (2003).
Littlewood et al., "A Modified Oestrogen Receptor Ligand-Binding Domain as an Improved Switch for the Regulation of Heterologous Proteins," *Nucleic Acids Res.* 23:1686-1690 (1995).
MacCorkle et al., "Synthetic Activation of Caspases: Artificial Death Switches," *Proc. Natl. Acad. Sci. USA* 95:3655-3660 (1998).
Madruga et al., "Dendritic Cells Conditionally Transformed by v-relER Oncogene Express Lymphoid Marker Genes," *Immunobiology* 202:394-407 (2000).
Mallet et al., "Conditional Cell Ablation by Tight Control of Caspase-3 Dimerization in Transgenic Mice," *Nat. Biotechnol.* 20:1234-1239 (2002).
Mangelsdorf et al., "The Nuclear Receptor Superfamily: The Second Decade," *Cell* 83:835-839 (1995).
Metzger et al., "Conditional Site-Specific Recombination in Mammalin Cells Using a Ligand-Dependent Chimeric Cre Recombinase," *Proc. Natl. Acad. Sci. USA* 92:6991-6995 (1995).
Minamino et al., "Inducible Gene Targeting in Postnatal Myocardium by Cardiac-Specific Expression of a Hormone-Activated Cre Fusion Protein," *Circ. Res.* 88:587-592 (2001).
Monastersky, "Gene Transfer Technology: Alternative Techniques and Applications," in Pinkert, *Transgenic Animal Technology: A Laboratory Handbook*, Academic Press, San Diego, USA pp. 177-220 (1994).
Mori et al., "Inducible Gene Deletion in Astroglia and Radial Glia—A Valuable Tool for Functional and Lineage Analysis," *Glia* 54:21-34 (2006).
Mosmann, "Rapid Colorimetric Assay for Cellular Growth and Survival: Application to Proliferation and Cytotoxicity Assays," *J. Immunol. Methods* 65:55-63 (1983).
Niculescu-Duvaz and Springer, "Introduction to the Background, Principles, and State of the Art in Suicide Gene Therapy," *Mol. Biotechnol.* 30:71-88 (2005).
Nishihara et al., "Treatment of Thyroid Carcinoma Cells with Four Different Suicide Gene/Prodrug Combinations in Vitro," *Anticancer Res.* 18:1521-1526 (1998).
Nör et al., "Ablation of Microvessels in Vivo Upon Dimerization of iCaspase-9," *Gene Ther.* 9:444-451 (2002).
Pajvani et al., "Fat Apoptosis Through Targeted Activation of Caspase 8: A New Mouse Model of Inducible and Reversible Lipatrophy," *Nat. Med.* 11:797-803 (2005).
Pearson and Lipman, "Improved Tools for Biological Sequence Comparison," *Proc. Natl. Acad. Sci. USA* 85:2444-2448 (1988).
Pelczar et al., "A Conditional Version of the Ets Transcription Factor Erm by Fusion to the Ligand Binding Domain of the Oestrogen Receptor," *Biochem. Biophys. Res. Commun.* 239:252-256 (1997).
Picard, "Regulation of Protein Function Through Expression of Chimaeric Proteins," *Curr. Opin. Biotechnol.* 5:511-515 (1994).
Polites and Pinkert, "DNA Mikroinjection and Transgenic Animal Production," Pinkert *Transgenic Animal Technology: A Laboratory Handbook* Academic Press, San Diego, USA pp. 15-68 (1994).
Portsmouth et al., "Suicide Genes for Cancer Therapy," *Mol. Aspects Med.* 28:4-41 (2007).
Pruschy et al., "Mechanistic Studies of a Signaling Pathway Activated by the Organic Dimerizer FK1012," *Chem. Biol.* 1:163-172 (1994).
Rindi et al., "Targeted Ablation of Secretin-Producing Cells in Transgenic Mice Reveals a Common Differentiation Pathway with Multiple Enteroendocrine Cell Lineages in the Small Intestine," *Development* 126:4149-4156 (1999).
Samuels et al., "Conditional Transformation of Cells and Rapid Activation of the Mitogen-Activated Protein Kinase Cascade by an Estradiol-Dependent Human Raf-1 Protein Kinase," *Mol. Cell. Biol.* 13:6241-6252 (1993).
Schwenk et al., "Temporally and Sptailly Regulated Somatic Mutagenesis in Mice," *Nucleic Acids Res.* 26:1427-1432 (1998).
Shariat et al., "Adenovirus-Mediated Transfer of Inducible Caspases: A Novel "Death Switch" Gene Therapeutic Approach to Prostate Cancer," *Cancer Res.*61:2562-2571 (2001).
Shi, "Caspase Activation: Revisiting the Induced Proximity Model," *Cell* 117:855-858 (2004).
Shi, "Mechanisms of Caspase Activation and Inhibition During Apoptosis," *Mol. Cell* 9 459-470 (2002).
Smith and Sestili, "Methods for Ligand-Receptor Assays in Clinical Chemistry," *Clin. Chem.* 26:543-550 (1980).
Smith and Waterman, "Comparison of Biotechniques," *Adv. Appl. Math.* 2:482-489 (1981).
Sofroniew et al., "Genetically-Targeted and Conditionally-Regulated Ablation of Astroglial Cells in the Central, Enteric and Peripheral Nervous Systems in Adult Transgenic Mice," *Brain Res.* 835:91-95 (1999).
Sohal et al., "Temporally Regulated and Tissue-Specific Gene Manipulations in the Adult and Embryonic Heart Using a Tamoxifen-Inducible Cre Protein," *Circ. Res.* 89:20-25 (2001).
Stoneman et al., "Monocyte/Macrophage Suppression in CD11b Diptheria Toxin Receptor Transgenic Mice Differentially Affects Atherogenesis and Established Plaques," *Circ. Res.* 100:884-893 (2007).
Takebayashi et al., "Hormone-Induced Apoptosis by Fas-Nuclear Receptor Fusion Proteins: Novel Biological Tools for Controlling Apoptosis in Vivo," *Cancer Res.* 56:4164-4170 (1996).
Thompson, "Apoptosis in the Pathogenesis and Treatment of Disease," *Science* 267:1456-1462 (1995).
Thornberry et al., "A Combinatorial Approach Defines Specificities of Member of the Caspase Family and Granzyme B," *J. Biol. Chem.* 272:17907-17911 (1997).
Tian et al., "An HSV-TK Transgenic Mouse Model to Evaluate Elimination of Fibroblasts for Fibrosis Therapy," *Am. J. Pathol.* 163:789-801 (2003).
Tomlinson et al., "A Conditional Form of Bruton's Tyrosine Kinase is Sufficient to Activate Multiple Downstream Signaling Pathways Via PLC Gamma 2 in B Cells," *BMC Immunol.* 2:4 (12 pages)(2001).
Visnjic et al., "Conditional Ablation of the Osteoblast Lineage in Col2.3Δtk Transgenic Mice," *J. Bone Miner. Res.* 16:2222-2231 (2001).
Vooijs et al., "A Highly Efficient Ligand-Regulated Cre Recombinase Mouse Line Shows that LoxP Recombination is Position Dependent," *EMBO Rep.* 2:292-297 (2001).
Wang et al., "A Regulatory System for Use in Gene Transfer," *Proc. Natl. Acad. Sci. USA* 91:8180-8184 (1994).
Weber et al., "Temporally Controlled Targeted Somatic Mutagenesis in the Mouse Brain," *Eur. J. Neurosci.* 14:1777-1783 (2001).
Wood, "Retrovirus-Mediated Gene Transfer," in Pinkett *Transgenic Animal Technology: A Laboratory Hanbook*, Academic Press, San Diego, USA pp. 147-176 (1994).
Yuan and Yankner, "Apoptosis in the Nervous System," *Nature* 407:802-809 (2000).
Zhang et al., "Development of an HSV-tk Transgenic Mouse Model for Study of Liver Damage," *FEBS J.* 272:2207-2215 (2005).

Zhao et al., "Tamoxifen-Inducible $Na_V$1.8-CreERT2 Recombinase Activity in Nociceptive Neurons of Dorsal Root Ganglia," *Genesis* 44:364-371 (2006).

International Search Report for PCT/EP2008/005013 mailed on Feb. 16, 2009.

Written Opinion for PCT/EP2008/005013.

Brocard et al., "Spatio-Temporally Controlled Site-Specific Somatic Mutagenesis in the Mouse," *Proc. Natl. Acad. Sci. U.S.A.* 94:14559-14563, 1997.

Buckley and Goa, "Tamoxifen. A Reappraisal of Its Pharmacodynamic and Pharmacokinetic Properties, and Therapeutic Use," *Drugs* 37:451-490, 1989.

Fillat et al., "Suicide Gene Therapy Mediated by the Herpes Simplex Virus Thymidine Kinase Gene/Ganciclovir System: Fifteen Years of Application," *Curr. Gene Ther*. 3:13-26, 2003.

Flamant et al., "International Union of Pharmacology. LIX. The Pharmacology and Classification of The Nuclear Receptor Superfamily: Thyroid Hormone Receptors," *Pharmacol. Rev*. 58:705-711, 2006.

Lu et al., "International Union of Pharmacology. LXV. The Pharmacology and Classification of the Nuclear Receptor Superfamily: Glucocorticoid, Mineralocorticoid, Progesterone, and Androgen Receptors," *Pharmacol. Rev*. 58:782-797, 2006.

* cited by examiner

Fig. 2 (continued)

| Sample | β-gal activity [RLU] | relative β-gal activity |
|---|---|---|
| **1) CreER 100 ng** | | |
| 1.1 without tamoxifen | **29315825** ± 860019 | **1** |
| 1.2 with $10^{-8}$ M tamoxifen | **28562925** ± 1106891 | **0.97** |
| **2) HAFasER 100 ng** | | |
| 2.1 without tamoxifen | **15341870** ± 1003335 | **0.52** |
| 2.2 with $10^{-8}$ M tamoxifen | **6685685** ± 425763 | **0.23** |
| **3) MFasER 100 ng** | | |
| 3.1 without tamoxifen | **17730580** ± 3702390 | **0.60** |
| 3.2 with $10^{-8}$ M tamoxifen | **7757925** ± 888649 | **0.26** |
| **4) BaxER 100 ng** | | |
| 4.1 without tamoxifen | **31115640** ± 2904717 | **1.06** |
| 4.2 with $10^{-8}$ M tamoxifen | **27390915** ± 1045358 | **0.93** |
| **5) ERBax 100 ng** | | |
| 5.1 without tamoxifen | **24607175** ± 96831 | **0.84** |
| 5.2 with $10^{-8}$ M tamoxifen | **24244460** ± 675655 | **0.83** |
| **6) Casp8ER 100 ng** | | |
| 6.1 without tamoxifen | **3135920** ± 57304 | **0.17** |
| 6.2 with $10^{-8}$ M tamoxifen | **625295** ± 13216 | **0.03** |
| **7) myrCasp8ER 100 ng** | | |
| 7.1 without tamoxifen | **1697988** ± 76700 | **0.06** |
| 7.2 with $10^{-8}$ M tamoxifen | **30688** ± 1054 | **0.001** |
| **8) Casp9fullER 50 ng** | | |
| 8.1 without tamoxifen | **11738755** ± 1092968 | **0.62** |
| 8.2 with $10^{-8}$ M tamoxifen | **1329815** ± 43720 | **0.07** |
| **9) Casp9truncER 50 ng** | | |
| 9.1 without tamoxifen | **13386220** ± 474242 | **0.70** |
| 9.2 with $10^{-8}$ M tamoxifen | **4247315** ± 204460 | **0.22** |
| **10) Casp3ER 100 ng** | | |
| 10.1 without tamoxifen | **7824046** ± 28175 | **0.52** |
| 10.2 with $10^{-8}$ M tamoxifen | **4188682** ± 7248 | **0.28** |
| **11) Casp3ED4ER 100 ng** | | |
| 11.1 without tamoxifen | **7579062** ± 1473448 | **0.51** |
| 11.2 with $10^{-8}$ M tamoxifen | **9712155** ± 1188726 | **0.65** |

A

B

C

D

E

F

Fig. 5 (continued)

| Sample | Viability [OD 570nm] |
|---|---|
| **1) M5N9 1.3 CreER** | |
| 1.1 without tamoxifen | 1.0035 ± 0.0417 |
| 1.2 with $10^{-8}$ M tamoxifen | 1.0095 ± 0.0742 |
| **2) M5N9 2.5 HAFasER** | |
| 2.1 without tamoxifen | 0.9180 ± 0.0778 |
| 2.2 with $10^{-8}$ M tamoxifen | 1.0145 ± 0.0247 |
| **3) M5N9 9.4 MfasER** | |
| 3.1 without tamoxifen | 0.9097 ± 0.0107 |
| 3.2 with $10^{-8}$ M tamoxifen | 0.9965 ± 0.0318 |
| **4) M5N9 4.6 ERBax** | |
| 4.1 without tamoxifen | 0.9863 ± 0.0876 |
| 4.2 with $10^{-8}$ M tamoxifen | 1.2430 ± 0.1541 |
| **5) M5N9 3.2 Casp8ER** | |
| 5.1 without tamoxifen | 0.9353 ± 0.0417 |
| 5.2 with $10^{-8}$ M tamoxifen | 0.2925 ± 0.0078 |
| **6) M5N9 7.4 myrCasp8ER** | |
| 6.1 without tamoxifen | 0.8905 ± 0.0092 |
| 6.2 with $10^{-8}$ M tamoxifen | 0.0813 ± 0.0105 |
| **7) M5N9 5.3 Casp9fullER** | |
| 7.1 without tamoxifen | 1.0255 ± 0.0233 |
| 7.2 with $10^{-8}$ M tamoxifen | 0.0600 ± 0.0046 |
| **8) M5N9 6.4 Casp9truncER** | |
| 8.1 without tamoxifen | 0.8610 ± 0.1039 |
| 8.2 with $10^{-8}$ M tamoxifen | 0.4993 ± 0.0186 |
| **9) M5N9 8.1 Casp3ER** | |
| 9.1 without tamoxifen | 1.0540 ± 0.0438 |
| 9.2 with $10^{-8}$ M tamoxifen | 1.0095 ± 0.0163 |

FUSION PROTEIN COMPRISING A CASPASE DOMAIN AND A NUCLEAR HORMONE RECEPTOR BINDING DOMAIN AND METHODS AND USES THEREOF

CROSS REFERENCED TO RELATED APPLICATIONS

This application is the U.S. National Stage of International Application No. PCT/EP2008/005013, filed Jun. 20, 2008, which claims the benefit of European Patent Application No. 07 012 138.9, filed Jun. 21, 2007, each of which is hereby incorporated by reference.

SEQUENCE LISTING

The present application contains a Sequence Listing which has been submitted in ASCII format via EFS-Web and is hereby incorporated by reference in its entirety. Said ASCII copy, created on Jul. 27, 2012, is named 50125163001.txt and is 329,640 bytes in size.

BACKGROUND OF THE INVENTION

The present invention relates to a fusion protein comprising a Caspase domain or a functionally active variant thereof and a ligand binding domain of a nuclear hormone receptor, a nucleic acid coding for the fusion protein, a vector or cell comprising the nucleic acid, a method of producing the fusion protein, a non-human transgenic animal containing the nucleic acid, the use of the fusion protein for ligand-mediated induction of apoptosis of a cell, or for studying the function of a cell, tissue and/or organ or the use of a transgenic organism for studying the function of a cell at various developmental stages or as a disease model, a method for inducing apoptosis of a cell expressing a fusion protein or for identifying a ligand, or a medicament comprising a fusion protein, the nucleic acid, the vector or the cell, particularly for the treatment of cancer or for or after transplantation, particularly as safety mechanism.

One target of genetic and genomic research is focused on the elucidation of function of individual genes within cells and organisms. Many genes are active only in certain cells and thereby contribute to the complex organisation of the mammalian body composed of hundreds of different cell types. At the level of the whole organism not single genes or gene families interact but population of cell types exist and fulfill biological functions.

To investigate these cellular functions experimentally, mutant analysis is a powerful tool. Like genetic mutants that are used to study the function of individual genes and to create models of genetic disease it is desirable to be able to create mutants for specific cell types or populations of cells in order to study their functional role in vivo. This aspect is of particular interest for the creation of animal models of human degenerative diseases that are characterized by the loss of specific cell populations, e.g. the loss of dopaminergic neurons in Parkinson's disease, or to mimic the damage of specific organs like heart or liver.

Furthermore, cells taken from a donor individual or cells grown in in vitro cultures can be transplanted or transferred into a recipient for research or therapeutic purposes. Upon cell transfer it is desirable to be able to ablate specifically all or some of the transplanted cells either to study the functions these cells fulfill in the recipient body or to enhance the safety of cell therapy if the transplanted cells thread the recipient by e.g. tumorigenesis or a graft versus host reaction (Cohen, et al., Immunol Today, 20, 172-176 (1999)) (Cohen, et al., Leuk Lymphoma, 34, 473-480 (1999)) (Cohen, et al., Hum Gene Ther, 10, 2701-2707 (1999) (Berger, et al., Blood, 103, 1261-1269 (2004)).

Moreover, in a cancer therapy termed suicide gene therapy tumor cells are equipped with an expression vector for a gene that allows to destroy these cells upon administration of a specific drug (Hurwitz, et al., Hum Gene Ther, 10, 441-448 (1999)) (Fillat, et al., Curr Gene Ther, 3, 13-26 (2003)) (Niculescu-Duvaz and Springer, Mol Biotechnol, 30, 71-88 (2005)) (Portsmouth, et al., Mol Aspects Med, 28, 4-41 (2007)).

In conclusion, it is an important aspect of biological and medical research to be able to manipulate the cellular composition of an organism such as the mammalian body. Ideally, methods would be available that enable cell ablation in a specific and also in a timed manner and that are safe, simple and universally applicable to all cell types and organs of the mammalian body.

Over the last two decades a variety of genetic methods has been developed to ablate selected cells in the body, mostly using the mouse as a model organism. These strategies can be classified into non-inducible methods that cannot be regulated from outside and lead to preprogrammed cell death during development and into inducible methods that employ initially innocent transgenes that are able mediate cell death upon administration of an inducer molecule.

The various methods are further distinguished by the biochemical mechanisms that lead to cell death, i.e. either by the accumulation of toxic products and necrotic cell death or by the use of endogenous pathways that lead to programmed cell death through apoptosis. The innate immune system reacts differently to cells that underwent pathological (necrosis) or physiological cell death (apoptosis) such that the clearance of necrotic cells is associated with proinflammatory responses of phagocytic macrophages (Cocco and Ucker, Mol Biol Cell, 12, 919-930 (2001)) (Krysko, et al., Apoptosis, 11, 1709-1726 (2006)). Therefore, the latter method is most appropriate to model disease processes that involve apoptotic cell death.

The strategies for non-inducible cell ablation in mice have used transgenes that employ the cell type specific expression of toxic proteins like the diphtheria toxin A chain (Breitman, et al., Science, 238, 1563-1565 (1987)) (Breitman, et al., Mol Cell Biol, 10, 474-479 (1990))(Kaur, et al., Development, 105, 613-619 (1989)) or Ricin (Landel, et al., Genes Dev, 2, 1168-1178 (1988)). This method was later refined such that the expression of diphtheria toxin can be controlled by the activity of Cre recombinase. In such double transgenic mice Cre recombinase is expressed from a cell type specific promoter while the diphtheria toxin transgene is under control of an ubiquitous active promoter but toxin expression occurs only upon Cre mediated deletion of an inhibitory DNA segment (Brockschnieder, et al., Mol Cell Biol, 24, 7636-7642 (2004)) (Brockschnieder, et al., Genesis, 44, 322-327 (2006)) (Ivanova, et al., Genesis, 43, 129-135 (2005)). Non-inducible cell ablation strategies rely solely on the activity of cell type specific promoter region, the activity of which cannot be further influenced in vivo. Thus, cell ablation occurs upon the initial activation of the utilised promoter region during embryonic development.

To gain also control on the timing of cell ablation a variety of inducible ablation strategies has been developed. Two of these methods are based on the transgenic expression of prokaryotic enzymes that modify specific prodrugs into cytotoxic derivates. The prodrugs are not recognised by mammalian enzymes. Thus, the cells expressing the prokaryotic enzyme are only killed upon the administration of the specific prodrug.

The use of a thymidine kinase derived from Herpes simplex virus (HSV-tk) enables to kill HSV-tk expressing, dividing cells by the administration of Ganciclovir (GANC) (Sofroniew, et al., Brain Res, 835, 91-95 (1999)) (Visnjic, et al., J Bone Miner Res, 16, 2222-2231 (2001)) (Rindi, et al., Development, 126, 4149-4156 (1999)) (Tian, et al., Am J Pathol, 163, 789-801 (2003)) (Ito, et al., Nat Med, 11, 1351-1354 (2005)) (Dancer, et al., Gene Ther, 10, 1170-1178 (2003)) (Lalancette-Hebert, et al., J Neurosci, 27, 2596-2605 (2007)) (Zhang, et al., Febs J, 272, 2207-2215 (2005)). GANC is phosphorylated only by HSV-tk and then blocks DNA replication leading to the death of mitotic cells. Post-mitotic, resting cells cannot be ablated with the HSV-tk/GANC system.

The use of the Nitroreductase (NTR) gene derived from *E. coli* enables to kill NTR expressing cells by the administration of the prodrug CB1954 (Clark, et al., Gene Ther, 4, 101-110 (1997)) (Cui, et al., Glia, 34, 272-282 (2001)) (Isles, et al., J Neurobiol, 47, 183-193 (2001)) (Gusterson, et al., Recent Results Cancer Res, 163, 31-45 (2003)). The cytotoxic derivative leads to the formation of interstrand DNA crosslinks which are poorly repaired by the cells. The NTR system is independent of the cell cycle and can be applied to non-dividing cells (Grove, et al., Cancer Res, 63, 5532-5537 (2003)). The prodrug CB1954, however, has evolved from cancer therapy and a significant bystander effect has been observed because of local spread of the activated prodrug that leads to the death of neighbored cells (Bridgewater, et al., Hum Gene Ther, 8, 709-717 (1997)) (Nishihara, et al., Anticancer Res, 18, 1521-1525 (1998)). While this effect is beneficial for cancer therapy it diminishes the utility of the NTR system for specific cell ablation.

In another inducible approach cells that express a receptor for diphtheria toxin (DTR) from a cell type specific transgene can be killed by the in vivo administration of diphtheria toxin A chain (DTA) (Buch, et al., Nat Methods, 2, 419-426 (2005)) (Chang and Yang, Sci STKE, 2003, PL1 (2003)) (Stoneman, et al., Circ Res, (2007)). DTA is toxic upon internalisation that is mediated by the transgenic DTR.

Besides the use of toxins or enzymes that lead to cytotoxic products two methods for inducible cell ablation have been developed that exploit endogenous cellular mechanisms of programmed cell death.

In the system described by Takebayashi (Takebayashi, et al., Cancer Res, 56, 4164-4170 (1996)) the transmembrane and intracellular domain of the Fas death receptor (amino acid 135-305) has been fused N-terminally to the ligand binding domain of the rat estrogen receptor. This fusion protein was constitutively expressed in L929 cells known to be sensitive to Fas-mediated apoptosis. From studies with wildtype estrogen receptor it has been found that upon ligand administration the ER domain undergoes a conformational change that leads to the dissociation of bound heat shock proteins and receptor dimerisation. The administration of estradiol to Fas-ER expressing L929 cells, T-lymphocytes or HeLa cells leads to cell death by apoptosis (Takebayashi, et al., Cancer Res, 56, 4164-4170 (1996)) (Kawaguchi, et al., Cancer Lett, 116, 53-59 (1997)) (Kametaka, et al., Cancer Sci, 94, 639-643 (2003)).

In a variation of this method the non-modified ER domain was replaced by a mutant murine ER ligand binding domain (amino acids 287-599) that harbours a single amino acid exchange (G525R). This mutation leads to a strongly reduced affinity to estradiol but the receptor can still be activated by 4-OH-tamoxifen. This Fas-ER(G525R) fusion protein was tested in the mouse cell line L929 (Kodaira, et al., Jpn J Cancer Res, 89, 741-747 (1998)). The Fas-ER method uses the extrinsic CD95 apoptosis pathway to induce cell death. Since this pathway is restricted in vivo largely to cells of the immune system (Krammer, Nature, 407, 789-795 (2000)) most other cell types in the body may be unresponsive to Fas-ER fusion proteins.

A cell ablation method that utilises ubiquitously expressed components of the intrinsic apoptosis pathways was first described by MacCorkle (MacCorkle, et al., Proc Natl Acad Sci USA, 95, 3655-3660 (1998)). For this method a domain of the FK506 binding protein FKBP was fused to the N-terminus of Caspase-1 or Caspase-3 and expressed in human Jurkat T cell lymphoma cells. Upon administration of dimeric FK506 (FK1012; Pruschy, et al., Chem Biol, 1, 163-172 (1994)), a chemical inducer of dimerisation (CID), the fusion proteins undergo oligomerisation and lead to cell death by apoptosis. This system was further developed by the fusion of one or more modified FKBP domains (Fv) to the N-terminus of Fas, Bax, Caspase-1, -3, -8 and -9 (Fan, et al., Hum Gene Ther, 10, 2273-2285 (1999)) (Hou and Hsu, Am J Physiol Heart Circ Physiol, 289, H477-487 (2005)). The Fv domain can be dimerised by the FK1012 analogs AP1903 (Fan, et al., Hum Gene Ther, 10, 2273-2285 (1999)) or AP20187 (Chang, et al., J Biol Chem, 278, 16466-16469 (2003)) that exhibit a higher affinity to the modified Fv domain than to the wildtype FKBP. However, FK506 and analogs that bind to FKBP exhibit a strong immunosuppressive action in vivo (Bierer, et al., Curr Opin Immunol, 5, 763-773 (1993)). The CID apoptosis system has been used for the ablation of transplanted endothelial cells in vivo that were transduced with a viral vector expressing a Fv-Caspase-9 fusion protein (Nor, et al., Gene Ther, 9, 444-451 (2002)) and to demonstrate suicide gene therapy of prostate cancer cells with a viral vector expressing a Fv-Caspase-1 protein (Shariat, et al., Cancer Res, 61, 2562-2571 (2001)). This system was further used in transgenic mice expressing a Fv-Caspase-3 fusion protein in hepatocytes as a model of inducible liver injury (Mallet, et al., Nat Biotechnol, 20, 1234-1239 (2002)) and in transgenic mice expressing a Fv-Caspase-8 fusion protein in adipocytes to create a model of inducible lipoatrophy (Pajvani, et al., Nat Med, 11, 797-803 (2005)).

Although great efforts have been undertaken to derive systems that allow inducible cell ablation in the mammalian body the existing technologies have severe limitations that limit their practical use:

1. The expression of diphtheria toxin from a cell type specific promoter or the activation of a diphtheria toxin gene through Cre recombinase expressed from a cell type specific promoter does not allow the induction of cell ablation from outside and does not provide control on the timing of cell ablation.
2. The ablation of cells expressing HSV-thymidine kinase by the administration of GANC enables induction from outside but this system is restricted to actively proliferating cells. Resting cells like mature neurons cannot be ablated.
3. The nitroreductase system is derived from cancer therapy and can lead to nonspecific cell death of neighbouring cells.
4. The activation of a diphtheria toxin receptor gene through Cre recombinase expressed from a cell type-specific promoter followed by administration of diphtheria toxin is impractical because it requires two independent transgenes and the generation of double transgenic mice.

5. The utility of the Fas-ER(G525R) fusion protein is restricted only to cells that are responsive to the CD95 extrinsic apoptosis pathway, i.e. mostly cells of the immune system.
6. The inducible CID system in combination with active Caspase domains has been developed for in vitro use and has limitations for in vivo application with respect to the pharmacology of the inducing compounds. The first generation inducer FK1012 (as a dimer of FK506; Pruschy, et al., Chem Biol, 1, 163-172 (1994)), and putatively also the analogs that bind to the endogenous FKPB protein, from which the CID dimeriser domain is derived, are immunosuppressive (Bierer, et al., Curr Opin Immunol, 5, 763-773 (1993)). The in vivo pharmacokinetics, metabolism and toxicity of these compounds (e.g. AP20187; (Chang, et al., J Biol Chem, 278, 16466-16469 (2003)) has not been characterised. Furthermore, it is not known whether any of these compounds penetrates the blood-brain barrier such that the utility of the CID system for use in the brain is unpredictable.

DETAILED DESCRIPTION OF THE INVENTION

In contrast to the diversity of biological and medical research application of inducible apoptosis systems for mammalian cells, very limited efforts have been made to optimise inducible apoptosis techniques towards a universal use in mammals. Alternative apoptosis induction systems of different ligand specificity could further enhance the flexibility of cell and tissue engineering in vivo.

The reason for this unsatisfying situation is readily explained by a number of requirements that should be fulfilled—at least in part—by a universally useful inducible apoptosis system in mammals:

I) it should act through a single polypeptide that can be expressed from a single transgene,
II) it should utilise mechanisms endogenous to the cell,
III) it should be able to induce cell death in at least most mammalian cell types and organs, especially also in brain cells,
IV) it should not include immunogenic peptide sequences,
V) it should be induced by compounds that have minimal effects on cells other than the target cells, and
VI) it should be induced by compounds that can preferably be applied also by oral administration, that are safe for use in humans and should act in preferably all organs, especially including the brain.

Therefore, it was an object of the present invention to provide an alternative fusion protein providing inducible apoptosis and preferably avoiding one or more of the above limitations. Particularly, the object to be solved by the invention of the present application is the provision of an inducible apoptosis system alternative to the Casp-FKBP and the Fas-ER systems, which has a different ligand binding domain or a different apoptosis inducing domain. Such an alternative inducible apoptosis system is particularly desirable for all those applications which require universal activation in any organ and any cell type of the mammalian body, including the brain.

Surprisingly, this object has been solved by a fusion protein comprising a Caspase domain or a functionally active variant thereof and a ligand binding domain of a nuclear hormone receptor or a functionally active variant thereof.

Given the limited knowledge on the protein biochemistry of steroid receptors and the molecular mechanisms of apoptosis, it is presently not possible to rationally design biological active and inducible apoptosis-inducing fusion proteins. In particular, it has not been described that a protein such as a Caspase that naturally requires proteolytic processing to develop enzymatic activity or that a protein that acts as a protease could be successfully fused with the ligand binding domain of a nuclear hormone receptor (LBD) into a ligand inducible fusion protein. In particular, upon fusion of a Caspase domain with a steroid receptor LBD it was unpredictable whether such a fusion protein developed biological activity since the molecular mechanism of Caspase activation are essentially unknown. For the only described example of the fusion of an apoptosis-related molecule, the Fas receptor, with the ER(T) LBD mutant, it is important to note that the intracytoplasmic domain of Fas receptor does not act as a protease and it has been found that a simple fusion of this domain with ER(T) is biologically inactive. Biological activity could be only detected in a fusion protein that also included the transmembrane region of the Fas receptor (Takebayashi, et al., Cancer Res, 56, 4164-4170 (1996)) such that it is unlikely that this fusion protein becomes only activated by heat shock protein dissociation or induced dimerisation but rather by a third, yet unknown mechanism. With regard to the above described Caspase fusion proteins with one or more FKBP-derived dimeriser (CID) domains it has been found that the forced oligomerisation leads to Caspase activation but the underlying mechanism remains unknown. In this system the CID domains have been fused onto the N-terminal end of Caspases or Caspase domains. Fusion proteins with dimeriser domains onto the C-terminal end of Caspases or Caspase domains have not been described and it is unknown whether such molecules would develop biological activity. The expression of a newly designed Caspase fusion protein in mammalian cells can be in general a difficult task since the two fusion protein domains may not acquire their native conformation during translation. Furthermore, the three-dimensional structure of such a fusion protein may be inappropriate for the interaction of a pair of Caspase domains, for the proteolytic activity of activated Caspase or for the ligand induced activation of the fusion partner. In addition, a newly designed fusion protein may exhibit a short half-life or form aggregates that lead to its rapid degradation by the proteasome machinery, or the fusion protein mRNA exhibits a short half-life or may contain cryptic splice sites.

Inventors could now show that fusion proteins comprising a Caspase domain, particularly a domain of Caspase 8 or 9, and a ligand binding domain of a nuclear hormone receptor, particularly mutant mammalian estrogen receptor ER(T2), expressed in mammalian cells induced apoptosis in these cells upon exposure to a ligand for that ligand binding domain of a nuclear hormone receptor, particularly the synthetic ligand 4-hydroxy-tamoxifen. It was proven that either full length Caspase or a functionally active fragment thereof can be used within the fusion protein.

Quantitative analysis of apoptosis upon ligand administration using the cells transiently expressing the fusion protein of the invention revealed that observed cell death in combination with the expression of the fusion proteins is a specific effect. In particular, the inventors provide first evidence for three highly efficient Caspase-ER(T2) fusion proteins: myrCasp8-ER(T2), Casp8-ER(T2) and Casp9full-ER(T2) (see Examples).

Also the stable genomic integration of active ER(T2) fusion proteins confirmed the results obtained for transient expression, namely the ability of the fusion protein to induce 4-OH-tamoxifen-dependent cell death in stably transfected cells.

Taken together, inventors have demonstrated for the first time that fusion constructs of Caspase domains and ligand binding domains of nuclear hormone receptor provide a highly efficient system to conditionally ablate mammalian cells. Moreover, since Caspases, particularly Caspase 8 and Caspase 9, are ubiquitously expressed in mammalian tissues and are both involved in different pathways of apoptosis, the potential universal application of nuclear hormone receptor fusions to Caspases, such as Caspase 8 or Caspase 9, for inducible cell ablation is of commercial relevance in biotechnology.

The present invention is the first disclosure of a protein that naturally requires proteolytic processing to develop enzymatic activity and that a fusion protein comprising a protein that acts as a protease, could be successfully fused with a steroid receptor LBD into a ligand inducible fusion protein.

The resulting Caspase nuclear hormone receptor ligand binding domain fusion proteins allow the highly efficient induction of Caspase activation leading to apoptosis in mammalian cells upon administration of a ligand that binds to the ligand binding domain.

The improved inducible apoptosis system of the present invention provides a universal apoptosis system for use in mammalian cells and organisms that allows to study the biological function of selected cells or a cell type in the mammalian body and thereby the creation of a wide range of animal models of human diseases. This apoptosis system further allows to remove transplanted cells that contain a fusion protein expression vector from the body of a recipient upon induction or to destroy tumor cells that were transduced or transfected with a fusion protein expression vector.

Accordingly, in a first aspect the present invention relates to a fusion protein comprising (a) a Caspase domain or a functionally active variant thereof and (b) a ligand binding domain of a nuclear hormone receptor or a functionally active variant thereof.

Thus, the present invention enables the highly efficient modification of the cellular composition of the mammalian body by cell type-specific, inducible apoptosis. Said process possesses the following advantages over current technology:

(i) the Caspase fusion protein, in particular the Caspase-8 or -9 fusion with the ER(T2) LBD, allows to induce Caspase activity and thereby apoptosis in dependence of steroid receptor ligands, in particular 4-OH-Tamoxifen, and (ii) the Caspase fusion protein, in particular the Caspase-8 or -9 fusion with the ER(T2) LBD, is the first described alternative inducible, Caspase-based apoptosis system with comparable efficiency to the FKBP dimeriser system for the modification of the cellular composition of the mammalian body.

In a preferred embodiment of the invention upon exposure to a ligand of the ligand binding domain of a nuclear hormone receptor, the fusion protein is capable of inducing apoptosis in a cell, preferably a eukaryotic cell, expressing the fusion protein.

Therefore, the first component of the fusion protein is a Caspase domain that is any domain of a Caspase capable of inducing apoptosis or a functionally active variant thereof.

Caspases are central components of the machinery for apoptosis. Apoptosis, or programmed cell death, plays a central role in the development and homeostasis of multicellular organisms (Jacobson, et al., Cell, 88, 347-354 (1997)). In humans, both excessive and insufficient apoptosis can lead to severe pathological consequences. Suppression of the apoptotic machinery causes autoimmune diseases and is a hallmark of cancer (Hanahan and Weinberg, Cell, 100, 57-70 (2000)) (Thompson, Science, 267, 1456-1462 (1995). On the other hand, abnormal upregulation of apoptosis contributes to neurological disorders (Yuan and Yankner, Nature, 407, 802-809 (2000)).

Fourteen distinct mammalian Caspases have been identified so far; at least 7 of these play important roles during apoptosis (Shi, Mol Cell, 9, 459-470 (2002)), namely Caspases 2, 3, 6, 7, 8, 9 and 10.

Caspases involved in apoptosis are generally divided into two categories, the initiator Caspases, which include without limitation Caspase 1, 8, 9, and 10, and the effector Caspases which include without limitation Caspase 3, 6, and 7.

An initiator Caspase is in general characterised by an extended N-terminal prodomain (>90 amino acids) important for its function, whereas an effector Caspase contains 20-30 residues in its prodomain sequence.

Caspases are produced in cells as catalytically inactive zymogens and must undergo proteolytic activation during apoptosis. The activation of an effector Caspase (e.g. Caspase 3) is performed by an initiator Caspase (e.g. Caspase 8 or 9) through cleavage at specific internal aspartate residues that separate the large and small subunits. The initiator Caspases are autoactivated; as this activation triggers a cascade of downstream Caspase activation, it is tightly regulated and requires the assembly of a multicomponent complex termed apoptosome (Bao and Shi, Cell Death Differ, 14, 56-65 (2007)). The initiator Caspases contain one of two protein-protein interaction motifs, the CARD (Caspase recruitment domain) or the DED (death effector domain). These motifs interact with similar motifs present on oligomerized adaptor proteins, bringing multiple initiator Caspase molecules into close proximity and facilitating their autoactivation (Shi, Mol Cell, 9, 459-470 (2002)).

However, the exact mechanisms by which the initiator Caspases are activated by the apoptosome remain elusive. Several models have been proposed: i) the induced proximity model summarizes the general process of initiator Caspase activation, ii) the proximity-driven dimerisation model describes how initiator Caspases respond to induced proximity, iii) the induced conformation model posits that the activated conformation for the active site of a initiator Caspase is attained through direct interaction with the apoptosome or through homo-oligomerization facilitated by the apoptosome (Bao and Shi, Cell Death Differ, 14, 56-65 (2007)). The functional Caspase unit is a homodimer, with each monomer comprising a large 20 kDa and a small 10 kDA subunit. Homodimerization is mediated by hydrophobic interactions, with 6 antiparallel beta-strands from each catalytic subunit forming a single contiguous 12-stranded beta-sheet. Several alpha-helices and short beta-strands are located on either side of the central beta-sheet, giving rise to a globular fold. The active sites, formed by four protruding loops from the scaffold, are located at two opposite ends of the beta-sheet (Shi, Mol Cell, 9, 459-470 (2002)). Once activated the effector Caspases are responsible for the proteolytic cleavage of a broad spectrum of cellular targets, leading ultimately to cell death.

In accordance with the present invention the first component of the fusion protein may also be a functionally active variant of a Caspase domain. Functional active variants are obtainable by changing the sequence of the Caspase domain as defined herein and are characterized by having a biological activity similar to that displayed by the Caspase domain from which it is derived, including the ability to induce apoptosis. Ability to induce apoptosis of a variant can be determined e.g. as described in the Examples, i.e. by producing a fusion protein as described in Example 1, wherein the variant is to be substituted for the Caspase domain, expressing the fusion protein and determining apoptosis in response to e.g. 4-OH-tamoxifen as described in Example 2 or 3.

Alternatively, the activity of a functionally active variant can be determined in vitro by the cleavage of chromophore-conjugated synthetic peptide substrates that mimic the cleavage site for the respective Caspase. Suitable tests, which can be used in order to determine activity of a variant are described in the art (see e.g. Kohler et al., J Immunol Methods, 265, 97-110 (2002)) (Thornberry et al., J Biol Chem, 272, 17907-11 (1997)).

The variant of an Caspase is functionally active in the context of the present invention, if the activity of the fragment amounts to at least 10%, preferably at least 25%, more preferably at least 50%, even more preferably at least 70%, still more preferably at least 80%, especially at least 90%, particularly at least 95%, most preferably at least 99% of the activity of the Caspase without sequence alteration.

A variant of the above Caspases in accordance with the present invention relates to a mutant of the respective original (viz. wild-type) Caspase having a Caspase activity as defined above (e.g. at least about 50% of said wild-type Caspase). Variants include truncated forms of the Caspase (such as N- or C-terminal truncated Caspase proteins), deletion-type mutants (where one or more amino acid residues or segments having more than one continuous amino acid residue have been deleted from the primary sequence of the wildtype Caspase), replacement-type mutants (where one or more amino acid residues or segments of the primary sequence of the wildtype Caspase have been replaced with alternative amino acid residues or segments), or the addition of signal peptides that alter intracellular localisation (where e.g. the myristoylation signal sequence GSSKSKPKDPSQR (SEQ ID NO: 82) have been added to the Caspase N-terminus) or combinations thereof.

In one embodiment of the present invention the Caspase domain or functionally active variant thereof may be a fragment. The fragment is characterized by being derived from a naturally occurring Caspase as defined below by one or more amino acid deletions. The deletion(s) may be C-terminally, N-terminally and/or internally. Preferably the fragment is obtained by at most 100, more preferably by at most 50, even more preferably at most 30, still more preferably at most 10, most preferably 1, 2, 3, 4 or 5 deletion(s).

The functional active fragment may be also characterized by its sequence homology to the wild type domain. Accordingly, in one preferred embodiment of the invention the functional active fragment consists of at least 60%, preferably at least 70%, more preferably at least 80%, still more preferably at least 90%, even more preferably at least 95%, most preferably 99% of any naturally occurring Caspase, e.g. those listed above. The functional active fragment as defined above may be derived from the peptide by one or more amino acid deletions. The deletions may be C-terminally, N-terminally and/or internally.

In another preferred embodiment of the invention the Caspase domain is a functionally active variant of a Caspase, wherein the variant is derived from any naturally occurring Caspase, e.g. those listed above, by one or more amino acid deletion(s), addition(s) and/or substitution(s) and preferably wherein the variant has at least 50% sequence identity to a naturally occurring Caspase domain. In a more preferred embodiment the functional active variant has a sequence identity of at least 60%, preferably at least 70%, more preferably at least 80%, still more preferably at least 90%, even more preferably at least 95%, most preferably 99% to any naturally occurring Caspase, e.g. those listed above.

The percentage of sequence identity can be determined e.g. by sequence alignment. Methods of alignment of sequences for comparison are well known in the art. Various programs and alignment algorithms have been described e.g. in Smith and Waterman, Adv. Appl. Math. 2: 482, 1981 or Pearson and Lipman, Proc. Natl. Acad. Sci. U.S.A. 85: 2444-2448, 1988.

The NCBI Basic Local Alignment Search Tool (BLAST) (Altschul et al., J. Mol. Biol. 215: 403-410, 1990) is available from several sources, including the National Center for Biotechnology Information (NCBI, Bethesda, Md.) and on the Internet, for use in connection with the sequence analysis programs blastp, blastn, blastx, tblastn and tblastx. Variants of any naturally occurring Caspase, e.g. those listed above, are typically characterized using the NCBI Blast 2.0, gapped blastp set to default parameters. For comparisons of amino acid sequences of at least 35 amino acids, the Blast 2 sequences function is employed using the default BLOSUM62 matrix set to default parameters, (gap existence cost of 11, and a per residue gap cost of 1).

As noted above, the functionally active variant of a Caspase is obtained by sequence alterations in the sequence of the Caspase, wherein the variant retains the function of the Caspase (see above). The term "functionally active variant" includes naturally occurring allelic variants, as well as mutants or any other non-naturally occurring variants.

However, if the variant is obtained from a Caspase by one or more substitution(s) conservative substitution(s) is/are preferred. Conservative substitutions are those that take place within a family of amino acids that are related in their side chains and chemical properties. Examples of such families are amino acids with basic side chains, with acidic side chains, with non-polar aliphatic side chains, with non-polar aromatic side chains, with uncharged polar side chains, with small side chains, with large side chains etc. In one embodiment, one conservative substitution is included in the variant. In another embodiment, two conservative substitutions or less are included in the peptide. In a further embodiment, three conservative substitutions or less are included in the variant.

Examples of conservative amino acid substitutions include, but are not limited to, the following: Ala→Ser; Arg→Lys; Asn→Gln or His; Asp→Glu; Cys→Ser; Gln→Asn; Glu→; His→Asn or Gln; Ile→Leu or Val; Leu→Ile or Val; Lys→Arg or Gln or Asn; Met→Leu or Ile; Phe→Met or Leu or Tyr; Ser→Thr; Thr→Ser; Trp→Tyr; Tyr→Trp or Phe; Val→Ile or Leu, wherein the amino acid mentioned first (before the arrow) indicates the original amino acid without substitution and the second amino acid(s) (after the arrow) indicate(s) the amino acid to be substituted for the respective first amino acid.

In case of one or more amino acid addition(s), these may result for the cloning of the Caspase or functionally active variant thereof, e.g. due to the use of particular restriction sites, and may or may not alter (increase or decrease) the activity of the Caspase. Alternatively, amino acids may be added in order to achieve a desired result, e.g. addition of a tag to provide for convenient purification.

Caspase proteins which can be used in the Caspase domain of the fusion protein of the present invention include, but are not limited to, a certain type of apoptosis inducing proteases belonging to the mammalian families of initiator and effector Caspases (Ho and Hawkins, Febs J, 272, 5436-5453 (2005)) (Bao and Shi, Cell Death Differ, 14, 56-65 (2007)) (Shi, Mol Cell, 9, 459-470 (2002)). These families include Caspase-3 (the amino acid sequences of said murine and human Caspase are shown in SEQ ID NOS: 58 and 59, respectively), Caspase-7 (the amino acid sequences of said murine and human Caspase are shown in SEQ ID NOS: 60 and 61, respectively), Caspase-6 (the amino acid sequences of said murine and human Caspase are shown in SEQ ID NOS: 62 and 63, respectively), Caspase-8 (the amino acid sequences of said murine and human Caspase are shown in SEQ ID NOS: 64 and 65, respectively), Caspase-10 (the amino acid sequence of said human Caspase is shown in SEQ ID NO: 66), Caspase-9 (the amino acid sequences of said murine and human Caspase are shown in SEQ ID NOS: 67 and 68, respectively), Caspase-2 (the amino acid sequences of said murine and human Caspase are shown in SEQ ID NOS: 69 and 70, respectively), Caspase-12 (the amino acid sequence of said murine Caspase is shown in SEQ ID NO: 71), and the like, or mutants thereof. Other vertebrate Caspases known in the art are also applicable.

Preferably, in the context of the present invention the Caspase domain is a Caspase or functionally active variant thereof selected from the group consisting of Caspase-2, Caspase-3, Caspase-6, Caspase-7, Caspase-8, Caspase-9, Caspase-10, and Caspase-12, or functionally active variant thereof, most preferably Caspase-8 or Caspase-9 or a functionally active variant thereof. More preferably, the Caspase is a mammalian Caspase, especially a murine or human Caspase, still more preferably selected from the group consisting of Caspase-2, Caspase-3, Caspase-6, Caspase-7, Caspase-8, Caspase-9, Caspase-10, and Caspase-12, most preferably Caspase-8 or Caspase-9, especially a murine or human Caspase-8 or Caspase-9. Preferred examples of sequences of Caspases are those of SEQ ID NO: 58 to 71, especially of SEQ ID NO: 64, SEQ ID NO: 65, SEQ ID NO: 67 or SEQ ID NO: 68.

In another preferred embodiment of the invention the Caspase domain of the fusion protein as defined above comprises or consists of the amino acid sequence of SEQ ID NO: 64, SEQ ID NO: 65, SEQ ID NO: 67 or SEQ ID NO: 68; or functionally active variants, particularly fragments thereof.

Most preferably, in the fusion protein of the invention the Caspase domain is preferably a murine Caspase-9 having the amino acid sequence shown in SEQ ID NO: 67 or a N-terminal truncated form thereof, or a murine Caspase-8 having the amino acid sequence shown in SEQ ID NO: 64 or a modified Caspase-8 that is fused with a myristoylation signal sequence at the N-terminus. Suitable truncated forms of the Caspase-9 comprise amino acid residues 92 to 454 of SEQ ID NO: 67; suitable modified Caspase-8 having an N-terminal fusion with a myristoylation signal peptide comprise the sequence GSSKSKPKDPSQR (SEQ ID NO: 82).

The second component of the fusion protein of the invention is the ligand binding domain of a nuclear hormone receptor (LBD) or a functionally active variant thereof. The LBD is located in the carboxyl-terminal half of the receptor, consists in general of about 300 amino acids.

It is noted that the ligand binding domain of a nuclear hormone receptor (LBD) or a functionally active variant thereof can be activated upon binding of a ligand to the LBD. In accordance with the present invention, the Caspase activity of the fusion protein in a cell is significantly higher in the presence of ligand as compared to its activity in the absence of ligand for the LBD or variant thereof.

A "significantly higher activity" in accordance with the present invention refers to an increase in death rate of at least 25%, preferably at least 50%, more preferably at least 75, most preferably at least 90%. The death rate may be determined as detailed in Example 2 or 3, wherein the respective fusion protein is to be used instead of those used for the Examples and the ligand is to be chosen in accordance with the LBD. For example, the death rate may be determined within 3 days in the presence of the ligand, e.g. 4-OH-Tamoxifen at a $10^{-6}$ molar (or lower) concentration to a MEF5 cell clone that expresses a stably integrated Caspase-ER(T2) fusion protein expression vector.

Fusion proteins including wild type and mutant steroid receptors have already been generated to regulate the activity of the fusion partner by natural or synthetic ligands (Picard, Curr Opin Biotechnol, 5, 511-515 (1994)). It is believed that the heat shock proteins that are bound to the ligand binding domain of a nuclear hormone receptor (LBD) and that dissociate upon ligand binding keep the fusion partner inactive in the absence of ligand (Picard, Curr Opin Biotechnol, 5, 511-515 (1994)). This inhibition could occur either by sterical hindrance or by partial unfolding of the protein structure. The exact mechanism of this phenomenon has not been resolved such that a predictable construction of regulated, inducible LBD fusion proteins is not possible (Picard, Curr Opin Biotechnol, 5, 511-515 (1994)).

Therefore, the derivation of new fusion proteins is presently rather an empirical approach than a theoretical approach. The only parameter known that might be important for the regulability of a fusion protein is the length of the connecting region between the fusion partner and the LBD (Picard, Curr Opin Biotechnol, 5, 511-515 (1994)). If the spacing is rather long the fusion partner may be active even in the absence of ligand but if the distance is too short the activity of the fusion partner can be completely abolished even in the presence of ligand. A second, intrinsic property of LBD fusion proteins is the presence of a hidden nuclear localisation function that becomes active only upon ligand binding such that fusion proteins usually accumulate in the nucleus.

Furthermore, it has been found that the wildtype estrogen receptor LBD forms a dimer upon binding of the natural ligand estradiol or the synthetic ligand 4-OH-Tamoxifen (Kumar and Chambon, Cell, 55, 145-156 (1988)), other synthetic ligands like ICI 164384 do not induce dimerisation (Fawell, et al., Cell, 60, 953-962 (1990)). The exact mechanism of the dimerisation process is not characterised but point mutants that are unable to dimerise have been described. These mutations fall into the same LBD subdomain that is also important for the specificity of ligand binding such that mutants that exhibit altered ligand binding properties may be also affected for dimerisation (Fawell, et al., Proc Natl Acad Sci USA, 87, 6883-6887 (1990)). For fusion partner proteins that act as monomer a forced dimerisation would be an unwanted but unavoidable effect, however, for the described inducible fusion proteins (see below) dimerisation does not severely interfere with protein function.

Inducible fusion proteins with steroid receptor LBD's have generated with the following functional types of proteins: transcription factors like E2F1, STAT6 and Ets (Agger, et al., Oncogene, 24, 780-789 (2005))(Kamogawa, et al., J Immunol, 161, 1074-1077 (1998)) (Pelczar, et al., Biochem Biophys Res Commun, 239, 252-256 (1997)), protein kinases like Raf or Btk (Samuels, et al., Mol Cell Biol, 13, 6241-6252 (1993)) (Tomlinson, et al., BMC Immunol, 2, 4 (2001)), oncogenes like Myc or Rel (Madruga, et al., Immunobiology, 202, 394-407 (2000)) (Littlewood, et al., Nucleic Acids Res, 23, 1686-1690 (1995)), and DNA recombinases like Cre recombinase (Metzger, et al., Proc Natl Acad Sci USA, 92, 6991-6995 (1995)) or FLP recombinase (Hunter, et al., Genesis, 41, 99-109 (2005)). The fusion of steroid receptor LBD's with proteins that require further processing to become active or that directly act as a protease has not been described.

In the context of the present invention a LBD of any nuclear hormone receptor may be used. Nuclear hormones receptors are a class of protein molecules found within the interior of cells that are responsible for sensing the presence of hormones and certain other molecules. Nuclear receptors have the ability to directly bind to DNA and regulate the expression of adjacent genes. The regulation of gene expression by nuclear receptors is ligand dependent. In other words, nuclear receptors normally are only active in the presence of ligand. More specifically, ligand binding to a nuclear receptor results in a conformational change in the receptor which in turn activates the receptor resulting in e.g. up-regulate of gene expression. Examples of nuclear hormone receptors of the estrogen-like receptor family, which is preferred, include without limitation estrogen receptor (estrogen receptor-α, estrogen receptor-β, an estrogen related receptor, a ketosteroid receptor such as the glucocorticoid receptor, the mineralocorticoid receptor, the progesterone receptor or the androgen receptor. Alternative receptor subfamilies are thyroid hormone receptor-like, retinoid X receptor-like, nerve growth factor IB-like, steroidogenic factor-like and germ cell nuclear factor-like receptors.

Regulated fusion proteins have particularly been constructed with the LBD of the well characterised estrogen receptor (ER), either in its wildtype form that responds to the natural ligand estradiol or by the use of receptor mutants that exhibit strongly reduced estradiol binding but can be activated by synthetic ligands like 4-OH-Tamoxifen. The use of such ER LBD mutants may be of importance for in vivo applications in mammals, if spontaneous activation of a fusion partner by naturally occurring estrogens is to be avoided.

The first mutant of this type was a murine ER LBD that contains a single point mutation replacing a glycine by an arginine residue at position 525 of the mouse or the analogous position 521 of the human estrogen receptor (ER(T)) (Brocard, et al., Proc Natl Acad Sci USA, 94, 14559-14563 (1997)) (Danielian, et al., Mol Endocrinol, 7, 232-240 (1993)). However, as compared to the wildtype ER LBD this mutation also lowers the affinity of the mutant LBD to the synthetic ligand 4-OH-Tamoxifen. A new human ER LBD mutant harbouring three point mutations (G400V/M543A/L544A, named ER(T2)) was described by Feil (Feil, et al., Biochem Biophys Res Commun, 237, 752-757 (1997)) and it was found in fusion with Cre recombinase to act in transgenic mice 10-fold more sensitive to 4-OH-Tamoxifen induction as compared to the ER(T) mutant (Indra, et al., Nucleic Acids Res, 27, 4324-4327 (1999)). The ER(T) (G525) mutant has been shown to dimerise with the ligand 4-OH-Tamoxifen (Danielian, et al., Mol Endocrinol, 7, 232-240 (1993)); for the triple mutant ER(T2) dimerisation has not been characterised.

Besides the estrogen receptor occasionally other steroid receptor mutants have been used to derive inducible fusion proteins, i.e. a mutant human progesterone receptor (Wang, et al., Proc Natl Acad Sci USA, 91, 8180-8184 (1994)) (Kellendonk, et al., Nucleic Acids Res, 24, 1404-1411 (1996)) (Kellendonk, et al., J Mol Biol, 285, 175-182 (1999)) a mutant glucocorticoid receptor (Brocard, et al., Nucleic Acids Res, 26, 4086-4090 (1998)) and a mutant androgen receptor (Kaczmarczyk and Green, Nucleic Acids Res, 31, e86 (2003)). Modified receptors are also described in US 2003/109683.

LBDs modified to only bind a compound selected from the group consisting of non-natural ligands, anti-hormones and non-native ligands are preferred.

The most frequently used ER fusion protein is Cre-ER(T2) consisting of Cre recombinase in fusion with the ER(T2) LBD in combination with the inducer 4-OH-Tamoxifen for in vitro or Tamoxifen for in vivo application. Cre-ER(T2) is frequently used in transgenic mice as a system that enables inducible DNA recombination in vivo. In such Cre-ER(T2) transgenic mice the fusion protein is expressed from a cell type specific promoter and allows the inactivation of a modified endogenous gene that has been flanked with two Cre (loxP) recognition sites. Inducible recombination with this system has been demonstrated in vivo for a variety of cell types and peripheral organs (Indra, et al., Nucleic Acids Res, 27, 4324-4327 (1999)) (Kuhbandner, et al., Genesis, 28, 15-22 (2000)) (Vooijs, et al., EMBO Rep, 2, 292-297 (2001)) (Minamino, et al., Circ Res, 88, 587-592 (2001)) (Sohali, et al., Circ Res, 89, 20-25 (2001)) (Imai, et al., Proc Natl Acad Sci USA, 98, 224-228 (2001)) (Bex, et al., J Urol, 168, 2641-2644 (2002)) (Bosenberg, et al., Genesis, 44, 262-267 (2006)) (Guo, et al., Genesis, 32, 8-18 (2002)) (Hayashi and McMahon, Dev Biol, 244, 305-318 (2002)). Important for applications to the central nervous system is the performance of the CreER(T2) system which has been shown for neurons and glia cells in the brain of adult mice (Weber, et al., Eur J Neurosci, 14, 1777-1783 (2001)) (Leone, et al., Mol Cell Neurosci, 22, 430-440 (2003)) (Doerflinger, et al., Genesis, 35, 63-72 (2003)) (Hirriinger, et al., Glia, 54, 11-20 (2006)) (Mori, et al., Glia, 54, 21-34 (2006)) (Zhao, et al., Genesis, 44, 364-371 (2006)). For in vivo applications usually Tamoxifen is used as inducing compound upon intraperitoneal, subcutaneous or oral administration. Tamoxifen is metabolised in the liver into the ER(T2) ligand 4-OH-Tamoxifen. The pharmacology of Tamoxifen in rodents and man is well established and it is used clinically for the therapy of female breast cancer (Fromson, et al., Xenobiotica, 3, 711-714 (1973)) (Fromson, et al., Xenobiotica, 3, 693-709 (1973)) (Etgen, Horm Behav, 13, 97-112 (1979)) (Furr and Jordan, Pharmacol Ther, 25, 127-205 (1984)) (Grainger and Metcalfe, Nat Med, 2, 381-385 (1996)) (Buckley and Goa, Drugs, 37, 451-490 (1989)).

Alternative nuclear receptor ligand binding domains (LBD) which can be used as the LBD domain of the fusion protein of the present invention belong to the nuclear receptor superfamily of proteins (Mangelsdorf, et al., Cell, 83, 835-839 (1995)) and include, but are not limited to, steroid hormone receptors, vitamin-A and -D receptors and retinoic receptors. The structure of the LBD of nuclear steroid receptors consists of a conserved arrangement of a series of 11-12 alpha-helices closely folded in a similar manner (Kumar and Thompson, Steroids, 64, 310-319 (1999)).

Preferably, in the context of the present invention the nuclear hormone receptor is selected from the group consisting of an estrogen receptor, a progesterone receptor, a glucocorticoid receptor, an androgen receptor and a functionally active variant thereof, particularly an estrogen receptor or a functionally active variant thereof as defined above. More preferably, the receptor is a mammalian nuclear hormone receptor, especially a human nuclear hormone receptor, still more preferably selected from the group consisting of an estrogen receptor, a progesterone receptor, a glucocorticoid receptor, an androgen receptor and a functionally active variant thereof. Examples of those include Estrogen receptors (the amino acid sequence of said mouse estrogen receptor alpha is shown in SEQ ID NO: 72, of which the LBD comprises the residues 355-547 and the sequence of said human estrogen receptor alpha is shown in SEQ ID NO: 73, of which the LBD comprises the residues 351-543), Progesterone receptors (the amino acid sequence of said mouse progesterone receptor is shown in SEQ ID NO: 74 and the sequence of said human progesterone receptor is shown in SEQ ID NO: 75, of which the LBD comprises the residues 641-891 or 641-933), Glucocorticoid receptors (the amino acid sequence of said murine glucocorticoid receptor is shown in SEQ ID NO: 76, and the sequence of said human glucocorticoid receptor is shown in SEQ ID NO: 77, of which the LBD comprises the residues 500-777), Androgen receptors (the amino acid sequence of said murine androgen receptor is shown in SEQ ID NO: 78, and the sequence of said human androgen receptor is shown in SEQ ID NO: 79), and the like, or mutants thereof. Other nuclear hormone and steroid receptor LBDs known in the art are also applicable. However, preferred examples of sequences of nuclear hormone receptor are those of SEQ ID NO: 72 to 80, especially SEQ ID NO: 80.

As detailed above, ligands to the LBD are needed in order to activate the LBD and induce apoptosis of a cell, in which the fusion protein is expressed.

Specific examples of compounds which bind the ligand binding domain include 5-alpha-pregnane-3,20-dione; 11[beta]-(4-dimethylaminophenyl)-17[beta]-hydroxy-17[alpha]-ropinyl-4,9-estradiene-3-one; 11[beta]-(4-dimethylaminophenyl)-17[alpha]-hydroxy-17[beta]-(3-hydroxypropyl)-13 [alpha]-methyl-4,9-gonadiene-3-one; 11[beta]-(4-acetylphenyl)-17[beta]-hydroxy-17[alpha]-(1-propinyl)-4,9-estradiene-3-one; 11 [beta]-(4-dimethylaminophenyl)-17[beta]-hydroxy-17[alpha]-(3-hydroxy-1(Z)-propenyl-estra-4,9-diene-3-one; (7[beta], 11[beta], 17 [beta])-11-(4-dimethylaminophenyl)-7-methyl-4',5'-dihydrospiro[ester-4,9-diene-17,2'(3'H)-furan]-3-one; (11[beta],14[beta], 17[alpha])-4',5'-dihydro-11-(4-dimethylaminophenyl)-[spiroestra-4,9-diene-17,2'(3'H)-furan]-3-one; Raloxifen, Naloxifen, 4-OH-tamoxifen or ICI 164384.

Particularly for mutant LBD the following ligands may be used in order to induce apoptosis:

ER(T2): 4-OH-Tamoxifen, Raloxifen, Naloxifen

Mutant progesterone receptor: RU486 (=Mifepristone), ORG31376, ORG31806, ZK98.229, ZK98.734, ZK112.993

Mutant glucocorticoid receptor: Dexamethasone, Triamcinolone acetonide, RU38486

Mutant androgen receptor: Mibolerone, OH-Flutamide

In accordance with the present invention the second component of the fusion protein may also be a functionally active variant of a LBD as defined above. Functional active variants are obtainable by changing the sequence of the LBD as defined herein and are characterized by having a biological activity similar to that displayed by the LBD from which it is derived, including the ability to be activated upon binding of a ligand. Ability to be activated can be determined e.g. as described in the Examples, i.e. by producing a fusion protein as described in Example 1, wherein the variant is to be substituted for the LBD, expressing the fusion protein and comparing apoptosis in presence and absence of a ligand for the respective LBD, e.g. 4-OH-tamoxifen, as described in Example 2 or 3. The variant of a LBD is functionally active in the context of the present invention, if the activity of the fragment amounts to at least 10%, preferably at least 25%, more preferably at least 50%, even more preferably at least 70%, still more preferably at least 80%, especially at least 90%, particularly at least 95%, most preferably at least 99% of the activity of the LBD without sequence alteration.

Alternatively, the ligand binding affinity of the wild-type LBD and the mutant LBD may be determined. The ligand binding affinity of such mutants can be determined by incubation of the LBD with radioactive labeled ligand at various concentrations in the presence or absence of unlabelled ligand and subsequent measurement of bound labeled ligand, e.g. as described by Smith and Sestili, Clin Chem 26, 543-50 (1980)). A functionally active variant of the above LBD in accordance with the present invention relates to a mutant of the respective original (viz. wild-type) LBD having a ligand binding affinity to the natural or a synthetic ligand of at least 0.1%, preferably at least 1%, more preferably at least 10% of that of said wild-type LBD.

Variants include truncated forms of the LBD (such as N- or C-terminal truncated LBD proteins), deletion-type mutants (where one or more amino acid residues or segments having more than one continuous amino acid residue have been deleted from the primary sequence of the wildtype LBD), replacement-type mutants (where one or more amino acid residues or segments of the primary sequence of the wildtype LBD have been replaced with alternative amino acid residues or segments), or the addition of signal peptides that alter intracellular localisation, or combinations thereof.

In one embodiment of the present invention the LBD or functionally active variant thereof may be a fragment. The fragment is characterized by being derived from a naturally occurring LBD as defined below by one or more amino acid deletions. The deletion(s) may be C-terminally, N-terminally and/or internally. Preferably, the fragment is obtained by at most 100, more preferably by at most 50, even more preferably at most 30, still more preferably at most 10, most preferably 1, 2, 3, 4 or 5 deletion(s).

The functionally active fragment may be also characterized by other structural similarity. Accordingly, in one preferred embodiment of the invention the functional active fragment consists of at least 60%, preferably at least 70%, more preferably at least 80%, still more preferably at least 90%, even more preferably at least 95%, most preferably 99% of any naturally occurring LBD, e.g. those listed above. The functional active fragment as defined above may be derived from the peptide by one or more amino acid deletions. The deletions may be C-terminally, N-terminally and/or internally. For progesterone receptor variants c terminal mutations are preferred, as those are more likely to effect reduction or abolishment of ligand binding.

In another preferred embodiment of the invention the LBD is a functionally active variant of a LBD, wherein the variant is derived from any naturally occurring LBD, e.g. those listed above, by one or more amino acid deletion(s), addition(s) and/or substitution(s) and preferably wherein the variant has at least 50% sequence identity to a naturally occurring LBD. In a more preferred embodiment the functional active variant has a sequence identity of at least 60%, preferably at least 70%, more preferably at least 80%, still more preferably at least 90%, even more preferably at least 95%, most preferably 99% to any naturally occurring LBD, e.g. those listed above.

The percentage of sequence identity can be determined as described above in connection with the variant of a Caspase.

As noted above, the functionally active variant of a LBD is obtained by sequence alterations in the sequence of the LBD, wherein the variant retains the function of the LBD (see above). The term "functionally active variant" includes naturally occurring allelic variants, as well as mutants or any other non-naturally occurring variants.

However, if the variant is obtained from a LBD by one or more substitution(s) conservative substitution(s) is/are preferred. Conservative substitutions are as detailed above.

In case of one or more amino acid addition(s), these may result for the cloning of the LBD or functionally active variant thereof, e.g. due to the use of particular restriction site, and may or may not alter (increase or decrease) the activity of the LBD. Alternatively, amino acids may be added in order to achieve a desired result, e.g. addition of a tag to provide for convenient purification.

As detailed above, particularly for in vivo application receptor mutants are preferred which may not be activated by the respective naturally occurring ligand in order to avoid induction of apoptosis upon the presence of the ligand in the body of the respective animal. In accordance with this, the above specified mutants are preferred in the context of the present invention. Particularly, estrogen receptors with single point mutation replacing a glycine by an arginine residue at position 525 of the mouse or the analogous position 521 of the human estrogen receptor (ER(T)) or with three point mutation (G400V/M543A/L544A, named ER(T2)) are preferred. Alternatives are the above specified mutant human progesterone receptor, the mutant glucocorticoid receptor and a mutant androgen receptor as well as any other mutant nuclear hormone receptor known to the skilled person.

In a very preferred embodiment of the invention the functionally active variant of the nuclear hormone receptor is the human estrogen receptor LBD mutant ER(T2) (residues 282-595 of the human estrogen receptor as published in: Feil, et al., Biochem Biophys Res Commun, 237, 752-757 (1997)) with amino acid exchanges from Glycine to Valine at position 400 (G400V), from Methionine to Alanine at position 543 (M543A), from Leucine to Alanine at position 544 and having the amino acid sequence shown in SEQ ID NO: 80.

The preferred ligands for the activation of the ER(T2) mutant LBD are non-steroidal antiestrogens, the most preferred ligand is 4-OH-Tamoxifen (chemical name: [trans-1-(4β-dimethylaminoethoxyphenyl) 1,2-diphenylbut-1-ene]). Alternatively, ICI 164384 may be used.

Within the fusion protein the binding domain of the nuclear hormone receptor ligand may be linked to the N-terminal or C-terminal of the Caspase domain; however, preferably the ligand binding domain of the nuclear hormone receptor is linked to the C-terminal of the Caspase domain. The ligand binding domain of the nuclear hormone receptor may be either linked to the Caspase domain directly or via a linker. Preferably, the linker is composed of amino acids.

In one embodiment of the invention the linker consists of 1 to 100 amino acid residues, preferably 1 to 40 amino acids, more preferably 1 to 10 amino acids, such as 1, 2, 3, 4, 5, 6, 7, 8, 9, or 10 amino acids. Especially, the linker consists essentially of neutral amino acids. An exemplary linker is composed of the glycine, alanine and/or valine or particularly consists of the sequence Ala-Asp-Gln (as shown in SEQ ID NO: 20).

An alternative linker comprises a part of the nuclear hormone receptor D and F domain sequences flanking the ligand binding domain (Metzger, et al., Proc Natl Acad Sci USA, 92, 6991-6995 (1995)).

In addition to the components listed and specified above, the fusion protein may comprise further components such as a myristoylation signal sequence such as GSSKSKPKDPSQR (SEQ ID NO: 82), a subcellular targeting signal like a nuclear localization sequence or any other suitable sequence such as a tag, e.g. for purification. Other suitable sequences are known to the skilled persons and it is within the knowledge of the skilled person to select and combine further sequences with the components of the fusion protein as defined above.

Myristoylation is an irreversible, post-translational protein modification found in animals, plants, fungi and viruses. In this protein modification a myristoyl group (derived from myristic acid) is covalently attached via an amide bond to the alpha-amino group of an N-terminal glycine residue of a nascent polypeptide. The modification is catalyzed by the enzyme N-myristoyltransferase, and occurs most commonly on glycine residues exposed during co-translational N-terminal methionine removal. Myristoylation plays a vital role in membrane targeting and signal transduction in plant responses to environmental stress. A myristoylation signal sequence may be included in order to increase the local concentration of the fusion protein at membranes which might lead to faster and more efficient induction of apoptosis.

A nuclear localization signal sequence provides for the active transport into the nucleus of eukaryotic cells. Such a signal peptide domain preferably has a length of 5 to 74, preferably 7 to 15 amino acid residues. More preferably, the signal peptide domain comprises a segment of 6 amino acid residues wherein at least 2 amino acid residues, preferably at least 3 amino acid residues are positively charged basic am9no acids. Basic amino acids include, but are not limited to, lysine, arginine, and histidine.

Highly preferred fusion proteins of the present invention comprise the amino acid sequence for a CASP8-ER(T2) protein shown in SEQ ID NO: 20 and a myrCASP8-ER(T2) protein shown in SEQ ID NO: 23 (suitable DNA sequence coding for said fusion proteins being shown in SEQ ID NO: 19 and 22, respectively), and the amino acid sequence for a CASP9full-ER(T2) protein shown in SEQ ID NO: 29 and a CASP9trunc-ER(T2) protein shown in SEQ ID NO: 32, (a suitable DNA sequence coding for said fusion protein being shown in SEQ ID NO: 28 and 31, respectively), and the amino acid sequence for a CASP3-ER(T2) protein shown in SEQ ID NO: 37 (a suitable DNA sequence coding for said fusion protein being shown in SEQ ID NO: 36).

Most preferred fusion proteins consist of an amino acid sequence selected from the group consisting of SEQ ID NO: 20, SEQ ID NO: 23, SEQ ID NO: 29, SEQ ID NO: 32 or SEQ ID NO: 37. Especially preferred fusion proteins consist of an amino acid sequence selected from the group consisting of SEQ ID NO: 20, SEQ ID NO: 23, SEQ ID NO: 29, SEQ ID NO: 32 or SEQ ID NO: 37.

A further subject of the invention relates to a nucleic acid coding for the fusion protein of the invention, wherein the nucleic acid may be comprised in a vector. The term nucleic acid includes DNA and RNA such as genomic DNA, cDNA and mRNA, or combinations thereof. The nucleic acid may comprise—in addition to the sequence coding for the fusion protein—further sequences e.g. required for the transcription and/or translation of the nucleic acid coding for the fusion protein. This may include a promoter, enhancer, transcription and/or translation initiation and/or termination sequences, selection markers, sequences protecting or directing the RNA or fusion protein within the cell. The selection and combination of these sequences is within the knowledge of the person skilled in the art and may be selected in accordance with the cell the nucleic acid or fusion protein is intended for. Sequences of preferred nucleic acids are identified in SEQ ID NO: 18, 21, 27, 30 and 35.

The term “vector” as used herein refers to a construction comprised of genetic material designed to direct transformation of a targeted cell. A vector contains multiple genetic elements positionally and sequentially oriented with other necessary elements such that the nucleic acid in a nucleic acid cassette can be transcribed and when necessary translated in the transfected cells. The term vector as used herein can refer to nucleic acid, e.g., DNA derived from a plasmid, cosmid, phagemid or bacteriophage, into which one or more fragments of nucleic acid may be inserted or cloned which encode for particular proteins. The term “plasmid” as used herein refers to a construction comprised of extrachromosomal genetic material, usually of a circular duplex of DNA which can replicate independently of chromosomal DNA. The plasmid does not necessarily replicate.

The vector can contain one or more unique restriction sites, and may be capable of autonomous replication in a defined host or organism such that the cloned sequence is reproduced.

The vector molecule can confer some well-defined phenotype on the host organism which is either selectable or readily detected. The vector may have a linear or circular configuration. The components of a vector can contain but is not limited to a DNA molecule incorporating: (1) DNA; (2) a sequence encoding the fusion protein of the invention; and (3) regulatory elements for transcription, translation, RNA processing, RNA stability, and replication.

The purpose of the vector is to provide expression of a nucleic acid sequence in cells or tissue. Expression includes the efficient transcription of an inserted gene or nucleic acid sequence. Expression products may be proteins, polypeptides, or RNA. The nucleic acid sequence can be contained in a nucleic acid cassette. Expression of the nucleic acid can be continuous, constitutive, or regulated. The vector can also be used as a prokaryotic element for replication of plasmid in bacteria and selection for maintenance of plasmid in bacteria.

In one embodiment the vector comprises the following elements linked sequentially at an appropriate distance to allow functional expression: a promoter, a 5' mRNA leader sequence, a translation initiation site, a nucleic acid cassette containing the sequence of the fusion protein to be expressed, a 3' mRNA untranslated region, and a polyadenylation signal sequence. As used herein the term "expression vector" refers to a DNA vector that contains all of the information necessary to produce a recombinant protein in a heterologous cell.

In addition, the term "vector" as used herein can also include viral vectors. A "viral vector" in this sense is one that is physically incorporated in a viral particle by the inclusion of a portion of a viral genome within the vector, e.g., a packaging signal, and is not merely DNA or a located gene taken from a portion of a viral nucleic acid. Thus, while a portion of a viral genome can be present in a vector of the present invention, that portion does not cause incorporation of the vector into a viral particle and thus is unable to produce an infective viral particle.

A vector as used herein can also include DNA sequence elements which enable extra-chromosomal (episomal) replication of the DNA. Vectors capable of episomal replication are maintained as extra-chromosomal molecules and can replicate. These vectors are not eliminated by simple degradation but continue to be copied. These elements may be derived from a viral or mammalian genome. These provide prolonged or "persistent" expression.

Examples of vectors are pCAG (see Examples), pBR322, the pUC series, pBluescript, pTZ, pSP and pGEM. The components of the nucleic acid or of the vector are selected in such a way that the nucleic acid is expressed and the fusion protein is produced by the target cell.

Another subject of the invention relates to a cell comprising the nucleic acid and/or vector of the present invention.

"Cells" and "eukaryotic cells" according to the present invention include cells isolated from the below defined living organism and cultured in vitro. These cells can be transformed (immortalized) or untransformed (directly derived from the living organism; primary cell culture).

"Microorganism" according to the present invention relates to prokaryotes (e.g. *E. coli*) and eukaryotic microorganisms (e.g. yeasts).

The "organisms" according to the present invention are multi-cell organisms and can be vertebrates such as mammals (humans and non-human animals including rodents such as mice or rats) or non-mammals (e.g. fish), or can be invertebrates such as insects or worms, or can be plants (higher plants, algae or fungi). Most preferred living organisms are mice and humans.

The term "mammal" as used in the context of the present invention includes non-human mammals and humans.

The cell can be any suitable cell, especially a eukaryotic cell, for example a fungal, plant or animal cell. Cell lines of these cells are also included. Preferably, it is a mammalian cell, especially a murine or human cell or cell line. Examples of such mammalian cells are HEK 293 cells, CHO cells, HeLa cells, CaCo cells, NIH 3T3 cells or mouse embryonic fibroblast cell line MEF5/N9 (see Examples). Examples of insect cells are SF9, drosophila, butterfly and bee cells. The cell may also be a cell line, which is particularly useful for studying apoptosis or identification of ligand for the LBD. The present invention also provides stable cell lines transformed with the plasmids of the present invention.

Another subject of the invention relates to a method for producing the fusion protein of the invention comprising culturing the cell of the invention as defined above comprising the nucleic acid and/or vector of the present invention under conditions conducive to the production of the fusion protein.

A cell of the invention as defined above comprising the nucleic acid and/or vector of the present invention and having been obtained from a cell line stably expressing the fusion protein of the invention or by transfection or transformation as defined above, may be grown and propagated in cell culture.

Cells that are cultured directly from an animal or person are known as primary cells. With the exception of some derived from tumors, most primary cell cultures have limited lifespan. After a certain number of population doublings cells undergo the process of senescence and stop dividing, while generally retaining viability.

An established or immortalised cell line has acquired the ability to proliferate indefinitely either through random mutation or deliberate modification, such as artificial expression of the telomerase gene. There are numerous well established cell lines representative of particular cell types and it is within the knowledge of the skilled person to select a suitable cell line.

For cultivation cells are grown and maintained at an appropriate temperature and gas mixture (typically, 37° C., 5% $CO_2$) in a cell incubator. Culture conditions vary widely for each cell type, and variation of conditions for a particular cell type can result in different phenotypes being expressed. Aside from temperature and gas mixture, the most commonly varied factor in culture systems is the growth medium. Recipes for growth media can vary in pH, glucose concentration, growth factors, and the presence of other nutrient components. Antibiotics can also be added to the growth media. Amongst the common manipulations carried out on culture cells are media changes and passaging cells. However, selection of suitable conditions is known to the skilled person. However, for producing the fusion protein the culturing is preferably carried out in the absence of a ligand for the LBD, which would induce apoptosis of the cells and therefore, be counterproductive.

If necessary, the fusion protein can also be isolated from the cells. If a sufficient amount of the fusion protein has been secreted into the medium (e.g. due to suitable secretory signal sequences), this can be separated from the cells, e.g. by removing the supernatant medium. Otherwise it may be necessary to disrupt the cells. This can be effected for example by lysis of the cells e.g. by means of ultrasound or hypotonic medium. To remove insoluble components, the sample obtained can for example be centrifuged, especially at 10000×g to 15000×g, and the supernatant obtained can be used.

Still another subject of the invention relates to a non-human transgenic organism, preferably a non-human transgenic mammal, containing the nucleic acid and/or vector of the present invention.

In general, transgenic animals of the invention exhibit an expression of fusion protein of the invention, optionally tissue-specifically e.g. by using a tissue-specific promoter; therefore, they are very suitable, for example for studying the function of a cell, tissue and/or organ, e.g. at various developmental stages. Preference is given to using transgenic mice. Other examples of a non-human mammal according to the invention is a rat, a guinea pig, a rabbit, a cow, a goat, a sheep, a horse, a pig, a dog, a cat or a monkey.

The transgenic non-human animal may be produced by a series of techniques known to the skilled person. For example, the method may comprise the following steps:

a. Introducing, into at least one oocyte, one stem cell, one precursor cell and/or one immortalized cell of a non-human mammal, on the one hand at least one nucleic acid encoding a fusion protein and/or at least one vector containing at least one said nucleic acid, with the fusion protein of the invention, and, optionally, on the other hand, at least one suitable transfection marker gene,
b. selecting the transfected cell from step a.,
c. introducing the cell which has been selected in accordance with step b. into at least one non-human mammalian blastocyte,
d. introducing the blastocyte from step c. into a non-human, preferably pseudopregnant, mammalian foster mother, and
e. identifying the transgenic non-human mammal which has developed from said blastocyte.

The methods for introducing blastocytes are known to the skilled person. The blastocyte can, for example, be introduced by injection (Hogan, B., Beddington, R., Constantini, F. and Lacy, E., A laboratory Manual (1994), Cold Spring Harbor Laboratory Press).

A transgenic non-human mammal can be identified, for example, by extracting genomic DNA from the transgenic non-human mammal, for example from the tail of a mouse. In a subsequent PCR (polymerase chain reaction), use is made of primers which specifically recognize the transgene for the nucleic acid according to the invention. Integration of the transgene can be detected in this way.

Another possibility for effecting the identification is by means of southern blotting. In this method, genomic DNA is transferred to a membrane and detected using DNA probes, for example radioactively labeled DNA probes, which are specific for the sought-after transgene.

Methods for producing a transgenic non-human mammal according to the invention by means of regenerating a non-human stem cell, oocyte, precursor cell or immortalized cell to give a transgenic non-human animal, in particular transgenic mice, are known to the skilled person from DE 196 25 049 and the U.S. Pat. No. 4,736,866; U.S. Pat. No. 5,625,122; U.S. Pat. No. 5,698,765; U.S. Pat. No. 5,583,278 and U.S. Pat. No. 5,750,825, and encompass transgenic animals which can be produced, for example, by directly injecting expression vectors according to the invention into embryos or spermatocytes or by transfecting expression vectors into embryonic stem cells (Polites and Pinkert: DNA Microinjection and Transgenic Animal Production, pages 15-68 in Pinkert, 1994: Transgenic Animal Technology: A Laboratory Handbook, Academic Press, San Diego, USA; Houdebine 1997, Harwood Academic Publishers, Amsterdam, The Netherlands; Doetschman: Gene Transfer in Embryonic Stem Cells, pages 115-146 in Pinkert, 1994, see above; Wood: Retrovirus-Mediated Gene Transfer, pages 147-176 in Pinkert, 1994, see above; Monastersky: Gene Transfer Technology: Alternative Techniques and Applications, pages 177-220 in Pinkert, 1994, see above).

A transgenic non-human mammal according to the invention can also be prepared by directly injecting a nucleic acid according to the invention into the pronucleus of a non-human mammal.

A large number of methods for preparing transgenic animals, in particular transgenic mice, are also known to the skilled person from, inter alia, WO 98/36052, WO 01/32855, DE 196 25 049, U.S. Pat. No. 4,736,866, U.S. Pat. No. 5,625,122, U.S. Pat. No. 5,698,765, U.S. Pat. No. 5,583,278 and U.S. Pat. No. 5,750,825 and encompass transgenic animals which can be produced, for example, by directly injecting vectors according to the invention into embryos or spermatocytes or by transfecting vectors or nucleic acids into embryonic stem cells (Polites and Pinkert, in Pinkert, (1994) Transgenic animal technology, A Laboratory Handbook, Academic Press, London, UK, pages 15 to 68; Doetschmann, in Pinkert, 1994, see above, pages 115 to 146).

A further subject of the invention relates to the use of the fusion protein according to any the invention for ligand-mediated induction of apoptosis of a cell, preferably a eukaryotic cell, more preferably a mammal cell, especially a human cell. In patent systems not allowing claims directed to therapeutic and/or diagnostic methods of the human or animal body, these therapeutic and/or diagnostic methods are excluded; however, e.g. research methods are included. The fusion protein e.g. may be used for studying the function of a cell, tissue and/or organ. Also the transgenic non-human organism according to the invention may be used for studying the function of a cell at various developmental stages or as a disease model.

The inducible apoptosis system of the invention provides a universal cell ablation system for use in mammalian cells and organisms that allows to study the biological function of selected cells or a cell type in the mammalian body and thereby the creation of a wide range of animal models of human diseases. Such an inducible apoptosis system is particularly desirable for all those applications which require its universal activation in any organ and any cell type of the mammalian body, including the brain. It is to be noted that the non-human transgenic animal can be used to study the function of cells, e.g. in mice, by inducible apoptosis. For this purpose the coding region of the fusion proteins of the invention may be combined with suitable sequences as detailed above, for example a cell type specific promoter region, and the fusion protein transgene be inserted into the mouse germline by pronuclear injection or other methods known in the art. The administration of ligand that activates the Caspase activity of the fusion protein leads to the complete or partial ablation of the selected target cells in fusion protein transgenic mice at any chosen ontogenetic stage. The prespecified temporal and/or spatial restricted cell death is of particular use to model neurodegenerative diseases in mice and to develop model therapies that compensate for the loss of cellular functions through enhanced regeneration or through cell transfer. Alternatively to the use of germline transgenic mice, the fusion protein coding region can be combined with a cell type specific or ubiquitous active promoter region and inserted into the genome of a viral vector that is used to transduce the fusion protein expression unit locally into somatic tissues of embryonic, juvenile or adult mice.

Another subject of the invention relates to a method for inducing apoptosis of a cell expressing a fusion protein according to the invention, the method comprising contacting the ligand binding domain of the nuclear hormone receptor of the cell with a ligand capable inducing apoptosis of the cell.

Particularly, the method may be used in order to treat a patient as described below. Alternatively, the method may be an in vitro method, allowing studying apoptosis in a cell, identifying new ligands for LBD etc. as described within the present description of the invention.

Another subject of the invention relates to a method for identifying a ligand to a ligand binding domain of a nuclear hormone receptor or a functionally active variant thereof, the method comprising contacting the ligand binding domain of the nuclear hormone receptor of the cell according to the invention with a substance; and identifying the substance as a ligand, depending on its capability to induce apoptosis of the cell.

In another application of the inducible apoptosis system of the invention further allows to identify a ligand to a LBD. Substances deemed to be potential agonists or antagonists of a LBD may be screened for substances that inhibit or induce Caspase activity using cells according to the invention. Cells expressing the fusion protein of the invention may be cultured in the presence of a substance. If the substances induced apoptosis, it is identified as an agonistic ligand of the respective LBD of the fusion protein.

If it is screened for an antagonistic ligand of the LBD, the substance is tested in the presence of an agonistic ligand for the LBD. If the substance is capable of inhibiting apoptosis induced by the agonistic ligand (i.e. a ligand capable of inducing apoptosis of a cell upon binding to the LBD of a fusion protein of the invention), it is identified as antagonistic ligand. Ligands, particularly agonistic ligands, may be chosen in accordance with the above description. The selection of suitable conditions for the methods for identifying a ligand is within the knowledge of the skilled person and/or may be chosen in accordance with Examples 2 and 3.

Furthermore, the in vivo efficacy of such compounds can be assessed in transgenic mice of the invention that express the fusion protein of the invention upon coadministration of a test substance and optionally an agonistic ligand.

Still another subject of the invention relates to a medicament comprising a fusion protein according to the invention, a nucleic acid according to the invention, a vector according to the invention and/or a cell according to the invention.

The medicament of the invention may be used for the treatment of a disease requiring enhancement of apoptosis, particularly for the treatment of cancer or for or after transplantation, particularly as safety mechanism.

The inducible apoptosis system of the invention further allows for specifically ablating cells such as cancer cells or transplanted cells that contain a fusion protein, nucleic acid or vector of the invention from the body of a recipient by the administration of a ligand that activates the fusion protein.

For this purpose, all or a selected population of cells that are transferred into a recipient for therapeutic purposes (e.g. bone marrow transplantation, neurons or keratinocytes grown in in vitro cultures) can e.g. be transduced with a viral fusion protein expression vector or other methods known in the art. In this context, the fusion protein of the invention may be used as a safety mechanism in case that the transplanted cells or their progeny thread the recipient by e.g. tumorigenesis or a graft versus host reaction.

In another application the inducible apoptosis system of the invention further allows to destroy tumor cells by suicide gene therapy e.g. upon transduction or transfection of these cells with a fusion protein expression vector and ligand administration.

The medicament of the present invention may encompass pharmaceutically acceptable carriers and/or excipients. The pharmaceutically acceptable carriers and/or excipients useful in this invention are conventional and may include buffers, stabilizers, diluents, preservatives, and solubilizers. Remington's Pharmaceutical Sciences, by E. W. Martin, Mack Publishing Co., Easton, Pa., 15th Edition (1975), describes compositions and formulations suitable for pharmaceutical delivery of the (poly)peptides herein disclosed. In general, the nature of the carrier or excipients will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g. powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Also encompassed by the present inventions are methods for treating or preventing the diseases specified herein by administering to a patient an effective amount of a fusion protein of the invention, a nucleic acid coding of the invention, a vector comprising the nucleic acid and/or a cell of the invention.

The medicament may be administered to a subject in need thereof, preferably mammals, and still more preferably humans, in any conventional manner, including oral, intranasal, intramuscular, intra-lymph node, intradermal, intraperitoneal, subcutaneous, and combinations thereof, but most preferably through local administration, such as local injection.

Nucleic acid delivery compositions and methods are known to those of skill in the art. The nucleic acid of the invention may be employed in the methods of this invention or in the compositions described herein as DNA sequences, either administered as naked DNA, associated with a pharmaceutically acceptable carrier or comprised in a vector. The nucleic may be administered therapeutically or as a safety mechanism e.g., by injection.

An "effective amount" of a medicament may be calculated as that amount capable of exhibiting an in vivo effect, e.g. preventing or ameliorating a sign or symptoms. Such amounts may be determined by one of skill in the art. Preferably, such a composition is administered directly to the intended site of action, e.g. directly into a tumor. However, it may also be formulated to be administered by any other suitable route. The selection of the route of delivery and dosage of such therapeutic compositions are within the skill of the art.

Treatment in the context of the present invention refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented.

The present invention is further illustrated by the following Figures and Examples which are, however, not to be construed as limiting the scope of the invention.

FIGURES BRIEF DESCRIPTION OF THE DRAWINGS

FIG. 1 shows expression vectors for fusion proteins of the mutant Estrogen receptor ligand binding domain ER(T2) with Caspase-8, -9, -3, Bax, Fas or Cre recombinase and the (3-galactosidase reporter vector used for transient transfections and the hygromycin resistance vector used for stable transfections.

A-D: Mammalian expression vectors for ER(T2) fusion proteins which contain the CAG promoter, the coding region of the fusion protein to be tested, and a bovine polyadenylation signal sequence (pA).

A: pCAG-Casp8-ER(T2)-pA containing the 1.74 kb coding region for an N-terminal fusion of murine Caspase-8 domain to the ER(T2) ligand binding domain. pCAG-myrCasp8-ER(T2)-pA containing the 1.78 kb coding region for an N-terminal fusion of a murine Caspase-8 domain, fused with a N-terminal sequence motif coding for myristoylation, to the ER(T2) ligand binding domain.

B: pCAG-Casp9full-ER(T2)-pA containing the 2.32 kb coding region for an N-terminal fusion of full length murine Caspase-9 protein to the ER(T2) ligand binding domain. pCAG-Casp9trunc-ER(T2)-pA containing the 2.04 kb coding region for an N-terminal fusion of truncated murine Caspase-9 protein without the CARD domain to the ER(T2) ligand binding domain.

C: pCAG-Casp3-ER(T2)-pA containing the 1.79 kb coding region for an N-terminal fusion of full length murine Caspase-3 protein to the ER(T2) ligand binding domain. pCAG-Casp3-ED4ER(T2)-pA containing the 1.71 kb coding region for an N-terminal fusion of full length murine Caspase-3 protein to the modified ER(T2) ligand binding domain with shortened N-terminus.

D: pCAG-Bax-ER(T2)-pA, pCAG-ER(T2)-Bax-pA containing the 1.53 kb coding region for an N-terminal fusion of full length murine Bax protein and the 1.45 kb coding region for an C-terminal fusion of Bax to the ER(T2) ligand binding domain.

E: pCAG-Cre-ER(T2)-pA containing the 1.98 kb coding region for an N-terminal fusion of Cre recombinase to the ER(T2) ligand binding domain, used as a negative control.

F: pCAG-HA-Fas-ER(T2)-pA containing the 1.5 kb coding region for N-terminal fusion of the transmembrane and intracellular domain of murine Fas to the ER(T2) ligand binding domain. A hemagglutinin epitope (HA) was N-terminally fusioned to Fas. pCAG-MFas-ER(T2)-pA containing the 1.53 kb coding region for N-terminal fusion of the transmembrane and intracellular domain of murine Fas to the ER(T2) ligand binding domain. This Fas-ER(T2) fusion variant contains a N-terminal signal peptide for cell membrane targeting.

These constructs were planned to be used as a positive control.

G: pCMV-β-gal-pA containing the β-galactosidase reporter gene under control of the CMV promoter.

H: pPgk-hygro-pA containing the hygromycin resistance gene under the control of the pgk promoter.

Figure 2:
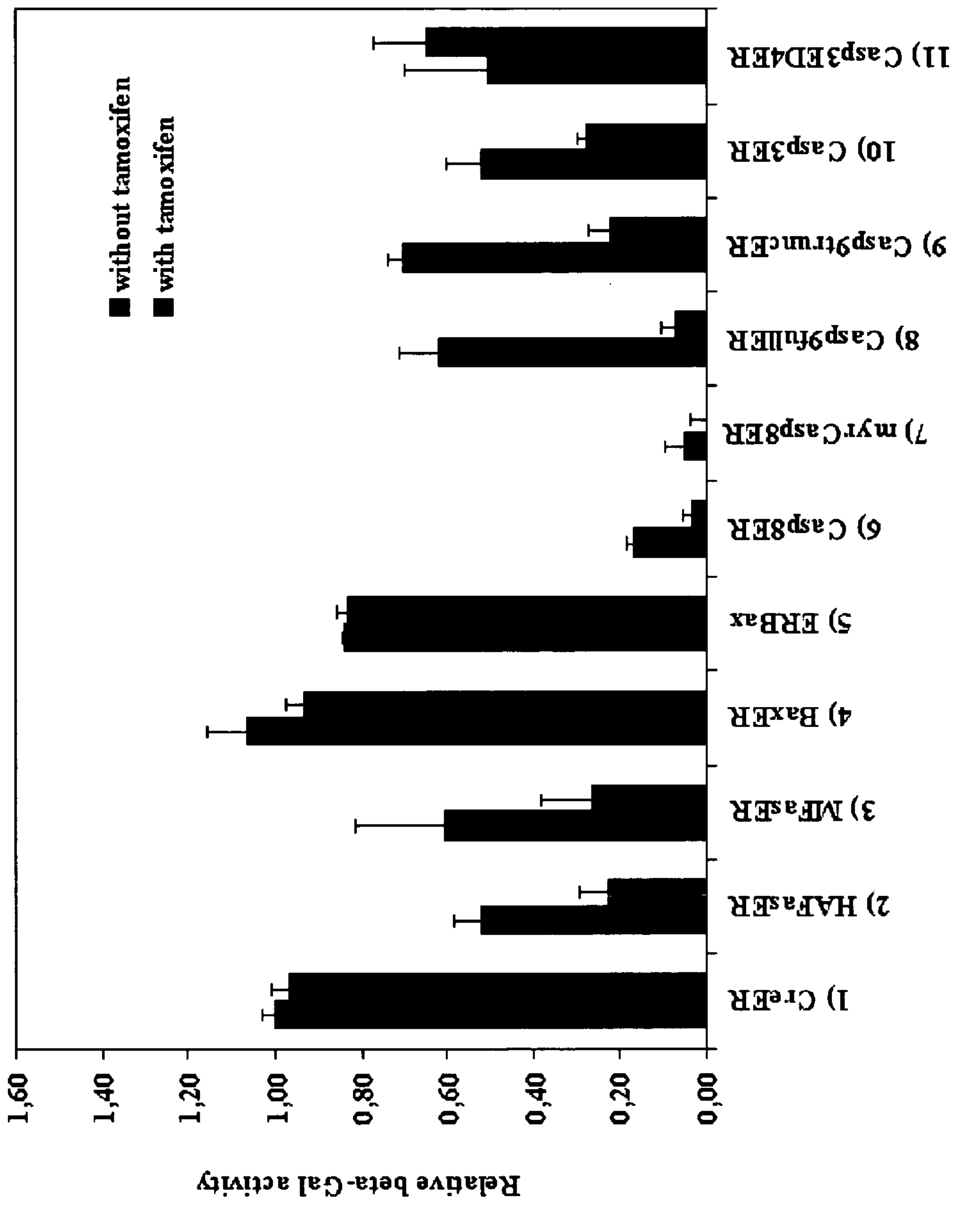

FIG. 2 shows results of transient transfections of expression vectors for ER(T2) fusion proteins with Caspase-8, -9, -3, Bax, Fas or Cre into MEF5/N9 cells.

All cotransfections were performed with a fixed amount of the reporter plasmid pCMV-β-gal-pA and 50 ng or 100 ng of the expression plasmids pCAG-Bax-ER(T2) (sample 4), pCAG-ER(T2)-Bax (sample 5), pCAG-Casp8-ER(T2) (sample 6), pCAG-myrCasp8-ER(T2) (sample 7), pCAG-Casp9full-ER(T2) (sample 8), pCAG-Casp9trunc-ER(T2) (sample 9), pCAG-Casp3-ER(T2) (sample 10), pCAG-Casp3-ED4ER(T2) (sample 11). Negative control: transfection with pCAG-Cre-ER(T2) (sample 1). Planned positive controls: transfection with the plasmids pCAG-HAFas-ER (T2) (sample 2) or pCAG-MFas-ER(T2) (sample 3).

The vertical rows show the mean values and standard deviation of "Relative light units" (RLU) obtained from cell lysates with the assay for β-galactosidase activity and the relative β-galactosidase activity of the cells transfected with various ER(T2) fusion constructs as compared to the negative control without tamoxifen defined as 1.1.

Figure 3:
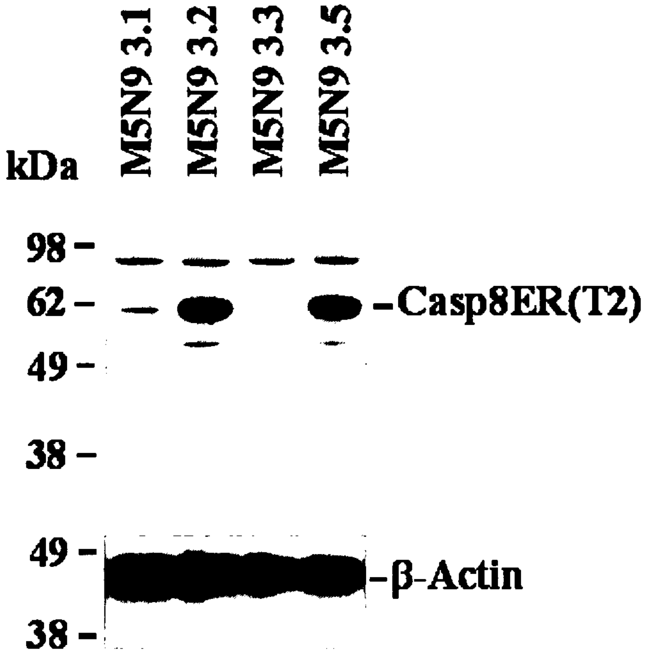
Figure 3:
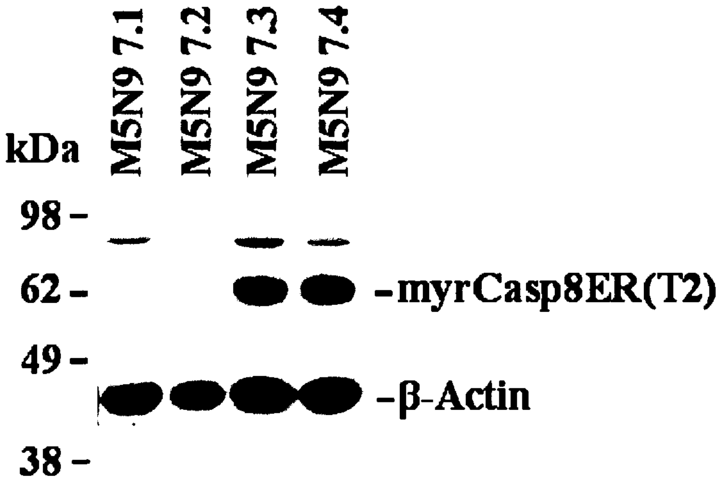
Figure 3:
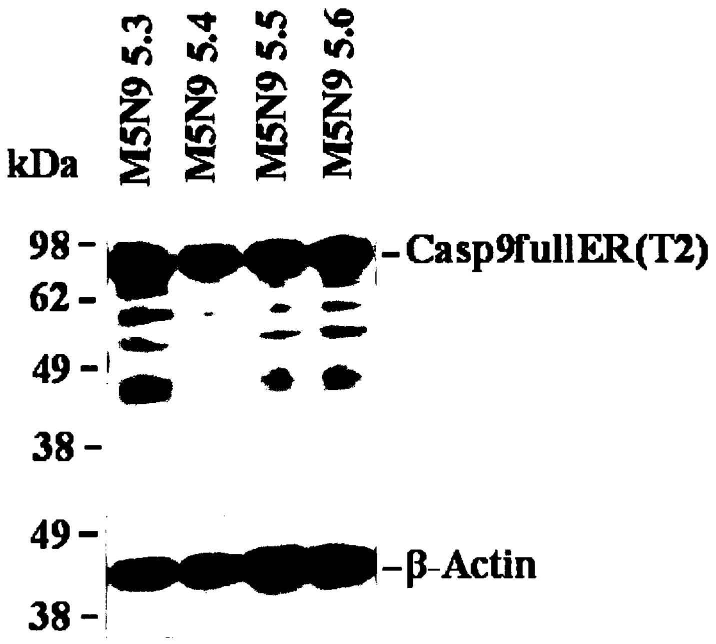
Figure 3:
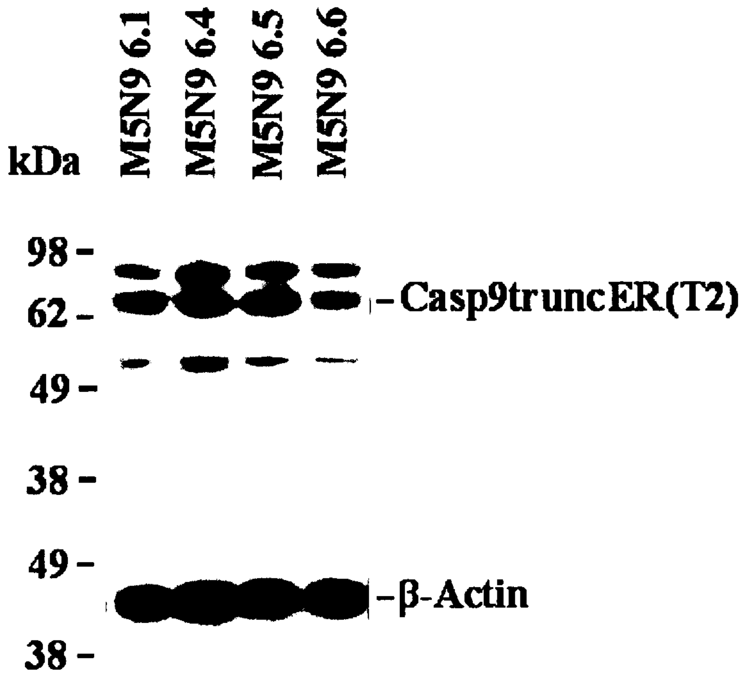
Figure 3:
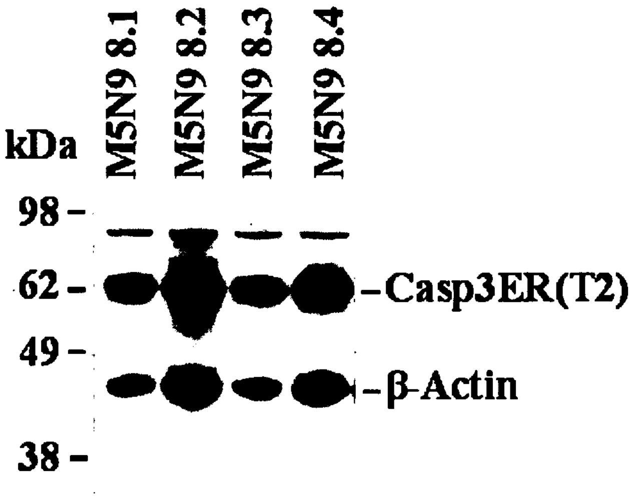
Figure 3:
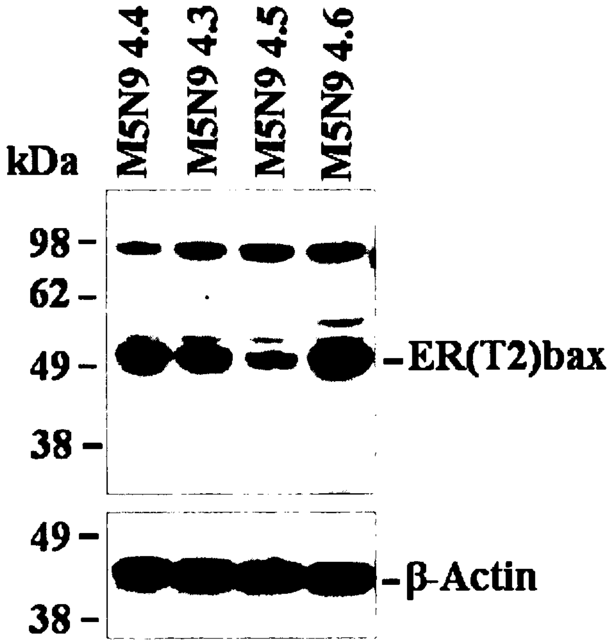
Figure 3:
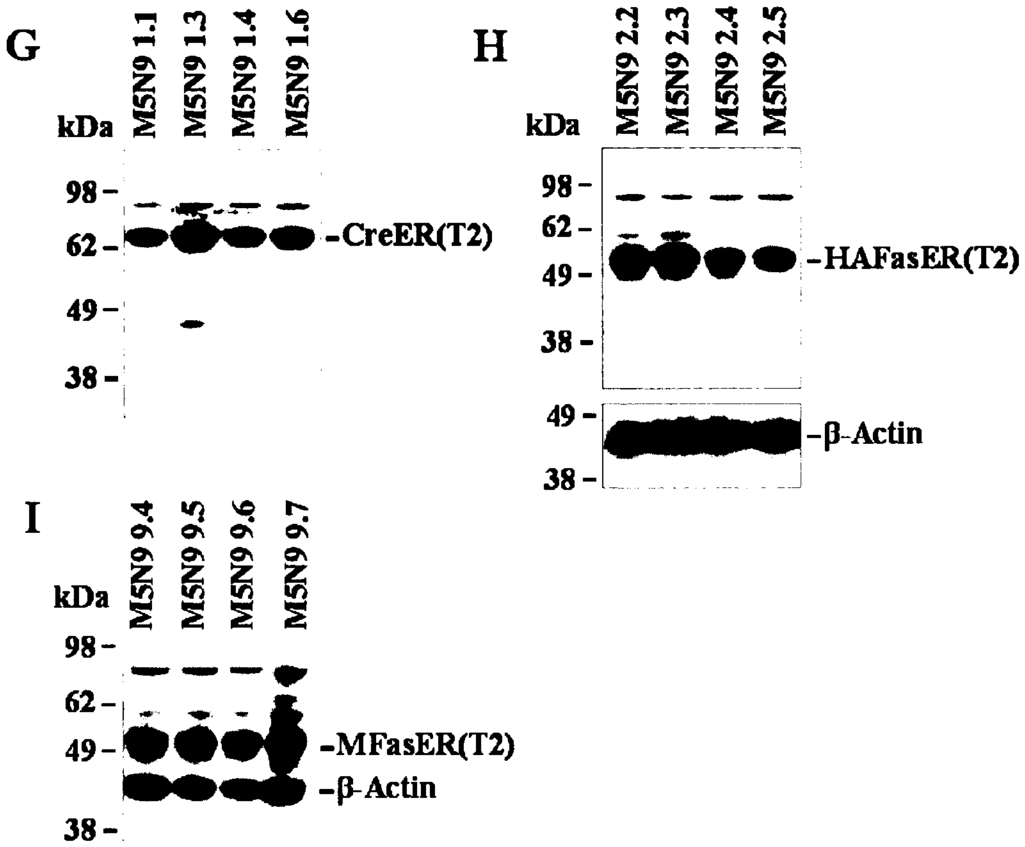

FIG. 3 shows the detection of stably expressed ER(T2) fusion proteins in MEF5/N9 clones by western blot analysis. MEF5/N9 cells were electroporated with 8 μg linearised pPgk-hygro for hygromycin selection of positive clones and 32 μg of linearised ER(T2) expression plasmids. Four stably transfected clones of each construct were selected for further analysis. Approximately $10^6$ cells were lysed and 40 μg protein of each sample was subjected to SDS-PAGE. The ER(T2) fusion proteins were detected by using an anti-ER antibody. Expressed ER(T2) fusion proteins are indicated by the arrows.

A-B: Stable expression of the 64 kDa Casp8-ER(T2) protein in M5N9 clones 3.2 and 3.6 and of the 65 kDa myrCasp8-ER(T2) protein in M5N9 clones 7.3 and 7.4.

C-D: Stable expression of the 85 kDa Casp9full-ER(T2) protein and of the 75 kDa Casp9trunc-ER(T2) protein in M5N9 clones.

E: Stable expression of the 65 kDa Casp3-ER(T2) protein in M5N9 clones.

F: Stable expression of the 53 kDa ER(T2)-Bax protein in M5N9 clones planned to be as negative control since the construct pCAG-ER(T2)-Bax showed no tamoxifen-dependent activity in transient transfection assays.

G: Stable expression of the 74 kDa Cre-ER(T2) protein in M5N9 clones.

H-I: Stable expression of the 54 kDa HAFas-ER(T2) protein and of the 56 kDa MFas-ER(T2) protein in M5N9 clones.

Figure 4:
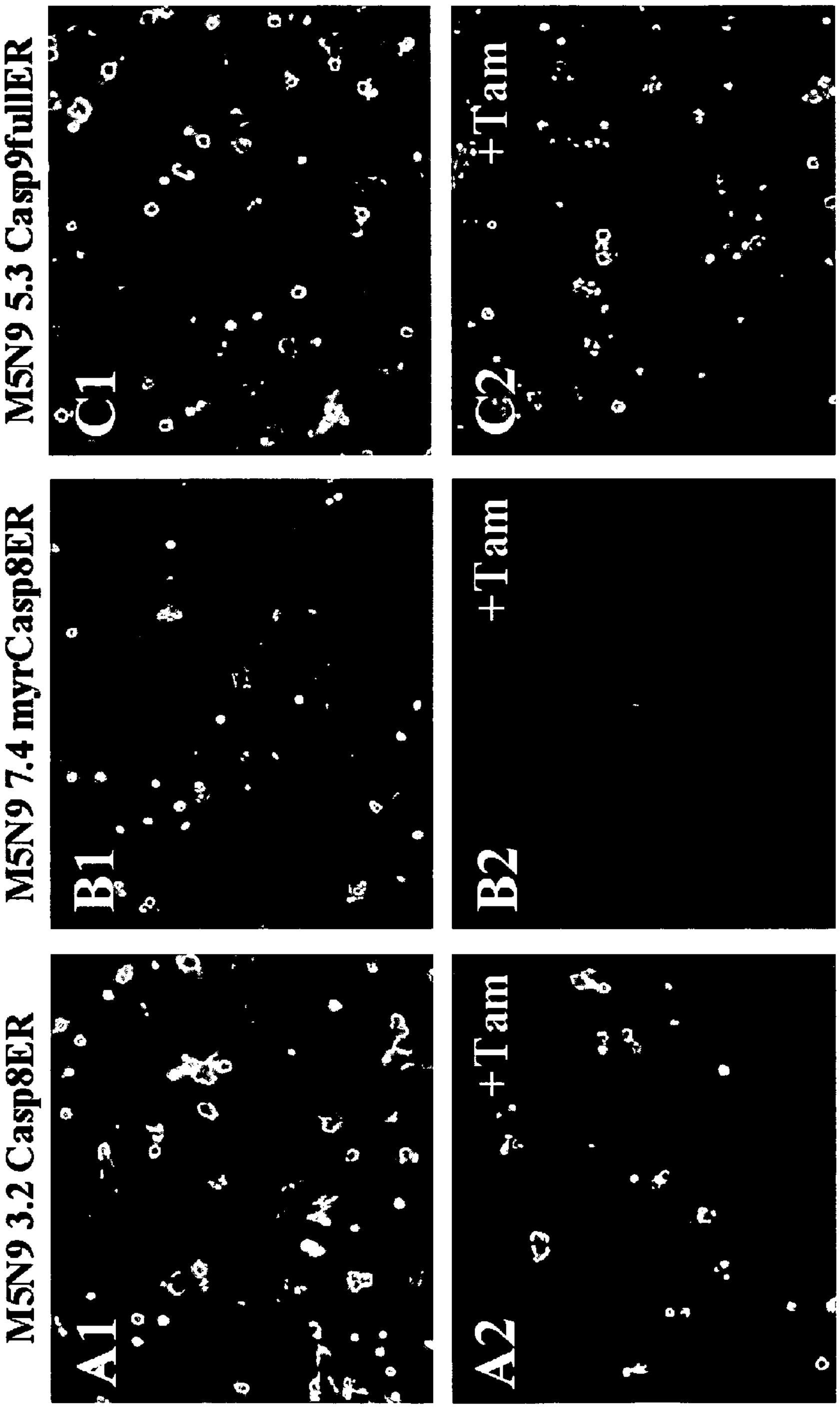
Figure 4:
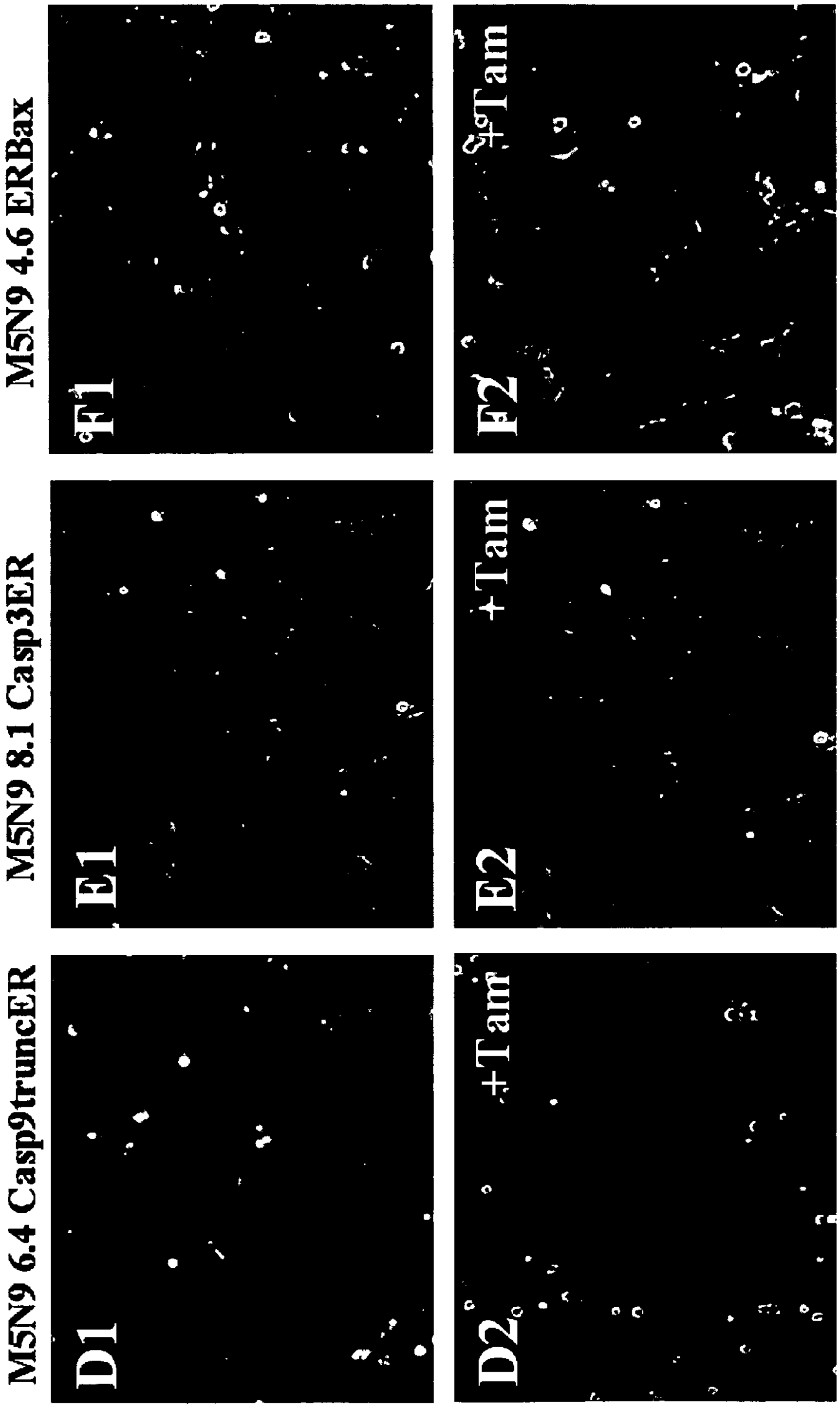
Figure 4:
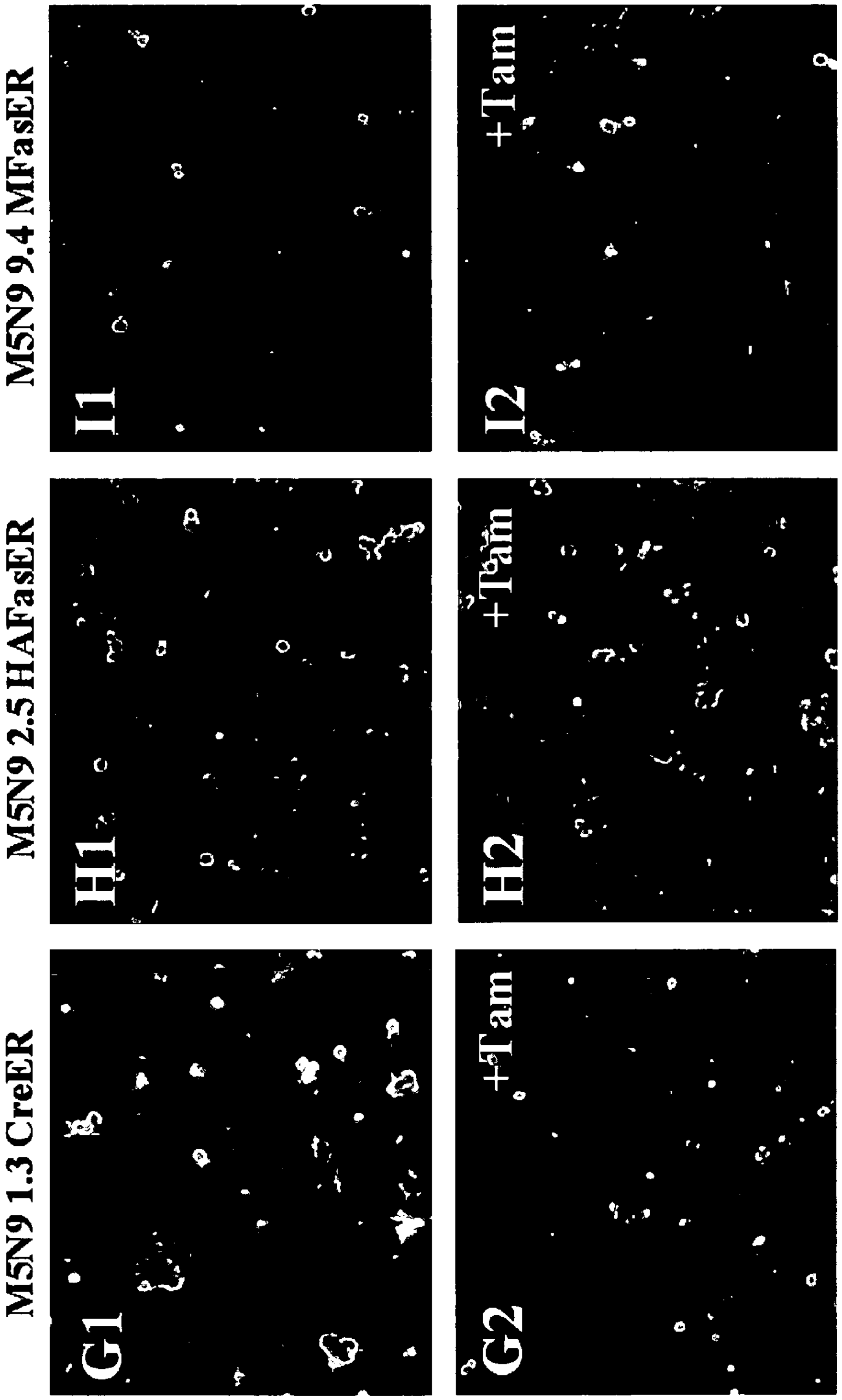

FIG. 4 illustrates visible phenotypic changes of MEF5/N9 clones on tamoxifen treatment. Cells were treated for 24 h with $10^{-8}$ M 4-OH-tamoxifen and photographed. The figure shows representative results obtained from two independently performed experiments. The upper panels demonstrate the phenotype of untreated cells which grew well in all clones. The lower panels display 4-OH-tamoxifen-treated cells and substantial cell death in the clones M5N9 3.2 Casp8ER (A2), M5N9 7.4 myrCasp8ER (B2), M5N9 5.3 Casp9fullER(C2) and M5N9 6.4 Casp9truncER (D2). The effect is weaker in the Casp9trunc-ER(T2) expressing clone. The negative controls M5N9 1.3 CreER (G2) and M5N9 4.6 ERBax (F2), further the clones M5N9 2.5 HAFasER(H2), M5N9 9.4 MfasER (I2) and M5N9 8.1 Casp3ER (E2) were not affected by the treatment with 4-OH-tamoxifen.

Figure 5:
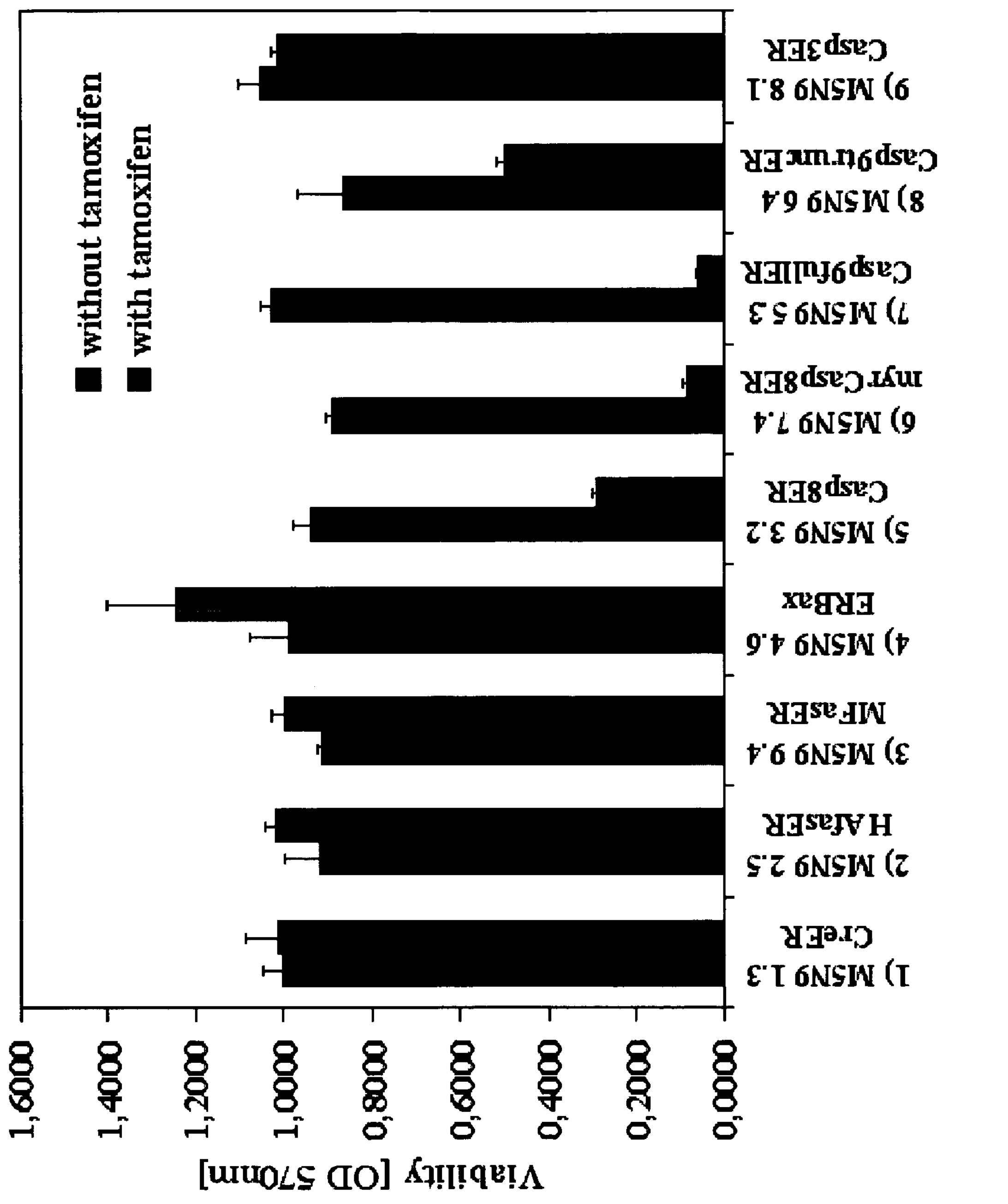

FIG. 5 shows the results derived from quantitative analysis of the cell viability of MEF5/N9 clones in the presence of 4-OH-tamoxifen. Following 48 h of incubation with $10^{-8}$ M 4-OH-tamoxifen, cell viabilities were analysis by the MTT cytotoxicity assay. The figure shows representative results obtained from two independently performed experiments. In the presence of 4-OH-tamoxifen, the cell viabilities of Casp8ER-(sample 5), myrCasp8ER-(sample 6), Casp9fullER-(sample 7) and Casp9truncER-(sample 8) expressing clones were reduced down to 31%, 9%, 6% and 58% respectively. In contrast, CreER-(negative control, sample 1), ERBax-(sample 4), Casp3ER-(sample 9), HAFasER-(sample 2) and MFasER-(sample 3) expressing clones were not affected by treatment with 4-OH-tamoxifen.

Figure 6:
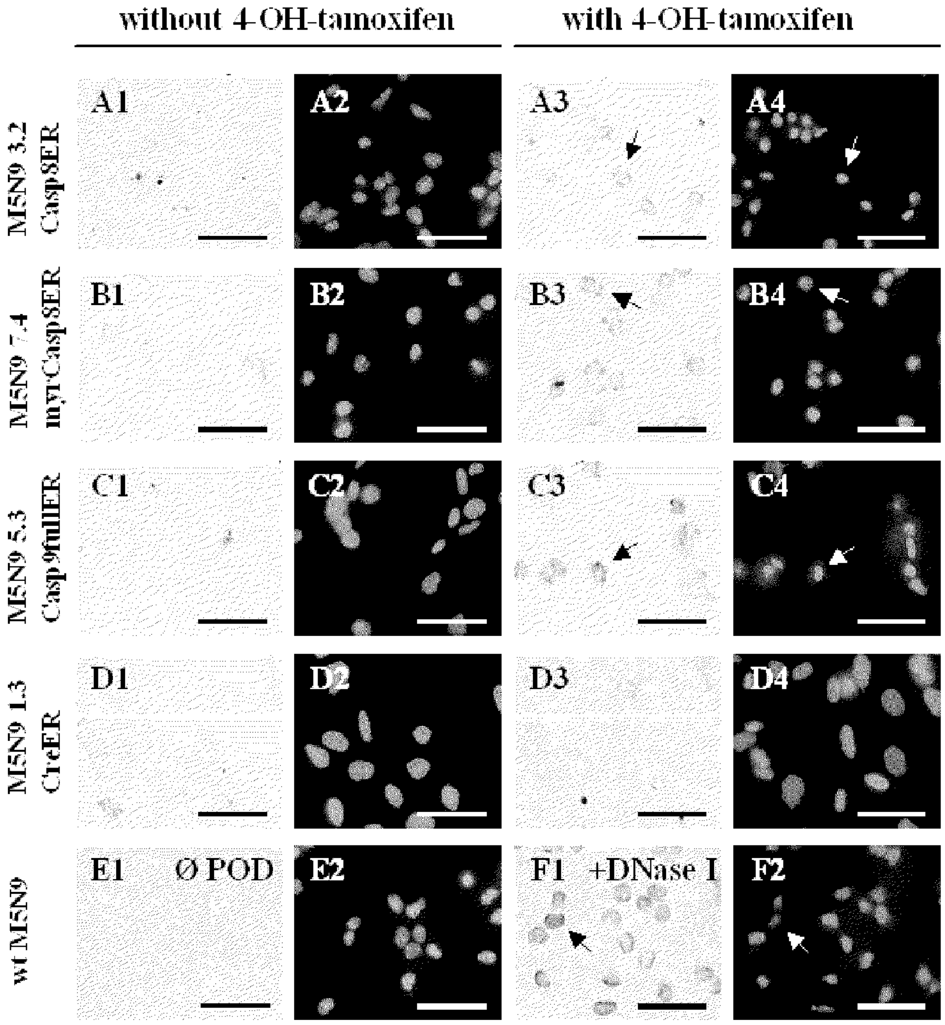

FIG. 6 shows the results derived from TUNEL (terminal deoxynucleotidyl transferase-mediated dUTP nick end-labeling) analysis of MEF5/N9 clones expressing Caspase-8 or -9 fusion proteins in the presence or absence of 4-OH-Tamoxifen. Cells were incubated with 4-OH-tamoxifen at a concentration of $10^{-8}$ M either for 3 hours or 7 hours, fixated in 4% PFA and permeabilized in Methanol at −20° C. DNA fragmentation was detected by incorporated fluorescein which was recognized by an anti-fluorescein antibody, conjugated with horse-radish peroxidase (POD). When reacted with the peroxidase, the substrate DAB yields an insoluble brown precipitate which was visualized under a light microscope. Nuclei were additionally stained with DAPI (A2-E2; A4-F4) and fluorescence was documented with a Zeiss Axioplan 2 fluorescence microscope. Positive control: Cells were incubated with DNase I to induce DNA strand breaks and were proceeded in the same manner as the other samples. TUNEL positive cells were stained dark brown (F1). As a negative control served a sample incubated with fluorescein and terminal deoxynucleotidyl transferase but that was not treated with POD (E1). Each sample was performed in duplicates. Note positive nuclei stained in brown (arrow). Cells expressing Casp8-ER (A3), myrCasp8-ER (B3) and Casp9fullER(C3) exhibited typical apoptotic morphology, indicated by an arrow. Slight brownish precipitates appearing in samples that were not treated with 4-OH-tamoxifen are unspecific. Original magnification: 40-fold. Scale bar: 50 μm.

Figure 7:
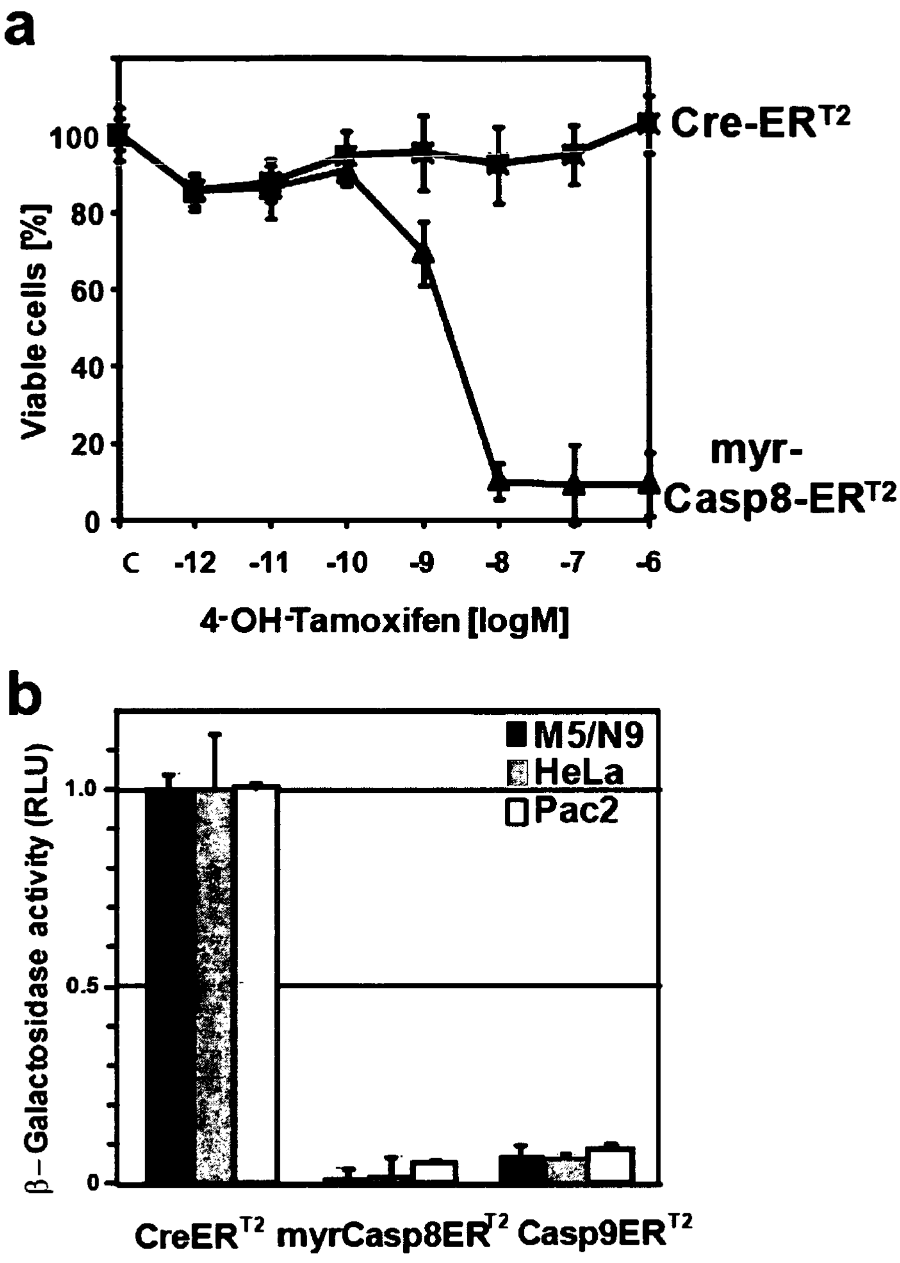

FIG. 7 shows dose response to 4-OH-tamoxifen of stable transfected murine fibroblasts and species specificity of the murine myrCasp8-ER(T2) fusion protein. (a) Cell viability in cultures of M5/N9 clones expressing myrCasp8-ER(T2) or Cre-ER(T2) in dependence of the concentration of 4-OH-tamoxifen, determined with the MTT assay at 48 h, in comparison to cultures that did not receive 4-OH-tamoxifen. Results are shown as mean values of triplicate samples with standard deviation. (b) Transient cotransfection of a β-galactosidase reporter with a Cre-ER(T2), myrCasp8-ER(T2), or Casp9-ER(T2) expression plasmid into murine M5/N9 (black columns), human HeLa (grey columns) or zebrafish Pac2 (open columns) cells. 12 h following transfection, cells were cultured for 36 h with 4-OH-tamoxifen at $10^{-8}$ M and the activity of β-galactosidase in cell lysates was determined. Values obtained from transfections of the Cre-ER(T2) vector were defined as reference. Results are shown as mean values of triplicate samples with standard deviation.

EXAMPLES

Example 1

Applications of an inducible cell ablation tool by using the chimeric system of Caspase-FKBP and Fas-ER have been efficiently demonstrated in several studies.

However, this system does not provide universal usage in any organ and any cell type of the mammalian body, including the brain. Here, we investigated an alternative inducible apoptosis system designed for universal application in mammalian cells and tissues, including the brain. To test the activity of different chimeric genes, we fused either a Caspase-8, -9, -3, or Bax domain to the ligand binding domain of the mutant mammalian estrogen receptor ER(T2) which is unable to bind estrogen yet retains high affinity for a synthetic ligand, 4-hydroxy-tamoxifen (Tm). Upon administration of the ligand which induces dimerisation of the ER(T2) domain, apoptosis should be directed by the activated Caspase or Bax domain. To compare and quantify the activity of the different CASP/Bax-ER(T2) expression vectors, these constructs were transiently introduced into the mouse fibroblast cell line MEF5/N9 together with a reporter vector encoding β-galactosidase.

A. Plasmid Constructions:

For the construction of pCAG-Cre-ER(T2)-bpA a 2.3 kb fragment coding for the Cre-ER(T2) fusion protein (Feil, et al., Biochem Biophys Res Commun, 237, 752-757 (1997)) was isolated from pSS1 (SEQ ID NO: 1; R. Kühn, unpublished) by digestion with PacI, PvuII and ScaI and ligated into pCAG-C31Int(NLS)-bpA (R. Kühn, unpublished; SEQ ID NO: 2), opened with SphI and PacI. pCAG-Cre-ER(T2)-bpA (SEQ ID NO: 3; FIG. 1E) contains a 1669 bp CAG promoter (position 432-2099), the Cre-ER(T2) fusion gene (SEQ ID NOS: 4 and 5; Cre: position 2139-3167; 3 AA linker: position 3168-3176; ER(T2): position 3177-4118), and a 265 bp bovine polyadenylation signal sequence (position 4181-4445). The sequence of the Cre-ER(T2) fusion gene was confirmed by DNA sequence analysis.

The expression vectors pCAG-HAFas-ER(T2) and pCAG-MFas-ER(T2) were constructed as following: mouse Fas insert encoding amino acids 135 to 305 for the transmembrane and intracellular domain of the Fas receptor was amplified by PCR (Phusion High-fidelity PCR kit, New England Biolabs) from the plasmid pDNR-LIB-Fas (RZPD GmbH, Berlin, Germany, clone ID: IRALp962N1053Q). To generate the 574 bp HAFas fragment, the oligonucleotides fasIER-A (SEQ ID NO: 6), containing the influenza virus hemagglutinin epitope, YPYDVPDYA (SEQ ID NO: 81), and fasER-B (SEQ ID NO: 7) were used. The 602 bp MFas variant was obtained by using the oligonucleotides fas2ER-A (SEQ ID NO: 8), containing a signal sequence for cell membrane targeting, and fasER-B. Both PCR fragments were flanked by a 5' PacI site and a 3' SalI site. The ends of the PCR products were digested with the respective enzymes and ligated into plasmid pCAG-Cre-ER(T2)-bpA, opened with PacI and XhoI, giving rise to the expression vectors pCAG-HAFas-ER(T2) (SEQ ID NO: 9) and pCAG-MFas-ER(T2) (SEQ ID NO: 10). pCAG-HAFas-ER(T2) (FIG. 1F) contains a 1669 bp CAG promoter (position 432-2099), the HAFas-ER(T2) fusion gene (SEQ ID NOS: 11 and 12; HA: position 2120-2152, Fas: position 2153-2665; 3 AA-linker: position: 2666-2674, ER(T2): position 2675-3616), and a 265 bp bovine polyadenylation signal sequence (position 3679-3943). pCAG-MFas-ER(T2) (FIG. 1F) contains a 1669 bp CAG promoter (position 432-2099), the MFas-ER(T2) fusion gene (SEQ ID NOS: 13 and 14; signal sequence: position 2120-2182, Fas: position 2183-2695; 3 AA-linker: position 2696-2704, ER(T2): position 2705-3646), and a 265 bp bovine polyadenylation signal sequence (position 3709-3973). The sequences of HAFas-ER(T2) and MFas-ER(T2) were confirmed by DNA sequence analysis.

Construction of the expression plasmids pCAG-Casp8-ER(T2)-bpA and pCAG-myrCasp8-ER(T2)-bpA: mouse Caspase 8 insert was PCR amplified from the plasmid pCMV-SPORT6-Casp8 (RZPD GmbH, Berlin, Germany, clone ID: IRAVp968E1193D). The 814 bp Casp8 PCR fragment was generated by using the oligonucleotides Casp8ER-A (SEQ ID NO: 15) and Casp8ER-B (SEQ ID NO: 16). The 853 bp myrCasp8 variant, containing a N-terminal myristoylation sequence motif, was obtained by using the oligonucleotides myrCasp8ER-A (SEQ ID NO: 17) and Casp8ER-B. Both PCR products were digested with PacI and XhoI and inserted into the PacI/XhoI cloning site of pCAG-Cre-ER(T2)-bpA, giving rise to the expression vectors pCAG-Casp8-ER(T2)- bpA and pCAG-myrCasp8-ER(T2)-bpA. pCAG-Casp8-ER (T2)-bpA (SEQ ID NO: 18; FIG. 1A) contains a 1669 bp CAG promoter (position 432-2099), the Casp8-ER(T2) fusion gene (SEQ ID NOS: 19 and 20; Caspase 8: position 2119-2907, 3 AA-linker: position 2908-2916, ER(T2): position 2917-3858), and a 265 bp bovine polyadenylation signal sequence (position 3921-4185). pCAG-myrCasp8-ER(T2)-bpA (SEQ ID NO: 21; FIG. 1A) consists of a 1669 bp CAG promoter (position 432-2099), the myrCasp8-ER(T2) fusion gene (SEQ ID NOS: 22 and 23; myristoylation motif: position 2119-2160, Caspase 8: position 2161-2946, 3 AA-linker: position 2947-2955, ER(T2): position 2956-3897), and a 265 bp bovine polyadenylation signal sequence (position 3960-4224). The sequences of Casp8-ER(T2) and myrCasp8-ER (T2) were confirmed by DNA sequence analysis.

The expression vectors pCAG-Casp9full-ER(T2)-bpA and pCAG-Casp9trunc-ER(T2)-bpA for the Caspase 9 ER(T2) fusion protein and a Caspase-activation recruitment domain (CARD) deleted form, referred to as truncated Caspase 9 ER(T2) fusion protein, were constructed as following: mouse Caspase 9 insert was PCR amplified from the plasmid pXY-Asc-Casp9 (RZPD GmbH, Berlin, Germany, clone ID: IRAVp968D06114D) by using the oligonucleotides Casp9fullER-A (SEQ ID NO: 24) and Casp9ER-B (SEQ ID NO: 25) for generating the 1.3 kb Casp9full fragment. To obtain the 1.1 kb truncated variant Casp9trunc, the oligonucleotides Casp9truncER-A (SEQ ID NO: 26) and Casp9ER-B were used. The PCR products were digested with PacI/SalI and ligated into the PacI/XhoI cloning site of pCAG-Cre-ER(T2)-bpA, giving rise to the expression vectors pCAG-Casp9full-ER(T2)-bpA and pCAG-Casp9trunc-ER(T2)-bpA. pCAG-Casp9full-ER(T2)-bpA (SEQ ID NO: 27; FIG. 1B) contains a 1669 bp CAG promoter (position 432-2099), the Casp9full-ER(T2) fusion gene (SEQ ID NOS: 28 and 29; Caspase 9: position 2119-3480, 3 AA-linker: position 3481-3489, ER(T2): position 3490-4439), and a 265 bp bovine polyadenylation signal sequence (position 4494-4758). pCAG-Casp9trunc-ER(T2)-bpA (SEQ ID NO: 30; FIG. 1B) consists of a 1669 bp CAG promoter (position 432-2099), the Casp9trunc-ER(T2) fusion gene (SEQ ID NOS: 31 and 32; CARD deleted Caspase 9: position 2119-3210, 3 AA-linker: position 3211-3219, ER(T2): position 3220-4161), and a 265 bp bovine polyadenylation signal sequence (position 4224-4488). The sequences of Casp9full-ER(T2) and Casp9trunc-ER(T2) were confirmed by DNA sequence analysis.

Construction of the expression plasmids pCAG-Casp3-ER (T2)-bpA and pCAG-Casp3-ED4ER(T2)-bpA: mouse Caspase 3 insert was amplified from the plasmid pFLCI-Casp3 (Open Biosystems, Huntsville, USA, clone ID: EMM1002-7378750). The 856 bp PCR fragment was obtained by using the oligonucleotides Casp3ER-A (SEQ ID NO: 33) and Casp3ER-B (SEQ ID NO: 34) and digested with PacI/XhoI. To generate the expression vector pCAG-Casp3-ER(T2)-bpA, the digested PCR product was inserted into pCAG-Cre-ER(T2), opened with PacI/XhoI. pCAG-Casp3-ER(T2)-bpA (SEQ ID NO: 35; FIG. 1C) contains a 1669 bp CAG promoter (position 432-2099), the Casp3-ER(T2) fusion gene (SEQ ID NO: 36 and 37; Caspase 3: position 2119-2949, 3 AA-linker: 2950-2958, position ER(T2): position 2959-3900), and a 265 bp bovine polyadenylation signal sequence (position 3963-4227). The vector pCAG-Casp3-ED4ER(T2)-bpA (SEQ ID NO: 38, encoding a Casp3-ER (T2) variant with a N-terminal shortened ER(T2) domain, referred to as ED4ER(T2), was constructed by ligating PacI/XhoI digested Caspase 3 PCR product into the plasmid pCAG-Cre-ED4ER(T2)-bpA (SEQ ID NO: 39), opened with PacI/XhoI. pCAG-Casp3-ED4ER(T2) (FIG. 1C) consists of a 1669 bp CAG promoter (position 432-2099), the Casp3-ED4ER(T2) fusion gene (SEQ ID NOS: 40 and 41; Caspase 3: position 2119-2955, ED4ER(T2): position 2956-3828), and a 265 bp bovine polyadenylation signal sequence (position 3891-4155). The expression plasmid pCAG-Cre-ED4ER (T2)-bpA was generated by substitution of the longer N-terminal fragment of ER(T2) by the N-terminal shortened ED4 part. The 298 bp ED4 fragment was PCR amplified by using the oligonucleotides ED4ER-A (SEQ ID NO: 42) and ED4ER-B (SEQ ID NO: 43), digested with XhoI/DraIII and ligated into the XhoI/DraIII site of pCAG-Cre-ER(T2)-bpA. The sequences of Casp3-ER(T2) and Casp3-ED4ER(T2) were confirmed by DNA sequence analysis.

Generation of the expression plasmid pCAG-Bax-ER(T2)-bpA occurred by PCR amplifying mouse Bax from the plasmid pCMV-SPORT6-bax (RZPD GmbH, Berlin, Germany, clone ID: IRAVp968B0795D) with the oligonucleotides BaxER-A (SEQ ID NO: 44) and BaxER-B (SEQ ID NO: 45). The 606 bp PCR product was digested with PacI/XhoI and ligated into the PacI/XhoI site of pCAG-Cre-ER(T2)-bpA. pCAG-Bax-ER(T2)-bpA (SEQ ID NO: 46; FIG. 1D) contains a 1669 bp CAG promoter (position 432-2099), the Bax-ER(T2) fusion gene (SEQ ID NOS: 47 and 48; Bax: position 2119-2697, 3 AA-linker: position 2698-2706, ER(T2): position 2707-3648), and a 265 bp bovine polyadenylation signal sequence (position 3711-3975). To construct the plasmid pCAG-ER(T2)-Bax-bpA coding for a fusion of Bax to the N-terminus of the ER(T2) domain, we applied fusion PCR with overlapping primers. First, the 913 bp ER(T2) part was PCR amplified from plasmid pCAG-Cre-ER(T2) using oligonucleotides ERbax-1 (SEQ ID NO: 49) and ERbax-2 (SEQ ID NO: 50). Simultaneously, the 590 bp PCR product coding for the Bax domain was generated by using the oligonucleotides ERbax-3 (SEQ ID NO: 51) and ERbax-4 (SEQ ID NO: 52) and the plasmid pCMV-SPORT6-bax (RZPD GmbH, Berlin, Germany, clone ID: IRAVp968B0795D) as template DNA. Since the primers ERbax-2 and ERbax-3 overlap, both PCR fragments were combined to the 1503 bp fusion PCR product ER(T2)-Bax by using the oligonucleotides ERbax-1 and ERbax-4. The end product was flanked by a 5'-PacI and a 3'-SalI site, digested with the respective enzymes and ligated into the plasmid pCAG-C31Int(NLS)-bpA, opened with PacI and SalI, giving rise to the expression vector pCAG-ER(T2)-Bax-bpA (SEQ ID NO: 53; FIG. 1D) which contains a 1669 bp CAG promoter (position 432-2099), the ER(T2)-Bax fusion gene (SEQ ID NOS: 54 and 55; ER(T2): position 2124-2999, Bax: position 3000-3575), and a 317 bp bovine polyadenylation signal sequence (position 3593-3909). The sequences of Bax-ER(T2) and ER(T2)-Bax were confirmed by DNA sequencing.

B. Cell Culture and Transient Transfections

The transformed mouse embryonic fibroblast cell line MEF5/N9 (Schwenk et al., Nucleic Acids Research, 26(6) 1427-1432 (1998)) was obtained from Michel Aguet (University of Zurich, Switzerland). The cells were grown in DMEM medium (Life Technologies) supplemented with 2 mM glutamate and 10% fetal calf serum at 37° C., 5% $CO_2$ in humid atmosphere and passaged upon trypsinization. One day before transient transfection $4 \cdot 10^4$ cells were plated into a 24-well plate (Falcon). For the transient transfection of MEF5/N9 cells with plasmids, each well received into 500 µl of medium a total amount of 150 ng or 200 ng supercoiled plasmid DNA complexed before with the FuGene6 transfection reagent (Roche Diagnostics GmbH, Mannheim, Germany) according to the manufacturer's protocol. Each 150 ng or 200 ng DNA preparation (FIG. 2 sample 1 to 11) contained 100 ng of the β-Galactosidase expression vector pCMV-β-gal-pA (pCMVβ, Clontech, FIG. 1G, SEQ ID NO: 56), and 100 ng of the fusion ER(T2) expression vectors to be tested (FIG. 2 sample 3-7, 10-11) and the control plasmids (FIG. 2 sample 1-3), except for the samples with the plasmids pCAG-Casp9full-ER(T2)-bpA (FIG. 2 sample 8) and pCAG-Casp9trunc-ER(T2)-bpA (FIG. 2 sample 9), respectively, that received 50 ng of the test vector. For each sample to be tested four individual wells were transfected. Five hours after the addition of the DNA preparations each well received additional 500 μl of growth medium. The following day, the medium of two wells of each sample was replaced by fresh medium. The other two wells received medium containing $10^{-8}$ M 4-hydroxy-tamoxifen (Sigma). 48 hours after induction with 4-OH-tamoxifen, the cells of each well were lysed with 200 μl lysate reagent supplemented with protease inhibitors (Roche Diagnostics GmbH). The lysates were centrifuged and 50 μl were used to determine the β-galactosidase activities using the β-galactosidase reporter gene assay (Roche Diagnostics GmbH) according to the manufacturer's protocol in a microplate luminometer (Berthold Detection Systems GmbH). The mean value and standard deviation of the samples was calculated from the β-galactosidase RLU values obtained from the two transfected wells of each sample. The relative β-galactosidase activity was obtained by comparison to the negative control (pCAG-Cre-ER(T2)-bpA) without 4-OH-tamoxifen.

Results:

To assess the efficacy of a novel approach for inducible cell death, we generated different fusion genes of Caspases or bax and the mutant mammalian estrogen receptor ER(T2), which dimerizes upon administration of the synthetic ligand 4-hydroxy-tamoxifen. We first constructed the plasmid pCAG-Cre-ER(T2) (see FIG. 1E) designed as a negative control which contains the 1.98 kb fusion gene Cre-ER(T2), driven by the CAG promoter and a bovine polyadenylation signal sequence. The Cre protein was fused to the N-terminus of the ligand binding domain of the mutant mammalian estrogen receptor, referred to as ER(T2) (282-595) (Feil, et al., Biochem Biophys Res Commun, 237, 752-757 (1997)). Both domains are separated by a linker consisting of three amino acids. In all other constructs tested, the Cre recombinase domain was replaced by the respective Caspase, bax or fas domain, resulting in identical backbone sequences with exception for the plasmids pCAG-Casp3-ED4ER(T2) and pCAG-ER(T2)-Bax. The plasmids pCAG-Casp8-ER(T2) and pCAG-myrCasp8-ER(T2) contained a mouse Caspase 8 domain fused to the N-terminus of ER(T2) (see FIG. 1A). The 1.78 kb myrCasp8-ER(T2) differed from the 1.74 kb Casp8-ER(T2) fusion gene by an additional myristoylation signal sequence to provide membrane attachment for Casp8-ER (T2) and therefore to effectively increase local concentrations of the fusion protein. pCAG-Casp9full-ER(T2) (see FIG. 1B) contained the full length sequence of mouse proCaspase 9, resulting in a fusion gene of 2.32 kb size. The variant pCAG-Casp9trunc-ER(T2) (see FIG. 1B) consisted of the 2.04 kb fusion gene Casp9trunc-ER(T2) which includes a mouse Caspase 9 domain without the Caspase activation recruitment domain (CARD). The plasmids pCAG-Casp3-ER(T2) and pCAG-Casp3-ED4ER(T2) contain the full length sequence of mouse proCaspase 3 (see FIG. 1C). The 1.79 kb Casp3-ER(T2) fusion gene includes the usual linker of three amino acids between both domains. In contrast, the 1.71 kb Casp3-ED4ER(T2) fusion gene results from a direct fusion of proCaspase 3 to a N-terminal shortened ER(T2) variant (305-595). The plasmids pCAG-Bax-ER(T2) and pCAG-ER(T2)-Bax contain the full length sequence of mouse Bax (see FIG. 1D). While the 1.53 kb bax-ER(T2) fusion gene encodes a N-terminal fusion protein of Bax and ER(T2), the 1.45 kb ER(T2)-Bax variant is a spaceless C-terminal fusion of Bax to ER(T2). The backbone sequence of pCAG-ER(T2)-Bax is identical to the vector pCAG-C31Int(NLS). The plasmids pCAG-HAFas-ER(T2) and pCAG-MFas-ER(T2) (see FIG. 1F) were planned as positive controls since the activity of the fas-ER fusion protein to induce ligand-dependent apoptosis has been demonstrated in several studies (Takebayashi et al., Cancer Research, 56, 4164-4170 (1996); Kawaguchi et al., Cancer Letters, 116, 53-59 (1997); Kodaira et al., Jpn. J. Cancer Res., 89, 741-747 (1998)). HAFas-ER(T2) (1.5 kb) is a fusion between an influenza virus HA epitope, followed by the transmembrane and cytoplasmic domains of mouse Fas (135-305) and ER(T2). The other variant MFas-ER(T2) (1.53 kb) is identical to HAFas-ER(T2) but contains instead of the HA epitope a signal peptide for cell membrane targeting.

To investigate the cell death effect of the different ER(T2) fusion constructs quantitatively, we performed transient cotransfections of the ER(T2) fusion protein expression vectors together with a fixed amount of a reporter plasmid coding for β-galactosidase in MEF5/N9 fibroblast cells. Transfected cells were treated 12 hours after transfection with 4-OH-tamoxifen at a concentration of $10^{-8}$ M. Following 48 hours of 4-OH-tamoxifen induction, the cells from the various samples were lysed and the activity of β-galactosidase in the lysates was determined by a chemiluminescence assay and expressed in "Relative Light Units" (RLU) (FIG. 2). As positive controls for 4-OH-tamoxifen-inducible cell death, we prepared samples transfected with the constructs pCAG-HAFas-ER(T2) or pCAG-MFas-ER(T2) together with the reporter plasmid and treatment with 4-OH-tamoxifen. As negative control for this assay served samples which received the reporter plasmid together with the expression vector pCAG-Cre-ER(T2) and that were treated with 4-OH-tamoxifen.

To determine the relative activity of the tested ER(T2) fusion constructs inducing apoptosis in the presence of 4-OH-tamoxifen, the RLU values of β-galactosidase activity were divided individually for each sample by the RLU value obtained from the sample which received the plasmid pCAG-Cre-ER(T2) but was not treated with 4-OH-tamoxifen (defined as negative control). The relative activity of the tested Caspase- or bax-ER(T2) fusion proteins was then compared to the negative control for 4-OH-tamoxifen-dependent cell death defined as an activity of 1.

FIG. 2 shows the representative results from at least two independently performed experiments. Only those results from samples which received the DNA amount with the lowest basal toxicity are shown in FIG. 2. Neither the expression of the negative control Cre-ER(T2) alone nor the combined treatment with 4-OH-tamoxifen at the concentration of $10^{-8}$ M displayed toxic side effects (sample 1.1 and 1.2), indicating that observed cell death in combination with the expression of the test constructs is a specific effect. Both Fas-ER (T2) variants designed as positive controls exhibited in presence of 4-OH-tamoxifen a relative β-galactosidase activity of only 23% for HAFas-ER(T2) and 26% for MFas-ER (T2) compared to the negative control. However, a basal toxicity, expressed in reduced β-galactosidase activities compared to the negative control in absence of 4-OH-tamoxifen, could be observed for both constructs. Considering slight experimental variation between transfections, 4-OH-tamoxifen-dependent basal toxicities had the following rankings: myrCasp8-ER(T2) (6%)>Casp8-ER(T2) (17%)>Casp3-ER (T2), Casp3-ED4ER(T2), HAFas-ER(T2) (52%)>MFas-ER (T2) (60%)>Casp9full-ER(T2) (62%)>Casp9trunc-ER(T2)

(70%)>ER(T2)-Bax (84%)>Bax-ER(T2) (100%). Sensitivity to 4-OH-tamoxifen-inducible activation follows a Blighty different order than basal activity: myrCasp8-ER(T2) (0.1%)>Casp8-ER(T2) (3%)>Casp9full-ER(T2) (7%)>Casp9trunc-ER(T2) (22%)>HAFas-ER(T2) (23%)>MFas-ER(T2) (26%)>Casp3-ER(T2) (28%). Normally, it was observed that a decreasing basal activity correlates with the reduction of 4-OH-tamoxifen-inducible activity. Both Caspase 8 ER(T2) fusion constructs demonstrated the highest efficiency for 4-OH-tamoxifen-dependent cell death among all ER(T2) fusion proteins but the strongest basal activity as well. Even when the amount of transfected expression plasmid was reduced to 5 ng per sample, a change in the basal activity could not be significantly detected (not shown). In contrast, both Caspase 9 ER(T2) constructs showed relative low basal toxicity but lower 4-OH-tamoxifen-dependent activity as well. Surprisingly, neither the N-terminal nor the C-terminal fusion of Bax to ER(T2) displayed any activity in the chosen test cell line. Unexpectedly, though Caspase 3 plays the role of the downstream executive Caspase in the apoptotic pathway, the ligand-dependent activity of the Casp3-ER(T2) variant was low compared to the Caspase 8 or Caspase 9 ER(T2) fusion variants. Moreover, the Casp3-ED4ER(T2) construct with deleted linker and a shortened ER(T2) N-terminus revealed basal toxicity but could not be regulated in presence of 4-OH-tamoxifen. Except for Bax-ER(T2) all constructs including the positive control Fas-ER(T2) showed slight till considerable basal toxicity in absence of 4-OH-tamoxifen. These findings could be explained by the high copy number of transfected Caspase- or fas-ER(T2) constructs giving rise to unphysiological concentrations of ER(T2) fusion proteins inside the cells.

Taken together, in the transient transfection system shown in FIG. 2 we could identify several Caspase-ER(T2) fusion constructs displaying high 4-OH-tamoxifen-dependent activity. However, not every arbitrary combination of different Caspases or bax molecules and ER(T2) was capable to induce cell death in the presence of 4-OH-tamoxifen and could be further regulated in a ligand-dependent manner. In particular, this assay provides first evidence for three highly efficient Caspase-ER(T2) fusion proteins: myrCasp8-ER(T2), Casp8-ER(T2) and Casp9full-ER(T2). The efficiency of an alternative fusion of the Caspases to ER(T2) instead of the FKBP domain is regarded as an invention of substantial use for biotechnology.

Example 2

Using the transient transfection system of Example 1, we identified Caspase-ER(T2) fusion constructs that exhibit 4-OH-tamoxifen-dependent activity. However, the high copy number of expression plasmids following transient transfection may lead to unphysiological high concentrations of the fusion proteins. We next transfected the constructs identified as active in Example 1 stably into the test cell line MEF5/N9, in short M5N9.

A. Plasmid Constructions

All plasmids and their purification are described in Example 1, except for the pPgk-hygro-pA plasmid (FIG. 1H; SEQ ID NO: 57) that was obtained from Paul Krimpenfort (National Cancer Institute, Amsterdam).

B. Cell Culture and Stable Transfections

To generate stably transfected MEF5/N9 cells, $2 \cdot 10^6$ cells were coelectroporated with 32 μg ER(T2) fusion plasmid DNA linearised with ScaI and 8 μg pPgk-hygro-pA plasmid DNA linearised with XhoI and plated into two 96-well plates. The cells were grown in DMEM medium (Invitrogen) supplemented with 2 mM Glutamine and 10% fetal calf serum at 37° C., 5% $CO_2$ in humid atmosphere, and passaged upon trypsinization. Two days after transfection the medium was supplemented with 250 U/ml of hygromycin (Calbiochem) for the selection of stable integrants. Upon the growth of resistant colonies these were individually expanded in the presence of hygromycin.

C. Immunoblot Detection of Er(T2) Fusion Proteins in Transfected Mef5/N9 Cells

To directly demonstrate expression of the transfected fusion protein vector, protein lysates of hygromycin resistant clones were prepared for western blot analysis.

One million cells were lysed in 500 μl of lysis buffer (50 mM Tris-HCl [pH 6.8], 50 mM dithiothreitol, 10% glycerol, 2% SDS) supplemented with protease inhibitor cocktail (Roche Diagnostics GmbH). Cell lysates were incubated for 7 min at 100° C. and sonificated for 10 s. Cell debris were pelleted by centrifugation and an aliquot of the supernatant was applied for protein concentration analysis by using the BCA protein assay kit (Pierce, Rockford, Ill.). 0.01% of bromphenolblue, diluted in lysis buffer was added to the remaining lysate. For western blot analysis, 40 μg protein was incubated for 3 min at 100° C. before separating the samples on a 10% SDS-polyacrylamide gel (NuPAGE® Novex Bis-Tris gels; Invitrogen). Electrophoresis was performed according to the manufacturer's protocol in MES running buffer (50 mM MES, 50 mM Tris-HCl, 1 mM EDTA, 0.1% SDS, [pH 7.2]). Following subsequent blotting to BioTrace PVDF transfer membrane (Pall Corporation) in blotting buffer (25 mM bicine, 25 mM bis-Tris, 1 mM EDTA, 0.005 mM chlorobutanol, 10% methanol), membranes were blocked in 5% skim milk (BD Biosciences) over night at 4° C. Western blot analysis was performed with the ECL kit (Amersham Biosciences) using either the rabbit anti-ERα antibody HC-20 (#SC543, Santa Cruz Biotechnology), diluted 1:1000 in 2.5% skim milk/TBST or mouse anti-β-actin antibody AC15 (BIOZOL, Eching, Germany), diluted 1:5000 in 2.5% skim milk/TBST. Between each incubation step and before signal detection, membranes were rinsed several times with TBST (25 mM Tris-HCl [pH 7.6], 137 mM NaCl, 0.1% Tween-20). Membrane stripping occurred for 5 min in stripping buffer (10% acetic acid, 10% methanol) on a shaker.

Results

To generate mammalian cell clones with a stable genomic integration of active ER(T2) fusion genes, the murine fibroblast cell line MEF5/N9 was electroporated with linearised DNA of ER(T2) fusion constructs together with the plasmid pPgk-hygro (FIG. 1; see also example 1) and subjected to selection in hygromycin containing growth medium. We transfected MEF5/N9 with pCAG-Cre-ER(T2) and pCAG-ER(T2)-Bax, respectively, designed as negative controls. We further transfected the cells with the constructs pCAG-myr-Casp8-ER(T2), pCAG-Casp8-ER(T2), pCAG-Casp9full-ER (T2), pCAG-Casp9trunc-ER(T2), pCAG-Casp3-ER(T2) and the putative positive controls pCAG-HAFas-ER(T2) and pCAG-MFas-ER(T2). For each construct four stably transfected clones were expanded and chosen for further analysis.

As shown in FIG. 3, expression of the fusion proteins was determined by western blot analysis using an anti-ER antibody. 40 μg of each sample was applied for SDS-PAGE. The anti-ER antibody specifically recognised the ER(T2) fusion proteins since endogenous estrogen receptor was not present in the untransfected cells (not shown). At least two of the four clones of each construct displayed high expression of the ER(T2) fusion proteins. This finding indicates firstly, that the designed fusion constructs could correctly be expressed, and secondly, that the stable expression of the fusion proteins showing high basal toxicity in transient transfection assays (Example 1) was not lethal for the cells. FIG. 1G demonstrates the expression of Cre-ER(T2) which was detected as a 74 kDa protein in all four clones. FIGS. 3H and 3I shows the expression of the 54 kDa HAFas-ER(T2) and the 56 kDa MFas-ER(T2) fusion proteins. Casp8-ER(T2) was detected as a 64 kDa protein in the clones M5N9 3.2 and 3.6 (see FIG. 1A). myrCasp8-ER(T2) was detected as a 65 kDa protein in the clones M5N9 7.3 and 7.4 (see FIG. 1B). Casp9full-ER (T2) and Casp9trunc-ER(T2), respectively was detected as a 85 kDa and as a 75 kDA protein in all four clones for each construct (FIG. 1C, D). Casp3-ER(T2) was expressed in all clones as a 65 kDa protein (see FIG. 1E). Expression of the ER(T2)-Bax protein is shown in FIG. 1F as a 53 kDa protein.

Example 3

We have shown in transient transfection assays (example 1) that fusions between ER(T2) and Caspase 8, myristoylated Caspase 8, proCaspase 9, Caspase 9 without CARD, or proCaspase 3, induced cell death under control of 4-OH-tamoxifen. However, this assay system does not provide final evidence for the efficacy of the various constructs. To investigate differences in the efficacy of the various expression plasmids, we generated stably transfected MEF5/N9 clones expressing the ER(T2) fusion proteins in a low copy number. Transfected MEF5/N9 clones were incubated with 4-OH-tamoxifen and examined for cell viability.

A. Viability of Transfected Mef5/N9 Cells Upon Treatment with 4-OH-Tamoxifen

To examine 4-OH-tamoxifen-dependent cell death, $1\cdot10^5$ MEF5/N9 cells expressing ER(T2) fusion proteins were plated into each well of a six-well plate. The following day, for each sample the medium in two of four individual wells were replaced with medium supplemented with $10^{-8}$ M 4-hydroxy-tamoxifen. 24 hours after induction with 4-OH-tamoxifen, cells were photographed through a Leica DMI6000B fluorescence microscope with phase contrast either at 10-fold or 20-fold magnification.

B. MTT Cytotoxicity Assay

To quantify 4-OH-tamoxifen-inducible cell death, we applied the colorimetric MTT assay (Mossman, J. Immunol. Methods, 65, 55 (1983)) allowing the quantification of cell survival. Cells ($4\cdot10^3$) were plated on 96-well plates. The assay was carried out in three replicas for each sample treated with and without 4-OH-tamoxifen. After 12 h, medium was replaced either with fresh medium or with medium supplemented with $10^{-8}$ M 4-OH-tamoxifen. Following 48 h of 4-OH-tamoxifen treatment, sterile filtered MTT reagent in PBS (Sigma) was added at the concentration of 0.5 mg/ml. Incubation occurred for 4 hours at 37° C. With ongoing reaction time, dark violet MTT formazan crystals appeared on the bottom of the wells containing living cells. The crystals were dissolved in 150 μl 0.04 N HCl/isopropanol to give a homogeneous blue solution suitable for absorbance measurement at a wavelength of 570 nm on the Synergy™ HT Multi-Detection Microplate Reader (BioTek).

Results

To examine 4-OH-tamoxifen-inducible apoptosis in stably transfected MEF5/N9 clones, we first visualized cell viability after 24 hours of incubation with 4-OH-tamoxifen at a concentration of $10^{-8}$ M. FIG. 4 shows representative results from two independently performed experiments. Since the responsiveness of the clones, transfected with the same construct, to 4-OH-tamoxifen differed only slightly from each other, only the results obtained from one clone for each construct are shown in the figure.

The results obtained from the transient transfection assays could partially be confirmed. Interestingly, only the fusion proteins of ER(T2) and proCaspase 9, myristoylated Caspase 8, Caspase 8 and Caspase 9 with deleted CARD were able to induce 4-OH-tamoxifen-dependent cell death in stably transfected MEF5/N9 cells. All clones tested were growing well, like the parental cell line, in absence of 4-OH-tamoxifen (FIG. 4, upper panels), whereas nearly all cells of the clones expressing Casp8-ER(T2) (FIG. 4 A2), myrCasp8-ER(T2) (FIG. 4 B2) and Casp9full-ER(T2) (FIG. 4 C2) died in the presence of 4-OH-tamoxifen within 24 h. MEF5/N9 cells expressing Casp9trunc-ER(T2) fusion protein displayed weaker susceptibility to 4-OH-tamoxifen (FIG. 4 D2) compared to cells expressing the highly efficient fusion protein Casp8-ER(T2), myrCasp8-ER(T2) or Casp9full-ER(T2). In contrast, cells expressing the fusion proteins Cre-ER(T2) or ER(T2)-Bax, that revealed to be inactive in transient transfection assays, did not respond to 4-OH-tamoxifen (see FIG. 4 G2, F2). Most surprisingly, neither the two Fas-ER(T2) variants (see FIG. 4 H2, I2) nor Casp3-ER(T2) (FIG. 4 E2) were able to induce apoptosis in the presence of 4-OH-tamoxifen. For these constructs, 4-OH-tamoxifen-dependent cell death could possibly only be observed if the fusion genes were available in a high copy number in the cells as it was the case in transient transfections (Example 1).

We further quantified cell viabilities by the MTT cytotoxicity assay following 48 h of incubation with $10^{-8}$ M 4-OH-tamoxifen. Representative results from two independently performed experiments are shown in FIG. 5. The results obtained from phenotypic examinations of stably transfected MEF5/N9 clones were confirmed in this assay. In the absence of 4-OH-tamoxifen, there was no apparent difference in growth rates between stable clones, but in the presence of 4-OH-tamoxifen, nearly all cells of the clones M5N9 3.2 Casp8ER (sample 5), M5N9 7.4 myrCasp8ER (sample 6) and M5N9 5.3 Casp9fullER (sample 7) died within 48 h of treatment. We observed a reduction of the cell viability down to 31% in clone M5N9 3.2 Casp8ER, to 9% in clone M5N9 7.4 myrCasp8ER and to 6% in clone M5N9 5.3 Casp9fullER in presence of 4-OH-tamoxifen. The clone M5N9 6.4 Casp9truncER (sample 8) displayed weaker susceptibility to 4-OH-tamoxifen-inducible cell death as it was already observed in the morphological examinations.

Taken together, we could identify three highly efficient ER(T2) fusion constructs, namely Casp8-ER(T2), myrCasp8-ER(T2) and Casp9full-ER(T2) inducing 4-OH-tamoxifen-dependent apoptosis in the test cell line MEF5/N9 within a short time. However, the reported activity of the Fas-ER(T2) fusion protein (Kodaira et al., Jpn. J. Cancer Res., 89, 741-747 (1998)) originally planned as a positive control could not be reproduced in the cell line MEF5/N9. This finding demonstrates that Fas-ER(T2) possibly shows activity only in specific cell types, namely in those expressing endogeneous fas receptor and in which apoptosis can be induced in a fas-dependent manner. In contrast, we have demonstrated for the first time that fusion constructs of ER(T2) and Caspases provide a highly efficient system to conditionally ablate mammalian cells. Moreover, since Caspase 8 and Caspase 9 are ubiquitously expressed in mammalian tissues and are both involved in different pathways of apoptosis, the potential universal application of ER(T2) fusions to Caspase 8 or 9 for inducible cell ablation is of commercial relevance in biotechnology.

Example 4

We could demonstrate in example 3 that 4-OH-tamoxifen induced cell death of MEF5 clones expressing Caspase fusion proteins. In order to provide direct evidence that the cell death occurs via induced apoptosis the TUNEL DNA fragmentation assay was used. This method detects DNA fragmentation, one of the late events that result from apoptotic signaling cascades. As shown in FIG. 6, the TUNEL analysis revealed that clones expressing Caspase-8 or -9 fusion proteins undergo apoptotic cell death in the presence of the inducer 4-OH-Tamoxifen.

In Situ Cell Death Detection Assay

TUNEL, or terminal deoxynucleotidyl transferase-mediated dUTP nick end-labeling, is acknowledged as a method of choice in the rapid detection of DNA fragmentation that results from apoptotic signaling cascades (Gavrieli et al., J. Cell Biol., 119(3), 493-501 (1992)). Cleavage of genomic DNA during apoptosis may yield double-stranded, low molecular weight DNA fragments as well as single strand breaks ("nicks") in high molecular weight DNA. Those DNA strand breaks can be identified by terminal deoxynucleotidyl transferase (TdT), which catalyzes polymerization of labeled nucleotides to free 3'-OH DNA ends in a template-independent manner. To detect 4-OH-tamoxifen induced cell death in MEF5/N9 cells, we applied the In Situ Cell Death Detection Kit, POD by Roche according to the manufacturer's instructions. Incorporated fluorescein is detected by anti-fluorescein antibody, conjugated with horse-radish peroxidase (POD). After substrate reaction, stained cells can be analyzed under light microscopy.

Two days prior to the TUNEL staining, round glass cover slips (12 min Ø) were sterilized with 70% EtOH, dried under laminar flow and coated with Poly-L-lysine at a concentration of 50 μg/ml over night at 37° C., which allows a better attachment of cells on the cover slips. The following day, the cover slips were rinsed 3 times with PBS and dried for 1 hour under laminar flow. $2.5 \cdot 10^5$ cells were seeded onto cover slips in a 6-well plate. On the test day, medium was replaced either by fresh medium or medium supplemented with $10^{-8}$ M 4-OH-tamoxifen. Cells were fixated in 4% PFA (diluted in PBS, pH 7.4) for 1 hour at room temperature following 2, 3 and 7 hours of incubation. After fixation, cells were rinsed three times in PBS, covered with 100% methanol and incubated for 10 min or over night in a freezer and rinsed in PBS. Endogenous peroxidase activity was blocked by immersing cover slips for 10 min in 3% $H_2O_2$ in methanol prior to cell permeabilization. Cells were subsequently rinsed with PBS and incubated in permeabilization solution (0.1% Triton X-100 in freshly prepared 0.1% sodium citrate) for 2 min on ice. To generate a positive control, DNA strand breaks were induced by incubating permeabilized cells with 2 U/ml DNase I in 50 mM Tris-HCl, pH 7.5, 10 mM $MgCl_2$, 1 mg/ml BSA for 10 min at room temperature, prior to labeling procedure. Cover slips were rinsed twice with PBS before incubating each sample with 25 μl TUNEL reaction mixture for 60 min at 37° C. in a humidified atmosphere in the dark. To avoid evaporative loss, cover slips were covered with parafilm. For a negative control 25 μl of Label solution without enzyme solution were added. Following labeling, cover slips were rinsed 3 times with PBS for 10 min each. To convert the fluorescence signal to a chromogenic signal, 25 μl of the POD solution were added on each sample which was covered with parafilm and incubated in a humidified chamber for 30 min at 37° C. Subsequently, cover slips were rinsed 3 times with PBS and incubated in freshly prepared 0.05% DAB in 0.1 M Tris-HCl (pH 7.4) supplemented with 0.02% $H_2O_2$ for 10-20 min at room temperature. The conversion procedure was controlled under a light microscope. The reaction was stopped with PBS until brown precipitates were well visible inside the cells. To remove DAB, cover slips were rinsed several times in PBS. Optionally, nuclear staining was performed by incubating cover slips for 15 min in 2.5 μg/ml DAPI diluted in PBS. Cover slips were mounted with a water-soluble, non-fluorescing mounting medium (Aqua-Poly/Mount; Polysciences Inc., Eppelheim, Germany) under SuperFrost slides (VWR International). Prior to the analysis of the samples under a light microscope, mounting medium was dried for 24 hours at room temperature.

Results

To provide direct evidence for 4-OH-tamoxifen-induced apoptosis in MEF5/N9 clones expressing Caspase-8 or -9 fusion proteins, an in situ application of the TUNEL assay was performed. This method detects DNA fragmentation, one of the late events that result from apoptotic signaling cascades. Cells were seeded onto cover slips and incubated with 4-OH-tamoxifen at a concentration of $10^{-8}$ M. Since general data of apoptotic kinetics do not exist so far, cells were fixated at different time points. Thus, cells were incubated with 4-OH-tamoxifen for 2, 3, 5 and 7 hours before fixation in 4% PFA and permeabilized in Methanol at −20° C. Fragmented DNA was labeled by incorporated fluorescein which was recognized by an anti-fluorescein antibody, conjugated with horse-radish-peroxidase (POD). POD converts the substrate DAB into insoluble brown precipitates which can be visualized under a light microscope. Samples were performed in duplicates and documented with a Zeiss Axioplan 2 fluorescence microscope. Nuclei were additionally stained with DAPI (A2-E2; A4-F4). As a positive control served wildtype MEF5/N9 cells that were incubated with DNase I to initiate DNA strand breaks. These cells were stained typically dark brown (see FIG. 6 F1). As a negative control served a sample incubated with fluorescein and terminal deoxynucleotidyl transferase but that was not treated with POD (E1). MEF5/N9 cells expressing Cre-ER(T2) fusion proteins were TUNEL negative at any point in time. A representative result is shown in FIG. 6 D1, D3, following 7 hours of treatment with 4-OH-tamoxifen. TUNEL positive cells, expressing myrCasp8ER (FIG. 6 B3) and Casp9fullER (FIG. 6 C3), could be detected as early as 3 hours following incubation with 4-OH-tamoxifen. In contrast, the induction of apoptosis was slower in cells expressing Casp8ER fusion proteins. TUNEL positive M5N9 Casp8ER expressing cells could be visualized not until 7 hours of treatment with 4-OH-tamoxifen (FIG. 6 A3). All three TUNEL positive clones exhibited typical apoptotic morphology of membrane bubbling, indicated by arrows in FIG. 6 A3, B3, C3. Slight brownish precipitates appearing in samples that were not treated with 4-OH-tamoxifen are unspecific.

Example 5

Transient transfections into M5/N9 and HeLa cells were performed with FuGene transfection reagent (Roche) following the manufacturer's instructions. Briefly, semiconfluent cultures in a 24-well plate were transfected in triplicate with 112 ng of the β-galactosidase expression vector CMVβ(Invitrogen) and the same amount of pCAG-Cre-ER(T2), pCAG-Casp8-ER(T2) or pCAG-Casp9-ER(T2) plasmid DNA. After 12 h 4-OH-tamoxifen was added at a concentration of $10^{-8}$ M and the cultures were lysed at 48 h. Cell lysis and the measurement of β-galactosidase activity by chemiluminescence were performed with the β-galactosidase reporter gene assay (Roche) using a Centro LB960 plate luminometer (Berthold).

PAC2 zebrafish fibroblasts were grown in Leibowitz's L15—with L-Glutamine medium supplemented with 1% Non-essential Amino Acids, 1% Penicillin/Streptomycin and 10% fetal calf serum (all Gibco) at 28° C. $3\times10^6$ Cells were transiently transfected with the plasmids CMVβ together with CAG-CreER(T2), CAG-myrCasp8ER(T2) or CAG-Casp9ER(T2) (500 ng each) using nanofectin transfection reagent (PAA). 24 hrs after transfection the medium was replaced and conditioned with $10^{-8}$ M 4-OH-tamoxifen. Before lysis, the cells were incubated for another 24 hrs at 28°.

Results

We examined the effects of various concentrations of 4-OHT and 17-β-estradiol ($E_2$), the natural ligand of the estrogen receptor, on the induction of cell death in M5/N9 cells expressing myrCasp8-$ER^{T2}$ as compared to control cells expressing Cre-ER(T2). Cell viability was determined following 48 hours of incubation with the respective ligand at concentrations ranging from $10^{-6}$ M to $10^{-12}$ M by using the MTT assay. 4-OHT at a concentration of $10^{-9}$ M reduced the viability of myrCasp8-ER(T2) expressing cells by 30% and led to complete cell death at $10^{-8}$ M or higher concentration (FIG. 7*a*). In contrast, concentrations of $10^{-7}$ M or higher of $E_2$ were required to induce cell death in myrCasp8-ER(T2) expressing cells (data not shown). This result showed that the sensitivity of the mutant ER(T2) ligand binding domain to 4-OHT, as described for the fusion with Cre recombinase (Feil et al., Biochem Biophys Res Commun 237:752-757 (1997)), is retained in the myrCasp8-ER(T2) fusion protein. Since the responsiveness of the ER(T2) domain to $E_2$ is at least 1000-fold reduced as compared to wildtype estrogen receptor and endogenous $E_2$ does not exceed levels of $10^{-10}$ M, even in female mice during pregnancy (Bergman et al. Endocrinology 130:1923-1930 (1992)), the Caspase-ER(T2) system seems to be well applicable in vivo.

To define whether fusion proteins of murine Caspases and the human ER(T2) domain induce apoptosis in cells of other vertebrates than mice we transiently transfected Caspase-ER (T2) or Cre-ER(T2) expression vectors with a β-galactosidase reporter plasmid into human HeLa cells and zebrafish Pac2 cells (Chen et al., J Virol 76:2192-2198 (2002)). The activity of β-Galactosidase cotransfected with Cre-ER(T2) was taken as positive control of cell viability and its decline as indication of the death of cotransfected cells. The levels of β-Galactosidase activity in HeLa and Pac2 cells were reduced by 95-99% for myrCasp8-ER(T2) and 91-93% for Casp9-ER (T2) in the presence of 4-OHT and reached the same values as obtained from murine M5/N9 fibroblasts (FIG. 7*b*). Thus, the murine Caspase fusion proteins are broadly active and can be used for inducible apoptosis in diverse vertebrates like mouse, zebrafish and humans.

Taking advantage of a mutant estrogen receptor ligand binding domain (ER(T2)) we developed novel Caspase fusion proteins for inducible apoptosis. We show that Caspase-ER(T2) fusion proteins become specifically activated by the synthetic ligand 4-OH-tamoxifen and rapidly induce apoptotic cell death in human, murine and zebrafish cells. This novel tool for targeted cell ablation greatly facilitates the generation of disease models as well as developmental and regeneration studies in model organisms.

The invention claimed is:

1. A fusion protein comprising (a) a Caspase domain comprising an amino acid sequence selected from the group consisting of SEQ ID NO: 64, SEQ ID NO: 65, SEQ ID NO: 67 and, SEQ ID NO: 68; and (b) a ligand binding domain of a nuclear hormone receptor or a functionally active variant thereof having the ability to be activated upon binding of a ligand, wherein upon exposure of the ligand binding domain of the nuclear hormone receptor to the ligand, the fusion protein is capable of inducing apoptosis in a cell.

2. The fusion protein of claim 1, wherein the nuclear hormone receptor is selected from the group consisting of an estrogen receptor, a progesterone receptor, a glucocorticoid receptor and an androgen receptor.

3. The fusion protein of claim 1, wherein the nuclear hormone receptor is a mammalian nuclear hormone receptor.

4. The fusion protein of claim 1, wherein the functionally active variant of the nuclear hormone receptor is mutant ER(T2) estrogen receptor.

5. The fusion protein of claim 1, wherein the binding domain of the nuclear hormone receptor ligand is linked to the N-terminal or C-terminal end of the Caspase domain.

6. The fusion protein of claim 1, wherein the ligand binding domain of the nuclear hormone receptor is linked to the Caspase domain directly.

7. The fusion protein of claim 1, wherein the ligand binding domain of the nuclear hormone receptor is linked to the Caspase domain via a linker.

8. The fusion protein of claim 1 comprising an amino acid sequence selected from the group consisting of SEQ ID NO: 20, SEQ ID NO: 23, SEQ ID NO: 29, SEQ ID NO: 32 and SEQ ID NO: 37.

9. A nucleic acid coding for the fusion protein according to claim 1.

10. A vector comprising the nucleic acid according to claim 9.

11. An isolated cell comprising the nucleic acid according to claim 9.

12. A method for producing the fusion protein according to claim 1 comprising culturing a cell comprising a nucleic acid coding for the fusion protein according to claim 1 under conditions conducive to the production of the fusion protein.

13. An in vitro method for ligand-mediated induction of apoptosis of a cell, the cell comprising a nucleic acid coding for the fusion protein according to claim 1, the method comprising contacting the fusion protein according to claim 1 on the surface of the cell with a ligand.

14. The method of claim 13, the method being used for studying the function of a cell, tissue or organ.

15. An in virtro method for identifying a ligand to a ligand binding domain of a nuclear hormone receptor or a functionally active variant thereof, the method comprising contacting the ligand binding domain of the nuclear hormone receptor of a cell comprising a nucleic acid coding for the fusion protein according to claim 1 with a substance; and identifying the substance as a ligand, depending on its capability to induce apoptosis of the cell.

16. A composition comprising (i) the fusion protein according to claim 1 or the nucleic acid according to claim 9 and (ii) a pharmaceutically acceptable carrier or excipient.

17. The fusion protein of claim 1, wherein the Caspase domain consists of an amino acid sequence selected from the group consisting of SEQ ID NO: 64, SEQ ID NO: 65, SEQ ID NO: 67 and SEQ ID NO: 68.

18. The fusion protein of claim 1, wherein the ligand binding domain comprises the ER(T2) estrogen receptor ligand binding domain.

19. The fusion protein of claim 1, comprising a deletion of the Caspase recruitment domain (CARD).

20. The fusion protein of claim 1, further comprising a myristoylation signal sequence.

* * * * *

UNITED STATES PATENT AND TRADEMARK OFFICE

CERTIFICATE OF CORRECTION

PATENT NO. : 8,530,168 B2
APPLICATION NO. : 12/665680
DATED : September 10, 2013
INVENTOR(S) : Chu et al.

It is certified that error appears in the above-identified patent and that said Letters Patent is hereby corrected as shown below:

In the Claims

Column 252, Claim 15, Line 52, replace “An in virtro” with --An in vitro--.

Signed and Sealed this
Fifteenth Day of April, 2014

Michelle K. Lee
*Deputy Director of the United States Patent and Trademark Office*

SEQUENCE LISTING

```
<160> NUMBER OF SEQ ID NOS: 82

<210> SEQ ID NO 1
<211> LENGTH: 7014
<212> TYPE: DNA
<213> ORGANISM: Artificial sequence
<220> FEATURE:
<223> OTHER INFORMATION: vector pSS1

<400> SEQUENCE: 1

gggtaccggg ccccccctcg aggtcgacgg tatcgataag cttgatatcg aattcgagct      60

cggtacccgg gggcgcgccg gatctcgaca ttgattattg actagttatt aatagtaatc     120

aattacgggg tcattagttc atagcccata tatggagttc cgcgttacat aacttacggt     180

aaatggcccg cctggctgac cgcccaacga cccccgccca ttgacgtcaa taatgacgta     240

tgttcccata gtaacgccaa tagggacttt ccattgacgt caatgggtgg actatttacg     300

gtaaactgcc cacttggcag tacatcaagt gtatcatatg ccaagtacgc cccctattga     360

cgtcaatgac ggtaaatggc ccgcctggca ttatgcccag tacatgacct tatgggactt     420

tcctacttgg cagtacatct acgtattagt catcgctatt accatgggtc gaggtgagcc     480

ccacgttctg cttcactctc cccatctccc ccccctcccc acccccaatt ttgtatttat     540

ttatttttta attattttgt gcagcgatgg gggcgggggg gggggggggcg cgcgccaggc     600

ggggcggggc ggggcgaggg gcggggcggg gcgaggcgga gaggtgcggc ggcagccaat     660

cagagcggcg cgctccgaaa gtttcctttt atggcgaggc ggcggcggcg gcggccctat     720

aaaaagcgaa gcgcgcggcg ggcgggagtc gctgcgttgc cttcgccccg tgccccgctc     780

cgcgccgcct cgcgccgccc gccccggctc tgactgaccg cgttactccc acaggtgagc     840

gggcgggacg gcccttctcc tccgggctgt aattagcgct tggtttaatg acggctcgtt     900
```

-continued

```
tcttttctgt ggctgcgtga aagccttaaa gggctccggg agggcccttt gtgcgggggg    960
gagcggctcg gggggtgcgt gcgtgtgtgt gtgcgtgggg agcgccgcgt gcggcccgcg   1020
ctgcccggcg gctgtgagcg ctgcgggcgc ggcgcggggc tttgtgcgct ccgcgtgtgc   1080
gcgaggggag cgcggccggg ggcggtgccc cgcggtgcgg gggggctgcg aggggaacaa   1140
aggctgcgtg cggggtgtgt gcgtgggggg gtgagcaggg ggtgtgggcg cggcggtcgg   1200
gctgtaaccc ccccctgcac ccccctcccc gagttgctga gcacggcccg gcttcgggtg   1260
cggggctccg tgcggggcgt ggcgcggggc tcgccgtgcc gggcgggggg tggcggcagg   1320
tgggggtgcc gggcggggcg gggccgcctc gggccgggga gggctcgggg gaggggcgcg   1380
gcggccccgg agcgccggcg gctgtcgagg cgcggcgagc cgcagccatt gccttttatg   1440
gtaatcgtgc gagagggcgc agggacttcc tttgtcccaa atctggcgga gccgaaatct   1500
gggaggcgcc gccgcacccc ctctagcggg cgcgggcgaa gcggtgcggc gccggcagga   1560
aggaaatggg cggggagggc cttcgtgcgt cgccgcgccg ccgtcccctt ctccctctcc   1620
agcctcgggg ctgtccgcgg ggggacggct gccttcgggg gggacggggc agggcggggt   1680
tcggcttctg gcgtgtgacc ggcggctcta gagcctctgc taaccatgtt catgccttct   1740
tctttttcct acagatcctt aattaagtct agagtcgact gtttaattcc accatgtcca   1800
atttactgac cgtacaccaa aatttgcctg cattaccggt cgatgcaacg agtgatgagg   1860
ttcgcaagaa cctgatggac atgttcaggg atcgccaggc gttttctgag catacctgga   1920
aaatgcttct gtccgtttgc cggtcgtggg cggcatggtg caagttgaat aaccggaaat   1980
ggtttcccgc agaacctgaa gatgttcgcg attatcttct atatcttcag gcgcgcggtc   2040
tggcagtaaa aactatccag caacatttgg gccagctaaa catgcttcat cgtcggtccg   2100
ggctgccacg accaagtgac agcaatgctg tttcactggt tatgcggcgg atccgaaaag   2160
aaaacgttga tgccggtgaa cgtgcaaaac aggctctagc gttcgaacgc actgatttcg   2220
accaggttcg ttcactcatg gaaaatagcg atcgctgcca ggatatacgt aatctggcat   2280
ttctggggat tgcttataac accctgttac gtatagccga aattgccagg atcagggtta   2340
aagatatctc acgtactgac ggtgggagaa tgttaatcca tattggcaga acgaaaacgc   2400
tggttagcac cgcaggtgta gagaaggcac ttagcctggg ggtaactaaa ctggtcgagc   2460
gatggatttc cgtctctggt gtagctgatg atccgaataa ctacctgttt tgccgggtca   2520
gaaaaaatgg tgttgccgcg ccatctgcca ccagccagct atcaactcgc gccctggaag   2580
ggatttttga agcaactcat cgattgattt acggcgctaa ggatgactct ggtcagagat   2640
acctggcctg gtctggacac agtgcccgtg tcggagccgc gcgagatatg gcccgcgctg   2700
gagtttcaat accggagatc atgcaagctg gtggctggac caatgtaaat attgtcatga   2760
actatatccg taacctggat agtgaaacag gggcaatggt gcgcctgctg gaagatggcg   2820
atctcgagcc atctgctgga gacatgagag ctgccaacct ttggccaagc ccgctcatga   2880
tcaaacgctc taagaagaac agcctggcct tgtccctgac ggccgaccag atggtcagtg   2940
ccttgttgga tgctgagccc cccatactct attccgagta tgatcctacc agacccttca   3000
gtgaagcttc gatgatgggc ttactgacca acctggcaga cagggagctg gttcacatga   3060
tcaactgggc gaagagggtg ccaggctttg tggatttgac cctccatgat caggtccacc   3120
ttctagaatg tgcctggcta gagatcctga tgattggtct cgtctggcgc tccatggagc   3180
acccagtgaa gctactgttt gctcctaact tgctcttgga caggaaccag ggaaaatgtg   3240
tagagggcat ggtggagatc ttcgacatgc tgctggctac atcatctcgg ttccgcatga   3300
```

-continued tgaatctgca gggagaggag tttgtgtgcc tcaaatctat tattttgctt aattctggag 3360
tgtacacatt tctgtccagc accctgaagt ctctggaaga gaaggaccat atccaccgag 3420
tcctggacaa gatcacagac actttgatcc acctgatggc caaggcaggc ctgaccctgc 3480
agcagcagca ccagcggctg gcccagctcc tcctcatcct ctcccacatc aggcacatga 3540
gtaacaaagg catggagcat ctgtacagca tgaagtgcaa gaacgtggtg cccctctatg 3600
acctgctgct ggaggcggcg gacgcccacc gcctacatgc gcccactagc cgtggagggg 3660
catccgtgga ggagacggac caaagccact tggccactgc gggctctact tcatcgcatt 3720
ccttgcaaaa gtattacatc acgggggagg cagagggttt ccctgccaca gcttgatgaa 3780
gatctgagct ccctggcgga attgcgtaaa tgattgcaga tccactagtt ctagagctcg 3840
ctgatcagcc tcgactgtgc cttctagttg ccagccatct gttgtttgcc cctcccccgt 3900
gccttccttg accctggaag gtgccactcc cactgtcctt tcctaataaa atgaggaaat 3960
tgcatcgcat tgtctgagta ggtgtcattc tattctgggg ggtggggtgg ggcaggacag 4020
caagggggag gattgggaag acaatagcag gcatgctggg gatgcggtgg gctctatggc 4080
ttctgaggcg gaaagaacca gctggggctc gagatccact agttctagcc tcgaggctag 4140
agcggccgcc accgcggtgg agctccaatt cgccctatag tgagtcgtat tacaattcac 4200
tggccgtcgt tttacaacgt cgtgactggg aaaaccctgg cgttacccaa cttaatcgcc 4260
ttgcagcaca tccccctttc gccagctggc gtaatagcga agaggcccgc accgatcgcc 4320
cttcccaaca gttgcgcagc ctgaatggcg aatgggacgc gccctgtagc ggcgcattaa 4380
gcgcggcggg tgtggtggtt acgcgcagcg tgaccgctac acttgccagc gccctagcgc 4440
ccgctccttt cgctttcttc ccttcctttc tcgccacgtt cgccggcttt ccccgtcaag 4500
ctctaaatcg ggggctccct ttagggttcc gatttagtgc tttacggcac ctcgacccca 4560
aaaaacttga ttagggtgat ggttcacgta gtgggccatc gccctgatag acggtttttc 4620
gccctttgac gttggagtcc acgttcttta atagtggact cttgttccaa actggaacaa 4680
cactcaaccc tatctcggtc tattcttttg atttataagg gattttgccg atttcggcct 4740
attggttaaa aaatgagctg atttaacaaa aatttaacgc gaattttaac aaaatattaa 4800
cgcttacaat ttaggtggca cttttcgggg aaatgtgcgc ggaaccccta tttgtttatt 4860
tttctaaata cattcaaata tgtatccgct catgagacaa taaccctgat aaatgcttca 4920
ataatattga aaaaggaaga gtatgagtat tcaacatttc cgtgtcgccc ttattccctt 4980
ttttgcggca ttttgccttc ctgtttttgc tcacccagaa acgctggtga aagtaaaaga 5040
tgctgaagat cagttgggtg cacgagtggg ttacatcgaa ctggatctca acagcggtaa 5100
gatccttgag agttttcgcc ccgaagaacg ttttccaatg atgagcactt ttaaagttct 5160
gctatgtggc gcggtattat cccgtattga cgccgggcaa gagcaactcg gtcgccgcat 5220
acactattct cagaatgact tggttgagta ctcaccagtc acagaaaagc atcttacgga 5280
tggcatgaca gtaagagaat tatgcagtgc tgccataacc atgagtgata acactgcggc 5340
caacttactt ctgacaacga tcggaggacc gaaggagcta accgcttttt tgcacaacat 5400
gggggatcat gtaactcgcc ttgatcgttg ggaaccggag ctgaatgaag ccataccaaa 5460
cgacgagcgt gacaccacga tgcctgtagc aatggcaaca acgttgcgca aactattaac 5520
tggcgaacta cttactctag cttcccggca acaattaata gactggatgg aggcggataa 5580
agttgcagga ccacttctgc gctcggccct tccggctggc tggtttattg ctgataaatc 5640
tggagccggt gagcgtgggt ctcgcggtat cattgcagca ctggggccag atggtaagcc 5700

```
ctcccgtatc gtagttatct acacgacggg gagtcaggca actatggatg aacgaaatag   5760
acagatcgct gagataggtg cctcactgat taagcattgg taactgtcag accaagttta   5820
ctcatatata ctttagattg atttaaaact tcatttttaa tttaaaagga tctaggtgaa   5880
gatccttttt gataatctca tgaccaaaat cccttaacgt gagttttcgt tccactgagc   5940
gtcagacccc gtagaaaaga tcaaaggatc ttcttgagat cctttttttc tgcgcgtaat   6000
ctgctgcttg caaacaaaaa aaccaccgct accagcggtg gtttgtttgc cggatcaaga   6060
gctaccaact ctttttccga aggtaactgg cttcagcaga gcgcagatac caaatactgt   6120
ccttctagtg tagccgtagt taggccacca cttcaagaac tctgtagcac cgcctacata   6180
cctcgctctg ctaatcctgt taccagtggc tgctgccagt ggcgataagt cgtgtcttac   6240
cgggttggac tcaagacgat agttaccgga taaggcgcag cggtcgggct gaacgggggg   6300
ttcgtgcaca cagcccagct tggagcgaac gacctacacc gaactgagat acctacagcg   6360
tgagctatga gaaagcgcca cgcttcccga agggagaaag gcggacaggt atccggtaag   6420
cggcagggtc ggaacaggag agcgcacgag ggagcttcca gggggaaacg cctggtatct   6480
ttatagtcct gtcgggtttc gccacctctg acttgagcgt cgatttttgt gatgctcgtc   6540
aggggggcgg agcctatgga aaaacgccag caacgcggcc tttttacggt tcctggcctt   6600
ttgctggcct tttgctcaca tgttctttcc tgcgttatcc cctgattctg tggataaccg   6660
tattaccgcc tttgagtgag ctgataccgc tcgccgcagc cgaacgaccg agcgcagcga   6720
gtcagtgagc gaggaagcgg aagagcgccc aatacgcaaa ccgcctctcc ccgcgcgttg   6780
gccgattcat taatgcagct ggcacgacag gtttcccgac tggaaagcgg gcagtgagcg   6840
caacgcaatt aatgtgagtt agctcactca ttaggcaccc caggctttac actttatgct   6900
tccggctcgt atgttgtgtg gaattgtgag cggataacaa tttcacacag gaaacagcta   6960
tgaccatgat tacgccaagc gcgcaattaa ccctcactaa agggaacaaa agct         7014
```

```
<210> SEQ ID NO 2
<211> LENGTH: 6576
<212> TYPE: DNA
<213> ORGANISM: Artificial sequence
<220> FEATURE:
<223> OTHER INFORMATION: vector pCAG-C31Int(NLS)-bpA
<220> FEATURE:
<221> NAME/KEY: misc_feature
<222> LOCATION: (4261)..(4263)
<223> OTHER INFORMATION: n is a, c, g, or t

<400> SEQUENCE: 2

tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgaatt cgagctcggt acccgggggc    420
gcgccggatc tcgacattga ttattgacta gttattaata gtaatcaatt acggggtcat    480
tagttcatag cccatatatg gagttccgcg ttacataact tacggtaaat ggcccgcctg    540
gctgaccgcc caacgacccc cgcccattga cgtcaataat gacgtatgtt cccatagtaa    600
cgccaatagg gactttccat tgacgtcaat gggtggacta tttacggtaa actgcccact    660
```

-continued

```
tggcagtaca tcaagtgtat catatgccaa gtacgccccc tattgacgtc aatgacggta    720
aatggcccgc ctggcattat gcccagtaca tgaccttatg ggactttcct acttggcagt    780
acatctacgt attagtcatc gctattacca tgggtcgagg tgagccccac gttctgcttc    840
actctcccca tctccccccc ctccccaccc ccaattttgt atttatttat tttttaatta    900
ttttgtgcag cgatgggggc gggggggggg ggggcgcgcg ccaggcgggg cggggcgggg    960
cgaggggcgg ggcggggcga ggcggagagg tgcggcggca gccaatcaga gcggcgcgct   1020
ccgaaagttt ccttttatgg cgaggcggcg gcggcggcgg ccctataaaa agcgaagcgc   1080
gcggcgggcg ggagtcgctg cgttgccttc gccccgtgcc ccgctccgcg ccgcctcgcg   1140
ccgcccgccc cggctctgac tgaccgcgtt actcccacag gtgagcgggc gggacggccc   1200
ttctcctccg ggctgtaatt agcgcttggt ttaatgacgg ctcgtttctt ttctgtggct   1260
gcgtgaaagc cttaaagggc tccgggaggg ccctttgtgc ggggggggagc ggctcggggg   1320
gtgcgtgcgt gtgtgtgtgc gtggggagcg ccgcgtgcgg cccgcgctgc ccggcggctg   1380
tgagcgctgc gggcgcggcg cggggctttg tgcgctccgc gtgtgcgcga ggggagcgcg   1440
gccgggggcg gtgccccgcg gtgcgggggg gctgcgaggg gaacaaaggc tgcgtgcggg   1500
gtgtgtgcgt ggggggggtga gcagggggtg tgggcgcggc ggtcgggctg taaccccccc   1560
ctgcaccccc ctccccgagt tgctgagcac ggcccggctt cgggtgcggg gctccgtgcg   1620
gggcgtggcg cggggctcgc cgtgccgggc ggggggtggc ggcaggtggg ggtgccgggc   1680
ggggcggggc cgcctcgggc cggggagggc tcgggggagg ggcgcggcgg ccccggagcg   1740
ccggcggctg tcgaggcgcg gcgagccgca gccattgcct tttatggtaa tcgtgcgaga   1800
gggcgcaggg acttcctttg tcccaaatct ggcggagccg aaatctggga ggcgccgccg   1860
cacccccctct agcgggcgcg ggcgaagcgg tgcggcgccg gcaggaagga aatgggcggg   1920
gagggccttc gtgcgtcgcc gcgccgccgt ccccttctcc atctccagcc tcggggctgc   1980
cgcagggggga cggctgcctt cggggggggac ggggcagggc ggggttcggc ttctggcgtg   2040
tgaccggcgg ctctagagcc tctgctaacc atgttcatgc cttcttcttt ttcctacaga   2100
tccttaatta agtctagacc gatatgacac aaggggttgt gaccggggtg gacacgtacg   2160
cgggtgctta cgaccgtcag tcgcgcgagc gcgagaattc gagcgcagca agcccagcga   2220
cacagcgtag cgccaacgaa gacaaggcgg ccgaccttca gcgcgaagtc gagcgcgacg   2280
ggggccggtt caggttcgtc gggcatttca gcgaagcgcc gggcacgtcg gcgttcggga   2340
cggcggagcg cccggagttc gaacgcatcc tgaacgaatg ccgcgccggg cggctcaaca   2400
tgatcattgt ctatgacgtg tcgcgcttct cgcgcctgaa ggtcatggac gcgattccga   2460
ttgtctcgga attgctcgcc ctgggcgtga cgattgtttc cactcaggaa ggcgtcttcc   2520
ggcagggaaa cgtcatggac ctgattcacc tgattatgcg gctcgacgcg tcgcacaaag   2580
aatcttcgct gaagtcggcg aagattctcg acacgaagaa ccttcagcgc gaattgggcg   2640
ggtacgtcgg cgggaaggcg ccttacggct tcgagcttgt ttcggagacg aaggagatca   2700
cgcgcaacgg ccgaatggtc aatgtcgtca tcaacaagct tgcgcactcg accactcccc   2760
ttaccggacc cttcgagttc gagcccgacg taatccggtg gtggtggcgt gagatcaaga   2820
cgcacaaaca ccttcccttc aagccgggca gtcaagccgc cattcacccg ggcagcatca   2880
cggggctttg taagcgcatg gacgctgacg ccgtgccgac ccggggcgag acgattggga   2940
agaagaccgc ttcaagcgcc tgggacccgg caaccgttat gcgaatcctt cgggacccgc   3000
gtattgcggg cttcgccgct gaggtgatct acaagaagaa gccggacggc acgccgacca   3060
```

-continued

```
cgaagattga gggttaccgc attcagcgcg acccgatcac gctccggccg gtcgagcttg   3120
attgcggacc gatcatcgag cccgctgagt ggtatgagct tcaggcgtgg ttggacggca   3180
gggggcgcgg caaggggctt tcccgggggc aagccattct gtccgccatg gacaagctgt   3240
actgcgagtg tggcgccgtc atgacttcga agcgcgggga agaatcgatc aaggactctt   3300
accgctgccg tcgccggaag gtggtcgacc cgtccgcacc tgggcagcac gaaggcacgt   3360
gcaacgtcag catggcggca ctcgacaagt tcgttgcgga acgcatcttc aacaagatca   3420
ggcacgccga aggcgacgaa gagacgttgg cgcttctgtg ggaagccgcc cgacgcttcg   3480
gcaagctcac tgaggcgcct gagaagagcg gcgaacgggc gaaccttgtt gcggagcgcg   3540
ccgacgccct gaacgccctt gaagagctgt acgaagaccg cgcggcaggc gcgtacgacg   3600
gacccgttgg caggaagcac ttccggaagc aacaggcagc gctgacgctc cggcagcaag   3660
gggcggaaga gcggcttgcc gaacttgaag ccgccgaagc cccgaagctt ccccttgacc   3720
aatggttccc cgaagacgcc gacgctgacc cgaccggccc taagtcgtgg tgggggcgcg   3780
cgtcagtaga cgacaagcgc gtgttcgtcg ggctcttcgt agacaagatc gttgtcacga   3840
agtcgactac gggcaggggg cagggaacgc ccatcgagaa gcgcgcttcg atcacgtggg   3900
cgaagccgcc gaccgacgac gacgaagacg acgcccagga cggcacggaa gacgtagcgg   3960
cgcctaagaa gaagaggaag gtttagtcta gagtcgactg tttctagagc tcgctgatca   4020
gcctcgactg tgccttctag ttgccagcca tctgttgttt gcccctcccc cgtgccttcc   4080
ttgaccctgg aaggtgccac tcccactgtc ctttcctaat aaaatgagga aattgcatcg   4140
cattgtctga gtaggtgtca ttctattctg gggggtgggg tggggcagga cagcaagggg   4200
gaggattggg aagacaatag caggcatgct ggggatgcgg tgggctctat ggcttctgag   4260
nnngaaagaa ccagctgggg ctcgagatcc actagttcta gcctcgaggc tagagcggcc   4320
aaacctgcag gcatgcaagc ttggcgtaat catggtcata gctgtttcct gtgtgaaatt   4380
gttatccgct cacaattcca cacaacatac gagccggaag cataaagtgt aaagcctggg   4440
gtgcctaatg agtgagctaa ctcacattaa ttgcgttgcg ctcactgccc gctttccagt   4500
cgggaaacct gtcgtgccag ctgcattaat gaatcggcca acgcgcgggg agaggcggtt   4560
tgcgtattgg gcgctcttcc gcttcctcgc tcactgactc gctgcgctcg gtcgttcggc   4620
tgcggcgagc ggtatcagct cactcaaagg cggtaatacg gttatccaca gaatcagggg   4680
ataacgcagg aaagaacatg tgagcaaaag gccagcaaaa ggccaggaac cgtaaaaagg   4740
ccgcgttgct ggcgtttttc cataggctcc gcccccctga cgagcatcac aaaaatcgac   4800
gctcaagtca gaggtggcga aacccgacag gactataaag ataccaggcg tttccccctg   4860
gaagctccct cgtgcgctct cctgttccga ccctgccgct taccggatac ctgtccgcct   4920
ttctcccttc gggaagcgtg gcgctttctc atagctcacg ctgtaggtat ctcagttcgg   4980
tgtaggtcgt tcgctccaag ctgggctgtg tgcacgaacc ccccgttcag cccgaccgct   5040
gcgccttatc cggtaactat cgtcttgagt ccaacccggt aagacacgac ttatcgccac   5100
tggcagcagc cactggtaac aggattagca gagcgaggta tgtaggcggt gctacagagt   5160
tcttgaagtg gtggcctaac tacggctaca ctagaaggac agtatttggt atctgcgctc   5220
tgctgaagcc agttaccttc ggaaaaagag ttggtagctc ttgatccggc aaacaaacca   5280
ccgctggtag cggtggtttt tttgtttgca agcagcagat tacgcgcaga aaaaaaggat   5340
ctcaagaaga tcctttgatc ttttctacgg ggtctgacgc tcagtggaac gaaaactcac   5400
gttaagggat tttggtcatg agattatcaa aaggatctt cacctagatc cttttaaatt   5460
```

aaaaatgaag ttttaaatca atctaaagta tatatgagta aacttggtct gacagttacc 5520
aatgcttaat cagtgaggca cctatctcag cgatctgtct atttcgttca tccatagttg 5580
cctgactccc cgtcgtgtag ataactacga tacgggaggg cttaccatct ggccccagtg 5640
ctgcaatgat accgcgagac ccacgctcac cggctccaga tttatcagca ataaaccagc 5700
cagccggaag ggccgagcgc agaagtggtc ctgcaacttt atccgcctcc atccagtcta 5760
ttaattgttg ccgggaagct agagtaagta gttcgccagt taatagtttg cgcaacgttg 5820
ttgccattgc tacaggcatc gtggtgtcac gctcgtcgtt tggtatggct tcattcagct 5880
ccggttccca acgatcaagg cgagttacat gatcccccat gttgtgcaaa aaagcggtta 5940
gctccttcgg tcctccgatc gttgtcagaa gtaagttggc cgcagtgtta tcactcatgg 6000
ttatggcagc actgcataat tctcttactg tcatgccatc cgtaagatgc ttttctgtga 6060
ctggtgagta ctcaaccaag tcattctgag aatagtgtat gcggcgaccg agttgctctt 6120
gcccggcgtc aatacgggat aataccgcgc cacatagcag aactttaaaa gtgctcatca 6180
ttggaaaacg ttcttcgggg cgaaaactct caaggatctt accgctgttg agatccagtt 6240
cgatgtaacc cactcgtgca cccaactgat cttcagcatc ttttactttc accagcgttt 6300
ctgggtgagc aaaaacagga aggcaaaatg ccgcaaaaaa gggaataagg gcgacacgga 6360
aatgttgaat actcatactc ttcctttttc aatattattg aagcatttat cagggttatt 6420
gtctcatgag cggatacata tttgaatgta tttagaaaaa taaacaaata ggggttccgc 6480
gcacatttcc ccgaaaagtg ccacctgacg tctaagaaac cattattatc atgacattaa 6540
cctataaaaa taggcgtatc acgaggccct ttcgtc 6576

<210> SEQ ID NO 3
<211> LENGTH: 6686
<212> TYPE: DNA
<213> ORGANISM: Artificial sequence
<220> FEATURE:
<223> OTHER INFORMATION: vector pCAG-Cre-ER(T2)-bpA

<400> SEQUENCE: 3
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcaggcgcc 240
attcgccatt caggctgcgc aactgttggg aagggcgatc ggtgcgggcc tcttcgctat 300
tacgccagct ggcgaaaggg ggatgtgctg caaggcgatt aagttgggta acgccagggt 360
tttcccagtc acgacgttgt aaaacgacgg ccagtgaatt cgagctcggt acccgggggc 420
gcgccggatc tcgacattga ttattgacta gttattaata gtaatcaatt acggggtcat 480
tagttcatag cccatatatg gagttccgcg ttacataact tacggtaaat ggcccgcctg 540
gctgaccgcc caacgacccc cgcccattga cgtcaataat gacgtatgtt cccatagtaa 600
cgccaatagg gactttccat tgacgtcaat gggtggacta tttacggtaa actgcccact 660
tggcagtaca tcaagtgtat catatgccaa gtacgccccc tattgacgtc aatgacggta 720
aatggcccgc ctggcattat gcccagtaca tgaccttatg ggactttcct acttggcagt 780
acatctacgt attagtcatc gctattacca tgggtcgagg tgagccccac gttctgcttc 840
actctcccca tctccccccc ctccccaccc ccaattttgt atttatttat tttttaatta 900
ttttgtgcag cgatgggggc gggggggggg ggggcgcgcg ccaggcgggg cggggcgggg 960

-continued

```
cgaggggcgg ggcggggcga ggcggagagg tgcggcggca gccaatcaga gcggcgcgct   1020
ccgaaagttt ccttttatgg cgaggcggcg gcggcggcgg ccctataaaa agcgaagcgc   1080
gcggcgggcg ggagtcgctg cgttgccttc gccccgtgcc ccgctccgcg ccgcctcgcg   1140
ccgcccgccc cggctctgac tgaccgcgtt actcccacag gtgagcgggc gggacggccc   1200
ttctcctccg ggctgtaatt agcgcttggt ttaatgacgg ctcgtttctt ttctgtggct   1260
gcgtgaaagc cttaaagggc tccgggaggg ccctttgtgc ggggggggagc ggctcggggg   1320
gtgcgtgcgt gtgtgtgtgc gtggggagcg ccgcgtgcgg cccgcgctgc ccggcggctg   1380
tgagcgctgc gggcgcggcg cggggctttg tgcgctccgc gtgtgcgcga ggggagcgcg   1440
gccgggggcg gtgccccgcg gtgcgggggg gctgcgaggg gaacaaaggc tgcgtgcggg   1500
gtgtgtgcgt gggggggtga gcagggggtg tgggcgcggc ggtcgggctg taaccccccc   1560
ctgcaccccc ctccccgagt tgctgagcac ggcccggctt cgggtgcggg gctccgtgcg   1620
gggcgtggcg cggggctcgc cgtgccgggc ggggggtggc ggcaggtggg ggtgccgggc   1680
ggggcggggc cgcctcgggc cggggagggc tcgggggagg ggcgcggcgg ccccggagcg   1740
ccggcggctg tcgaggcgcg gcgagccgca gccattgcct tttatggtaa tcgtgcgaga   1800
gggcgcaggg acttcctttg tcccaaatct ggcggagccg aaatctggga ggcgccgccg   1860
caccccctct agcgggcgcg ggcgaagcgg tgcggcgccg gcaggaagga aatgggcggg   1920
gagggccttc gtgcgtcgcc gcgccgccgt ccccttctcc atctccagcc tcggggctgc   1980
cgcaggggga cggctgcctt cgggggggac ggggcagggc ggggttcggc ttctggcgtg   2040
tgaccggcgg ctctagagcc tctgctaacc atgttcatgc cttcttcttt ttcctacaga   2100
tccttaatta agtctagagt cgactgttta attccaccat gtccaattta ctgaccgtac   2160
accaaaattt gcctgcatta ccggtcgatg caacgagtga tgaggttcgc aagaacctga   2220
tggacatgtt cagggatcgc caggcgtttt ctgagcatac ctggaaaatg cttctgtccg   2280
tttgccggtc gtgggcggca tggtgcaagt tgaataaccg gaaatggttt cccgcagaac   2340
ctgaagatgt tcgcgattat cttctatatc ttcaggcgcg cggtctggca gtaaaaacta   2400
tccagcaaca tttgggccag ctaaacatgc ttcatcgtcg gtccgggctg ccacgaccaa   2460
gtgacagcaa tgctgtttca ctggttatgc ggcggatccg aaaagaaaac gttgatgccg   2520
gtgaacgtgc aaaacaggct ctagcgttcg aacgcactga tttcgaccag gttcgttcac   2580
tcatggaaaa tagcgatcgc tgccaggata tacgtaatct ggcatttctg gggattgctt   2640
ataacaccct gttacgtata gccgaaattg ccaggatcag ggttaaagat atctcacgta   2700
ctgacggtgg gagaatgtta atccatattg gcagaacgaa aacgctggtt agcaccgcag   2760
gtgtagagaa ggcacttagc ctgggggtaa ctaaactggt cgagcgatgg atttccgtct   2820
ctggtgtagc tgatgatccg aataactacc tgttttgccg ggtcagaaaa aatggtgttg   2880
ccgcgccatc tgccaccagc cagctatcaa ctcgcgccct ggaagggatt tttgaagcaa   2940
ctcatcgatt gatttacggc gctaaggatg actctggtca gagatacctg gcctggtctg   3000
gacacagtgc ccgtgtcgga gccgcgcgag atatggcccg cgctggagtt tcaataccgg   3060
agatcatgca agctggtggc tggaccaatg taaatattgt catgaactat atccgtaacc   3120
tggatagtga aacaggggca atggtgcgcc tgctggaaga tggcgatctc gagccatctg   3180
ctggagacat gagagctgcc aacctttggc caagcccgct catgatcaaa cgctctaaga   3240
agaacagcct ggccttgtcc ctgacggccg accagatggt cagtgccttg ttggatgctg   3300
agccccccat actctattcc gagtatgatc ctaccagacc cttcagtgaa gcttcgatga   3360
```

-continued

```
tgggcttact gaccaacctg gcagacaggg agctggttca catgatcaac tgggcgaaga   3420
gggtgccagg ctttgtggat ttgaccctcc atgatcaggt ccaccttcta gaatgtgcct   3480
ggctagagat cctgatgatt ggtctcgtct ggcgctccat ggagcaccca gtgaagctac   3540
tgtttgctcc taacttgctc ttggacagga accagggaaa atgtgtagag ggcatggtgg   3600
agatcttcga catgctgctg gctacatcat ctcggttccg catgatgaat ctgcagggag   3660
aggagtttgt gtgcctcaaa tctattattt tgcttaattc tggagtgtac acatttctgt   3720
ccagcaccct gaagtctctg gaagagaagg accatatcca ccgagtcctg gacaagatca   3780
cagacacttt gatccacctg atggccaagg caggcctgac cctgcagcag cagcaccagc   3840
ggctggccca gctcctcctc atcctctccc acatcaggca catgagtaac aaaggcatgg   3900
agcatctgta cagcatgaag tgcaagaacg tggtgcccct ctatgacctg ctgctggagg   3960
cggcggacgc ccaccgccta catgcgccca ctagccgtgg aggggcatcc gtggaggaga   4020
cggaccaaag ccacttggcc actgcgggct ctacttcatc gcattccttg caaaagtatt   4080
acatcacggg ggaggcagag ggtttccctg ccacagcttg atgaagatct gagctccctg   4140
gcggaattgc gtaaatgatt gcagatccac tagttctaga gctcgctgat cagcctcgac   4200
tgtgccttct agttgccagc catctgttgt ttgcccctcc cccgtgcctt ccttgaccct   4260
ggaaggtgcc actcccactg tcctttccta ataaaatgag gaaattgcat cgcattgtct   4320
gagtaggtgt cattctattc tggggggtgg ggtggggcag gacagcaagg gggaggattg   4380
ggaagacaat agcaggcatg ctggggatgc ggtgggctct atggcttctg aggcggaaag   4440
aaccagaagc ttggcgtaat catggtcata gctgtttcct gtgtgaaatt gttatccgct   4500
cacaattcca cacaacatac gagccggaag cataaagtgt aaagcctggg gtgcctaatg   4560
agtgagctaa ctcacattaa ttgcgttgcg ctcactgccc gctttccagt cgggaaacct   4620
gtcgtgccag ctgcattaat gaatcggcca acgcgcgggg agaggcggtt tgcgtattgg   4680
gcgctcttcc gcttcctcgc tcactgactc gctgcgctcg gtcgttcggc tgcggcgagc   4740
ggtatcagct cactcaaagg cggtaatacg gttatccaca gaatcagggg ataacgcagg   4800
aaagaacatg tgagcaaaag gccagcaaaa ggccaggaac cgtaaaaagg ccgcgttgct   4860
ggcgtttttc cataggctcc gcccccctga cgagcatcac aaaaatcgac gctcaagtca   4920
gaggtggcga aacccgacag gactataaag ataccaggcg tttccccctg gaagctccct   4980
cgtgcgctct cctgttccga ccctgccgct taccggatac ctgtccgcct ttctcccttc   5040
gggaagcgtg gcgctttctc atagctcacg ctgtaggtat ctcagttcgg tgtaggtcgt   5100
tcgctccaag ctgggctgtg tgcacgaacc ccccgttcag cccgaccgct gcgccttatc   5160
cggtaactat cgtcttgagt ccaacccggt aagacacgac ttatcgccac tggcagcagc   5220
cactggtaac aggattagca gagcgaggta tgtaggcggt gctacagagt tcttgaagtg   5280
gtggcctaac tacggctaca ctagaaggac agtatttggt atctgcgctc tgctgaagcc   5340
agttaccttc ggaaaaagag ttggtagctc ttgatccggc aaacaaacca ccgctggtag   5400
cggtggtttt tttgtttgca agcagcagat tacgcgcaga aaaaaaggat ctcaagaaga   5460
tcctttgatc ttttctacgg ggtctgacgc tcagtggaac gaaaactcac gttaagggat   5520
tttggtcatg agattatcaa aaaggatctt cacctagatc cttttaaatt aaaaatgaag   5580
ttttaaatca atctaaagta tatatgagta aacttggtct gacagttacc aatgcttaat   5640
cagtgaggca cctatctcag cgatctgtct atttcgttca tccatagttg cctgactccc   5700
cgtcgtgtag ataactacga tacgggaggg cttaccatct ggccccagtg ctgcaatgat   5760
```

-continued

```
accgcgagac ccacgctcac cggctccaga tttatcagca ataaaccagc cagccggaag   5820

ggccgagcgc agaagtggtc ctgcaacttt atccgcctcc atccagtcta ttaattgttg   5880

ccgggaagct agagtaagta gttcgccagt taatagtttg cgcaacgttg ttgccattgc   5940

tacaggcatc gtggtgtcac gctcgtcgtt tggtatggct tcattcagct ccggttccca   6000

acgatcaagg cgagttacat gatcccccat gttgtgcaaa aaagcggtta gctccttcgg   6060

tcctccgatc gttgtcagaa gtaagttggc cgcagtgtta tcactcatgg ttatggcagc   6120

actgcataat tctcttactg tcatgccatc cgtaagatgc ttttctgtga ctggtgagta   6180

ctcaaccaag tcattctgag aatagtgtat gcggcgaccg agttgctctt gcccggcgtc   6240

aatacgggat aataccgcgc cacatagcag aactttaaaa gtgctcatca ttggaaaacg   6300

ttcttcgggg cgaaaactct caaggatctt accgctgttg agatccagtt cgatgtaacc   6360

cactcgtgca cccaactgat cttcagcatc ttttactttc accagcgttt ctgggtgagc   6420

aaaaacagga aggcaaaatg ccgcaaaaaa gggaataagg gcgacacgga aatgttgaat   6480

actcatactc ttcctttttc aatattattg aagcatttat cagggttatt gtctcatgag   6540

cggatacata tttgaatgta tttagaaaaa taaacaaata ggggttccgc gcacatttcc   6600

ccgaaaagtg ccacctgacg tctaagaaac cattattatc atgacattaa cctataaaaa   6660

taggcgtatc acgaggccct ttcgtc                                        6686
```

```
<210> SEQ ID NO 4
<211> LENGTH: 1983
<212> TYPE: DNA
<213> ORGANISM: Artificial sequence
<220> FEATURE:
<223> OTHER INFORMATION: DNA sequence coding for fusion protein
      Cre-ER(T2)

<400> SEQUENCE: 4
```

```
atgtccaatt tactgaccgt acaccaaaat ttgcctgcat taccggtcga tgcaacgagt     60

gatgaggttc gcaagaacct gatggacatg ttcagggatc gccaggcgtt ttctgagcat    120

acctggaaaa tgcttctgtc cgtttgccgg tcgtgggcgg catggtgcaa gttgaataac    180

cggaaatggt ttcccgcaga acctgaagat gttcgcgatt atcttctata tcttcaggcg    240

cgcggtctgg cagtaaaaac tatccagcaa catttgggcc agctaaacat gcttcatcgt    300

cggtccgggc tgccacgacc aagtgacagc aatgctgttt cactggttat gcggcggatc    360

cgaaaagaaa acgttgatgc cggtgaacgt gcaaaacagg ctctagcgtt cgaacgcact    420

gatttcgacc aggttcgttc actcatggaa aatagcgatc gctgccagga tatacgtaat    480

ctggcatttc tggggattgc ttataacacc ctgttacgta tagccgaaat tgccaggatc    540

agggttaaag atatctcacg tactgacggt gggagaatgt taatccatat tggcagaacg    600

aaaacgctgg ttagcaccgc aggtgtagag aaggcactta gcctgggggt aactaaactg    660

gtcgagcgat ggatttccgt ctctggtgta gctgatgatc cgaataacta cctgttttgc    720

cgggtcagaa aaaatggtgt tgccgcgcca tctgccacca gccagctatc aactcgcgcc    780

ctggaaggga tttttgaagc aactcatcga ttgatttacg gcgctaagga tgactctggt    840

cagagatacc tggcctggtc tggacacagt gcccgtgtcg gagccgcgcg agatatggcc    900

cgcgctggag tttcaatacc ggagatcatg caagctggtg gctggaccaa tgtaaatatt    960

gtcatgaact atatccgtaa cctggatagt gaaacagggg caatggtgcg cctgctggaa   1020

gatggcgatc tcgagccatc tgctggagac atgagagctg ccaacctttg gccaagcccg   1080
```

-continued

```
ctcatgatca aacgctctaa gaagaacagc ctggccttgt ccctgacggc cgaccagatg   1140

gtcagtgcct tgttggatgc tgagcccccc atactctatt ccgagtatga tcctaccaga   1200

cccttcagtg aagcttcgat gatgggctta ctgaccaacc tggcagacag ggagctggtt   1260

cacatgatca actgggcgaa gagggtgcca ggctttgtgg atttgaccct ccatgatcag   1320

gtccaccttc tagaatgtgc ctggctagag atcctgatga ttggtctcgt ctggcgctcc   1380

atggagcacc cagtgaagct actgtttgct cctaacttgc tcttggacag gaaccaggga   1440

aaatgtgtag agggcatggt ggagatcttc gacatgctgc tggctacatc atctcggttc   1500

cgcatgatga atctgcaggg agaggagttt gtgtgcctca aatctattat tttgcttaat   1560

tctggagtgt acacatttct gtccagcacc ctgaagtctc tggaagagaa ggaccatatc   1620

caccgagtcc tggacaagat cacagacact ttgatccacc tgatggccaa ggcaggcctg   1680

accctgcagc agcagcacca gcggctggcc cagctcctcc tcatcctctc ccacatcagg   1740

cacatgagta acaaaggcat ggagcatctg tacagcatga agtgcaagaa cgtggtgccc   1800

ctctatgacc tgctgctgga ggcggcggac gcccaccgcc tacatgcgcc cactagccgt   1860

ggaggggcat ccgtggagga gacggaccaa agccacttgg ccactgcggg ctctacttca   1920

tcgcattcct tgcaaaagta ttacatcacg gggggaggcag agggtttccc tgccacagct   1980

tga                                                                 1983
```

<210> SEQ ID NO 5
<211> LENGTH: 660
<212> TYPE: PRT
<213> ORGANISM: Artificial sequence
<220> FEATURE:
<223> OTHER INFORMATION: fusion protein Cre-ER(T2)

<400> SEQUENCE: 5

```
Met Ser Asn Leu Leu Thr Val His Gln Asn Leu Pro Ala Leu Pro Val
1               5                   10                  15

Asp Ala Thr Ser Asp Glu Val Arg Lys Asn Leu Met Asp Met Phe Arg
            20                  25                  30

Asp Arg Gln Ala Phe Ser Glu His Thr Trp Lys Met Leu Leu Ser Val
        35                  40                  45

Cys Arg Ser Trp Ala Ala Trp Cys Lys Leu Asn Asn Arg Lys Trp Phe
    50                  55                  60

Pro Ala Glu Pro Glu Asp Val Arg Asp Tyr Leu Leu Tyr Leu Gln Ala
65                  70                  75                  80

Arg Gly Leu Ala Val Lys Thr Ile Gln Gln His Leu Gly Gln Leu Asn
                85                  90                  95

Met Leu His Arg Arg Ser Gly Leu Pro Arg Pro Ser Asp Ser Asn Ala
            100                 105                 110

Val Ser Leu Val Met Arg Arg Ile Arg Lys Glu Asn Val Asp Ala Gly
        115                 120                 125

Glu Arg Ala Lys Gln Ala Leu Ala Phe Glu Arg Thr Asp Phe Asp Gln
    130                 135                 140

Val Arg Ser Leu Met Glu Asn Ser Asp Arg Cys Gln Asp Ile Arg Asn
145                 150                 155                 160

Leu Ala Phe Leu Gly Ile Ala Tyr Asn Thr Leu Leu Arg Ile Ala Glu
                165                 170                 175

Ile Ala Arg Ile Arg Val Lys Asp Ile Ser Arg Thr Asp Gly Gly Arg
            180                 185                 190

Met Leu Ile His Ile Gly Arg Thr Lys Thr Leu Val Ser Thr Ala Gly
        195                 200                 205
```

-continued

```
Val Glu Lys Ala Leu Ser Leu Gly Val Thr Lys Leu Val Glu Arg Trp
    210                 215                 220

Ile Ser Val Ser Gly Val Ala Asp Asp Pro Asn Asn Tyr Leu Phe Cys
225                 230                 235                 240

Arg Val Arg Lys Asn Gly Val Ala Ala Pro Ser Ala Thr Ser Gln Leu
                245                 250                 255

Ser Thr Arg Ala Leu Glu Gly Ile Phe Glu Ala Thr His Arg Leu Ile
            260                 265                 270

Tyr Gly Ala Lys Asp Asp Ser Gly Gln Arg Tyr Leu Ala Trp Ser Gly
        275                 280                 285

His Ser Ala Arg Val Gly Ala Ala Arg Asp Met Ala Arg Ala Gly Val
    290                 295                 300

Ser Ile Pro Glu Ile Met Gln Ala Gly Gly Trp Thr Asn Val Asn Ile
305                 310                 315                 320

Val Met Asn Tyr Ile Arg Asn Leu Asp Ser Glu Thr Gly Ala Met Val
                325                 330                 335

Arg Leu Leu Glu Asp Gly Asp Leu Glu Pro Ser Ala Gly Asp Met Arg
            340                 345                 350

Ala Ala Asn Leu Trp Pro Ser Pro Leu Met Ile Lys Arg Ser Lys Lys
        355                 360                 365

Asn Ser Leu Ala Leu Ser Leu Thr Ala Asp Gln Met Val Ser Ala Leu
    370                 375                 380

Leu Asp Ala Glu Pro Pro Ile Leu Tyr Ser Glu Tyr Asp Pro Thr Arg
385                 390                 395                 400

Pro Phe Ser Glu Ala Ser Met Met Gly Leu Leu Thr Asn Leu Ala Asp
                405                 410                 415

Arg Glu Leu Val His Met Ile Asn Trp Ala Lys Arg Val Pro Gly Phe
            420                 425                 430

Val Asp Leu Thr Leu His Asp Gln Val His Leu Leu Glu Cys Ala Trp
        435                 440                 445

Leu Glu Ile Leu Met Ile Gly Leu Val Trp Arg Ser Met Glu His Pro
    450                 455                 460

Val Lys Leu Leu Phe Ala Pro Asn Leu Leu Leu Asp Arg Asn Gln Gly
465                 470                 475                 480

Lys Cys Val Glu Gly Met Val Glu Ile Phe Asp Met Leu Leu Ala Thr
                485                 490                 495

Ser Ser Arg Phe Arg Met Met Asn Leu Gln Gly Glu Glu Phe Val Cys
            500                 505                 510

Leu Lys Ser Ile Ile Leu Leu Asn Ser Gly Val Tyr Thr Phe Leu Ser
        515                 520                 525

Ser Thr Leu Lys Ser Leu Glu Glu Lys Asp His Ile His Arg Val Leu
    530                 535                 540

Asp Lys Ile Thr Asp Thr Leu Ile His Leu Met Ala Lys Ala Gly Leu
545                 550                 555                 560

Thr Leu Gln Gln Gln His Gln Arg Leu Ala Gln Leu Leu Leu Ile Leu
                565                 570                 575

Ser His Ile Arg His Met Ser Asn Lys Gly Met Glu His Leu Tyr Ser
            580                 585                 590

Met Lys Cys Lys Asn Val Val Pro Leu Tyr Asp Leu Leu Leu Glu Ala
        595                 600                 605

Ala Asp Ala His Arg Leu His Ala Pro Thr Ser Arg Gly Gly Ala Ser
    610                 615                 620

Val Glu Glu Thr Asp Gln Ser His Leu Ala Thr Ala Gly Ser Thr Ser
```

-continued 625 630 635 640

Ser His Ser Leu Gln Lys Tyr Tyr Ile Thr Gly Glu Ala Glu Gly Phe
645 650 655

Pro Ala Thr Ala
660

<210> SEQ ID NO 6
<211> LENGTH: 74
<212> TYPE: DNA
<213> ORGANISM: Artificial sequence
<220> FEATURE:
<223> OTHER INFORMATION: primer fas1ER-A

<400> SEQUENCE: 6
atccttaatt aaattccacc atgggctacc cctacgacgt gcccgactac gccaccagca 60
atacaaactg cagg 74

<210> SEQ ID NO 7
<211> LENGTH: 29
<212> TYPE: DNA
<213> ORGANISM: Artificial sequence
<220> FEATURE:
<223> OTHER INFORMATION: primer fasER-B

<400> SEQUENCE: 7
gggtcgacca gacattgtcc ttcattttc 29

<210> SEQ ID NO 8
<211> LENGTH: 102
<212> TYPE: DNA
<213> ORGANISM: Artificial sequence
<220> FEATURE:
<223> OTHER INFORMATION: primer fas2ER-A

<400> SEQUENCE: 8
ccttaattaa attccaccat gctgtggatc tgggctgtcc tgcctctggt gcttgctggc 60
tcacagttaa gagttcatac taccagcaat acaaactgca gg 102

<210> SEQ ID NO 9
<211> LENGTH: 6184
<212> TYPE: DNA
<213> ORGANISM: Artificial sequence
<220> FEATURE:
<223> OTHER INFORMATION: vector pCAG-HAFas-ER(T2)-bpA

<400> SEQUENCE: 9
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcaggcgcc 240
attcgccatt caggctgcgc aactgttggg aagggcgatc ggtgcgggcc tcttcgctat 300
tacgccagct ggcgaaaggg ggatgtgctg caaggcgatt aagttgggta acgccagggt 360
tttcccagtc acgacgttgt aaaacgacgg ccagtgaatt cgagctcggt acccgggggc 420
gcgccggatc tcgacattga ttattgacta gttattaata gtaatcaatt acggggtcat 480
tagttcatag cccatatatg gagttccgcg ttacataact tacggtaaat ggcccgcctg 540
gctgaccgcc caacgacccc cgcccattga cgtcaataat gacgtatgtt cccatagtaa 600
cgccaatagg gactttccat tgacgtcaat gggtggacta tttacggtaa actgcccact 660

-continued

```
tggcagtaca tcaagtgtat catatgccaa gtacgccccc tattgacgtc aatgacggta    720
aatggcccgc ctggcattat gcccagtaca tgaccttatg ggactttcct acttggcagt    780
acatctacgt attagtcatc gctattacca tgggtcgagg tgagccccac gttctgcttc    840
actctcccca tctccccccc ctccccaccc ccaattttgt atttatttat tttttaatta    900
ttttgtgcag cgatgggggc gggggggggg ggggcgcgcg ccaggcgggg cggggcgggg    960
cgaggggcgg ggcggggcga ggcggagagg tgcggcggca gccaatcaga gcggcgcgct   1020
ccgaaagttt ccttttatgg cgaggcggcg gcggcggcgg ccctataaaa agcgaagcgc   1080
gcggcgggcg ggagtcgctg cgttgccttc gccccgtgcc ccgctccgcg ccgcctcgcg   1140
ccgcccgccc cggctctgac tgaccgcgtt actcccacag gtgagcgggc gggacggccc   1200
ttctcctccg ggctgtaatt agcgcttggt ttaatgacgg ctcgtttctt ttctgtggct   1260
gcgtgaaagc cttaaagggc tccgggaggg ccctttgtgc ggggggggagc ggctcggggg   1320
gtgcgtgcgt gtgtgtgtgc gtggggagcg ccgcgtgcgg cccgcgctgc ccggcggctg   1380
tgagcgctgc gggcgcggcg cggggctttg tgcgctccgc gtgtgcgcga ggggagcgcg   1440
gccgggggcg gtgccccgcg gtgcgggggg gctgcgaggg gaacaaaggc tgcgtgcggg   1500
gtgtgtgcgt gggggggtga gcagggggtg tgggcgcggc ggtcgggctg taaccccccc   1560
ctgcaccccc ctccccgagt tgctgagcac ggcccggctt cgggtgcggg gctccgtgcg   1620
gggcgtggcg cggggctcgc cgtgccgggc ggggggtggc ggcaggtggg ggtgccgggc   1680
ggggcggggc cgcctcgggc cggggagggc tcgggggagg ggcgcggcgg ccccggagcg   1740
ccggcggctg tcgaggcgcg gcgagccgca gccattgcct tttatggtaa tcgtgcgaga   1800
gggcgcaggg acttcctttg tcccaaatct ggcggagccg aaatctggga ggcgccgccg   1860
caccccctct agcgggcgcg ggcgaagcgg tgcggcgccg gcaggaagga aatgggcggg   1920
gagggccttc gtgcgtcgcc gcgccgccgt ccccttctcc atctccagcc tcggggctgc   1980
cgcaggggga cggctgcctt cgggggggac ggggcagggc ggggttcggc ttctggcgtg   2040
tgaccggcgg ctctagagcc tctgctaacc atgttcatgc cttcttcttt ttcctacaga   2100
tccttaatta aattccacca tgggctaccc ctacgacgtg cccgactacg ccaccagcaa   2160
tacaaactgc aggaaacaaa gtcccagaaa tcgcctatgg ttgttgacca tccttgtttt   2220
gttaattcca cttgtattta tatatcgaaa gtaccggaaa agaaagtgct ggaaaaggag   2280
acaggatgac cctgaatcta gaacctccag tcgtgaaacc ataccaatga atgcctcaaa   2340
tcttagcttg agtaaataca tcccgagaat tgctgaagac atgacaatcc aggaagctaa   2400
aaaatttgct cgagaaaata acatcaagga gggcaagata gatgagatca tgcatgacag   2460
catccaagac acagctgagc agaaagtcca gctgctcctg tgctggtacc aatctcatgg   2520
gaagagtgat gcatatcaag atttaatcaa gggtctcaaa aaagccgaat gtcgcagaac   2580
cttagataaa tttcaggaca tggtccagaa ggaccttgga aaatcaaccc cagacactgg   2640
aaatgaaaat gaaggacaat gtctggtcga gccatctgct ggagacatga gagctgccaa   2700
cctttggcca agcccgctca tgatcaaacg ctctaagaag aacagcctgg ccttgtccct   2760
gacggccgac cagatggtca gtgccttgtt ggatgctgag ccccccatac tctattccga   2820
gtatgatcct accagaccct tcagtgaagc ttcgatgatg ggcttactga ccaacctggc   2880
agacagggag ctggttcaca tgatcaactg ggcgaagagg gtgccaggct ttgtggattt   2940
gaccctccat gatcaggtcc accttctaga atgtgcctgg ctagagatcc tgatgattgg   3000
tctcgtctgg cgctccatgg agcacccagt gaagctactg tttgctccta acttgctctt   3060
```

-continued

```
ggacaggaac cagggaaaat gtgtagaggg catggtggag atcttcgaca tgctgctggc   3120
tacatcatct cggttccgca tgatgaatct gcagggagag gagtttgtgt gcctcaaatc   3180
tattattttg cttaattctg gagtgtacac atttctgtcc agcaccctga agtctctgga   3240
agagaaggac catatccacc gagtcctgga caagatcaca gacactttga tccacctgat   3300
ggccaaggca ggcctgaccc tgcagcagca gcaccagcgg ctggcccagc tcctcctcat   3360
cctctcccac atcaggcaca tgagtaacaa aggcatggag catctgtaca gcatgaagtg   3420
caagaacgtg gtgcccctct atgacctgct gctggaggcg gcggacgccc accgcctaca   3480
tgcgcccact agccgtggag gggcatccgt ggaggagacg gaccaaagcc acttggccac   3540
tgcgggctct acttcatcgc attccttgca aaagtattac atcacggggg aggcagaggg   3600
tttccctgcc acagcttgat gaagatctga gctccctggc ggaattgcgt aaatgattgc   3660
agatccacta gttctagagc tcgctgatca gcctcgactg tgccttctag ttgccagcca   3720
tctgttgttt gcccctcccc cgtgccttcc ttgaccctgg aaggtgccac tcccactgtc   3780
ctttcctaat aaaatgagga aattgcatcg cattgtctga gtaggtgtca ttctattctg   3840
gggggtgggg tggggcagga cagcaagggg gaggattggg aagacaatag caggcatgct   3900
ggggatgcgg tgggctctat ggcttctgag gcggaaagaa ccagaagctt ggcgtaatca   3960
tggtcatagc tgtttcctgt gtgaaattgt tatccgctca caattccaca caacatacga   4020
gccggaagca taaagtgtaa agcctggggt gcctaatgag tgagctaact cacattaatt   4080
gcgttgcgct cactgcccgc tttccagtcg ggaaacctgt cgtgccagct gcattaatga   4140
atcggccaac gcgcggggag aggcggtttg cgtattgggc gctcttccgc ttcctcgctc   4200
actgactcgc tgcgctcggt cgttcggctg cggcgagcgg tatcagctca ctcaaaggcg   4260
gtaatacggt tatccacaga atcaggggat aacgcaggaa agaacatgtg agcaaaaggc   4320
cagcaaaagg ccaggaaccg taaaaaggcc gcgttgctgg cgtttttcca taggctccgc   4380
ccccctgacg agcatcacaa aaatcgacgc tcaagtcaga ggtggcgaaa cccgacagga   4440
ctataaagat accaggcgtt tccccctgga agctccctcg tgcgctctcc tgttccgacc   4500
ctgccgctta ccggatacct gtccgccttt ctcccttcgg gaagcgtggc gctttctcat   4560
agctcacgct gtaggtatct cagttcggtg taggtcgttc gctccaagct gggctgtgtg   4620
cacgaacccc ccgttcagcc cgaccgctgc gccttatccg gtaactatcg tcttgagtcc   4680
aacccggtaa gacacgactt atcgccactg gcagcagcca ctggtaacag gattagcaga   4740
gcgaggtatg taggcggtgc tacagagttc ttgaagtggt ggcctaacta cggctacact   4800
agaaggacag tatttggtat ctgcgctctg ctgaagccag ttaccttcgg aaaaagagtt   4860
ggtagctctt gatccggcaa acaaaccacc gctggtagcg gtggtttttt tgtttgcaag   4920
cagcagatta cgcgcagaaa aaaaggatct caagaagatc ctttgatctt ttctacgggg   4980
tctgacgctc agtggaacga aaactcacgt taagggattt tggtcatgag attatcaaaa   5040
aggatcttca cctagatcct tttaaattaa aaatgaagtt ttaaatcaat ctaaagtata   5100
tatgagtaaa cttggtctga cagttaccaa tgcttaatca gtgaggcacc tatctcagcg   5160
atctgtctat ttcgttcatc catagttgcc tgactccccg tcgtgtagat aactacgata   5220
cgggagggct taccatctgg ccccagtgct gcaatgatac cgcgagaccc acgctcaccg   5280
gctccagatt tatcagcaat aaaccagcca gccggaaggg ccgagcgcag aagtggtcct   5340
gcaactttat ccgcctccat ccagtctatt aattgttgcc gggaagctag agtaagtagt   5400
tcgccagtta atagtttgcg caacgttgtt gccattgcta caggcatcgt ggtgtcacgc   5460
```

-continued tcgtcgtttg gtatggcttc attcagctcc ggttcccaac gatcaaggcg agttacatga 5520
tcccccatgt tgtgcaaaaa agcggttagc tccttcggtc ctccgatcgt tgtcagaagt 5580
aagttggccg cagtgttatc actcatggtt atggcagcac tgcataattc tcttactgtc 5640
atgccatccg taagatgctt ttctgtgact ggtgagtact caaccaagtc attctgagaa 5700
tagtgtatgc ggcgaccgag ttgctcttgc ccggcgtcaa tacgggataa taccgcgcca 5760
catagcagaa ctttaaaagt gctcatcatt ggaaaacgtt cttcggggcg aaaactctca 5820
aggatcttac cgctgttgag atccagttcg atgtaaccca ctcgtgcacc caactgatct 5880
tcagcatctt ttactttcac cagcgtttct gggtgagcaa aaacaggaag gcaaaatgcc 5940
gcaaaaaagg gaataagggc gacacggaaa tgttgaatac tcatactctt cctttttcaa 6000
tattattgaa gcatttatca gggttattgt ctcatgagcg gatacatatt tgaatgtatt 6060
tagaaaaata aacaaatagg ggttccgcgc acatttcccc gaaaagtgcc acctgacgtc 6120
taagaaacca ttattatcat gacattaacc tataaaaata ggcgtatcac gaggcccttt 6180
cgtc 6184

<210> SEQ ID NO 10
<211> LENGTH: 6214
<212> TYPE: DNA
<213> ORGANISM: Artificial sequence
<220> FEATURE:
<223> OTHER INFORMATION: vector pCAG-MFas-ER(T2)-bpA

<400> SEQUENCE: 10
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcaggcgcc 240
attcgccatt caggctgcgc aactgttggg aagggcgatc ggtgcgggcc tcttcgctat 300
tacgccagct ggcgaaaggg ggatgtgctg caaggcgatt aagttgggta acgccagggt 360
tttcccagtc acgacgttgt aaaacgacgg ccagtgaatt cgagctcggt acccgggggc 420
gcgccggatc tcgacattga ttattgacta gttattaata gtaatcaatt acggggtcat 480
tagttcatag cccatatatg gagttccgcg ttacataact tacggtaaat ggcccgcctg 540
gctgaccgcc caacgacccc cgcccattga cgtcaataat gacgtatgtt cccatagtaa 600
cgccaatagg gactttccat tgacgtcaat gggtggacta tttacggtaa actgcccact 660
tggcagtaca tcaagtgtat catatgccaa gtacgccccc tattgacgtc aatgacggta 720
aatggcccgc ctggcattat gcccagtaca tgaccttatg ggactttcct acttggcagt 780
acatctacgt attagtcatc gctattacca tgggtcgagg tgagccccac gttctgcttc 840
actctcccca tctccccccc ctccccaccc ccaattttgt atttatttat tttttaatta 900
ttttgtgcag cgatgggggc gggggggggg ggggcgcgcg ccaggcgggg cggggcgggg 960
cgaggggcgg ggcggggcga ggcggagagg tgcggcggca gccaatcaga gcggcgcgct 1020
ccgaaagttt ccttttatgg cgaggcggcg gcggcggcgg ccctataaaa agcgaagcgc 1080
gcggcgggcg ggagtcgctg cgttgccttc gccccgtgcc ccgctccgcg ccgcctcgcg 1140
ccgcccgccc cggctctgac tgaccgcgtt actcccacag gtgagcgggc gggacggccc 1200
ttctcctccg ggctgtaatt agcgcttggt ttaatgacgg ctcgtttctt ttctgtggct 1260
gcgtgaaagc cttaaagggc tccgggaggg ccctttgtgc ggggggggagc ggctcggggg 1320

-continued gtgcgtgcgt gtgtgtgtgc gtggggagcg ccgcgtgcgg cccgcgctgc ccggcggctg 1380
tgagcgctgc gggcgcggcg cggggctttg tgcgctccgc gtgtgcgcga ggggagcgcg 1440
gccgggggcg gtgccccgcg gtgcgggggg gctgcgaggg gaacaaaggc tgcgtgcggg 1500
gtgtgtgcgt gggggggtga gcagggggtg tgggcgcggc ggtcgggctg taacccccc 1560 ctgcaccccc ctccccgagt tgctgagcac ggcccggctt cgggtgcggg gctccgtgcg 1620
gggcgtggcg cggggctcgc cgtgccgggc ggggggtggc ggcaggtggg ggtgccgggc 1680
ggggcggggc cgcctcgggc cggggagggc tcgggggagg ggcgcggcgg ccccggagcg 1740
ccggcggctg tcgaggcgcg gcgagccgca gccattgcct tttatggtaa tcgtgcgaga 1800
gggcgcaggg acttcctttg tcccaaatct ggcggagccg aaatctggga ggcgccgccg 1860 cacccccctct agcgggcgcg ggcgaagcgg tgcggcgccg gcaggaagga aatgggcggg 1920
gagggccttc gtgcgtcgcc gcgccgccgt ccccttctcc atctccagcc tcggggctgc 1980
cgcaggggga cggctgcctt cgggggggac ggggcagggc ggggttcggc ttctggcgtg 2040
tgaccggcgg ctctagagcc tctgctaacc atgttcatgc cttcttcttt ttcctacaga 2100
tccttaatta aattccacca tgctgtggat ctgggctgtc ctgcctctgg tgcttgctgg 2160
ctcacagtta agagttcata ctaccagcaa tacaaactgc aggaaacaaa gtcccagaaa 2220
tcgcctatgg ttgttgacca tccttgtttt gttaattcca cttgtattta tatatcgaaa 2280
gtaccggaaa agaaagtgct ggaaaaggag acaggatgac cctgaatcta gaacctccag 2340
tcgtgaaacc ataccaatga atgcctcaaa tcttagcttg agtaaataca tcccgagaat 2400
tgctgaagac atgacaatcc aggaagctaa aaaatttgct cgagaaaata acatcaagga 2460
gggcaagata gatgagatca tgcatgacag catccaagac acagctgagc agaaagtcca 2520
gctgctcctg tgctggtacc aatctcatgg gaagagtgat gcatatcaag atttaatcaa 2580
gggtctcaaa aaagccgaat gtcgcagaac cttagataaa tttcaggaca tggtccagaa 2640
ggaccttgga aaatcaaccc cagacactgg aaatgaaaat gaaggacaat gtctggtcga 2700
gccatctgct ggagacatga gagctgccaa cctttggcca agcccgctca tgatcaaacg 2760
ctctaagaag aacagcctgg ccttgtccct gacggccgac cagatggtca gtgccttgtt 2820
ggatgctgag ccccccatac tctattccga gtatgatcct accagaccct tcagtgaagc 2880
ttcgatgatg ggcttactga ccaacctggc agacagggag ctggttcaca tgatcaactg 2940
ggcgaagagg gtgccaggct ttgtggattt gaccctccat gatcaggtcc accttctaga 3000
atgtgcctgg ctagagatcc tgatgattgg tctcgtctgg cgctccatgg agcacccagt 3060
gaagctactg tttgctccta acttgctctt ggacaggaac cagggaaaat gtgtagaggg 3120
catggtggag atcttcgaca tgctgctggc tacatcatct cggttccgca tgatgaatct 3180
gcagggagag gagtttgtgt gcctcaaatc tattattttg cttaattctg gagtgtacac 3240
atttctgtcc agcaccctga agtctctgga agagaaggac catatccacc gagtcctgga 3300
caagatcaca gacactttga tccacctgat ggccaaggca ggcctgaccc tgcagcagca 3360
gcaccagcgg ctggcccagc tcctcctcat cctctcccac atcaggcaca tgagtaacaa 3420
aggcatggag catctgtaca gcatgaagtg caagaacgtg gtgcccctct atgacctgct 3480
gctggaggcg gcggacgccc accgcctaca tgcgcccact agccgtggag gggcatccgt 3540
ggaggagacg gaccaaagcc acttggccac tgcgggctct acttcatcgc attccttgca 3600
aaagtattac atcacggggg aggcagaggg tttccctgcc acagcttgat gaagatctga 3660
gctccctggc ggaattgcgt aaatgattgc agatccacta gttctagagc tcgctgatca 3720

-continued

```
gcctcgactg tgccttctag ttgccagcca tctgttgttt gcccctcccc cgtgccttcc   3780
ttgaccctgg aaggtgccac tcccactgtc ctttcctaat aaaatgagga aattgcatcg   3840
cattgtctga gtaggtgtca ttctattctg gggggtgggg tggggcagga cagcaagggg   3900
gaggattggg aagacaatag caggcatgct ggggatgcgg tgggctctat ggcttctgag   3960
gcggaaagaa ccagaagctt ggcgtaatca tggtcatagc tgtttcctgt gtgaaattgt   4020
tatccgctca caattccaca caacatacga gccggaagca taaagtgtaa agcctggggt   4080
gcctaatgag tgagctaact cacattaatt gcgttgcgct cactgcccgc tttccagtcg   4140
ggaaacctgt cgtgccagct gcattaatga atcggccaac gcgcggggag aggcggtttg   4200
cgtattgggc gctcttccgc ttcctcgctc actgactcgc tgcgctcggt cgttcggctg   4260
cggcgagcgg tatcagctca ctcaaaggcg gtaatacggt tatccacaga atcaggggat   4320
aacgcaggaa agaacatgtg agcaaaaggc cagcaaaagg ccaggaaccg taaaaaggcc   4380
gcgttgctgg cgtttttcca taggctccgc ccccctgacg agcatcacaa aaatcgacgc   4440
tcaagtcaga ggtggcgaaa cccgacagga ctataaagat accaggcgtt tccccctgga   4500
agctccctcg tgcgctctcc tgttccgacc ctgccgctta ccggatacct gtccgccttt   4560
ctcccttcgg gaagcgtggc gctttctcat agctcacgct gtaggtatct cagttcggtg   4620
taggtcgttc gctccaagct gggctgtgtg cacgaacccc ccgttcagcc cgaccgctgc   4680
gccttatccg gtaactatcg tcttgagtcc aacccggtaa gacacgactt atcgccactg   4740
gcagcagcca ctggtaacag gattagcaga gcgaggtatg taggcggtgc tacagagttc   4800
ttgaagtggt ggcctaacta cggctacact agaaggacag tatttggtat ctgcgctctg   4860
ctgaagccag ttaccttcgg aaaaagagtt ggtagctctt gatccggcaa acaaaccacc   4920
gctggtagcg gtggtttttt tgtttgcaag cagcagatta cgcgcagaaa aaaaggatct   4980
caagaagatc ctttgatctt ttctacgggg tctgacgctc agtggaacga aaactcacgt   5040
taagggattt tggtcatgag attatcaaaa aggatcttca cctagatcct tttaaattaa   5100
aaatgaagtt ttaaatcaat ctaaagtata tatgagtaaa cttggtctga cagttaccaa   5160
tgcttaatca gtgaggcacc tatctcagcg atctgtctat ttcgttcatc catagttgcc   5220
tgactccccg tcgtgtagat aactacgata cgggagggct taccatctgg ccccagtgct   5280
gcaatgatac cgcgagaccc acgctcaccg gctccagatt tatcagcaat aaaccagcca   5340
gccggaaggg ccgagcgcag aagtggtcct gcaactttat ccgcctccat ccagtctatt   5400
aattgttgcc gggaagctag agtaagtagt tcgccagtta atagtttgcg caacgttgtt   5460
gccattgcta caggcatcgt ggtgtcacgc tcgtcgtttg gtatggcttc attcagctcc   5520
ggttcccaac gatcaaggcg agttacatga tcccccatgt tgtgcaaaaa agcggttagc   5580
tccttcggtc ctccgatcgt tgtcagaagt aagttggccg cagtgttatc actcatggtt   5640
atggcagcac tgcataattc tcttactgtc atgccatccg taagatgctt ttctgtgact   5700
ggtgagtact caaccaagtc attctgagaa tagtgtatgc ggcgaccgag ttgctcttgc   5760
ccggcgtcaa tacgggataa taccgcgcca catagcagaa ctttaaaagt gctcatcatt   5820
ggaaaacgtt cttcggggcg aaaactctca aggatcttac cgctgttgag atccagttcg   5880
atgtaaccca ctcgtgcacc caactgatct tcagcatctt ttactttcac cagcgtttct   5940
gggtgagcaa aaacaggaag gcaaaatgcc gcaaaaaagg gaataagggc gacacggaaa   6000
tgttgaatac tcatactctt cctttttcaa tattattgaa gcatttatca gggttattgt   6060
ctcatgagcg gatacatatt tgaatgtatt tagaaaaata aacaaatagg ggttccgcgc   6120
```

-continued acatttcccc gaaaagtgcc acctgacgtc taagaaacca ttattatcat gacattaacc 6180
tataaaaata ggcgtatcac gaggcccttt cgtc 6214

<210> SEQ ID NO 11
<211> LENGTH: 1500
<212> TYPE: DNA
<213> ORGANISM: Artificial sequence
<220> FEATURE:
<223> OTHER INFORMATION: DNA sequence coding for fusion protein HAFas-ER(T2)

<400> SEQUENCE: 11
atgggctacc cctacgacgt gcccgactac gccaccagca atacaaactg caggaaacaa 60
agtcccagaa atcgcctatg gttgttgacc atccttgttt tgttaattcc acttgtattt 120
atatatcgaa agtaccggaa aagaaagtgc tggaaaagga gacaggatga ccctgaatct 180
agaacctcca gtcgtgaaac cataccaatg aatgcctcaa atcttagctt gagtaaatac 240
atcccgagaa ttgctgaaga catgacaatc caggaagcta aaaaatttgc tcgagaaaat 300
aacatcaagg agggcaagat agatgagatc atgcatgaca gcatccaaga cacagctgag 360
cagaaagtcc agctgctcct gtgctggtac caatctcatg ggaagagtga tgcatatcaa 420
gatttaatca agggtctcaa aaaagccgaa tgtcgcagaa ccttagataa atttcaggac 480
atggtccaga aggaccttgg aaaatcaacc ccagacactg gaaatgaaaa tgaaggacaa 540
tgtctggtcg agccatctgc tggagacatg agagctgcca acctttggcc aagcccgctc 600
atgatcaaac gctctaagaa gaacagcctg gccttgtccc tgacggccga ccagatggtc 660
agtgccttgt tggatgctga gcccccccata ctctattccg agtatgatcc taccagaccc 720
ttcagtgaag cttcgatgat gggcttactg accaacctgg cagacaggga gctggttcac 780
atgatcaact gggcgaagag ggtgccaggc tttgtggatt tgaccctcca tgatcaggtc 840
caccttctag aatgtgcctg gctagagatc ctgatgattg gtctcgtctg gcgctccatg 900
gagcacccag tgaagctact gtttgctcct aacttgctct tggacaggaa ccagggaaaa 960
tgtgtagagg gcatggtgga gatcttcgac atgctgctgg ctacatcatc tcggttccgc 1020
atgatgaatc tgcagggaga ggagtttgtg tgcctcaaat ctattatttt gcttaattct 1080
ggagtgtaca catttctgtc cagcaccctg aagtctctgg aagagaagga ccatatccac 1140
cgagtcctgg acaagatcac agacactttg atccacctga tggccaaggc aggcctgacc 1200
ctgcagcagc agcaccagcg gctggcccag ctcctcctca tcctctccca catcaggcac 1260
atgagtaaca aaggcatgga gcatctgtac agcatgaagt gcaagaacgt ggtgcccctc 1320
tatgacctgc tgctggaggc ggcggacgcc caccgcctac atgcgcccac tagccgtgga 1380
ggggcatccg tggaggagac ggaccaaagc cacttggcca ctgcgggctc tacttcatcg 1440
cattccttgc aaaagtatta catcacgggg gaggcagagg gtttccctgc cacagcttga 1500

<210> SEQ ID NO 12
<211> LENGTH: 499
<212> TYPE: PRT
<213> ORGANISM: Artificial sequence
<220> FEATURE:
<223> OTHER INFORMATION: fusion protein HAFas-ER(T2)

<400> SEQUENCE: 12

Met Gly Tyr Pro Tyr Asp Val Pro Asp Tyr Ala Thr Ser Asn Thr Asn
1 5 10 15

Cys Arg Lys Gln Ser Pro Arg Asn Arg Leu Trp Leu Leu Thr Ile Leu
20 25 30

-continued

```
Val Leu Leu Ile Pro Leu Val Phe Ile Tyr Arg Lys Tyr Arg Lys Arg
        35                  40                  45

Lys Cys Trp Lys Arg Arg Gln Asp Asp Pro Glu Ser Arg Thr Ser Ser
    50                  55                  60

Arg Glu Thr Ile Pro Met Asn Ala Ser Asn Leu Ser Leu Ser Lys Tyr
65                  70                  75                  80

Ile Pro Arg Ile Ala Glu Asp Met Thr Ile Gln Glu Ala Lys Lys Phe
                85                  90                  95

Ala Arg Glu Asn Asn Ile Lys Glu Gly Lys Ile Asp Glu Ile Met His
            100                 105                 110

Asp Ser Ile Gln Asp Thr Ala Glu Gln Lys Val Gln Leu Leu Leu Cys
        115                 120                 125

Trp Tyr Gln Ser His Gly Lys Ser Asp Ala Tyr Gln Asp Leu Ile Lys
    130                 135                 140

Gly Leu Lys Lys Ala Glu Cys Arg Arg Thr Leu Asp Lys Phe Gln Asp
145                 150                 155                 160

Met Val Gln Lys Asp Leu Gly Lys Ser Thr Pro Asp Thr Gly Asn Glu
                165                 170                 175

Asn Glu Gly Gln Cys Leu Val Glu Pro Ser Ala Gly Asp Met Arg Ala
            180                 185                 190

Ala Asn Leu Trp Pro Ser Pro Leu Met Ile Lys Arg Ser Lys Lys Asn
        195                 200                 205

Ser Leu Ala Leu Ser Leu Thr Ala Asp Gln Met Val Ser Ala Leu Leu
    210                 215                 220

Asp Ala Glu Pro Pro Ile Leu Tyr Ser Glu Tyr Asp Pro Thr Arg Pro
225                 230                 235                 240

Phe Ser Glu Ala Ser Met Met Gly Leu Leu Thr Asn Leu Ala Asp Arg
                245                 250                 255

Glu Leu Val His Met Ile Asn Trp Ala Lys Arg Val Pro Gly Phe Val
            260                 265                 270

Asp Leu Thr Leu His Asp Gln Val His Leu Leu Glu Cys Ala Trp Leu
        275                 280                 285

Glu Ile Leu Met Ile Gly Leu Val Trp Arg Ser Met Glu His Pro Val
    290                 295                 300

Lys Leu Leu Phe Ala Pro Asn Leu Leu Leu Asp Arg Asn Gln Gly Lys
305                 310                 315                 320

Cys Val Glu Gly Met Val Glu Ile Phe Asp Met Leu Leu Ala Thr Ser
                325                 330                 335

Ser Arg Phe Arg Met Met Asn Leu Gln Gly Glu Glu Phe Val Cys Leu
            340                 345                 350

Lys Ser Ile Ile Leu Leu Asn Ser Gly Val Tyr Thr Phe Leu Ser Ser
        355                 360                 365

Thr Leu Lys Ser Leu Glu Glu Lys Asp His Ile His Arg Val Leu Asp
    370                 375                 380

Lys Ile Thr Asp Thr Leu Ile His Leu Met Ala Lys Ala Gly Leu Thr
385                 390                 395                 400

Leu Gln Gln Gln His Gln Arg Leu Ala Gln Leu Leu Leu Ile Leu Ser
                405                 410                 415

His Ile Arg His Met Ser Asn Lys Gly Met Glu His Leu Tyr Ser Met
            420                 425                 430

Lys Cys Lys Asn Val Val Pro Leu Tyr Asp Leu Leu Leu Glu Ala Ala
        435                 440                 445

Asp Ala His Arg Leu His Ala Pro Thr Ser Arg Gly Gly Ala Ser Val
```

```
    450                 455                 460

Glu Glu Thr Asp Gln Ser His Leu Ala Thr Ala Gly Ser Thr Ser Ser
465                 470                 475                 480

His Ser Leu Gln Lys Tyr Tyr Ile Thr Gly Glu Ala Glu Gly Phe Pro
                485                 490                 495

Ala Thr Ala


<210> SEQ ID NO 13
<211> LENGTH: 1530
<212> TYPE: DNA
<213> ORGANISM: Artificial sequence
<220> FEATURE:
<223> OTHER INFORMATION: DNA sequence coding for fusion protein
      MFas-ER(T2)

<400> SEQUENCE: 13

atgctgtgga tctgggctgt cctgcctctg gtgcttgctg gctcacagtt aagagttcat     60

actaccagca atacaaactg caggaaacaa agtcccagaa atcgcctatg gttgttgacc    120

atccttgttt tgttaattcc acttgtattt atatatcgaa agtaccggaa aagaaagtgc    180

tggaaaagga gacaggatga ccctgaatct agaacctcca gtcgtgaaac cataccaatg    240

aatgcctcaa atcttagctt gagtaaatac atcccgagaa ttgctgaaga catgacaatc    300

caggaagcta aaaaatttgc tcgagaaaat aacatcaagg agggcaagat agatgagatc    360

atgcatgaca gcatccaaga cacagctgag cagaaagtcc agctgctcct gtgctggtac    420

caatctcatg ggaagagtga tgcatatcaa gatttaatca agggtctcaa aaaagccgaa    480

tgtcgcagaa ccttagataa atttcaggac atggtccaga aggaccttgg aaaatcaacc    540

ccagacactg gaaatgaaaa tgaaggacaa tgtctggtcg agccatctgc tggagacatg    600

agagctgcca acctttggcc aagcccgctc atgatcaaac gctctaagaa gaacagcctg    660

gccttgtccc tgacggccga ccagatggtc agtgccttgt tggatgctga gccccccata    720

ctctattccg agtatgatcc taccagaccc ttcagtgaag cttcgatgat gggcttactg    780

accaacctgg cagacaggga gctggttcac atgatcaact gggcgaagag ggtgccaggc    840

tttgtggatt tgaccctcca tgatcaggtc caccttctag aatgtgcctg gctagagatc    900

ctgatgattg gtctcgtctg gcgctccatg gagcacccag tgaagctact gtttgctcct    960

aacttgctct tggacaggaa ccagggaaaa tgtgtagagg gcatggtgga gatcttcgac   1020

atgctgctgg ctacatcatc tcggttccgc atgatgaatc tgcagggaga ggagtttgtg   1080

tgcctcaaat ctattatttt gcttaattct ggagtgtaca catttctgtc cagcaccctg   1140

aagtctctgg aagagaagga ccatatccac cgagtcctgg acaagatcac agacactttg   1200

atccacctga tggccaaggc aggcctgacc ctgcagcagc agcaccagcg gctggcccag   1260

ctcctcctca tcctctccca catcaggcac atgagtaaca aaggcatgga gcatctgtac   1320

agcatgaagt gcaagaacgt ggtgcccctc tatgacctgc tgctggaggc ggcggacgcc   1380

caccgcctac atgcgcccac tagccgtgga ggggcatccg tggaggagac ggaccaaagc   1440

cacttggcca ctgcgggctc tacttcatcg cattccttgc aaaagtatta catcacgggg   1500

gaggcagagg gtttccctgc cacagcttga                                    1530


<210> SEQ ID NO 14
<211> LENGTH: 509
<212> TYPE: PRT
<213> ORGANISM: Artificial sequence
<220> FEATURE:
<223> OTHER INFORMATION: fusion protein MFas-ER(T2)
```

<400> SEQUENCE: 14

```
Met Leu Trp Ile Trp Ala Val Leu Pro Leu Val Leu Ala Gly Ser Gln
1               5                   10                  15

Leu Arg Val His Thr Thr Ser Asn Thr Asn Cys Arg Lys Gln Ser Pro
            20                  25                  30

Arg Asn Arg Leu Trp Leu Leu Thr Ile Leu Val Leu Leu Ile Pro Leu
        35                  40                  45

Val Phe Ile Tyr Arg Lys Tyr Arg Lys Arg Lys Cys Trp Lys Arg Arg
    50                  55                  60

Gln Asp Asp Pro Glu Ser Arg Thr Ser Ser Arg Glu Thr Ile Pro Met
65                  70                  75                  80

Asn Ala Ser Asn Leu Ser Leu Ser Lys Tyr Ile Pro Arg Ile Ala Glu
                85                  90                  95

Asp Met Thr Ile Gln Glu Ala Lys Lys Phe Ala Arg Glu Asn Asn Ile
            100                 105                 110

Lys Glu Gly Lys Ile Asp Glu Ile Met His Asp Ser Ile Gln Asp Thr
        115                 120                 125

Ala Glu Gln Lys Val Gln Leu Leu Leu Cys Trp Tyr Gln Ser His Gly
    130                 135                 140

Lys Ser Asp Ala Tyr Gln Asp Leu Ile Lys Gly Leu Lys Lys Ala Glu
145                 150                 155                 160

Cys Arg Arg Thr Leu Asp Lys Phe Gln Asp Met Val Gln Lys Asp Leu
                165                 170                 175

Gly Lys Ser Thr Pro Asp Thr Gly Asn Glu Asn Glu Gly Gln Cys Leu
            180                 185                 190

Val Glu Pro Ser Ala Gly Asp Met Arg Ala Ala Asn Leu Trp Pro Ser
        195                 200                 205

Pro Leu Met Ile Lys Arg Ser Lys Lys Asn Ser Leu Ala Leu Ser Leu
    210                 215                 220

Thr Ala Asp Gln Met Val Ser Ala Leu Leu Asp Ala Glu Pro Pro Ile
225                 230                 235                 240

Leu Tyr Ser Glu Tyr Asp Pro Thr Arg Pro Phe Ser Glu Ala Ser Met
                245                 250                 255

Met Gly Leu Leu Thr Asn Leu Ala Asp Arg Glu Leu Val His Met Ile
            260                 265                 270

Asn Trp Ala Lys Arg Val Pro Gly Phe Val Asp Leu Thr Leu His Asp
        275                 280                 285

Gln Val His Leu Leu Glu Cys Ala Trp Leu Glu Ile Leu Met Ile Gly
    290                 295                 300

Leu Val Trp Arg Ser Met Glu His Pro Val Lys Leu Leu Phe Ala Pro
305                 310                 315                 320

Asn Leu Leu Leu Asp Arg Asn Gln Gly Lys Cys Val Glu Gly Met Val
                325                 330                 335

Glu Ile Phe Asp Met Leu Leu Ala Thr Ser Ser Arg Phe Arg Met Met
            340                 345                 350

Asn Leu Gln Gly Glu Glu Phe Val Cys Leu Lys Ser Ile Ile Leu Leu
        355                 360                 365

Asn Ser Gly Val Tyr Thr Phe Leu Ser Ser Thr Leu Lys Ser Leu Glu
    370                 375                 380

Glu Lys Asp His Ile His Arg Val Leu Asp Lys Ile Thr Asp Thr Leu
385                 390                 395                 400

Ile His Leu Met Ala Lys Ala Gly Leu Thr Leu Gln Gln Gln His Gln
                405                 410                 415
```

```
Arg Leu Ala Gln Leu Leu Leu Ile Leu Ser His Ile Arg His Met Ser
            420                 425                 430

Asn Lys Gly Met Glu His Leu Tyr Ser Met Lys Cys Lys Asn Val Val
        435                 440                 445

Pro Leu Tyr Asp Leu Leu Leu Glu Ala Ala Asp Ala His Arg Leu His
    450                 455                 460

Ala Pro Thr Ser Arg Gly Gly Ala Ser Val Glu Glu Thr Asp Gln Ser
465                 470                 475                 480

His Leu Ala Thr Ala Gly Ser Thr Ser Ser His Ser Leu Gln Lys Tyr
                485                 490                 495

Tyr Ile Thr Gly Glu Ala Glu Gly Phe Pro Ala Thr Ala
            500                 505


<210> SEQ ID NO 15
<211> LENGTH: 39
<212> TYPE: DNA
<213> ORGANISM: Artificial sequence
<220> FEATURE:
<223> OTHER INFORMATION: primer Casp8ER-A

<400> SEQUENCE: 15

ccttaattaa ttccaccatg agtgagtcac ggacttcag                             39


<210> SEQ ID NO 16
<211> LENGTH: 27
<212> TYPE: DNA
<213> ORGANISM: Artificial sequence
<220> FEATURE:
<223> OTHER INFORMATION: primer Casp8ER-B

<400> SEQUENCE: 16

ggctcgaggg gagggaagaa gagcttc                                          27


<210> SEQ ID NO 17
<211> LENGTH: 78
<212> TYPE: DNA
<213> ORGANISM: Artificial sequence
<220> FEATURE:
<223> OTHER INFORMATION: myrCasp8ER-A

<400> SEQUENCE: 17

ccttaattaa ttccaccatg ggagtagca agagcaagcc taaggacccc agccagcgca     60

gtgagtcacg gacttcag                                                    78


<210> SEQ ID NO 18
<211> LENGTH: 6426
<212> TYPE: DNA
<213> ORGANISM: Artificial sequence
<220> FEATURE:
<223> OTHER INFORMATION: vector pCAG-Casp8-ER(T2)-bpA

<400> SEQUENCE: 18

tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accatatgcg gtgtgaaata ccgcacagat gcgtaaggag aaaataccgc atcaggcgcc    240

attcgccatt caggctgcgc aactgttggg aagggcgatc ggtgcgggcc tcttcgctat    300

tacgccagct ggcgaaaggg ggatgtgctg caaggcgatt aagttgggta acgccagggt    360

tttcccagtc acgacgttgt aaaacgacgg ccagtgaatt cgagctcggt acccgggggc    420
```

-continued

```
gcgccggatc tcgacattga ttattgacta gttattaata gtaatcaatt acggggtcat    480
tagttcatag cccatatatg gagttccgcg ttacataact tacggtaaat ggcccgcctg    540
gctgaccgcc caacgacccc cgcccattga cgtcaataat gacgtatgtt cccatagtaa    600
cgccaatagg gactttccat tgacgtcaat gggtggacta tttacggtaa actgcccact    660
tggcagtaca tcaagtgtat catatgccaa gtacgccccc tattgacgtc aatgacggta    720
aatggcccgc ctggcattat gcccagtaca tgaccttatg ggactttcct acttggcagt    780
acatctacgt attagtcatc gctattacca tgggtcgagg tgagccccac gttctgcttc    840
actctcccca tctccccccc ctccccaccc ccaattttgt atttatttat tttttaatta    900
ttttgtgcag cgatgggggc gggggggggg ggggcgcgcg ccaggcgggg cggggcgggg    960
cgaggggcgg ggcggggcga ggcggagagg tgcggcggca gccaatcaga gcggcgcgct   1020
ccgaaagttt ccttttatgg cgaggcggcg gcggcggcgg ccctataaaa agcgaagcgc   1080
gcggcgggcg ggagtcgctg cgttgccttc gccccgtgcc ccgctccgcg ccgcctcgcg   1140
ccgcccgccc cggctctgac tgaccgcgtt actcccacag gtgagcgggc gggacggccc   1200
ttctcctccg ggctgtaatt agcgcttggt ttaatgacgg ctcgtttctt ttctgtggct   1260
gcgtgaaagc cttaaagggc tccgggaggg ccctttgtgc ggggggggagc ggctcggggg   1320
gtgcgtgcgt gtgtgtgtgc gtggggagcg ccgcgtgcgg cccgcgctgc ccggcggctg   1380
tgagcgctgc gggcgcggcg cggggctttg tgcgctccgc gtgtgcgcga ggggagcgcg   1440
gccgggggcg gtgccccgcg gtgcgggggg gctgcgaggg gaacaaaggc tgcgtgcggg   1500
gtgtgtgcgt gggggggtga gcagggggtg tgggcgcggc ggtcgggctg taaccccccc   1560
ctgcaccccc ctccccgagt tgctgagcac ggcccggctt cgggtgcggg gctccgtgcg   1620
gggcgtggcg cggggctcgc cgtgccgggc ggggggtggc ggcaggtggg ggtgccgggc   1680
ggggcggggc cgcctcgggc cggggagggc tcgggggagg ggcgcggcgg ccccggagcg   1740
ccggcggctg tcgaggcgcg gcgagccgca gccattgcct tttatggtaa tcgtgcgaga   1800
gggcgcaggg acttcctttg tcccaaatct ggcggagccg aaatctggga ggcgccgccg   1860
caccccctct agcgggcgcg ggcgaagcgg tgcggcgccg gcaggaagga aatgggcggg   1920
gagggccttc gtgcgtcgcc gcgccgccgt ccccttctcc atctccagcc tcggggctgc   1980
cgcagggggga cggctgcctt cgggggggac ggggcagggc ggggttcggc ttctggcgtg   2040
tgaccggcgg ctctagagcc tctgctaacc atgttcatgc cttcttcttt ttcctacaga   2100
tccttaatta attccaccat gagtgagtca cggacttcag acaaagttta ccaaatgaag   2160
aacaaacctc ggggatactg tctgatcatc aacaatcatg atttcagcaa ggcccgggaa   2220
gacataaccc aactccgaaa aatgaaggac agaaaaggaa cagactgtga taaagaggct   2280
ctgagtaaga cctttaagga gcttcatttt gagatagtat cttacgacga ctgcactgca   2340
aatgaaatcc acgagattct agaaggctac caaagcgcag accacaagaa caaagactgc   2400
ttcatctgct gtatcctatc ccacggtgac aagggtgtcg tctatggaac ggatgggaag   2460
gaggcctcca tctatgacct gacatcttac ttcactggtt caaagtgccc ttccctgtct   2520
gggaaaccca agatcttttt cattcaggct tgccaaggaa gtaacttcca gaaaggagtg   2580
cctgatgagg caggcttcga gcaacagaac cacactttag aagtggattc atcatctcac   2640
aagaactata ttccggatga ggcagacttt ctgctgggaa tggctacggt gaagaactgc   2700
gtttcctacc gagatcctgt gaatggaacc tggtatattc agtcactttg ccagagcctg   2760
agggaaagat gtcctcaagg agatgacatt cttagcatcc tgactggcgt gaactatgac   2820
```

-continued

```
gtgagcaata aagacgacag gaggaacaag ggaaagcaga tgccacagcc caccttcaca   2880
ctacggaaga agctcttctt ccctccccctc gagccatctg ctggagacat gagagctgcc   2940
aacctttggc caagcccgct catgatcaaa cgctctaaga agaacagcct ggccttgtcc   3000
ctgacggccg accagatggt cagtgccttg ttggatgctg agccccccat actctattcc   3060
gagtatgatc ctaccagacc cttcagtgaa gcttcgatga tgggcttact gaccaacctg   3120
gcagacaggg agctggttca catgatcaac tgggcgaaga gggtgccagg ctttgtggat   3180
ttgaccctcc atgatcaggt ccaccttcta gaatgtgcct ggctagagat cctgatgatt   3240
ggtctcgtct ggcgctccat ggagcaccca gtgaagctac tgtttgctcc taacttgctc   3300
ttggacagga accagggaaa atgtgtagag ggcatggtgg agatcttcga catgctgctg   3360
gctacatcat ctcggttccg catgatgaat ctgcagggag aggagtttgt gtgcctcaaa   3420
tctattattt tgcttaattc tggagtgtac acatttctgt ccagcaccct gaagtctctg   3480
gaagagaagg accatatcca ccgagtcctg gacaagatca cagacacttt gatccacctg   3540
atggccaagg caggcctgac cctgcagcag cagcaccagc ggctggccca gctcctcctc   3600
atcctctccc acatcaggca catgagtaac aaaggcatgg agcatctgta cagcatgaag   3660
tgcaagaacg tggtgcccct ctatgacctg ctgctggagg cggcggacgc ccaccgccta   3720
catgcgccca ctagccgtgg aggggcatcc gtggaggaga cggaccaaag ccacttggcc   3780
actgcgggct ctacttcatc gcattccttg caaaagtatt acatcacggg ggaggcagag   3840
ggtttccctg ccacagcttg atgaagatct gagctccctg gcggaattgc gtaaatgatt   3900
gcagatccac tagttctaga gctcgctgat cagcctcgac tgtgccttct agttgccagc   3960
catctgttgt ttgcccctcc cccgtgcctt ccttgaccct ggaaggtgcc actcccactg   4020
tcctttccta ataaaatgag gaaattgcat cgcattgtct gagtaggtgt cattctattc   4080
tggggggtgg ggtggggcag gacagcaagg gggaggattg ggaagacaat agcaggcatg   4140
ctggggatgc ggtgggctct atggcttctg aggcggaaag aaccagaagc ttggcgtaat   4200
catggtcata gctgtttcct gtgtgaaatt gttatccgct cacaattcca cacaacatac   4260
gagccggaag cataaagtgt aaagcctggg gtgcctaatg agtgagctaa ctcacattaa   4320
ttgcgttgcg ctcactgccc gctttccagt cgggaaacct gtcgtgccag ctgcattaat   4380
gaatcggcca acgcgcgggg agaggcggtt tgcgtattgg gcgctcttcc gcttcctcgc   4440
tcactgactc gctgcgctcg gtcgttcggc tgcggcgagc ggtatcagct cactcaaagg   4500
cggtaatacg gttatccaca gaatcagggg ataacgcagg aaagaacatg tgagcaaaag   4560
gccagcaaaa ggccaggaac cgtaaaaagg ccgcgttgct ggcgtttttc cataggctcc   4620
gcccccctga cgagcatcac aaaaatcgac gctcaagtca gaggtggcga aacccgacag   4680
gactataaag ataccaggcg tttccccctg gaagctccct cgtgcgctct cctgttccga   4740
ccctgccgct taccggatac ctgtccgcct ttctcccttc gggaagcgtg gcgctttctc   4800
atagctcacg ctgtaggtat ctcagttcgg tgtaggtcgt tcgctccaag ctgggctgtg   4860
tgcacgaacc ccccgttcag cccgaccgct gcgccttatc cggtaactat cgtcttgagt   4920
ccaacccggt aagacacgac ttatcgccac tggcagcagc cactggtaac aggattagca   4980
gagcgaggta tgtaggcggt gctacagagt tcttgaagtg gtggcctaac tacggctaca   5040
ctagaaggac agtatttggt atctgcgctc tgctgaagcc agttaccttc ggaaaaagag   5100
ttggtagctc ttgatccggc aaacaaacca ccgctggtag cggtggtttt tttgtttgca   5160
agcagcagat tacgcgcaga aaaaaaggat ctcaagaaga tcctttgatc ttttctacgg   5220
```

ggtctgacgc tcagtggaac gaaaactcac gttaagggat tttggtcatg agattatcaa 5280
aaaggatctt cacctagatc cttttaaatt aaaaatgaag ttttaaatca atctaaagta 5340
tatatgagta aacttggtct gacagttacc aatgcttaat cagtgaggca cctatctcag 5400
cgatctgtct atttcgttca tccatagttg cctgactccc cgtcgtgtag ataactacga 5460
tacgggaggg cttaccatct ggccccagtg ctgcaatgat accgcgagac ccacgctcac 5520
cggctccaga tttatcagca ataaaccagc cagccggaag ggccgagcgc agaagtggtc 5580
ctgcaacttt atccgcctcc atccagtcta ttaattgttg ccgggaagct agagtaagta 5640
gttcgccagt taatagtttg cgcaacgttg ttgccattgc tacaggcatc gtggtgtcac 5700
gctcgtcgtt tggtatggct tcattcagct ccggttccca acgatcaagg cgagttacat 5760
gatcccccat gttgtgcaaa aaagcggtta gctccttcgg tcctccgatc gttgtcagaa 5820
gtaagttggc cgcagtgtta tcactcatgg ttatggcagc actgcataat tctcttactg 5880
tcatgccatc cgtaagatgc ttttctgtga ctggtgagta ctcaaccaag tcattctgag 5940
aatagtgtat gcggcgaccg agttgctctt gcccggcgtc aatacgggat aataccgcgc 6000
cacatagcag aactttaaaa gtgctcatca ttggaaaacg ttcttcgggg cgaaaactct 6060
caaggatctt accgctgttg agatccagtt cgatgtaacc cactcgtgca cccaactgat 6120
cttcagcatc ttttactttc accagcgttt ctgggtgagc aaaaacagga aggcaaaatg 6180
ccgcaaaaaa gggaataagg gcgacacgga aatgttgaat actcatactc ttcctttttc 6240
aatattattg aagcatttat cagggttatt gtctcatgag cggatacata tttgaatgta 6300
tttagaaaaa taaacaaata ggggttccgc gcacatttcc ccgaaaagtg ccacctgacg 6360
tctaagaaac cattattatc atgacattaa cctataaaaa taggcgtatc acgaggccct 6420
ttcgtc 6426

<210> SEQ ID NO 19
<211> LENGTH: 1743
<212> TYPE: DNA
<213> ORGANISM: Artificial sequence
<220> FEATURE:
<223> OTHER INFORMATION: DNA sequence coding for fusion protein Casp8-ER(T2)

<400> SEQUENCE: 19
atgagtgagt cacggacttc agacaaagtt taccaaatga agaacaaacc tcggggatac 60
tgtctgatca tcaacaatca tgatttcagc aaggcccggg aagacataac ccaactccga 120
aaaatgaagg acagaaaagg aacagactgt gataaagagg ctctgagtaa gacctttaag 180
gagcttcatt ttgagatagt atcttacgac gactgcactg caaatgaaat ccacgagatt 240
ctagaaggct accaaagcgc agaccacaag aacaaagact gcttcatctg ctgtatccta 300
tcccacggtg acaagggtgt cgtctatgga acggatggga aggaggcctc catctatgac 360
ctgacatctt acttcactgg ttcaaagtgc ccttccctgt ctgggaaacc caagatcttt 420
ttcattcagg cttgccaagg aagtaacttc cagaaaggag tgcctgatga ggcaggcttc 480
gagcaacaga accacacttt agaagtggat tcatcatctc acaagaacta tattccggat 540
gaggcagact ttctgctggg aatggctacg gtgaagaact gcgtttccta ccgagatcct 600
gtgaatggaa cctggtatat tcagtcactt tgccagagcc tgagggaaag atgtcctcaa 660
ggagatgaca ttcttagcat cctgactggc gtgaactatg acgtgagcaa taaagacgac 720
aggaggaaca agggaaagca gatgccacag cccaccttca cactacggaa gaagctcttc 780

```
ttccctcccc tcgagccatc tgctggagac atgagagctg ccaacctttg gccaagcccg    840

ctcatgatca aacgctctaa gaagaacagc ctggccttgt ccctgacggc cgaccagatg    900

gtcagtgcct tgttggatgc tgagcccccc atactctatt ccgagtatga tcctaccaga    960

cccttcagtg aagcttcgat gatgggctta ctgaccaacc tggcagacag ggagctggtt   1020

cacatgatca actgggcgaa gagggtgcca ggctttgtgg atttgaccct ccatgatcag   1080

gtccaccttc tagaatgtgc ctggctagag atcctgatga ttggtctcgt ctggcgctcc   1140

atggagcacc cagtgaagct actgtttgct cctaacttgc tcttggacag gaaccaggga   1200

aaatgtgtag agggcatggt ggagatcttc gacatgctgc tggctacatc atctcggttc   1260

cgcatgatga atctgcaggg agaggagttt gtgtgcctca aatctattat tttgcttaat   1320

tctggagtgt acacatttct gtccagcacc ctgaagtctc tggaagagaa ggaccatatc   1380

caccgagtcc tggacaagat cacagacact ttgatccacc tgatggccaa ggcaggcctg   1440

accctgcagc agcagcacca gcggctggcc cagctcctcc tcatcctctc ccacatcagg   1500

cacatgagta acaaaggcat ggagcatctg tacagcatga agtgcaagaa cgtggtgccc   1560

ctctatgacc tgctgctgga ggcggcggac gcccaccgcc tacatgcgcc cactagccgt   1620

ggaggggcat ccgtggagga gacggaccaa agccacttgg ccactgcggg ctctacttca   1680

tcgcattcct tgcaaaagta ttacatcacg gggggaggcag agggtttccc tgccacagct   1740

tga                                                                 1743
```

<210> SEQ ID NO 20
<211> LENGTH: 580
<212> TYPE: PRT
<213> ORGANISM: Artificial sequence
<220> FEATURE:
<223> OTHER INFORMATION: fusion protein Casp8-ER(T2)

<400> SEQUENCE: 20

```
Met Ser Glu Ser Arg Thr Ser Asp Lys Val Tyr Gln Met Lys Asn Lys
1               5                   10                  15

Pro Arg Gly Tyr Cys Leu Ile Ile Asn Asn His Asp Phe Ser Lys Ala
            20                  25                  30

Arg Glu Asp Ile Thr Gln Leu Arg Lys Met Lys Asp Arg Lys Gly Thr
        35                  40                  45

Asp Cys Asp Lys Glu Ala Leu Ser Lys Thr Phe Lys Glu Leu His Phe
    50                  55                  60

Glu Ile Val Ser Tyr Asp Asp Cys Thr Ala Asn Glu Ile His Glu Ile
65                  70                  75                  80

Leu Glu Gly Tyr Gln Ser Ala Asp His Lys Asn Lys Asp Cys Phe Ile
                85                  90                  95

Cys Cys Ile Leu Ser His Gly Asp Lys Gly Val Val Tyr Gly Thr Asp
            100                 105                 110

Gly Lys Glu Ala Ser Ile Tyr Asp Leu Thr Ser Tyr Phe Thr Gly Ser
        115                 120                 125

Lys Cys Pro Ser Leu Ser Gly Lys Pro Lys Ile Phe Phe Ile Gln Ala
    130                 135                 140

Cys Gln Gly Ser Asn Phe Gln Lys Gly Val Pro Asp Glu Ala Gly Phe
145                 150                 155                 160

Glu Gln Gln Asn His Thr Leu Glu Val Asp Ser Ser Ser His Lys Asn
                165                 170                 175

Tyr Ile Pro Asp Glu Ala Asp Phe Leu Leu Gly Met Ala Thr Val Lys
            180                 185                 190
```

-continued

```
Asn Cys Val Ser Tyr Arg Asp Pro Val Asn Gly Thr Trp Tyr Ile Gln
        195                 200                 205

Ser Leu Cys Gln Ser Leu Arg Glu Arg Cys Pro Gln Gly Asp Asp Ile
    210                 215                 220

Leu Ser Ile Leu Thr Gly Val Asn Tyr Asp Val Ser Asn Lys Asp Asp
225                 230                 235                 240

Arg Arg Asn Lys Gly Lys Gln Met Pro Gln Pro Thr Phe Thr Leu Arg
                245                 250                 255

Lys Lys Leu Phe Phe Pro Pro Leu Glu Pro Ser Ala Gly Asp Met Arg
            260                 265                 270

Ala Ala Asn Leu Trp Pro Ser Pro Leu Met Ile Lys Arg Ser Lys Lys
        275                 280                 285

Asn Ser Leu Ala Leu Ser Leu Thr Ala Asp Gln Met Val Ser Ala Leu
    290                 295                 300

Leu Asp Ala Glu Pro Pro Ile Leu Tyr Ser Glu Tyr Asp Pro Thr Arg
305                 310                 315                 320

Pro Phe Ser Glu Ala Ser Met Met Gly Leu Leu Thr Asn Leu Ala Asp
                325                 330                 335

Arg Glu Leu Val His Met Ile Asn Trp Ala Lys Arg Val Pro Gly Phe
            340                 345                 350

Val Asp Leu Thr Leu His Asp Gln Val His Leu Leu Glu Cys Ala Trp
        355                 360                 365

Leu Glu Ile Leu Met Ile Gly Leu Val Trp Arg Ser Met Glu His Pro
    370                 375                 380

Val Lys Leu Leu Phe Ala Pro Asn Leu Leu Leu Asp Arg Asn Gln Gly
385                 390                 395                 400

Lys Cys Val Glu Gly Met Val Glu Ile Phe Asp Met Leu Leu Ala Thr
                405                 410                 415

Ser Ser Arg Phe Arg Met Met Asn Leu Gln Gly Glu Glu Phe Val Cys
            420                 425                 430

Leu Lys Ser Ile Ile Leu Leu Asn Ser Gly Val Tyr Thr Phe Leu Ser
        435                 440                 445

Ser Thr Leu Lys Ser Leu Glu Glu Lys Asp His Ile His Arg Val Leu
    450                 455                 460

Asp Lys Ile Thr Asp Thr Leu Ile His Leu Met Ala Lys Ala Gly Leu
465                 470                 475                 480

Thr Leu Gln Gln Gln His Gln Arg Leu Ala Gln Leu Leu Leu Ile Leu
                485                 490                 495

Ser His Ile Arg His Met Ser Asn Lys Gly Met Glu His Leu Tyr Ser
            500                 505                 510

Met Lys Cys Lys Asn Val Val Pro Leu Tyr Asp Leu Leu Leu Glu Ala
        515                 520                 525

Ala Asp Ala His Arg Leu His Ala Pro Thr Ser Arg Gly Gly Ala Ser
    530                 535                 540

Val Glu Glu Thr Asp Gln Ser His Leu Ala Thr Ala Gly Ser Thr Ser
545                 550                 555                 560

Ser His Ser Leu Gln Lys Tyr Tyr Ile Thr Gly Glu Ala Glu Gly Phe
                565                 570                 575

Pro Ala Thr Ala
            580
```

<210> SEQ ID NO 21
<211> LENGTH: 6465
<212> TYPE: DNA
<213> ORGANISM: Artificial sequence
<220> FEATURE:
<223> OTHER INFORMATION: vector pCAG-myrCasp8-ER(T2)

<400> SEQUENCE: 21
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcaggcgcc 240
attcgccatt caggctgcgc aactgttggg aagggcgatc ggtgcgggcc tcttcgctat 300
tacgccagct ggcgaaaggg ggatgtgctg caaggcgatt aagttgggta acgccagggt 360
tttcccagtc acgacgttgt aaaacgacgg ccagtgaatt cgagctcggt acccgggggc 420
gcgccggatc tcgacattga ttattgacta gttattaata gtaatcaatt acggggtcat 480
tagttcatag cccatatatg gagttccgcg ttacataact tacggtaaat ggcccgcctg 540
gctgaccgcc caacgacccc cgcccattga cgtcaataat gacgtatgtt cccatagtaa 600
cgccaatagg gactttccat tgacgtcaat gggtggacta tttacggtaa actgcccact 660
tggcagtaca tcaagtgtat catatgccaa gtacgccccc tattgacgtc aatgacggta 720
aatggcccgc ctggcattat gcccagtaca tgaccttatg ggactttcct acttggcagt 780
acatctacgt attagtcatc gctattacca tgggtcgagg tgagccccac gttctgcttc 840
actctcccca tctccccccc ctccccaccc ccaattttgt atttatttat tttttaatta 900
ttttgtgcag cgatgggggc gggggggggg ggggcgcgcg ccaggcgggg cggggcgggg 960
cgaggggcgg ggcggggcga ggcggagagg tgcggcggca gccaatcaga gcggcgcgct 1020
ccgaaagttt ccttttatgg cgaggcggcg gcggcggcgg ccctataaaa agcgaagcgc 1080
gcggcgggcg ggagtcgctg cgttgccttc gccccgtgcc ccgctccgcg ccgcctcgcg 1140
ccgcccgccc cggctctgac tgaccgcgtt actcccacag gtgagcgggc gggacggccc 1200
ttctcctccg ggctgtaatt agcgcttggt ttaatgacgg ctcgtttctt ttctgtggct 1260
gcgtgaaagc cttaaagggc tccgggaggg ccctttgtgc ggggggggagc ggctcggggg 1320 gtgcgtgcgt gtgtgtgtgc gtggggagcg ccgcgtgcgg cccgcgctgc ccggcggctg 1380
tgagcgctgc gggcgcggcg cggggctttg tgcgctccgc gtgtgcgcga ggggagcgcg 1440
gccgggggcg gtgccccgcg gtgcgggggg gctgcgaggg gaacaaaggc tgcgtgcggg 1500
gtgtgtgcgt gggggggtga gcagggggtg tgggcgcggc ggtcgggctg taaccccccc 1560
ctgcaccccc ctccccgagt tgctgagcac ggcccggctt cgggtgcggg gctccgtgcg 1620
gggcgtggcg cggggctcgc cgtgccgggc ggggggtggc ggcaggtggg ggtgccgggc 1680
ggggcggggc cgcctcgggc cggggagggc tcgggggagg ggcgcggcgg ccccggagcg 1740
ccggcggctg tcgaggcgcg gcgagccgca gccattgcct tttatggtaa tcgtgcgaga 1800
gggcgcaggg acttcctttg tcccaaatct ggcggagccg aaatctggga ggcgccgccg 1860
caccccctct agcgggcgcg ggcgaagcgg tgcggcgccg gcaggaagga aatgggcggg 1920
gagggccttc gtgcgtcgcc gcgccgccgt ccccttctcc atctccagcc tcggggctgc 1980 cgcagggggga cggctgcctt cggggggggac ggggcagggc ggggttcggc ttctggcgtg 2040
tgaccggcgg ctctagagcc tctgctaacc atgttcatgc cttcttcttt ttcctacaga 2100
tccttaatta attccaccat ggggagtagc aagagcaagc ctaaggaccc cagccagcgc 2160
agtgagtcac ggacttcaga caaagtttac caaatgaaga acaaacctcg gggatactgt 2220
ctgatcatca acaatcatga tttcagcaag gcccgggaag acataaccca actccgaaaa 2280

-continued

```
atgaaggaca gaaaaggaac agactgtgat aaagaggctc tgagtaagac ctttaaggag   2340
cttcattttg agatagtatc ttacgacgac tgcactgcaa atgaaatcca cgagattcta   2400
gaaggctacc aaagcgcaga ccacaagaac aaagactgct tcatctgctg tatcctatcc   2460
cacggtgaca agggtgtcgt ctatggaacg gatgggaagg aggcctccat ctatgacctg   2520
acatcttact tcactggttc aaagtgccct tccctgtctg ggaaacccaa gatctttttc   2580
attcaggctt gccaaggaag taacttccag aaaggagtgc ctgatgaggc aggcttcgag   2640
caacagaacc acactttaga agtggattca tcatctcaca agaactatat tccggatgag   2700
gcagactttc tgctgggaat ggctacggtg aagaactgcg tttcctaccg agatcctgtg   2760
aatggaacct ggtatattca gtcactttgc cagagcctga gggaaagatg tcctcaagga   2820
gatgacattc ttagcatcct gactggcgtg aactatgacg tgagcaataa agacgacagg   2880
aggaacaagg gaaagcagat gccacagccc accttcacac tacggaagaa gctcttcttc   2940
cctcccctcg agccatctgc tggagacatg agagctgcca acctttggcc aagcccgctc   3000
atgatcaaac gctctaagaa gaacagcctg gccttgtccc tgacggccga ccagatggtc   3060
agtgccttgt tggatgctga gcccccata ctctattccg agtatgatcc taccagaccc   3120
ttcagtgaag cttcgatgat gggcttactg accaacctgg cagacaggga gctggttcac   3180
atgatcaact gggcgaagag ggtgccaggc tttgtggatt tgaccctcca tgatcaggtc   3240
caccttctag aatgtgcctg gctagagatc ctgatgattg gtctcgtctg gcgctccatg   3300
gagcacccag tgaagctact gtttgctcct aacttgctct tggacaggaa ccagggaaaa   3360
tgtgtagagg gcatggtgga gatcttcgac atgctgctgg ctacatcatc tcggttccgc   3420
atgatgaatc tgcagggaga ggagtttgtg tgcctcaaat ctattatttt gcttaattct   3480
ggagtgtaca catttctgtc cagcaccctg aagtctctgg aagagaagga ccatatccac   3540
cgagtcctgg acaagatcac agacactttg atccacctga tggccaaggc aggcctgacc   3600
ctgcagcagc agcaccagcg gctggcccag ctcctcctca tcctctccca catcaggcac   3660
atgagtaaca aaggcatgga gcatctgtac agcatgaagt gcaagaacgt ggtgcccctc   3720
tatgacctgc tgctggaggc ggcggacgcc caccgcctac atgcgcccac tagccgtgga   3780
ggggcatccg tggaggagac ggaccaaagc cacttggcca ctgcgggctc tacttcatcg   3840
cattccttgc aaaagtatta catcacgggg gaggcagagg gtttccctgc cacagcttga   3900
tgaagatctg agctccctgg cggaattgcg taaatgattg cagatccact agttctagag   3960
ctcgctgatc agcctcgact gtgccttcta gttgccagcc atctgttgtt tgcccctccc   4020
ccgtgccttc cttgaccctg gaaggtgcca ctcccactgt cctttcctaa taaaatgagg   4080
aaattgcatc gcattgtctg agtaggtgtc attctattct ggggggtggg gtggggcagg   4140
acagcaaggg ggaggattgg gaagacaata gcaggcatgc tggggatgcg gtgggctcta   4200
tggcttctga ggcggaaaga accagaagct tggcgtaatc atggtcatag ctgtttcctg   4260
tgtgaaattg ttatccgctc acaattccac acaacatacg agccggaagc ataaagtgta   4320
aagcctgggg tgcctaatga gtgagctaac tcacattaat tgcgttgcgc tcactgcccg   4380
ctttccagtc gggaaacctg tcgtgccagc tgcattaatg aatcggccaa cgcgcgggga   4440
gaggcggttt gcgtattggg cgctcttccg cttcctcgct cactgactcg ctgcgctcgg   4500
tcgttcggct gcggcgagcg gtatcagctc actcaaaggc ggtaatacgg ttatccacag   4560
aatcagggga taacgcagga aagaacatgt gagcaaaagg ccagcaaaag gccaggaacc   4620
gtaaaaaggc cgcgttgctg gcgtttttcc ataggctccg cccccctgac gagcatcaca   4680
```

```
aaaatcgacg ctcaagtcag aggtggcgaa acccgacagg actataaaga taccaggcgt   4740

ttcccctgg aagctccctc gtgcgctctc ctgttccgac cctgccgctt accggatacc   4800

tgtccgcctt tctcccttcg ggaagcgtgg cgctttctca tagctcacgc tgtaggtatc   4860

tcagttcggt gtaggtcgtt cgctccaagc tgggctgtgt gcacgaaccc cccgttcagc   4920

ccgaccgctg cgccttatcc ggtaactatc gtcttgagtc caacccggta agacacgact   4980

tatcgccact ggcagcagcc actggtaaca ggattagcag agcgaggtat gtaggcggtg   5040

ctacagagtt cttgaagtgg tggcctaact acggctacac tagaaggaca gtatttggta   5100

tctgcgctct gctgaagcca gttaccttcg gaaaaagagt tggtagctct tgatccggca   5160

aacaaaccac cgctggtagc ggtggttttt ttgtttgcaa gcagcagatt acgcgcagaa   5220

aaaaaggatc tcaagaagat cctttgatct tttctacggg gtctgacgct cagtggaacg   5280

aaaactcacg ttaagggatt ttggtcatga gattatcaaa aaggatcttc acctagatcc   5340

ttttaaatta aaaatgaagt tttaaatcaa tctaaagtat atatgagtaa acttggtctg   5400

acagttacca atgcttaatc agtgaggcac ctatctcagc gatctgtcta tttcgttcat   5460

ccatagttgc ctgactcccc gtcgtgtaga taactacgat acgggagggc ttaccatctg   5520

gccccagtgc tgcaatgata ccgcgagacc cacgctcacc ggctccagat ttatcagcaa   5580

taaaccagcc agccggaagg gccgagcgca gaagtggtcc tgcaacttta tccgcctcca   5640

tccagtctat taattgttgc cgggaagcta gagtaagtag ttcgccagtt aatagtttgc   5700

gcaacgttgt tgccattgct acaggcatcg tggtgtcacg ctcgtcgttt ggtatggctt   5760

cattcagctc cggttcccaa cgatcaaggc gagttacatg atcccccatg ttgtgcaaaa   5820

aagcggttag ctccttcggt cctccgatcg ttgtcagaag taagttggcc gcagtgttat   5880

cactcatggt tatggcagca ctgcataatt ctcttactgt catgccatcc gtaagatgct   5940

tttctgtgac tggtgagtac tcaaccaagt cattctgaga atagtgtatg cggcgaccga   6000

gttgctcttg cccggcgtca atacgggata ataccgcgcc acatagcaga actttaaaag   6060

tgctcatcat tggaaaacgt tcttcggggc gaaaactctc aaggatctta ccgctgttga   6120

gatccagttc gatgtaaccc actcgtgcac ccaactgatc ttcagcatct tttactttca   6180

ccagcgtttc tgggtgagca aaaacaggaa ggcaaaatgc cgcaaaaaag ggaataaggg   6240

cgacacggaa atgttgaata ctcatactct tcctttttca atattattga agcatttatc   6300

agggttattg tctcatgagc ggatacatat ttgaatgtat ttagaaaaat aaacaaatag   6360

gggttccgcg cacatttccc cgaaaagtgc cacctgacgt ctaagaaacc attattatca   6420

tgacattaac ctataaaaat aggcgtatca cgaggccctt tcgtc                   6465
```

<210> SEQ ID NO 22
<211> LENGTH: 1782
<212> TYPE: DNA
<213> ORGANISM: Artificial sequence
<220> FEATURE:
<223> OTHER INFORMATION: DNA sequence coding for fusion protein myrCasp8-ER(T2)

<400> SEQUENCE: 22

```
atggggagta gcaagagcaa gcctaaggac cccagccagc gcagtgagtc acggacttca     60

gacaaagttt accaaatgaa gaacaaacct cggggatact gtctgatcat caacaatcat    120

gatttcagca aggcccggga agacataacc caactccgaa aaatgaagga cagaaaagga    180

acagactgtg ataaagaggc tctgagtaag acctttaagg agcttcattt tgagatagta    240
```

-continued

```
tcttacgacg actgcactgc aaatgaaatc cacgagattc tagaaggcta ccaaagcgca    300

gaccacaaga acaaagactg cttcatctgc tgtatcctat cccacggtga caagggtgtc    360

gtctatggaa cggatgggaa ggaggcctcc atctatgacc tgacatctta cttcactggt    420

tcaaagtgcc cttccctgtc tgggaaaccc aagatctttt tcattcaggc ttgccaagga    480

agtaacttcc agaaaggagt gcctgatgag gcaggcttcg agcaacagaa ccacacttta    540

gaagtggatt catcatctca caagaactat attccggatg aggcagactt tctgctggga    600

atggctacgg tgaagaactg cgtttcctac cgagatcctg tgaatggaac ctggtatatt    660

cagtcacttt gccagagcct gagggaaaga tgtcctcaag gagatgacat tcttagcatc    720

ctgactggcg tgaactatga cgtgagcaat aaagacgaca ggaggaacaa gggaaagcag    780

atgccacagc ccaccttcac actacggaag aagctcttct tccctcccct cgagccatct    840

gctggagaca tgagagctgc caacctttgg ccaagcccgc tcatgatcaa acgctctaag    900

aagaacagcc tggccttgtc cctgacggcc gaccagatgg tcagtgcctt gttggatgct    960

gagcccccca tactctattc cgagtatgat cctaccagac ccttcagtga agcttcgatg   1020

atgggcttac tgaccaacct ggcagacagg gagctggttc acatgatcaa ctgggcgaag   1080

agggtgccag gctttgtgga tttgaccctc catgatcagg tccaccttct agaatgtgcc   1140

tggctagaga tcctgatgat tggtctcgtc tggcgctcca tggagcaccc agtgaagcta   1200

ctgtttgctc ctaacttgct cttggacagg aaccagggaa aatgtgtaga gggcatggtg   1260

gagatcttcg acatgctgct ggctacatca tctcggttcc gcatgatgaa tctgcaggga   1320

gaggagtttg tgtgcctcaa atctattatt ttgcttaatt ctggagtgta cacatttctg   1380

tccagcaccc tgaagtctct ggaagagaag gaccatatcc accgagtcct ggacaagatc   1440

acagacactt tgatccacct gatggccaag gcaggcctga ccctgcagca gcagcaccag   1500

cggctggccc agctcctcct catcctctcc cacatcaggc acatgagtaa caaaggcatg   1560

gagcatctgt acagcatgaa gtgcaagaac gtggtgcccc tctatgacct gctgctggag   1620

gcggcggacg cccaccgcct acatgcgccc actagccgtg gaggggcatc cgtggaggag   1680

acggaccaaa gccacttggc cactgcgggc tctacttcat cgcattcctt gcaaaagtat   1740

tacatcacgg gggaggcaga gggtttccct gccacagctt ga                      1782
```

```
<210> SEQ ID NO 23
<211> LENGTH: 593
<212> TYPE: PRT
<213> ORGANISM: Artificial sequence
<220> FEATURE:
<223> OTHER INFORMATION: fusion protein myrCasp8-ER(T2)

<400> SEQUENCE: 23

Met Gly Ser Ser Lys Ser Lys Pro Lys Asp Pro Ser Gln Arg Ser Glu
1               5                   10                  15

Ser Arg Thr Ser Asp Lys Val Tyr Gln Met Lys Asn Lys Pro Arg Gly
            20                  25                  30

Tyr Cys Leu Ile Ile Asn Asn His Asp Phe Ser Lys Ala Arg Glu Asp
        35                  40                  45

Ile Thr Gln Leu Arg Lys Met Lys Asp Arg Lys Gly Thr Asp Cys Asp
    50                  55                  60

Lys Glu Ala Leu Ser Lys Thr Phe Lys Glu Leu His Phe Glu Ile Val
65                  70                  75                  80

Ser Tyr Asp Asp Cys Thr Ala Asn Glu Ile His Glu Ile Leu Glu Gly
                85                  90                  95
```

-continued

```
Tyr Gln Ser Ala Asp His Lys Asn Lys Asp Cys Phe Ile Cys Cys Ile
            100                 105                 110

Leu Ser His Gly Asp Lys Gly Val Val Tyr Gly Thr Asp Gly Lys Glu
        115                 120                 125

Ala Ser Ile Tyr Asp Leu Thr Ser Tyr Phe Thr Gly Ser Lys Cys Pro
    130                 135                 140

Ser Leu Ser Gly Lys Pro Lys Ile Phe Phe Ile Gln Ala Cys Gln Gly
145                 150                 155                 160

Ser Asn Phe Gln Lys Gly Val Pro Asp Glu Ala Gly Phe Glu Gln Gln
                165                 170                 175

Asn His Thr Leu Glu Val Asp Ser Ser Ser His Lys Asn Tyr Ile Pro
            180                 185                 190

Asp Glu Ala Asp Phe Leu Leu Gly Met Ala Thr Val Lys Asn Cys Val
        195                 200                 205

Ser Tyr Arg Asp Pro Val Asn Gly Thr Trp Tyr Ile Gln Ser Leu Cys
    210                 215                 220

Gln Ser Leu Arg Glu Arg Cys Pro Gln Gly Asp Asp Ile Leu Ser Ile
225                 230                 235                 240

Leu Thr Gly Val Asn Tyr Asp Val Ser Asn Lys Asp Asp Arg Arg Asn
                245                 250                 255

Lys Gly Lys Gln Met Pro Gln Pro Thr Phe Thr Leu Arg Lys Lys Leu
            260                 265                 270

Phe Phe Pro Pro Leu Glu Pro Ser Ala Gly Asp Met Arg Ala Ala Asn
        275                 280                 285

Leu Trp Pro Ser Pro Leu Met Ile Lys Arg Ser Lys Lys Asn Ser Leu
    290                 295                 300

Ala Leu Ser Leu Thr Ala Asp Gln Met Val Ser Ala Leu Leu Asp Ala
305                 310                 315                 320

Glu Pro Pro Ile Leu Tyr Ser Glu Tyr Asp Pro Thr Arg Pro Phe Ser
                325                 330                 335

Glu Ala Ser Met Met Gly Leu Leu Thr Asn Leu Ala Asp Arg Glu Leu
            340                 345                 350

Val His Met Ile Asn Trp Ala Lys Arg Val Pro Gly Phe Val Asp Leu
        355                 360                 365

Thr Leu His Asp Gln Val His Leu Leu Glu Cys Ala Trp Leu Glu Ile
    370                 375                 380

Leu Met Ile Gly Leu Val Trp Arg Ser Met Glu His Pro Val Lys Leu
385                 390                 395                 400

Leu Phe Ala Pro Asn Leu Leu Leu Asp Arg Asn Gln Gly Lys Cys Val
                405                 410                 415

Glu Gly Met Val Glu Ile Phe Asp Met Leu Leu Ala Thr Ser Ser Arg
            420                 425                 430

Phe Arg Met Met Asn Leu Gln Gly Glu Glu Phe Val Cys Leu Lys Ser
        435                 440                 445

Ile Ile Leu Leu Asn Ser Gly Val Tyr Thr Phe Leu Ser Ser Thr Leu
    450                 455                 460

Lys Ser Leu Glu Glu Lys Asp His Ile His Arg Val Leu Asp Lys Ile
465                 470                 475                 480

Thr Asp Thr Leu Ile His Leu Met Ala Lys Ala Gly Leu Thr Leu Gln
                485                 490                 495

Gln Gln His Gln Arg Leu Ala Gln Leu Leu Leu Ile Leu Ser His Ile
            500                 505                 510

Arg His Met Ser Asn Lys Gly Met Glu His Leu Tyr Ser Met Lys Cys
        515                 520                 525
```

```
Lys Asn Val Val Pro Leu Tyr Asp Leu Leu Leu Glu Ala Ala Asp Ala
    530                 535                 540

His Arg Leu His Ala Pro Thr Ser Arg Gly Gly Ala Ser Val Glu Glu
545                 550                 555                 560

Thr Asp Gln Ser His Leu Ala Thr Ala Gly Ser Thr Ser Ser His Ser
                565                 570                 575

Leu Gln Lys Tyr Tyr Ile Thr Gly Glu Ala Glu Gly Phe Pro Ala Thr
            580                 585                 590

Ala


<210> SEQ ID NO 24
<211> LENGTH: 39
<212> TYPE: DNA
<213> ORGANISM: Artificial sequence
<220> FEATURE:
<223> OTHER INFORMATION: primer Casp9fullER-A

<400> SEQUENCE: 24

ccttaattaa ttccaccatg gacgaggcgg accggcagc                             39


<210> SEQ ID NO 25
<211> LENGTH: 27
<212> TYPE: DNA
<213> ORGANISM: Artificial sequence
<220> FEATURE:
<223> OTHER INFORMATION: primer Casp9ER-B

<400> SEQUENCE: 25

ggctcgactg aagttttaaa aaacagc                                          27


<210> SEQ ID NO 26
<211> LENGTH: 42
<212> TYPE: DNA
<213> ORGANISM: Artificial sequence
<220> FEATURE:
<223> OTHER INFORMATION: primer Casp9truncER-A

<400> SEQUENCE: 26

ccttaattaa ttccaccatg ggtcggcaag cagccaagca gg                         42


<210> SEQ ID NO 27
<211> LENGTH: 6999
<212> TYPE: DNA
<213> ORGANISM: Artificial sequence
<220> FEATURE:
<223> OTHER INFORMATION: vector pCAG-Casp9full-ER(T2)-bpA

<400> SEQUENCE: 27

tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accatatgcg gtgtgaaata ccgcacagat gcgtaaggag aaaataccgc atcaggcgcc    240

attcgccatt caggctgcgc aactgttggg aagggcgatc ggtgcgggcc tcttcgctat    300

tacgccagct ggcgaaaggg ggatgtgctg caaggcgatt aagttgggta acgccagggt    360

tttcccagtc acgacgttgt aaaacgacgg ccagtgaatt cgagctcggt acccgggggc    420

gcgccggatc tcgacattga ttattgacta gttattaata gtaatcaatt acggggtcat    480

tagttcatag cccatatatg gagttccgcg ttacataact tacggtaaat ggcccgcctg    540

gctgaccgcc caacgacccc cgcccattga cgtcaataat gacgtatgtt cccatagtaa    600
```

-continued

```
cgccaatagg gactttccat tgacgtcaat gggtggacta tttacggtaa actgcccact    660
tggcagtaca tcaagtgtat catatgccaa gtacgccccc tattgacgtc aatgacggta    720
aatggcccgc ctggcattat gcccagtaca tgaccttatg ggactttcct acttggcagt    780
acatctacgt attagtcatc gctattacca tgggtcgagg tgagccccac gttctgcttc    840
actctcccca tctccccccc ctccccaccc ccaattttgt atttatttat tttttaatta    900
ttttgtgcag cgatgggggc gggggggggg ggggcgcgcg ccaggcgggg cggggcgggg    960
cgaggggcgg ggcggggcga ggcggagagg tgcggcggca gccaatcaga gcggcgcgct   1020
ccgaaagttt ccttttatgg cgaggcggcg gcggcggcgg ccctataaaa agcgaagcgc   1080
gcggcgggcg ggagtcgctg cgttgccttc gccccgtgcc ccgctccgcg ccgcctcgcg   1140
ccgcccgccc cggctctgac tgaccgcgtt actcccacag gtgagcgggc gggacggccc   1200
ttctcctccg ggctgtaatt agcgcttggt ttaatgacgg ctcgtttctt ttctgtggct   1260
gcgtgaaagc cttaaagggc tccgggaggg ccctttgtgc ggggggggagc ggctcggggg   1320
gtgcgtgcgt gtgtgtgtgc gtggggagcg ccgcgtgcgg cccgcgctgc ccggcggctg   1380
tgagcgctgc gggcgcggcg cggggctttg tgcgctccgc gtgtgcgcga ggggagcgcg   1440
gccgggggcg gtgccccgcg gtgcgggggg gctgcgaggg gaacaaaggc tgcgtgcggg   1500
gtgtgtgcgt gggggggtga gcagggggtg tgggcgcggc ggtcgggctg taaccccccc   1560
ctgcaccccc ctccccgagt tgctgagcac ggcccggctt cgggtgcggg gctccgtgcg   1620
gggcgtggcg cggggctcgc cgtgccgggc ggggggtggc ggcaggtggg ggtgccgggc   1680
ggggcggggc cgcctcgggc cggggagggc tcgggggagg ggcgcggcgg ccccggagcg   1740
ccggcggctg tcgaggcgcg gcgagccgca gccattgcct tttatggtaa tcgtgcgaga   1800
gggcgcaggg acttcctttg tcccaaatct ggcggagccg aaatctggga ggcgccgccg   1860
caccccctct agcgggcgcg ggcgaagcgg tgcggcgccg gcaggaagga aatgggcggg   1920
gagggccttc gtgcgtcgcc gcgccgccgt ccccttctcc atctccagcc tcggggctgc   1980
cgcagggggga cggctgcctt cgggggggac ggggcagggc ggggttcggc ttctggcgtg   2040
tgaccggcgg ctctagagcc tctgctaacc atgttcatgc cttcttcttt ttcctacaga   2100
tccttaatta attccaccat ggacgaggcg gaccggcagc tcctgcggcg atgcagggtg   2160
cgcctagtga gcgagctgca agtcgcggag ctctgggacg ctctgctgag tcgagagctc   2220
ttcacgcgcg acatgatcga ggatattcag caggcaggat ctgggtctcg gcgggatcag   2280
gccaggcagc tggtcacaga ccttgagacc cgagggaggc aggcccttcc tctcttcatc   2340
tcctgcttag aggacacagg ccaaggcacc ctggcttcac tcttgcaaag cggtcggcaa   2400
gcagccaagc aggatccaga ggctgttaaa cccctagacc acctggtgcc tgtggtcctg   2460
ggaccaatgg gactcacagc aaaggagcag agagtagtga agctggaccc gtcacagcct   2520
gccgtgggaa acctcacccc agtggtgctg gggccagaag agctctggcc tgctcggctc   2580
aagccagagg ttctcagacc agaaacaccc aggcccgtgg acattggttc tggcggagct   2640
catgatgtct gtgttccagg gaagatcagg ggacatgcag atatggcata caccctggat   2700
tcggatccct gtggccactg cctcatcatc aacaatgtga acttctgccc ttcctcgggg   2760
ctcggcacac gcacgggctc caacttggac cgtgacaaac tcgagcaccg attccgctgg   2820
ctgcgcttca tggtggaggt gaagaacgac ctgactgcca agaaaatggt cacggctttg   2880
atggagatgg cacaccggaa ccaccgtgcc ctggactgct ttgtggtggt catcctctct   2940
catggctgcc aggccagcca cctccagttc ccgggtgctg tctatgggac agatggatgc   3000
```

-continued tccgtgtcca ttgagaaaat tgtgaatatc ttcaacggga gcggctgccc cagcctggga 3060
gggaagccca agctcttctt catccaggcc tgcggtggtg agcagaaaga ccatggcttt 3120
gaggtggcct gcacttcctc tcaaggcagg accttggaca gtgactctga gccagatgct 3180
gtccccctatc aggaaggccc aaggcccttg gaccagctgg atgctgtgtc aagtttgcct 3240
acccccagtg acatccttgt gtcctactcc accttcccag gttttgtctc ctggagggac 3300
aagaaaagtg gctcctggta catcgagacc ttggatggca ttctggagca gtgggctcgc 3360
tctgaagacc tgcagtccct ccttctcagg gttgccaatg ctgtttctgc gaaagggact 3420
tacaagcaga ttcctggctg ttttaacttc ctccggaaaa agctgttttt taaaacttca 3480
gtcgagccat ctgctggaga catgagagct gccaaccttt ggccaagccc gctcatgatc 3540
aaacgctcta agaagaacag cctggccttg tccctgacgg ccgaccagat ggtcagtgcc 3600
ttgttggatg ctgagccccc catactctat tccgagtatg atcctaccag acccttcagt 3660
gaagcttcga tgatgggctt actgaccaac ctggcagaca gggagctggt tcacatgatc 3720
aactgggcga agagggtgcc aggctttgtg gatttgaccc tccatgatca ggtccacctt 3780
ctagaatgtg cctggctaga gatcctgatg attggtctcg tctggcgctc catggagcac 3840
ccagtgaagc tactgtttgc tcctaacttg ctcttggaca ggaaccaggg aaaatgtgta 3900
gagggcatgg tggagatctt cgacatgctg ctggctacat catctcggtt ccgcatgatg 3960
aatctgcagg gagaggagtt tgtgtgcctc aaatctatta ttttgcttaa ttctggagtg 4020
tacacatttc tgtccagcac cctgaagtct ctggaagaga aggaccatat ccaccgagtc 4080
ctggacaaga tcacagacac tttgatccac ctgatggcca aggcaggcct gaccctgcag 4140
cagcagcacc agcggctggc ccagctcctc ctcatcctct cccacatcag gcacatgagt 4200
aacaaaggca tggagcatct gtacagcatg aagtgcaaga acgtggtgcc cctctatgac 4260
ctgctgctgg aggcggcgga cgcccaccgc ctacatgcgc ccactagccg tggaggggca 4320
tccgtggagg agacggacca aagccacttg gccactgcgg gctctacttc atcgcattcc 4380
ttgcaaaagt attacatcac gggggaggca gagggtttcc ctgccacagc ttgatgaaga 4440
tctgagctcc ctggcggaat tgcgtaaatg attgcagatc cactagttct agagctcgct 4500
gatcagcctc gactgtgcct tctagttgcc agccatctgt tgtttgcccc tcccccgtgc 4560
cttccttgac cctggaaggt gccactccca ctgtcctttc ctaataaaat gaggaaattg 4620
catcgcattg tctgagtagg tgtcattcta ttctgggggg tggggtgggg caggacagca 4680
agggggagga ttgggaagac aatagcaggc atgctgggga tgcggtgggc tctatggctt 4740
ctgaggcgga aagaaccaga agcttggcgt aatcatggtc atagctgttt cctgtgtgaa 4800
attgttatcc gctcacaatt ccacacaaca tacgagccgg aagcataaag tgtaaagcct 4860
ggggtgccta atgagtgagc taactcacat taattgcgtt gcgctcactg cccgctttcc 4920
agtcgggaaa cctgtcgtgc cagctgcatt aatgaatcgg ccaacgcgcg gggagaggcg 4980
gtttgcgtat tgggcgctct tccgcttcct cgctcactga ctcgctgcgc tcggtcgttc 5040
ggctgcggcg agcggtatca gctcactcaa aggcggtaat acggttatcc acagaatcag 5100
gggataacgc aggaaagaac atgtgagcaa aaggccagca aaaggccagg aaccgtaaaa 5160
aggccgcgtt gctggcgttt ttccataggc tccgcccccc tgacgagcat cacaaaaatc 5220
gacgctcaag tcagaggtgg cgaaacccga caggactata aagataccag gcgtttcccc 5280
ctggaagctc cctcgtgcgc tctcctgttc cgaccctgcc gcttaccgga tacctgtccg 5340
cctttctccc ttcgggaagc gtggcgcttt ctcatagctc acgctgtagg tatctcagtt 5400

```
cggtgtaggt cgttcgctcc aagctgggct gtgtgcacga accccccgtt cagcccgacc   5460
gctgcgcctt atccggtaac tatcgtcttg agtccaaccc ggtaagacac gacttatcgc   5520
cactggcagc agccactggt aacaggatta gcagagcgag gtatgtaggc ggtgctacag   5580
agttcttgaa gtggtggcct aactacggct acactagaag gacagtattt ggtatctgcg   5640
ctctgctgaa gccagttacc ttcggaaaaa gagttggtag ctcttgatcc ggcaaacaaa   5700
ccaccgctgg tagcggtggt ttttttgttt gcaagcagca gattacgcgc agaaaaaaag   5760
gatctcaaga agatcctttg atcttttcta cggggtctga cgctcagtgg aacgaaaact   5820
cacgttaagg gattttggtc atgagattat caaaaaggat cttcacctag atccttttaa   5880
attaaaaatg aagttttaaa tcaatctaaa gtatatatga gtaaacttgg tctgacagtt   5940
accaatgctt aatcagtgag gcacctatct cagcgatctg tctatttcgt tcatccatag   6000
ttgcctgact ccccgtcgtg tagataacta cgatacggga gggcttacca tctggcccca   6060
gtgctgcaat gataccgcga gacccacgct caccggctcc agatttatca gcaataaacc   6120
agccagccgg aagggccgag cgcagaagtg gtcctgcaac tttatccgcc tccatccagt   6180
ctattaattg ttgccgggaa gctagagtaa gtagttcgcc agttaatagt ttgcgcaacg   6240
ttgttgccat tgctacaggc atcgtggtgt cacgctcgtc gtttggtatg gcttcattca   6300
gctccggttc ccaacgatca aggcgagtta catgatcccc catgttgtgc aaaaaagcgg   6360
ttagctcctt cggtcctccg atcgttgtca gaagtaagtt ggccgcagtg ttatcactca   6420
tggttatggc agcactgcat aattctctta ctgtcatgcc atccgtaaga tgcttttctg   6480
tgactggtga gtactcaacc aagtcattct gagaatagtg tatgcggcga ccgagttgct   6540
cttgcccggc gtcaatacgg gataataccg cgccacatag cagaacttta aaagtgctca   6600
tcattggaaa acgttcttcg gggcgaaaac tctcaaggat cttaccgctg ttgagatcca   6660
gttcgatgta acccactcgt gcacccaact gatcttcagc atcttttact ttcaccagcg   6720
tttctgggtg agcaaaaaca ggaaggcaaa atgccgcaaa aaagggaata agggcgacac   6780
ggaaatgttg aatactcata ctcttccttt ttcaatatta ttgaagcatt tatcagggtt   6840
attgtctcat gagcggatac atatttgaat gtatttagaa aaataaacaa ataggggttc   6900
cgcgcacatt tccccgaaaa gtgccacctg acgtctaaga aaccattatt atcatgacat   6960
taacctataa aaataggcgt atcacgaggc cctttcgtc                          6999
```

<210> SEQ ID NO 28
<211> LENGTH: 2316
<212> TYPE: DNA
<213> ORGANISM: Artificial sequence
<220> FEATURE:
<223> OTHER INFORMATION: DNA sequence coding for fusion protein Casp9full-ER(T2)

<400> SEQUENCE: 28

```
atggacgagg cggaccggca gctcctgcgg cgatgcaggg tgcgcctagt gagcgagctg     60
caagtcgcgg agctctggga cgctctgctg agtcgagagc tcttcacgcg cgacatgatc    120
gaggatattc agcaggcagg atctgggtct cggcgggatc aggccaggca gctggtcaca    180
gaccttgaga cccgagggag gcaggccctt cctctcttca tctcctgctt agaggacaca    240
ggccaaggca ccctggcttc actcttgcaa agcggtcggc aagcagccaa gcaggatcca    300
gaggctgtta aacccctaga ccacctggtg cctgtggtcc tgggaccaat gggactcaca    360
gcaaaggagc agagagtagt gaagctggac ccgtcacagc ctgccgtggg aaacctcacc    420
```

```
ccagtggtgc tggggccaga agagctctgg cctgctcggc tcaagccaga ggttctcaga    480
ccagaaacac ccaggcccgt ggacattggt tctggcggag ctcatgatgt ctgtgttcca    540
gggaagatca ggggacatgc agatatggca tacaccctgg attcggatcc ctgtggccac    600
tgcctcatca tcaacaatgt gaacttctgc ccttcctcgg ggctcggcac acgcacgggc    660
tccaacttgg accgtgacaa actcgagcac cgattccgct ggctgcgctt catggtggag    720
gtgaagaacg acctgactgc caagaaaatg gtcacggctt tgatggagat ggcacaccgg    780
aaccaccgtg ccctggactg ctttgtggtg gtcatcctct ctcatggctg ccaggccagc    840
cacctccagt tcccgggtgc tgtctatggg acagatggat gctccgtgtc cattgagaaa    900
attgtgaata tcttcaacgg gagcggctgc ccccagcctgg gagggaagcc caagctcttc    960
ttcatccagg cctgcggtgg tgagcagaaa gaccatggct ttgaggtggc ctgcacttcc   1020
tctcaaggca ggaccttgga cagtgactct gagccagatg ctgtccccta tcaggaaggc   1080
ccaaggccct tggaccagct ggatgctgtg tcaagtttgc ctacccccag tgacatcctt   1140
gtgtcctact ccaccttccc aggttttgtc tcctggaggg acaagaaaag tggctcctgg   1200
tacatcgaga ccttggatgg cattctggag cagtgggctc gctctgaaga cctgcagtcc   1260
ctccttctca gggttgccaa tgctgtttct gcgaaaggga cttacaagca gattcctggc   1320
tgttttaact tcctccggaa aaagctgttt tttaaaactt cagtcgagcc atctgctgga   1380
gacatgagag ctgccaacct ttggccaagc ccgctcatga tcaaacgctc taagaagaac   1440
agcctggcct tgtccctgac ggccgaccag atggtcagtg ccttgttgga tgctgagccc   1500
cccatactct attccgagta tgatcctacc agacccttca gtgaagcttc gatgatgggc   1560
ttactgacca acctggcaga cagggagctg gttcacatga tcaactgggc gaagagggtg   1620
ccaggctttg tggatttgac cctccatgat caggtccacc ttctagaatg tgcctggcta   1680
gagatcctga tgattggtct cgtctggcgc tccatggagc acccagtgaa gctactgttt   1740
gctcctaact tgctcttgga caggaaccag ggaaaatgtg tagagggcat ggtggagatc   1800
ttcgacatgc tgctggctac atcatctcgg ttccgcatga tgaatctgca gggagaggag   1860
tttgtgtgcc tcaaatctat tattttgctt aattctggag tgtacacatt tctgtccagc   1920
accctgaagt ctctggaaga gaaggaccat atccaccgag tcctggacaa gatcacagac   1980
actttgatcc acctgatggc caaggcaggc ctgaccctgc agcagcagca ccagcggctg   2040
gcccagctcc tcctcatcct ctcccacatc aggcacatga gtaacaaagg catggagcat   2100
ctgtacagca tgaagtgcaa gaacgtggtg cccctctatg acctgctgct ggaggcggcg   2160
gacgcccacc gcctacatgc gcccactagc cgtggagggg catccgtgga ggagacggac   2220
caaagccact tggccactgc gggctctact tcatcgcatt ccttgcaaaa gtattacatc   2280
acgggggagg cagagggttt ccctgccaca gcttga                             2316
```

<210> SEQ ID NO 29
<211> LENGTH: 771
<212> TYPE: PRT
<213> ORGANISM: Artificial sequence
<220> FEATURE:
<223> OTHER INFORMATION: fusion protein Casp9full-ER(T2)

<400> SEQUENCE: 29

```
Met Asp Glu Ala Asp Arg Gln Leu Leu Arg Arg Cys Arg Val Arg Leu
1               5                   10                  15

Val Ser Glu Leu Gln Val Ala Glu Leu Trp Asp Ala Leu Leu Ser Arg
            20                  25                  30
```

```
Glu Leu Phe Thr Arg Asp Met Ile Glu Asp Ile Gln Gln Ala Gly Ser
        35                  40                  45

Gly Ser Arg Arg Asp Gln Ala Arg Gln Leu Val Thr Asp Leu Glu Thr
    50                  55                  60

Arg Gly Arg Gln Ala Leu Pro Leu Phe Ile Ser Cys Leu Glu Asp Thr
65                  70                  75                  80

Gly Gln Gly Thr Leu Ala Ser Leu Leu Gln Ser Gly Arg Gln Ala Ala
                85                  90                  95

Lys Gln Asp Pro Glu Ala Val Lys Pro Leu Asp His Leu Val Pro Val
            100                 105                 110

Val Leu Gly Pro Met Gly Leu Thr Ala Lys Glu Gln Arg Val Val Lys
        115                 120                 125

Leu Asp Pro Ser Gln Pro Ala Val Gly Asn Leu Thr Pro Val Val Leu
    130                 135                 140

Gly Pro Glu Glu Leu Trp Pro Ala Arg Leu Lys Pro Glu Val Leu Arg
145                 150                 155                 160

Pro Glu Thr Pro Arg Pro Val Asp Ile Gly Ser Gly Gly Ala His Asp
                165                 170                 175

Val Cys Val Pro Gly Lys Ile Arg Gly His Ala Asp Met Ala Tyr Thr
            180                 185                 190

Leu Asp Ser Asp Pro Cys Gly His Cys Leu Ile Ile Asn Asn Val Asn
        195                 200                 205

Phe Cys Pro Ser Ser Gly Leu Gly Thr Arg Thr Gly Ser Asn Leu Asp
    210                 215                 220

Arg Asp Lys Leu Glu His Arg Phe Arg Trp Leu Arg Phe Met Val Glu
225                 230                 235                 240

Val Lys Asn Asp Leu Thr Ala Lys Lys Met Val Thr Ala Leu Met Glu
                245                 250                 255

Met Ala His Arg Asn His Arg Ala Leu Asp Cys Phe Val Val Val Ile
            260                 265                 270

Leu Ser His Gly Cys Gln Ala Ser His Leu Gln Phe Pro Gly Ala Val
        275                 280                 285

Tyr Gly Thr Asp Gly Cys Ser Val Ser Ile Glu Lys Ile Val Asn Ile
    290                 295                 300

Phe Asn Gly Ser Gly Cys Pro Ser Leu Gly Gly Lys Pro Lys Leu Phe
305                 310                 315                 320

Phe Ile Gln Ala Cys Gly Gly Glu Gln Lys Asp His Gly Phe Glu Val
                325                 330                 335

Ala Cys Thr Ser Ser Gln Gly Arg Thr Leu Asp Ser Asp Ser Glu Pro
            340                 345                 350

Asp Ala Val Pro Tyr Gln Glu Gly Pro Arg Pro Leu Asp Gln Leu Asp
        355                 360                 365

Ala Val Ser Ser Leu Pro Thr Pro Ser Asp Ile Leu Val Ser Tyr Ser
    370                 375                 380

Thr Phe Pro Gly Phe Val Ser Trp Arg Asp Lys Lys Ser Gly Ser Trp
385                 390                 395                 400

Tyr Ile Glu Thr Leu Asp Gly Ile Leu Glu Gln Trp Ala Arg Ser Glu
                405                 410                 415

Asp Leu Gln Ser Leu Leu Leu Arg Val Ala Asn Ala Val Ser Ala Lys
            420                 425                 430

Gly Thr Tyr Lys Gln Ile Pro Gly Cys Phe Asn Phe Leu Arg Lys Lys
        435                 440                 445

Leu Phe Phe Lys Thr Ser Val Glu Pro Ser Ala Gly Asp Met Arg Ala
    450                 455                 460
```

Ala Asn Leu Trp Pro Ser Pro Leu Met Ile Lys Arg Ser Lys Lys Asn
465 470 475 480

Ser Leu Ala Leu Ser Leu Thr Ala Asp Gln Met Val Ser Ala Leu Leu
485 490 495

Asp Ala Glu Pro Pro Ile Leu Tyr Ser Glu Tyr Asp Pro Thr Arg Pro
500 505 510

Phe Ser Glu Ala Ser Met Met Gly Leu Leu Thr Asn Leu Ala Asp Arg
515 520 525

Glu Leu Val His Met Ile Asn Trp Ala Lys Arg Val Pro Gly Phe Val
530 535 540

Asp Leu Thr Leu His Asp Gln Val His Leu Leu Glu Cys Ala Trp Leu
545 550 555 560

Glu Ile Leu Met Ile Gly Leu Val Trp Arg Ser Met Glu His Pro Val
565 570 575

Lys Leu Leu Phe Ala Pro Asn Leu Leu Leu Asp Arg Asn Gln Gly Lys
580 585 590

Cys Val Glu Gly Met Val Glu Ile Phe Asp Met Leu Leu Ala Thr Ser
595 600 605

Ser Arg Phe Arg Met Met Asn Leu Gln Gly Glu Glu Phe Val Cys Leu
610 615 620

Lys Ser Ile Ile Leu Leu Asn Ser Gly Val Tyr Thr Phe Leu Ser Ser
625 630 635 640

Thr Leu Lys Ser Leu Glu Glu Lys Asp His Ile His Arg Val Leu Asp
645 650 655

Lys Ile Thr Asp Thr Leu Ile His Leu Met Ala Lys Ala Gly Leu Thr
660 665 670

Leu Gln Gln Gln His Gln Arg Leu Ala Gln Leu Leu Leu Ile Leu Ser
675 680 685

His Ile Arg His Met Ser Asn Lys Gly Met Glu His Leu Tyr Ser Met
690 695 700

Lys Cys Lys Asn Val Val Pro Leu Tyr Asp Leu Leu Leu Glu Ala Ala
705 710 715 720

Asp Ala His Arg Leu His Ala Pro Thr Ser Arg Gly Gly Ala Ser Val
725 730 735

Glu Glu Thr Asp Gln Ser His Leu Ala Thr Ala Gly Ser Thr Ser Ser
740 745 750

His Ser Leu Gln Lys Tyr Tyr Ile Thr Gly Glu Ala Glu Gly Phe Pro
755 760 765

Ala Thr Ala
770

<210> SEQ ID NO 30
<211> LENGTH: 6729
<212> TYPE: DNA
<213> ORGANISM: Artificial sequence
<220> FEATURE:
<223> OTHER INFORMATION: vector pCAG-Casp9trunc-ER(T2)-bpA

<400> SEQUENCE: 30
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcaggcgcc 240
attcgccatt caggctgcgc aactgttggg aagggcgatc ggtgcgggcc tcttcgctat 300
tacgccagct ggcgaaaggg ggatgtgctg caaggcgatt aagttgggta acgccagggt 360
tttcccagtc acgacgttgt aaaacgacgg ccagtgaatt cgagctcggt acccgggggc 420
gcgccggatc tcgacattga ttattgacta gttattaata gtaatcaatt acggggtcat 480
tagttcatag cccatatatg gagttccgcg ttacataact tacggtaaat ggcccgcctg 540
gctgaccgcc caacgacccc cgcccattga cgtcaataat gacgtatgtt cccatagtaa 600
cgccaatagg gactttccat tgacgtcaat gggtggacta tttacggtaa actgcccact 660
tggcagtaca tcaagtgtat catatgccaa gtacgccccc tattgacgtc aatgacggta 720
aatggcccgc ctggcattat gcccagtaca tgaccttatg ggactttcct acttggcagt 780
acatctacgt attagtcatc gctattacca tgggtcgagg tgagccccac gttctgcttc 840
actctcccca tctccccccc ctccccaccc ccaattttgt atttatttat tttttaatta 900
ttttgtgcag cgatgggggc gggggggggg ggggcgcgcg ccaggcgggg cggggcgggg 960
cgaggggcgg ggcggggcga ggcggagagg tgcggcggca gccaatcaga gcggcgcgct 1020
ccgaaagttt ccttttatgg cgaggcggcg gcggcggcgg ccctataaaa agcgaagcgc 1080
gcggcgggcg ggagtcgctg cgttgccttc gccccgtgcc ccgctccgcg ccgcctcgcg 1140
ccgcccgccc cggctctgac tgaccgcgtt actcccacag gtgagcgggc gggacggccc 1200
ttctcctccg ggctgtaatt agcgcttggt ttaatgacgg ctcgtttctt ttctgtggct 1260
gcgtgaaagc cttaaagggc tccgggaggg ccctttgtgc ggggggggagc ggctcggggg 1320
gtgcgtgcgt gtgtgtgtgc gtggggagcg ccgcgtgcgg cccgcgctgc ccggcggctg 1380
tgagcgctgc gggcgcggcg cggggctttg tgcgctccgc gtgtgcgcga ggggagcgcg 1440
gccgggggcg gtgccccgcg gtgcgggggg gctgcgaggg gaacaaaggc tgcgtgcggg 1500
gtgtgtgcgt gggggggtga gcagggggtg tgggcgcggc ggtcgggctg taaccccccc 1560
ctgcaccccc ctccccgagt tgctgagcac ggcccggctt cgggtgcggg gctccgtgcg 1620
gggcgtggcg cggggctcgc cgtgccgggc ggggggtggc ggcaggtggg ggtgccgggc 1680
ggggcggggc cgcctcgggc cggggagggc tcgggggagg ggcgcggcgg ccccggagcg 1740
ccggcggctg tcgaggcgcg gcgagccgca gccattgcct tttatggtaa tcgtgcgaga 1800
gggcgcaggg acttcctttg tcccaaatct ggcggagccg aaatctggga ggcgccgccg 1860
caccccctct agcgggcgcg ggcgaagcgg tgcggcgccg gcaggaagga aatgggcggg 1920
gagggccttc gtgcgtcgcc gcgccgccgt ccccttctcc atctccagcc tcggggctgc 1980
cgcaggggga cggctgcctt cgggggggac ggggcagggc ggggttcggc ttctggcgtg 2040
tgaccggcgg ctctagagcc tctgctaacc atgttcatgc cttcttcttt ttcctacaga 2100
tccttaatta attccaccat gggtcggcaa gcagccaagc aggatccaga ggctgttaaa 2160
cccctagacc acctggtgcc tgtggtcctg ggaccaatgg gactcacagc aaaggagcag 2220
agagtagtga agctggaccc gtcacagcct gccgtgggaa acctcacccc agtggtgctg 2280
gggccagaag agctctggcc tgctcggctc aagccagagg ttctcagacc agaaacaccc 2340
aggcccgtgg acattggttc tggcggagct catgatgtct gtgttccagg gaagatcagg 2400
ggacatgcag atatggcata caccctggat tcggatccct gtggccactg cctcatcatc 2460
aacaatgtga acttctgccc ttcctcgggg ctcggcacac gcacgggctc caacttggac 2520
cgtgacaaac tcgagcaccg attccgctgg ctgcgcttca tggtggaggt gaagaacgac 2580
ctgactgcca agaaaatggt cacggctttg atggagatgg cacaccggaa ccaccgtgcc 2640
ctggactgct ttgtggtggt catcctctct catggctgcc aggccagcca cctccagttc 2700

-continued

```
ccgggtgctg tctatgggac agatggatgc tccgtgtcca ttgagaaaat tgtgaatatc   2760
ttcaacggga gcggctgccc cagcctggga gggaagccca agctcttctt catccaggcc   2820
tgcggtggtg agcagaaaga ccatggcttt gaggtggcct gcacttcctc tcaaggcagg   2880
accttggaca gtgactctga gccagatgct gtcccctatc aggaaggccc aaggcccttg   2940
gaccagctgg atgctgtgtc aagtttgcct acccccagtg acatccttgt gtcctactcc   3000
accttcccag gttttgtctc ctggagggac aagaaaagtg gctcctggta catcgagacc   3060
ttggatggca ttctggagca gtgggctcgc tctgaagacc tgcagtccct ccttctcagg   3120
gttgccaatg ctgtttctgc gaaagggact tacaagcaga ttcctggctg ttttaacttc   3180
ctccggaaaa agctgttttt taaaacttca gtcgagccat ctgctggaga catgagagct   3240
gccaaccttt ggccaagccc gctcatgatc aaacgctcta agaagaacag cctggccttg   3300
tccctgacgg ccgaccagat ggtcagtgcc ttgttggatg ctgagccccc catactctat   3360
tccgagtatg atcctaccag acccttcagt gaagcttcga tgatgggctt actgaccaac   3420
ctggcagaca gggagctggt tcacatgatc aactgggcga agagggtgcc aggctttgtg   3480
gatttgaccc tccatgatca ggtccacctt ctagaatgtg cctggctaga gatcctgatg   3540
attggtctcg tctggcgctc catggagcac ccagtgaagc tactgtttgc tcctaacttg   3600
ctcttggaca ggaaccaggg aaaatgtgta gagggcatgg tggagatctt cgacatgctg   3660
ctggctacat catctcggtt ccgcatgatg aatctgcagg gagaggagtt tgtgtgcctc   3720
aaatctatta ttttgcttaa ttctggagtg tacacatttc tgtccagcac cctgaagtct   3780
ctggaagaga aggaccatat ccaccgagtc ctggacaaga tcacagacac tttgatccac   3840
ctgatggcca aggcaggcct gaccctgcag cagcagcacc agcggctggc ccagctcctc   3900
ctcatcctct cccacatcag gcacatgagt aacaaaggca tggagcatct gtacagcatg   3960
aagtgcaaga acgtggtgcc cctctatgac ctgctgctgg aggcggcgga cgcccaccgc   4020
ctacatgcgc ccactagccg tggaggggca tccgtggagg agacggacca aagccacttg   4080
gccactgcgg gctctacttc atcgcattcc ttgcaaaagt attacatcac gggggaggca   4140
gagggtttcc ctgccacagc ttgatgaaga tctgagctcc ctggcggaat tgcgtaaatg   4200
attgcagatc cactagttct agagctcgct gatcagcctc gactgtgcct tctagttgcc   4260
agccatctgt tgtttgcccc tcccccgtgc cttccttgac cctggaaggt gccactccca   4320
ctgtcctttc ctaataaaat gaggaaattg catcgcattg tctgagtagg tgtcattcta   4380
ttctgggggg tggggtgggg caggacagca agggggagga ttgggaagac aatagcaggc   4440
atgctgggga tgcggtgggc tctatggctt ctgaggcgga aagaaccaga agcttggcgt   4500
aatcatggtc atagctgttt cctgtgtgaa attgttatcc gctcacaatt ccacacaaca   4560
tacgagccgg aagcataaag tgtaaagcct ggggtgccta atgagtgagc taactcacat   4620
taattgcgtt gcgctcactg cccgctttcc agtcgggaaa cctgtcgtgc cagctgcatt   4680
aatgaatcgg ccaacgcgcg gggagaggcg gtttgcgtat tgggcgctct tccgcttcct   4740
cgctcactga ctcgctgcgc tcggtcgttc ggctgcggcg agcggtatca gctcactcaa   4800
aggcggtaat acggttatcc acagaatcag gggataacgc aggaaagaac atgtgagcaa   4860
aaggccagca aaaggccagg aaccgtaaaa aggccgcgtt gctggcgttt ttccataggc   4920
tccgcccccc tgacgagcat cacaaaaatc gacgctcaag tcagaggtgg cgaaacccga   4980
caggactata aagataccag gcgtttcccc ctggaagctc cctcgtgcgc tctcctgttc   5040
cgaccctgcc gcttaccgga tacctgtccg cctttctccc ttcgggaagc gtggcgcttt   5100
```

ctcatagctc acgctgtagg tatctcagtt cggtgtaggt cgttcgctcc aagctgggct 5160
gtgtgcacga acccccgtt cagcccgacc gctgcgcctt atccggtaac tatcgtcttg 5220
agtccaaccc ggtaagacac gacttatcgc cactggcagc agccactggt aacaggatta 5280
gcagagcgag gtatgtaggc ggtgctacag agttcttgaa gtggtggcct aactacggct 5340
acactagaag gacagtattt ggtatctgcg ctctgctgaa gccagttacc ttcggaaaaa 5400
gagttggtag ctcttgatcc ggcaaacaaa ccaccgctgg tagcggtggt tttttgttt 5460 gcaagcagca gattacgcgc agaaaaaaag gatctcaaga agatcctttg atcttttcta 5520
cggggtctga cgctcagtgg aacgaaaact cacgttaagg gattttggtc atgagattat 5580
caaaaaggat cttcacctag atccttttaa attaaaaatg aagttttaaa tcaatctaaa 5640
gtatatatga gtaaacttgg tctgacagtt accaatgctt aatcagtgag gcacctatct 5700
cagcgatctg tctatttcgt tcatccatag ttgcctgact ccccgtcgtg tagataacta 5760
cgatacggga gggcttacca tctggcccca gtgctgcaat gataccgcga gacccacgct 5820
caccggctcc agatttatca gcaataaacc agccagccgg aagggccgag cgcagaagtg 5880
gtcctgcaac tttatccgcc tccatccagt ctattaattg ttgccgggaa gctagagtaa 5940
gtagttcgcc agttaatagt ttgcgcaacg ttgttgccat tgctacaggc atcgtggtgt 6000
cacgctcgtc gtttggtatg gcttcattca gctccggttc ccaacgatca aggcgagtta 6060
catgatcccc catgttgtgc aaaaaagcgg ttagctcctt cggtcctccg atcgttgtca 6120
gaagtaagtt ggccgcagtg ttatcactca tggttatggc agcactgcat aattctctta 6180
ctgtcatgcc atccgtaaga tgcttttctg tgactggtga gtactcaacc aagtcattct 6240
gagaatagtg tatgcggcga ccgagttgct cttgcccggc gtcaatacgg gataataccg 6300
cgccacatag cagaacttta aaagtgctca tcattggaaa acgttcttcg gggcgaaaac 6360
tctcaaggat cttaccgctg ttgagatcca gttcgatgta acccactcgt gcacccaact 6420
gatcttcagc atcttttact ttcaccagcg tttctgggtg agcaaaaaca ggaaggcaaa 6480
atgccgcaaa aaagggaata agggcgacac ggaaatgttg aatactcata ctcttccttt 6540
ttcaatatta ttgaagcatt tatcagggtt attgtctcat gagcggatac atatttgaat 6600
gtatttagaa aaataaacaa ataggggttc cgcgcacatt tccccgaaaa gtgccacctg 6660
acgtctaaga aaccattatt atcatgacat taacctataa aaataggcgt atcacgaggc 6720
cctttcgtc 6729

<210> SEQ ID NO 31
<211> LENGTH: 2046
<212> TYPE: DNA
<213> ORGANISM: Artificial sequence
<220> FEATURE:
<223> OTHER INFORMATION: DNA sequence coding for fusion protein
Casp9trunc-ER(T2)

<400> SEQUENCE: 31
atgggtcggc aagcagccaa gcaggatcca gaggctgtta aacccctaga ccacctggtg 60
cctgtggtcc tgggaccaat gggactcaca gcaaaggagc agagagtagt gaagctggac 120
ccgtcacagc ctgccgtggg aaacctcacc ccagtggtgc tggggccaga agagctctgg 180
cctgctcggc tcaagccaga ggttctcaga ccagaaacac ccaggcccgt ggacattggt 240
tctggcggag ctcatgatgt ctgtgttcca gggaagatca ggggacatgc agatatggca 300
tacaccctgg attcggatcc ctgtggccac tgcctcatca tcaacaatgt gaacttctgc 360

-continued

```
ccttcctcgg ggctcggcac acgcacgggc tccaacttgg accgtgacaa actcgagcac    420

cgattccgct ggctgcgctt catggtggag gtgaagaacg acctgactgc caagaaaatg    480

gtcacggctt tgatggagat ggcacaccgg aaccaccgtg ccctggactg ctttgtggtg    540

gtcatcctct ctcatggctg ccaggccagc cacctccagt tcccgggtgc tgtctatggg    600

acagatggat gctccgtgtc cattgagaaa attgtgaata tcttcaacgg gagcggctgc    660

cccagcctgg gagggaagcc caagctcttc ttcatccagg cctgcggtgg tgagcagaaa    720

gaccatggct ttgaggtggc ctgcacttcc tctcaaggca ggaccttgga cagtgactct    780

gagccagatg ctgtccccta tcaggaaggc ccaaggccct tggaccagct ggatgctgtg    840

tcaagtttgc ctacccccag tgacatcctt gtgtcctact ccaccttccc aggttttgtc    900

tcctggaggg acaagaaaag tggctcctgg tacatcgaga ccttggatgg cattctggag    960

cagtgggctc gctctgaaga cctgcagtcc ctccttctca gggttgccaa tgctgtttct   1020

gcgaaaggga cttacaagca gattcctggc tgttttaact tcctccggaa aaagctgttt   1080

tttaaaactt cagtcgagcc atctgctgga gacatgagag ctgccaacct ttggccaagc   1140

ccgctcatga tcaaacgctc taagaagaac agcctggcct tgtccctgac ggccgaccag   1200

atggtcagtg ccttgttgga tgctgagccc cccatactct attccgagta tgatcctacc   1260

agacccttca gtgaagcttc gatgatgggc ttactgacca acctggcaga cagggagctg   1320

gttcacatga tcaactgggc gaagagggtg ccaggctttg tggatttgac cctccatgat   1380

caggtccacc ttctagaatg tgcctggcta gagatcctga tgattggtct cgtctggcgc   1440

tccatggagc acccagtgaa gctactgttt gctcctaact tgctcttgga caggaaccag   1500

ggaaaatgtg tagagggcat ggtggagatc ttcgacatgc tgctggctac atcatctcgg   1560

ttccgcatga tgaatctgca gggagaggag tttgtgtgcc tcaaatctat tattttgctt   1620

aattctggag tgtacacatt tctgtccagc accctgaagt ctctggaaga gaaggaccat   1680

atccaccgag tcctggacaa gatcacagac actttgatcc acctgatggc caaggcaggc   1740

ctgaccctgc agcagcagca ccagcggctg gcccagctcc tcctcatcct ctcccacatc   1800

aggcacatga gtaacaaagg catggagcat ctgtacagca tgaagtgcaa gaacgtggtg   1860

cccctctatg acctgctgct ggaggcggcg gacgcccacc gcctacatgc gcccactagc   1920

cgtggagggg catccgtgga ggagacggac caaagccact tggccactgc gggctctact   1980

tcatcgcatt ccttgcaaaa gtattacatc acgggggagg cagagggttt ccctgccaca   2040

gcttga                                                              2046
```

```
<210> SEQ ID NO 32
<211> LENGTH: 681
<212> TYPE: PRT
<213> ORGANISM: Artificial sequence
<220> FEATURE:
<223> OTHER INFORMATION: fusion protein Casp9trunc-ER(T2)

<400> SEQUENCE: 32

Met Gly Arg Gln Ala Ala Lys Gln Asp Pro Glu Ala Val Lys Pro Leu
1               5                   10                  15

Asp His Leu Val Pro Val Val Leu Gly Pro Met Gly Leu Thr Ala Lys
            20                  25                  30

Glu Gln Arg Val Val Lys Leu Asp Pro Ser Gln Pro Ala Val Gly Asn
        35                  40                  45

Leu Thr Pro Val Val Leu Gly Pro Glu Glu Leu Trp Pro Ala Arg Leu
    50                  55                  60
```

-continued

```
Lys Pro Glu Val Leu Arg Pro Glu Thr Pro Arg Pro Val Asp Ile Gly
65                  70                  75                  80

Ser Gly Gly Ala His Asp Val Cys Val Pro Gly Lys Ile Arg Gly His
                85                  90                  95

Ala Asp Met Ala Tyr Thr Leu Asp Ser Asp Pro Cys Gly His Cys Leu
            100                 105                 110

Ile Ile Asn Asn Val Asn Phe Cys Pro Ser Ser Gly Leu Gly Thr Arg
        115                 120                 125

Thr Gly Ser Asn Leu Asp Arg Asp Lys Leu Glu His Arg Phe Arg Trp
    130                 135                 140

Leu Arg Phe Met Val Glu Val Lys Asn Asp Leu Thr Ala Lys Lys Met
145                 150                 155                 160

Val Thr Ala Leu Met Glu Met Ala His Arg Asn His Arg Ala Leu Asp
                165                 170                 175

Cys Phe Val Val Val Ile Leu Ser His Gly Cys Gln Ala Ser His Leu
            180                 185                 190

Gln Phe Pro Gly Ala Val Tyr Gly Thr Asp Gly Cys Ser Val Ser Ile
        195                 200                 205

Glu Lys Ile Val Asn Ile Phe Asn Gly Ser Gly Cys Pro Ser Leu Gly
    210                 215                 220

Gly Lys Pro Lys Leu Phe Phe Ile Gln Ala Cys Gly Gly Glu Gln Lys
225                 230                 235                 240

Asp His Gly Phe Glu Val Ala Cys Thr Ser Ser Gln Gly Arg Thr Leu
                245                 250                 255

Asp Ser Asp Ser Glu Pro Asp Ala Val Pro Tyr Gln Glu Gly Pro Arg
            260                 265                 270

Pro Leu Asp Gln Leu Asp Ala Val Ser Ser Leu Pro Thr Pro Ser Asp
        275                 280                 285

Ile Leu Val Ser Tyr Ser Thr Phe Pro Gly Phe Val Ser Trp Arg Asp
    290                 295                 300

Lys Lys Ser Gly Ser Trp Tyr Ile Glu Thr Leu Asp Gly Ile Leu Glu
305                 310                 315                 320

Gln Trp Ala Arg Ser Glu Asp Leu Gln Ser Leu Leu Leu Arg Val Ala
                325                 330                 335

Asn Ala Val Ser Ala Lys Gly Thr Tyr Lys Gln Ile Pro Gly Cys Phe
            340                 345                 350

Asn Phe Leu Arg Lys Lys Leu Phe Phe Lys Thr Ser Val Glu Pro Ser
        355                 360                 365

Ala Gly Asp Met Arg Ala Ala Asn Leu Trp Pro Ser Pro Leu Met Ile
    370                 375                 380

Lys Arg Ser Lys Lys Asn Ser Leu Ala Leu Ser Leu Thr Ala Asp Gln
385                 390                 395                 400

Met Val Ser Ala Leu Leu Asp Ala Glu Pro Pro Ile Leu Tyr Ser Glu
                405                 410                 415

Tyr Asp Pro Thr Arg Pro Phe Ser Glu Ala Ser Met Met Gly Leu Leu
            420                 425                 430

Thr Asn Leu Ala Asp Arg Glu Leu Val His Met Ile Asn Trp Ala Lys
        435                 440                 445

Arg Val Pro Gly Phe Val Asp Leu Thr Leu His Asp Gln Val His Leu
    450                 455                 460

Leu Glu Cys Ala Trp Leu Glu Ile Leu Met Ile Gly Leu Val Trp Arg
465                 470                 475                 480

Ser Met Glu His Pro Val Lys Leu Leu Phe Ala Pro Asn Leu Leu Leu
                485                 490                 495
```

-continued

```
Asp Arg Asn Gln Gly Lys Cys Val Glu Gly Met Val Glu Ile Phe Asp
            500                 505                 510

Met Leu Leu Ala Thr Ser Ser Arg Phe Arg Met Met Asn Leu Gln Gly
        515                 520                 525

Glu Glu Phe Val Cys Leu Lys Ser Ile Ile Leu Leu Asn Ser Gly Val
    530                 535                 540

Tyr Thr Phe Leu Ser Ser Thr Leu Lys Ser Leu Glu Glu Lys Asp His
545                 550                 555                 560

Ile His Arg Val Leu Asp Lys Ile Thr Asp Thr Leu Ile His Leu Met
                565                 570                 575

Ala Lys Ala Gly Leu Thr Leu Gln Gln Gln His Gln Arg Leu Ala Gln
            580                 585                 590

Leu Leu Leu Ile Leu Ser His Ile Arg His Met Ser Asn Lys Gly Met
        595                 600                 605

Glu His Leu Tyr Ser Met Lys Cys Lys Asn Val Val Pro Leu Tyr Asp
    610                 615                 620

Leu Leu Leu Glu Ala Ala Asp Ala His Arg Leu His Ala Pro Thr Ser
625                 630                 635                 640

Arg Gly Gly Ala Ser Val Glu Glu Thr Asp Gln Ser His Leu Ala Thr
                645                 650                 655

Ala Gly Ser Thr Ser Ser His Ser Leu Gln Lys Tyr Tyr Ile Thr Gly
            660                 665                 670

Glu Ala Glu Gly Phe Pro Ala Thr Ala
        675                 680


<210> SEQ ID NO 33
<211> LENGTH: 37
<212> TYPE: DNA
<213> ORGANISM: Artificial sequence
<220> FEATURE:
<223> OTHER INFORMATION: primer Casp3ER-A

<400> SEQUENCE: 33

ccttaattaa ttccaccatg gagaacaaca aaacctc                              37


<210> SEQ ID NO 34
<211> LENGTH: 30
<212> TYPE: DNA
<213> ORGANISM: Artificial sequence
<220> FEATURE:
<223> OTHER INFORMATION: primer Casp3ER-B

<400> SEQUENCE: 34

ggctcgaggt gataaaagta cagttctttc                                      30


<210> SEQ ID NO 35
<211> LENGTH: 6468
<212> TYPE: DNA
<213> ORGANISM: Artificial sequence
<220> FEATURE:
<223> OTHER INFORMATION: vector pCAG-Casp3-ER(T2)-bpA

<400> SEQUENCE: 35

tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accatatgcg gtgtgaaata ccgcacagat gcgtaaggag aaaataccgc atcaggcgcc    240

attcgccatt caggctgcgc aactgttggg aagggcgatc ggtgcgggcc tcttcgctat    300
```

-continued

```
tacgccagct ggcgaaaggg ggatgtgctg caaggcgatt aagttgggta acgccagggt    360
tttcccagtc acgacgttgt aaaacgacgg ccagtgaatt cgagctcggt acccgggggc    420
gcgccggatc tcgacattga ttattgacta gttattaata gtaatcaatt acggggtcat    480
tagttcatag cccatatatg gagttccgcg ttacataact tacggtaaat ggcccgcctg    540
gctgaccgcc caacgacccc cgcccattga cgtcaataat gacgtatgtt cccatagtaa    600
cgccaatagg gactttccat tgacgtcaat gggtggacta tttacggtaa actgcccact    660
tggcagtaca tcaagtgtat catatgccaa gtacgccccc tattgacgtc aatgacggta    720
aatggcccgc ctggcattat gcccagtaca tgaccttatg ggactttcct acttggcagt    780
acatctacgt attagtcatc gctattacca tgggtcgagg tgagccccac gttctgcttc    840
actctcccca tctccccccc ctccccaccc ccaattttgt atttatttat tttttaatta    900
ttttgtgcag cgatgggggc gggggggggg ggggcgcgcg ccaggcgggg cggggcgggg    960
cgaggggcgg ggcggggcga ggcggagagg tgcggcggca gccaatcaga gcggcgcgct   1020
ccgaaagttt ccttttatgg cgaggcggcg gcggcggcgg ccctataaaa agcgaagcgc   1080
gcggcgggcg ggagtcgctg cgttgccttc gccccgtgcc ccgctccgcg ccgcctcgcg   1140
ccgcccgccc cggctctgac tgaccgcgtt actcccacag gtgagcgggc gggacggccc   1200
ttctcctccg ggctgtaatt agcgcttggt ttaatgacgg ctcgtttctt ttctgtggct   1260
gcgtgaaagc cttaaagggc tccgggaggg ccctttgtgc ggggggggagc ggctcggggg   1320
gtgcgtgcgt gtgtgtgtgc gtggggagcg ccgcgtgcgg cccgcgctgc ccggcggctg   1380
tgagcgctgc gggcgcggcg cggggctttg tgcgctccgc gtgtgcgcga ggggagcgcg   1440
gccgggggcg gtgccccgcg gtgcgggggg gctgcgaggg gaacaaaggc tgcgtgcggg   1500
gtgtgtgcgt ggggggggtga gcagggggtg tgggcgcggc ggtcgggctg taaccccccc   1560
ctgcaccccc ctccccgagt tgctgagcac ggcccggctt cgggtgcggg gctccgtgcg   1620
gggcgtggcg cggggctcgc cgtgccgggc ggggggtggc ggcaggtggg ggtgccgggc   1680
ggggcggggc cgcctcgggc cggggagggc tcgggggagg ggcgcggcgg ccccggagcg   1740
ccggcggctg tcgaggcgcg gcgagccgca gccattgcct tttatggtaa tcgtgcgaga   1800
gggcgcaggg acttcctttg tcccaaatct ggcggagccg aaatctggga ggcgccgccg   1860
caccccctct agcgggcgcg ggcgaagcgg tgcggcgccg gcaggaagga aatgggcggg   1920
gagggccttc gtgcgtcgcc gcgccgccgt ccccttctcc atctccagcc tcggggctgc   1980
cgcagggggga cggctgcctt cgggggggac ggggcagggc ggggttcggc ttctggcgtg   2040
tgaccggcgg ctctagagcc tctgctaacc atgttcatgc cttcttcttt ttcctacaga   2100
tccttaatta attccaccat ggagaacaac aaaacctcag tggattcaaa atccattaat   2160
aattttgaag taaagaccat acatgggagc aagtcagtgg actctgggat ctatctggac   2220
agtagttaca aaatggatta tcctgaaatg ggcatatgca taataattaa taataagaac   2280
ttccataaga gcactggaat gtcatctcgc tctggtacgg atgtggacgc agccaacctc   2340
agagagacat tcatgggcct gaaataccaa gtcaggaata aaaatgatct tactcgtgaa   2400
gacattttgg aattaatgga tagtgtttct aaggaagatc atagcaaaag gagcagcttt   2460
gtgtgtgtga ttctaagcca tggtgatgaa ggggtcattt atgggacaaa tgggcctgtt   2520
gaactgaaaa agttgactag cttcttcaga ggcgactact gccggagtct gactggaaag   2580
ccgaaactct tcatcattca ggcctgccgg ggtacggagc tggactgtgg cattgagaca   2640
gacagtggga ctgatgagga gatggcttgc cagaagatac cggtggaggc tgacttcctg   2700
```

-continued

```
tatgcttact ctacagcacc tggttactat tcctggagaa attcaaagga cgggtcgtgg   2760
ttcatccagt ccctttgcag catgctgaag ctgtacgcgc acaagctaga atttatgcac   2820
attctcactc gcgttaacag gaaggtggca acggaattcg agtccttctc cctggactcc   2880
actttccacg caaagaaaca gatcccgtgt attgtgtcca tgctcacgaa agaactgtac   2940
ttttatcacc tcgagccatc tgctggagac atgagagctg ccaacctttg gccaagcccg   3000
ctcatgatca aacgctctaa gaagaacagc ctggccttgt ccctgacggc cgaccagatg   3060
gtcagtgcct tgttggatgc tgagcccccc atactctatt ccgagtatga tcctaccaga   3120
cccttcagtg aagcttcgat gatgggctta ctgaccaacc tggcagacag ggagctggtt   3180
cacatgatca actgggcgaa gagggtgcca ggctttgtgg atttgaccct ccatgatcag   3240
gtccaccttc tagaatgtgc ctggctagag atcctgatga ttggtctcgt ctggcgctcc   3300
atggagcacc cagtgaagct actgtttgct cctaacttgc tcttggacag gaaccaggga   3360
aaatgtgtag agggcatggt ggagatcttc gacatgctgc tggctacatc atctcggttc   3420
cgcatgatga atctgcaggg agaggagttt gtgtgcctca aatctattat tttgcttaat   3480
tctggagtgt acacatttct gtccagcacc ctgaagtctc tggaagagaa ggaccatatc   3540
caccgagtcc tggacaagat cacagacact ttgatccacc tgatggccaa ggcaggcctg   3600
accctgcagc agcagcacca gcggctggcc cagctcctcc tcatcctctc ccacatcagg   3660
cacatgagta acaaaggcat ggagcatctg tacagcatga agtgcaagaa cgtggtgccc   3720
ctctatgacc tgctgctgga ggcggcggac gcccaccgcc tacatgcgcc cactagccgt   3780
ggaggggcat ccgtggagga gacggaccaa agccacttgg ccactgcggg ctctacttca   3840
tcgcattcct tgcaaaagta ttacatcacg gggggaggcag agggtttccc tgccacagct   3900
tgatgaagat ctgagctccc tggcggaatt gcgtaaatga ttgcagatcc actagttcta   3960
gagctcgctg atcagcctcg actgtgcctt ctagttgcca gccatctgtt gtttgcccct   4020
cccccgtgcc ttccttgacc ctggaaggtg ccactcccac tgtcctttcc taataaaatg   4080
aggaaattgc atcgcattgt ctgagtaggt gtcattctat tctggggggt ggggtggggc   4140
aggacagcaa gggggaggat tgggaagaca atagcaggca tgctggggat gcggtgggct   4200
ctatggcttc tgaggcggaa agaaccagaa gcttggcgta atcatggtca tagctgtttc   4260
ctgtgtgaaa ttgttatccg ctcacaattc cacacaacat acgagccgga agcataaagt   4320
gtaaagcctg gggtgcctaa tgagtgagct aactcacatt aattgcgttg cgctcactgc   4380
ccgctttcca gtcgggaaac ctgtcgtgcc agctgcatta atgaatcggc caacgcgcgg   4440
ggagaggcgg tttgcgtatt gggcgctctt ccgcttcctc gctcactgac tcgctgcgct   4500
cggtcgttcg gctgcggcga gcggtatcag ctcactcaaa ggcggtaata cggttatcca   4560
cagaatcagg ggataacgca ggaaagaaca tgtgagcaaa aggccagcaa aaggccagga   4620
accgtaaaaa ggccgcgttg ctggcgtttt tccataggct ccgcccccct gacgagcatc   4680
acaaaaatcg acgctcaagt cagaggtggc gaaacccgac aggactataa agataccagg   4740
cgtttccccc tggaagctcc ctcgtgcgct ctcctgttcc gaccctgccg cttaccggat   4800
acctgtccgc ctttctccct tcgggaagcg tggcgctttc tcatagctca cgctgtaggt   4860
atctcagttc ggtgtaggtc gttcgctcca agctgggctg tgtgcacgaa ccccccgttc   4920
agcccgaccg ctgcgcctta tccggtaact atcgtcttga gtccaacccg gtaagacacg   4980
acttatcgcc actggcagca gccactggta acaggattag cagagcgagg tatgtaggcg   5040
gtgctacaga gttcttgaag tggtggccta actacggcta cactagaagg acagtatttg   5100
```

```
gtatctgcgc tctgctgaag ccagttacct tcggaaaaag agttggtagc tcttgatccg   5160

gcaaacaaac caccgctggt agcggtggtt tttttgtttg caagcagcag attacgcgca   5220

gaaaaaaagg atctcaagaa gatcctttga tcttttctac ggggtctgac gctcagtgga   5280

acgaaaactc acgttaaggg attttggtca tgagattatc aaaaaggatc ttcacctaga   5340

tccttttaaa ttaaaaatga agttttaaat caatctaaag tatatatgag taaacttggt   5400

ctgacagtta ccaatgctta atcagtgagg cacctatctc agcgatctgt ctatttcgtt   5460

catccatagt tgcctgactc cccgtcgtgt agataactac gatacgggag ggcttaccat   5520

ctggccccag tgctgcaatg ataccgcgag acccacgctc accggctcca gatttatcag   5580

caataaacca gccagccgga agggccgagc gcagaagtgg tcctgcaact ttatccgcct   5640

ccatccagtc tattaattgt tgccgggaag ctagagtaag tagttcgcca gttaatagtt   5700

tgcgcaacgt tgttgccatt gctacaggca tcgtggtgtc acgctcgtcg tttggtatgg   5760

cttcattcag ctccggttcc caacgatcaa ggcgagttac atgatccccc atgttgtgca   5820

aaaaagcggt tagctccttc ggtcctccga tcgttgtcag aagtaagttg gccgcagtgt   5880

tatcactcat ggttatggca gcactgcata attctcttac tgtcatgcca tccgtaagat   5940

gcttttctgt gactggtgag tactcaacca agtcattctg agaatagtgt atgcggcgac   6000

cgagttgctc ttgcccggcg tcaatacggg ataataccgc gccacatagc agaactttaa   6060

aagtgctcat cattggaaaa cgttcttcgg ggcgaaaact ctcaaggatc ttaccgctgt   6120

tgagatccag ttcgatgtaa cccactcgtg cacccaactg atcttcagca tcttttactt   6180

tcaccagcgt ttctgggtga gcaaaaacag gaaggcaaaa tgccgcaaaa aagggaataa   6240

gggcgacacg gaaatgttga atactcatac tcttcctttt tcaatattat tgaagcattt   6300

atcagggtta ttgtctcatg agcggataca tatttgaatg tatttagaaa aataaacaaa   6360

taggggttcc gcgcacattt ccccgaaaag tgccacctga cgtctaagaa accattatta   6420

tcatgacatt aacctataaa aataggcgta tcacgaggcc ctttcgtc                6468
```

```
<210> SEQ ID NO 36
<211> LENGTH: 1785
<212> TYPE: DNA
<213> ORGANISM: Artificial sequence
<220> FEATURE:
<223> OTHER INFORMATION: DNA sequence coding for fusion gene
      Casp3-ER(T2)

<400> SEQUENCE: 36

atggagaaca acaaaacctc agtggattca aaatccatta ataattttga agtaaagacc     60

atacatggga gcaagtcagt ggactctggg atctatctgg acagtagtta caaaatggat    120

tatcctgaaa tgggcatatg cataataatt aataataaga acttccataa gagcactgga    180

atgtcatctc gctctggtac ggatgtggac gcagccaacc tcagagagac attcatgggc    240

ctgaaatacc aagtcaggaa taaaaatgat cttactcgtg aagacatttt ggaattaatg    300

gatagtgttt ctaaggaaga tcatagcaaa aggagcagct ttgtgtgtgt gattctaagc    360

catggtgatg aaggggtcat ttatgggaca aatgggcctg ttgaactgaa aaagttgact    420

agcttcttca gaggcgacta ctgccggagt ctgactggaa agccgaaact cttcatcatt    480

caggcctgcc ggggtacgga gctggactgt ggcattgaga cagacagtgg gactgatgag    540

gagatggctt gccagaagat accggtggag gctgacttcc tgtatgctta ctctacagca    600

cctggttact attcctggag aaattcaaag gacgggtcgt ggttcatcca gtccctttgc    660
```

agcatgctga agctgtacgc gcacaagcta gaatttatgc acattctcac tcgcgttaac 720
aggaaggtgg caacggaatt cgagtccttc tccctggact ccactttcca cgcaaagaaa 780
cagatcccgt gtattgtgtc catgctcacg aaagaactgt acttttatca cctcgagcca 840
tctgctggag acatgagagc tgccaacctt tggccaagcc cgctcatgat caaacgctct 900
aagaagaaca gcctggcctt gtccctgacg gccgaccaga tggtcagtgc cttgttggat 960
gctgagcccc ccatactcta ttccgagtat gatcctacca gacccttcag tgaagcttcg 1020
atgatgggct tactgaccaa cctggcagac agggagctgg ttcacatgat caactgggcg 1080
aagagggtgc caggctttgt ggatttgacc ctccatgatc aggtccacct tctagaatgt 1140
gcctggctag agatcctgat gattggtctc gtctggcgct ccatggagca cccagtgaag 1200
ctactgtttg ctcctaactt gctcttggac aggaaccagg gaaaatgtgt agagggcatg 1260
gtggagatct tcgacatgct gctggctaca tcatctcggt tccgcatgat gaatctgcag 1320
ggagaggagt ttgtgtgcct caaatctatt attttgctta attctggagt gtacacattt 1380
ctgtccagca ccctgaagtc tctggaagag aaggaccata tccaccgagt cctggacaag 1440
atcacagaca ctttgatcca cctgatggcc aaggcaggcc tgaccctgca gcagcagcac 1500
cagcggctgg cccagctcct cctcatcctc tcccacatca ggcacatgag taacaaaggc 1560
atggagcatc tgtacagcat gaagtgcaag aacgtggtgc ccctctatga cctgctgctg 1620
gaggcggcgg acgcccaccg cctacatgcg cccactagcc gtggaggggc atccgtggag 1680
gagacggacc aaagccactt ggccactgcg ggctctactt catcgcattc cttgcaaaag 1740
tattacatca cgggggaggc agagggtttc cctgccacag cttga 1785

<210> SEQ ID NO 37
<211> LENGTH: 594
<212> TYPE: PRT
<213> ORGANISM: Artificial sequence
<220> FEATURE:
<223> OTHER INFORMATION: fusion gene Casp3-ER(T2)

<400> SEQUENCE: 37

Met Glu Asn Asn Lys Thr Ser Val Asp Ser Lys Ser Ile Asn Asn Phe
1 5 10 15

Glu Val Lys Thr Ile His Gly Ser Lys Ser Val Asp Ser Gly Ile Tyr
20 25 30

Leu Asp Ser Ser Tyr Lys Met Asp Tyr Pro Glu Met Gly Ile Cys Ile
35 40 45

Ile Ile Asn Asn Lys Asn Phe His Lys Ser Thr Gly Met Ser Ser Arg
50 55 60

Ser Gly Thr Asp Val Asp Ala Ala Asn Leu Arg Glu Thr Phe Met Gly
65 70 75 80

Leu Lys Tyr Gln Val Arg Asn Lys Asn Asp Leu Thr Arg Glu Asp Ile
85 90 95

Leu Glu Leu Met Asp Ser Val Ser Lys Glu Asp His Ser Lys Arg Ser
100 105 110

Ser Phe Val Cys Val Ile Leu Ser His Gly Asp Glu Gly Val Ile Tyr
115 120 125

Gly Thr Asn Gly Pro Val Glu Leu Lys Lys Leu Thr Ser Phe Phe Arg
130 135 140

Gly Asp Tyr Cys Arg Ser Leu Thr Gly Lys Pro Lys Leu Phe Ile Ile
145 150 155 160

Gln Ala Cys Arg Gly Thr Glu Leu Asp Cys Gly Ile Glu Thr Asp Ser
165 170 175

-continued

```
Gly Thr Asp Glu Glu Met Ala Cys Gln Lys Ile Pro Val Glu Ala Asp
            180                 185                 190

Phe Leu Tyr Ala Tyr Ser Thr Ala Pro Gly Tyr Tyr Ser Trp Arg Asn
        195                 200                 205

Ser Lys Asp Gly Ser Trp Phe Ile Gln Ser Leu Cys Ser Met Leu Lys
    210                 215                 220

Leu Tyr Ala His Lys Leu Glu Phe Met His Ile Leu Thr Arg Val Asn
225                 230                 235                 240

Arg Lys Val Ala Thr Glu Phe Glu Ser Phe Ser Leu Asp Ser Thr Phe
                245                 250                 255

His Ala Lys Lys Gln Ile Pro Cys Ile Val Ser Met Leu Thr Lys Glu
            260                 265                 270

Leu Tyr Phe Tyr His Leu Glu Pro Ser Ala Gly Asp Met Arg Ala Ala
        275                 280                 285

Asn Leu Trp Pro Ser Pro Leu Met Ile Lys Arg Ser Lys Lys Asn Ser
    290                 295                 300

Leu Ala Leu Ser Leu Thr Ala Asp Gln Met Val Ser Ala Leu Leu Asp
305                 310                 315                 320

Ala Glu Pro Pro Ile Leu Tyr Ser Glu Tyr Asp Pro Thr Arg Pro Phe
                325                 330                 335

Ser Glu Ala Ser Met Met Gly Leu Leu Thr Asn Leu Ala Asp Arg Glu
            340                 345                 350

Leu Val His Met Ile Asn Trp Ala Lys Arg Val Pro Gly Phe Val Asp
        355                 360                 365

Leu Thr Leu His Asp Gln Val His Leu Leu Glu Cys Ala Trp Leu Glu
    370                 375                 380

Ile Leu Met Ile Gly Leu Val Trp Arg Ser Met Glu His Pro Val Lys
385                 390                 395                 400

Leu Leu Phe Ala Pro Asn Leu Leu Leu Asp Arg Asn Gln Gly Lys Cys
                405                 410                 415

Val Glu Gly Met Val Glu Ile Phe Asp Met Leu Leu Ala Thr Ser Ser
            420                 425                 430

Arg Phe Arg Met Met Asn Leu Gln Gly Glu Glu Phe Val Cys Leu Lys
        435                 440                 445

Ser Ile Ile Leu Leu Asn Ser Gly Val Tyr Thr Phe Leu Ser Ser Thr
    450                 455                 460

Leu Lys Ser Leu Glu Glu Lys Asp His Ile His Arg Val Leu Asp Lys
465                 470                 475                 480

Ile Thr Asp Thr Leu Ile His Leu Met Ala Lys Ala Gly Leu Thr Leu
                485                 490                 495

Gln Gln Gln His Gln Arg Leu Ala Gln Leu Leu Leu Ile Leu Ser His
            500                 505                 510

Ile Arg His Met Ser Asn Lys Gly Met Glu His Leu Tyr Ser Met Lys
        515                 520                 525

Cys Lys Asn Val Val Pro Leu Tyr Asp Leu Leu Leu Glu Ala Ala Asp
    530                 535                 540

Ala His Arg Leu His Ala Pro Thr Ser Arg Gly Gly Ala Ser Val Glu
545                 550                 555                 560

Glu Thr Asp Gln Ser His Leu Ala Thr Ala Gly Ser Thr Ser Ser His
                565                 570                 575

Ser Leu Gln Lys Tyr Tyr Ile Thr Gly Glu Ala Glu Gly Phe Pro Ala
            580                 585                 590

Thr Ala
```

<210> SEQ ID NO 38
<211> LENGTH: 6396
<212> TYPE: DNA
<213> ORGANISM: Artificial sequence
<220> FEATURE:
<223> OTHER INFORMATION: vector pCAG-Casp3-ED4ER(T2)-bpA

<400> SEQUENCE: 38
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcaggcgcc 240
attcgccatt caggctgcgc aactgttggg aagggcgatc ggtgcgggcc tcttcgctat 300
tacgccagct ggcgaaaggg ggatgtgctg caaggcgatt aagttgggta acgccagggt 360
tttcccagtc acgacgttgt aaaacgacgg ccagtgaatt cgagctcggt acccgggggc 420
gcgccggatc tcgacattga ttattgacta gttattaata gtaatcaatt acggggtcat 480
tagttcatag cccatatatg gagttccgcg ttacataact tacggtaaat ggcccgcctg 540
gctgaccgcc caacgacccc cgcccattga cgtcaataat gacgtatgtt cccatagtaa 600
cgccaatagg gactttccat tgacgtcaat gggtggacta tttacggtaa actgcccact 660
tggcagtaca tcaagtgtat catatgccaa gtacgccccc tattgacgtc aatgacggta 720
aatggcccgc ctggcattat gcccagtaca tgaccttatg ggactttcct acttggcagt 780
acatctacgt attagtcatc gctattacca tgggtcgagg tgagccccac gttctgcttc 840
actctcccca tctccccccc ctccccaccc ccaattttgt atttatttat tttttaatta 900
ttttgtgcag cgatgggggc gggggggggg ggggcgcgcg ccaggcgggg cggggcgggg 960
cgaggggcgg ggcggggcga ggcggagagg tgcggcggca gccaatcaga gcggcgcgct 1020
ccgaaagttt ccttttatgg cgaggcggcg gcggcggcgg ccctataaaa agcgaagcgc 1080
gcggcgggcg ggagtcgctg cgttgccttc gccccgtgcc ccgctccgcg ccgcctcgcg 1140
ccgcccgccc cggctctgac tgaccgcgtt actcccacag gtgagcgggc gggacggccc 1200
ttctcctccg ggctgtaatt agcgcttggt ttaatgacgg ctcgtttctt ttctgtggct 1260
gcgtgaaagc cttaaagggc tccgggaggg ccctttgtgc ggggggggagc ggctcggggg 1320 gtgcgtgcgt gtgtgtgtgc gtggggagcg ccgcgtgcgg cccgcgctgc ccggcggctg 1380
tgagcgctgc gggcgcggcg cggggctttg tgcgctccgc gtgtgcgcga ggggagcgcg 1440
gccgggggcg gtgccccgcg gtgcgggggg gctgcgaggg gaacaaaggc tgcgtgcggg 1500
gtgtgtgcgt gggggggtga gcagggggtg tgggcgcggc ggtcgggctg taaccccccc 1560
ctgcaccccc ctccccgagt tgctgagcac ggcccggctt cgggtgcggg gctccgtgcg 1620
gggcgtggcg cggggctcgc cgtgccgggc ggggggtggc ggcaggtggg ggtgccgggc 1680
ggggcggggc cgcctcgggc cggggagggc tcgggggagg ggcgcggcgg ccccggagcg 1740
ccggcggctg tcgaggcgcg gcgagccgca gccattgcct tttatggtaa tcgtgcgaga 1800
gggcgcaggg acttcctttg tcccaaatct ggcggagccg aaatctggga ggcgccgccg 1860
caccccctct agcgggcgcg ggcgaagcgg tgcggcgccg gcaggaagga aatgggcggg 1920
gagggccttc gtgcgtcgcc gcgccgccgt ccccttctcc atctccagcc tcggggctgc 1980
cgcaggggga cggctgcctt cgggggggac ggggcagggc ggggttcggc ttctggcgtg 2040
tgaccggcgg ctctagagcc tctgctaacc atgttcatgc cttcttcttt ttcctacaga 2100

-continued

```
tccttaatta attccaccat ggagaacaac aaaacctcag tggattcaaa atccattaat   2160
aattttgaag taaagaccat acatgggagc aagtcagtgg actctgggat ctatctggac   2220
agtagttaca aaatggatta tcctgaaatg ggcatatgca taataattaa taataagaac   2280
ttccataaga gcactggaat gtcatctcgc tctggtacgg atgtggacgc agccaacctc   2340
agagagacat tcatgggcct gaaataccaa gtcaggaata aaaatgatct tactcgtgaa   2400
gacattttgg aattaatgga tagtgtttct aaggaagatc atagcaaaag gagcagcttt   2460
gtgtgtgtga ttctaagcca tggtgatgaa ggggtcattt atgggacaaa tgggcctgtt   2520
gaactgaaaa agttgactag cttcttcaga ggcgactact gccggagtct gactggaaag   2580
ccgaaactct tcatcattca ggcctgccgg ggtacggagc tggactgtgg cattgagaca   2640
gacagtggga ctgatgagga gatggcttgc cagaagatac cggtggaggc tgacttcctg   2700
tatgcttact ctacagcacc tggttactat tcctggagaa attcaaagga cgggtcgtgg   2760
ttcatccagt ccctttgcag catgctgaag ctgtacgcgc acaagctaga atttatgcac   2820
attctcactc gcgttaacag gaaggtggca acggaattcg agtccttctc cctggactcc   2880
actttccacg caaagaaaca gatcccgtgt attgtgtcca tgctcacgaa agaactgtac   2940
ttttatcacc tcgagagcct ggccttgtcc ctgacggccg accagatggt cagtgccttg   3000
ttggatgctg agcccccat actctattcc gagtatgatc ctaccagacc cttcagtgaa   3060
gcttcgatga tgggcttact gaccaacctg gcagacaggg agctggttca catgatcaac   3120
tgggcgaaga gggtgccagg ctttgtggat ttgaccctcc atgatcaggt ccaccttcta   3180
gaatgtgcct ggctagagat cctgatgatt ggtctcgtct ggcgctccat ggagcaccca   3240
gtgaagctac tgtttgctcc taacttgctc ttggacagga accagggaaa atgtgtagag   3300
ggcatggtgg agatcttcga catgctgctg gctacatcat ctcggttccg catgatgaat   3360
ctgcagggag aggagtttgt gtgcctcaaa tctattattt tgcttaattc tggagtgtac   3420
acatttctgt ccagcaccct gaagtctctg gaagagaagg accatatcca ccgagtcctg   3480
gacaagatca cagacacttt gatccacctg atggccaagg caggcctgac cctgcagcag   3540
cagcaccagc ggctggccca gctcctcctc atcctctccc acatcaggca catgagtaac   3600
aaaggcatgg agcatctgta cagcatgaag tgcaagaacg tggtgcccct ctatgacctg   3660
ctgctggagg cggcggacgc ccaccgccta catgcgccca ctagccgtgg aggggcatcc   3720
gtggaggaga cggaccaaag ccacttggcc actgcgggct ctacttcatc gcattccttg   3780
caaaagtatt acatcacggg ggaggcagag ggtttccctg ccacagcttg atgaagatct   3840
gagctccctg gcggaattgc gtaaatgatt gcagatccac tagttctaga gctcgctgat   3900
cagcctcgac tgtgccttct agttgccagc catctgttgt ttgcccctcc cccgtgcctt   3960
ccttgaccct ggaaggtgcc actcccactg tcctttccta ataaaatgag gaaattgcat   4020
cgcattgtct gagtaggtgt cattctattc tggggggtgg ggtggggcag gacagcaagg   4080
gggaggattg ggaagacaat agcaggcatg ctggggatgc ggtgggctct atggcttctg   4140
aggcggaaag aaccagaagc ttggcgtaat catggtcata gctgtttcct gtgtgaaatt   4200
gttatccgct cacaattcca cacaacatac gagccggaag cataaagtgt aaagcctggg   4260
gtgcctaatg agtgagctaa ctcacattaa ttgcgttgcg ctcactgccc gctttccagt   4320
cgggaaacct gtcgtgccag ctgcattaat gaatcggcca acgcgcgggg agaggcggtt   4380
tgcgtattgg gcgctcttcc gcttcctcgc tcactgactc gctgcgctcg gtcgttcggc   4440
tgcggcgagc ggtatcagct cactcaaagg cggtaatacg gttatccaca gaatcagggg   4500
```

ataacgcagg aaagaacatg tgagcaaaag gccagcaaaa ggccaggaac cgtaaaaagg 4560
ccgcgttgct ggcgtttttc cataggctcc gcccccctga cgagcatcac aaaaatcgac 4620
gctcaagtca gaggtggcga aacccgacag gactataaag ataccaggcg tttccccctg 4680
gaagctccct cgtgcgctct cctgttccga ccctgccgct taccggatac ctgtccgcct 4740
ttctcccttc gggaagcgtg gcgctttctc atagctcacg ctgtaggtat ctcagttcgg 4800
tgtaggtcgt tcgctccaag ctgggctgtg tgcacgaacc ccccgttcag cccgaccgct 4860
gcgccttatc cggtaactat cgtcttgagt ccaacccggt aagacacgac ttatcgccac 4920
tggcagcagc cactggtaac aggattagca gagcgaggta tgtaggcggt gctacagagt 4980
tcttgaagtg gtggcctaac tacggctaca ctagaaggac agtatttggt atctgcgctc 5040
tgctgaagcc agttaccttc ggaaaaagag ttggtagctc ttgatccggc aaacaaacca 5100
ccgctggtag cggtggtttt tttgtttgca agcagcagat tacgcgcaga aaaaaaggat 5160
ctcaagaaga tcctttgatc ttttctacgg ggtctgacgc tcagtggaac gaaaactcac 5220
gttaagggat tttggtcatg agattatcaa aaaggatctt cacctagatc cttttaaatt 5280
aaaaatgaag ttttaaatca atctaaagta tatatgagta aacttggtct gacagttacc 5340
aatgcttaat cagtgaggca cctatctcag cgatctgtct atttcgttca tccatagttg 5400
cctgactccc cgtcgtgtag ataactacga tacgggaggg cttaccatct ggccccagtg 5460
ctgcaatgat accgcgagac ccacgctcac cggctccaga tttatcagca ataaaccagc 5520
cagccggaag ggccgagcgc agaagtggtc ctgcaacttt atccgcctcc atccagtcta 5580
ttaattgttg ccgggaagct agagtaagta gttcgccagt taatagtttg cgcaacgttg 5640
ttgccattgc tacaggcatc gtggtgtcac gctcgtcgtt tggtatggct tcattcagct 5700
ccggttccca acgatcaagg cgagttacat gatcccccat gttgtgcaaa aaagcggtta 5760
gctccttcgg tcctccgatc gttgtcagaa gtaagttggc cgcagtgtta tcactcatgg 5820
ttatggcagc actgcataat tctcttactg tcatgccatc cgtaagatgc ttttctgtga 5880
ctggtgagta ctcaaccaag tcattctgag aatagtgtat gcggcgaccg agttgctctt 5940
gcccggcgtc aatacgggat aataccgcgc cacatagcag aactttaaaa gtgctcatca 6000
ttggaaaacg ttcttcgggg cgaaaactct caaggatctt accgctgttg agatccagtt 6060
cgatgtaacc cactcgtgca cccaactgat cttcagcatc ttttactttc accagcgttt 6120
ctgggtgagc aaaaacagga aggcaaaatg ccgcaaaaaa gggaataagg gcgacacgga 6180
aatgttgaat actcatactc ttcctttttc aatattattg aagcatttat cagggttatt 6240
gtctcatgag cggatacata tttgaatgta tttagaaaaa taaacaaata ggggttccgc 6300
gcacatttcc ccgaaaagtg ccacctgacg tctaagaaac cattattatc atgacattaa 6360
cctataaaaa taggcgtatc acgaggccct ttcgtc 6396

<210> SEQ ID NO 39
<211> LENGTH: 6619
<212> TYPE: DNA
<213> ORGANISM: Artificial sequence
<220> FEATURE:
<223> OTHER INFORMATION: vector pCAG-Cre-ED4ER(T2)-bpA

<400> SEQUENCE: 39
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcaggcgcc 240
attcgccatt caggctgcgc aactgttggg aagggcgatc ggtgcgggcc tcttcgctat 300
tacgccagct ggcgaaaggg ggatgtgctg caaggcgatt aagttgggta acgccagggt 360
tttcccagtc acgacgttgt aaaacgacgg ccagtgaatt cgagctcggt acccgggggc 420
gcgccggatc tcgacattga ttattgacta gttattaata gtaatcaatt acggggtcat 480
tagttcatag cccatatatg gagttccgcg ttacataact tacggtaaat ggcccgcctg 540
gctgaccgcc caacgacccc cgcccattga cgtcaataat gacgtatgtt cccatagtaa 600
cgccaatagg gactttccat tgacgtcaat gggtggacta tttacggtaa actgcccact 660
tggcagtaca tcaagtgtat catatgccaa gtacgccccc tattgacgtc aatgacggta 720
aatggcccgc ctggcattat gcccagtaca tgaccttatg ggactttcct acttggcagt 780
acatctacgt attagtcatc gctattacca tgggtcgagg tgagccccac gttctgcttc 840
actctcccca tctccccccc ctccccaccc ccaattttgt atttatttat tttttaatta 900
ttttgtgcag cgatgggggc gggggggggg ggggcgcgcg ccaggcgggg cggggcgggg 960
cgaggggcgg ggcggggcga ggcggagagg tgcggcggca gccaatcaga gcggcgcgct 1020
ccgaaagttt ccttttatgg cgaggcggcg gcggcggcgg ccctataaaa agcgaagcgc 1080
gcggcgggcg ggagtcgctg cgttgccttc gccccgtgcc ccgctccgcg ccgcctcgcg 1140
ccgcccgccc cggctctgac tgaccgcgtt actcccacag gtgagcgggc gggacggccc 1200
ttctcctccg ggctgtaatt agcgcttggt ttaatgacgg ctcgtttctt ttctgtggct 1260
gcgtgaaagc cttaaagggc tccgggaggg ccctttgtgc ggggggggagc ggctcggggg 1320 gtgcgtgcgt gtgtgtgtgc gtggggagcg ccgcgtgcgg cccgcgctgc ccggcggctg 1380
tgagcgctgc gggcgcggcg cggggctttg tgcgctccgc gtgtgcgcga ggggagcgcg 1440
gccgggggcg gtgccccgcg gtgcgggggg gctgcgaggg gaacaaaggc tgcgtgcggg 1500
gtgtgtgcgt gggggggtga gcagggggtg tgggcgcggc ggtcgggctg taaccccccc 1560
ctgcaccccc ctccccgagt tgctgagcac ggcccggctt cgggtgcggg gctccgtgcg 1620
gggcgtggcg cggggctcgc cgtgccgggc ggggggtggc ggcaggtggg ggtgccgggc 1680
ggggcggggc cgcctcgggc cggggagggc tcgggggagg ggcgcggcgg ccccggagcg 1740
ccggcggctg tcgaggcgcg gcgagccgca gccattgcct tttatggtaa tcgtgcgaga 1800
gggcgcaggg acttcctttg tcccaaatct ggcggagccg aaatctggga ggcgccgccg 1860
caccccctct agcgggcgcg ggcgaagcgg tgcggcgccg gcaggaagga aatgggcggg 1920
gagggccttc gtgcgtcgcc gcgccgccgt ccccttctcc atctccagcc tcggggctgc 1980
cgcaggggga cggctgcctt cgggggggac ggggcagggc ggggttcggc ttctggcgtg 2040
tgaccggcgg ctctagagcc tctgctaacc atgttcatgc cttcttcttt ttcctacaga 2100
tccttaatta agtctagagt cgactgttta attccaccat gtccaattta ctgaccgtac 2160
accaaaattt gcctgcatta ccggtcgatg caacgagtga tgaggttcgc aagaacctga 2220
tggacatgtt cagggatcgc caggcgtttt ctgagcatac ctggaaaatg cttctgtccg 2280
tttgccggtc gtgggcggca tggtgcaagt tgaataaccg gaaatggttt cccgcagaac 2340
ctgaagatgt tcgcgattat cttctatatc ttcaggcgcg cggtctggca gtaaaaacta 2400
tccagcaaca tttgggccag ctaaacatgc ttcatcgtcg gtccgggctg ccacgaccaa 2460
gtgacagcaa tgctgtttca ctggttatgc ggcggatccg aaaagaaaac gttgatgccg 2520
gtgaacgtgc aaaacaggct ctagcgttcg aacgcactga tttcgaccag gttcgttcac 2580

```
tcatggaaaa tagcgatcgc tgccaggata tacgtaatct ggcatttctg ggattgctt   2640
ataacaccct gttacgtata gccgaaattg ccaggatcag ggttaaagat atctcacgta  2700
ctgacggtgg gagaatgtta atccatattg gcagaacgaa aacgctggtt agcaccgcag  2760
gtgtagagaa ggcacttagc ctgggggtaa ctaaactggt cgagcgatgg atttccgtct  2820
ctggtgtagc tgatgatccg aataactacc tgttttgccg ggtcagaaaa aatggtgttg  2880
ccgcgccatc tgccaccagc cagctatcaa ctcgcgccct ggaagggatt tttgaagcaa  2940
ctcatcgatt gatttacggc gctaaggatg actctggtca gagatacctg gcctggtctg  3000
gacacagtgc ccgtgtcgga gccgcgcgag atatggcccg cgctggagtt tcaataccgg  3060
agatcatgca agctggtggc tggaccaatg taaatattgt catgaactat atccgtaacc  3120
tggatagtga aacaggggca atggtgcgcc tgctggaaga tggcgatctc gagagcctgg  3180
ccttgtccct gacggccgac cagatggtca gtgccttgtt ggatgctgag cccccccatac 3240
tctattccga gtatgatcct accagaccct tcagtgaagc ttcgatgatg ggcttactga  3300
ccaacctggc agacagggag ctggttcaca tgatcaactg ggcgaagagg gtgccaggct  3360
ttgtggattt gaccctccat gatcaggtcc accttctaga atgtgcctgg ctagagatcc  3420
tgatgattgg tctcgtctgg cgctccatgg agcacccagt gaagctactg tttgctccta  3480
acttgctctt ggacaggaac cagggaaaat gtgtagaggg catggtggag atcttcgaca  3540
tgctgctggc tacatcatct cggttccgca tgatgaatct gcagggagag gagtttgtgt  3600
gcctcaaatc tattattttg cttaattctg gagtgtacac atttctgtcc agcaccctga  3660
agtctctgga agagaaggac catatccacc gagtcctgga caagatcaca gacactttga  3720
tccacctgat ggccaaggca ggcctgaccc tgcagcagca gcaccagcgg ctggcccagc  3780
tcctcctcat cctctcccac atcaggcaca tgagtaacaa aggcatggag catctgtaca  3840
gcatgaagtg caagaacgtg gtgcccctct atgacctgct gctggaggcg gcggacgccc  3900
accgcctaca tgcgcccact agccgtggag ggcatccgt ggaggagacg gaccaaagcc   3960
acttggccac tgcgggctct acttcatcgc attccttgca aaagtattac atcacggggg  4020
aggcagaggg tttccctgcc acagcttgat gaagatctga gctccctggc ggaattgcgt  4080
aaatgattgc agatccacta gttctagagc tcgctgatca gcctcgactg tgccttctag  4140
ttgccagcca tctgttgttt gcccctcccc cgtgccttcc ttgaccctgg aaggtgccac  4200
tcccactgtc ctttcctaat aaaatgagga aattgcatcg cattgtctga gtaggtgtca  4260
ttctattctg gggggtgggg tggggcagga cagcaagggg gaggattggg aagacaatag  4320
caggcatgct ggggatgcgg tgggctctat ggcttctgag gcggaaagaa ccagcatgca  4380
agcttggcgt aatcatggtc atagctgttt cctgtgtgaa attgttatcc gctcacaatt  4440
ccacacaaca tacgagccgg aagcataaag tgtaaagcct ggggtgccta atgagtgagc  4500
taactcacat taattgcgtt gcgctcactg cccgctttcc agtcgggaaa cctgtcgtgc  4560
cagctgcatt aatgaatcgg ccaacgcgcg gggagaggcg gtttgcgtat tgggcgctct  4620
tccgcttcct cgctcactga ctcgctgcgc tcggtcgttc ggctgcggcg agcggtatca  4680
gctcactcaa aggcggtaat acggttatcc acagaatcag gggataacgc aggaaagaac  4740
atgtgagcaa aaggccagca aaaggccagg aaccgtaaaa aggccgcgtt gctggcgttt  4800
ttccataggc tccgcccccc tgacgagcat cacaaaaatc gacgctcaag tcagaggtgg  4860
cgaaacccga caggactata aagataccag gcgtttcccc ctggaagctc cctcgtgcgc  4920
tctcctgttc cgaccctgcc gcttaccgga tacctgtccg cctttctccc ttcgggaagc  4980
```

gtggcgcttt ctcatagctc acgctgtagg tatctcagtt cggtgtaggt cgttcgctcc 5040
aagctgggct gtgtgcacga accccccgtt cagcccgacc gctgcgcctt atccggtaac 5100
tatcgtcttg agtccaaccc ggtaagacac gacttatcgc cactggcagc agccactggt 5160
aacaggatta gcagagcgag gtatgtaggc ggtgctacag agttcttgaa gtggtggcct 5220
aactacggct acactagaag gacagtattt ggtatctgcg ctctgctgaa gccagttacc 5280
ttcggaaaaa gagttggtag ctcttgatcc ggcaaacaaa ccaccgctgg tagcggtggt 5340 tttttgttt gcaagcagca gattacgcgc agaaaaaaag gatctcaaga agatcctttg 5400
atcttttcta cggggtctga cgctcagtgg aacgaaaact cacgttaagg gattttggtc 5460
atgagattat caaaaaggat cttcacctag atccttttaa attaaaaatg aagttttaaa 5520
tcaatctaaa gtatatatga gtaaacttgg tctgacagtt accaatgctt aatcagtgag 5580
gcacctatct cagcgatctg tctatttcgt tcatccatag ttgcctgact ccccgtcgtg 5640
tagataacta cgatacggga gggcttacca tctggcccca gtgctgcaat gataccgcga 5700
gacccacgct caccggctcc agatttatca gcaataaacc agccagccgg aagggccgag 5760
cgcagaagtg gtcctgcaac tttatccgcc tccatccagt ctattaattg ttgccgggaa 5820
gctagagtaa gtagttcgcc agttaatagt ttgcgcaacg ttgttgccat tgctacaggc 5880
atcgtggtgt cacgctcgtc gtttggtatg gcttcattca gctccggttc ccaacgatca 5940
aggcgagtta catgatcccc catgttgtgc aaaaaagcgg ttagctcctt cggtcctccg 6000
atcgttgtca gaagtaagtt ggccgcagtg ttatcactca tggttatggc agcactgcat 6060
aattctctta ctgtcatgcc atccgtaaga tgcttttctg tgactggtga gtactcaacc 6120
aagtcattct gagaatagtg tatgcggcga ccgagttgct cttgcccggc gtcaatacgg 6180
gataataccg cgccacatag cagaacttta aaagtgctca tcattggaaa acgttcttcg 6240
gggcgaaaac tctcaaggat cttaccgctg ttgagatcca gttcgatgta acccactcgt 6300
gcacccaact gatcttcagc atcttttact ttcaccagcg tttctgggtg agcaaaaaca 6360
ggaaggcaaa atgccgcaaa aaagggaata agggcgacac ggaaatgttg aatactcata 6420
ctcttccttt ttcaatatta ttgaagcatt tatcagggtt attgtctcat gagcggatac 6480
atatttgaat gtatttagaa aaataaacaa ataggggttc cgcgcacatt tccccgaaaa 6540
gtgccacctg acgtctaaga aaccattatt atcatgacat taacctataa aaataggcgt 6600
atcacgaggc cctttcgtc 6619

<210> SEQ ID NO 40
<211> LENGTH: 1713
<212> TYPE: DNA
<213> ORGANISM: Artificial sequence
<220> FEATURE:
<223> OTHER INFORMATION: DNA sequence coding for fusion gene Casp3-ED4ER(T2)

<400> SEQUENCE: 40
atggagaaca acaaaacctc agtggattca aaatccatta ataattttga agtaaagacc 60
atacatggga gcaagtcagt ggactctggg atctatctgg acagtagtta caaaatggat 120
tatcctgaaa tgggcatatg cataataatt aataataaga acttccataa gagcactgga 180
atgtcatctc gctctggtac ggatgtggac gcagccaacc tcagagagac attcatgggc 240
ctgaaatacc aagtcaggaa taaaaatgat cttactcgtg aagacatttt ggaattaatg 300
gatagtgttt ctaaggaaga tcatagcaaa aggagcagct ttgtgtgtgt gattctaagc 360

```
catggtgatg aaggggtcat ttatgggaca aatgggcctg ttgaactgaa aaagttgact    420

agcttcttca gaggcgacta ctgccggagt ctgactggaa agccgaaact cttcatcatt    480

caggcctgcc ggggtacgga gctggactgt ggcattgaga cagacagtgg gactgatgag    540

gagatggctt gccagaagat accggtggag gctgacttcc tgtatgctta ctctacagca    600

cctggttact attcctggag aaattcaaag gacgggtcgt ggttcatcca gtccctttgc    660

agcatgctga agctgtacgc gcacaagcta gaatttatgc acattctcac tcgcgttaac    720

aggaaggtgg caacggaatt cgagtccttc tccctggact ccactttcca cgcaaagaaa    780

cagatcccgt gtattgtgtc catgctcacg aaagaactgt acttttatca cctcgagagc    840

ctggccttgt ccctgacggc cgaccagatg gtcagtgcct tgttggatgc tgagcccccc    900

atactctatt ccgagtatga tcctaccaga cccttcagtg aagcttcgat gatgggctta    960

ctgaccaacc tggcagacag ggagctggtt cacatgatca actgggcgaa gagggtgcca   1020

ggctttgtgg atttgaccct ccatgatcag gtccaccttc tagaatgtgc ctggctagag   1080

atcctgatga ttggtctcgt ctggcgctcc atggagcacc cagtgaagct actgtttgct   1140

cctaacttgc tcttggacag gaaccaggga aaatgtgtag agggcatggt ggagatcttc   1200

gacatgctgc tggctacatc atctcggttc cgcatgatga atctgcaggg agaggagttt   1260

gtgtgcctca aatctattat tttgcttaat tctggagtgt acacatttct gtccagcacc   1320

ctgaagtctc tggaagagaa ggaccatatc caccgagtcc tggacaagat cacagacact   1380

ttgatccacc tgatggccaa ggcaggcctg accctgcagc agcagcacca gcggctggcc   1440

cagctcctcc tcatcctctc ccacatcagg cacatgagta acaaaggcat ggagcatctg   1500

tacagcatga agtgcaagaa cgtggtgccc ctctatgacc tgctgctgga ggcggcggac   1560

gcccaccgcc tacatgcgcc cactagccgt ggaggggcat ccgtggagga gacggaccaa   1620

agccacttgg ccactgcggg ctctacttca tcgcattcct tgcaaaagta ttacatcacg   1680

ggggaggcag agggtttccc tgccacagct tga                                1713
```

```
<210> SEQ ID NO 41
<211> LENGTH: 570
<212> TYPE: PRT
<213> ORGANISM: Artificial sequence
<220> FEATURE:
<223> OTHER INFORMATION: fusion gene Casp3-ED4ER(T2)

<400> SEQUENCE: 41

Met Glu Asn Asn Lys Thr Ser Val Asp Ser Lys Ser Ile Asn Asn Phe
1               5                   10                  15

Glu Val Lys Thr Ile His Gly Ser Lys Ser Val Asp Ser Gly Ile Tyr
            20                  25                  30

Leu Asp Ser Ser Tyr Lys Met Asp Tyr Pro Glu Met Gly Ile Cys Ile
        35                  40                  45

Ile Ile Asn Asn Lys Asn Phe His Lys Ser Thr Gly Met Ser Ser Arg
    50                  55                  60

Ser Gly Thr Asp Val Asp Ala Ala Asn Leu Arg Glu Thr Phe Met Gly
65                  70                  75                  80

Leu Lys Tyr Gln Val Arg Asn Lys Asn Asp Leu Thr Arg Glu Asp Ile
                85                  90                  95

Leu Glu Leu Met Asp Ser Val Ser Lys Glu Asp His Ser Lys Arg Ser
            100                 105                 110

Ser Phe Val Cys Val Ile Leu Ser His Gly Asp Glu Gly Val Ile Tyr
        115                 120                 125
```

-continued

```
Gly Thr Asn Gly Pro Val Glu Leu Lys Lys Leu Thr Ser Phe Phe Arg
    130                 135                 140

Gly Asp Tyr Cys Arg Ser Leu Thr Gly Lys Pro Lys Leu Phe Ile Ile
145                 150                 155                 160

Gln Ala Cys Arg Gly Thr Glu Leu Asp Cys Gly Ile Glu Thr Asp Ser
                165                 170                 175

Gly Thr Asp Glu Glu Met Ala Cys Gln Lys Ile Pro Val Glu Ala Asp
            180                 185                 190

Phe Leu Tyr Ala Tyr Ser Thr Ala Pro Gly Tyr Tyr Ser Trp Arg Asn
        195                 200                 205

Ser Lys Asp Gly Ser Trp Phe Ile Gln Ser Leu Cys Ser Met Leu Lys
    210                 215                 220

Leu Tyr Ala His Lys Leu Glu Phe Met His Ile Leu Thr Arg Val Asn
225                 230                 235                 240

Arg Lys Val Ala Thr Glu Phe Glu Ser Phe Ser Leu Asp Ser Thr Phe
                245                 250                 255

His Ala Lys Lys Gln Ile Pro Cys Ile Val Ser Met Leu Thr Lys Glu
            260                 265                 270

Leu Tyr Phe Tyr His Leu Glu Ser Leu Ala Leu Ser Leu Thr Ala Asp
        275                 280                 285

Gln Met Val Ser Ala Leu Leu Asp Ala Glu Pro Pro Ile Leu Tyr Ser
    290                 295                 300

Glu Tyr Asp Pro Thr Arg Pro Phe Ser Glu Ala Ser Met Met Gly Leu
305                 310                 315                 320

Leu Thr Asn Leu Ala Asp Arg Glu Leu Val His Met Ile Asn Trp Ala
                325                 330                 335

Lys Arg Val Pro Gly Phe Val Asp Leu Thr Leu His Asp Gln Val His
            340                 345                 350

Leu Leu Glu Cys Ala Trp Leu Glu Ile Leu Met Ile Gly Leu Val Trp
        355                 360                 365

Arg Ser Met Glu His Pro Val Lys Leu Leu Phe Ala Pro Asn Leu Leu
    370                 375                 380

Leu Asp Arg Asn Gln Gly Lys Cys Val Glu Gly Met Val Glu Ile Phe
385                 390                 395                 400

Asp Met Leu Leu Ala Thr Ser Ser Arg Phe Arg Met Met Asn Leu Gln
                405                 410                 415

Gly Glu Glu Phe Val Cys Leu Lys Ser Ile Ile Leu Leu Asn Ser Gly
            420                 425                 430

Val Tyr Thr Phe Leu Ser Ser Thr Leu Lys Ser Leu Glu Glu Lys Asp
        435                 440                 445

His Ile His Arg Val Leu Asp Lys Ile Thr Asp Thr Leu Ile His Leu
    450                 455                 460

Met Ala Lys Ala Gly Leu Thr Leu Gln Gln Gln His Gln Arg Leu Ala
465                 470                 475                 480

Gln Leu Leu Leu Ile Leu Ser His Ile Arg His Met Ser Asn Lys Gly
                485                 490                 495

Met Glu His Leu Tyr Ser Met Lys Cys Lys Asn Val Val Pro Leu Tyr
            500                 505                 510

Asp Leu Leu Leu Glu Ala Ala Asp Ala His Arg Leu His Ala Pro Thr
        515                 520                 525

Ser Arg Gly Gly Ala Ser Val Glu Glu Thr Asp Gln Ser His Leu Ala
    530                 535                 540

Thr Ala Gly Ser Thr Ser Ser His Ser Leu Gln Lys Tyr Tyr Ile Thr
545                 550                 555                 560
```

Gly Glu Ala Glu Gly Phe Pro Ala Thr Ala
565 570

<210> SEQ ID NO 42
<211> LENGTH: 29
<212> TYPE: DNA
<213> ORGANISM: Artificial sequence
<220> FEATURE:
<223> OTHER INFORMATION: primer ED4ER-A

<400> SEQUENCE: 42
acctcgagag cctggccttg tccctgacg 29

<210> SEQ ID NO 43
<211> LENGTH: 23
<212> TYPE: DNA
<213> ORGANISM: Artificial sequence
<220> FEATURE:
<223> OTHER INFORMATION: primer ED4ER-B

<400> SEQUENCE: 43
ttcactgggt gctccatgga gcg 23

<210> SEQ ID NO 44
<211> LENGTH: 44
<212> TYPE: DNA
<213> ORGANISM: Artificial sequence
<220> FEATURE:
<223> OTHER INFORMATION: primer baxER-A

<400> SEQUENCE: 44
ccttaattaa ttccaccatg ggcgacgggt ccggggagca gctt 44

<210> SEQ ID NO 45
<211> LENGTH: 28
<212> TYPE: DNA
<213> ORGANISM: Artificial sequence
<220> FEATURE:
<223> OTHER INFORMATION: primer baxER-B

<400> SEQUENCE: 45
ggctcgaggc ccatcttctt ccagatgg 28

<210> SEQ ID NO 46
<211> LENGTH: 6216
<212> TYPE: DNA
<213> ORGANISM: Artificial sequence
<220> FEATURE:
<223> OTHER INFORMATION: vector pCAG-Bax-ER(T2)-bpA

<400> SEQUENCE: 46
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcaggcgcc 240
attcgccatt caggctgcgc aactgttggg aagggcgatc ggtgcgggcc tcttcgctat 300
tacgccagct ggcgaaaggg ggatgtgctg caaggcgatt aagttgggta acgccagggt 360
tttcccagtc acgacgttgt aaaacgacgg ccagtgaatt cgagctcggt acccgggggc 420
gcgccggatc tcgacattga ttattgacta gttattaata gtaatcaatt acggggtcat 480
tagttcatag cccatatatg gagttccgcg ttacataact tacggtaaat ggcccgcctg 540

```
gctgaccgcc caacgacccc cgcccattga cgtcaataat gacgtatgtt cccatagtaa    600
cgccaatagg gactttccat tgacgtcaat gggtggacta tttacggtaa actgcccact    660
tggcagtaca tcaagtgtat catatgccaa gtacgccccc tattgacgtc aatgacggta    720
aatggcccgc ctggcattat gcccagtaca tgaccttatg ggactttcct acttggcagt    780
acatctacgt attagtcatc gctattacca tgggtcgagg tgagccccac gttctgcttc    840
actctcccca tctccccccc ctccccaccc ccaattttgt atttatttat tttttaatta    900
ttttgtgcag cgatgggggc gggggggggg ggggcgcgcg ccaggcgggg cggggcgggg    960
cgaggggcgg ggcggggcga ggcggagagg tgcggcggca gccaatcaga gcggcgcgct   1020
ccgaaagttt ccttttatgg cgaggcggcg gcggcggcgg ccctataaaa agcgaagcgc   1080
gcggcgggcg ggagtcgctg cgttgccttc gccccgtgcc ccgctccgcg ccgcctcgcg   1140
ccgcccgccc cggctctgac tgaccgcgtt actcccacag gtgagcgggc gggacggccc   1200
ttctcctccg ggctgtaatt agcgcttggt ttaatgacgg ctcgtttctt ttctgtggct   1260
gcgtgaaagc cttaaagggc tccgggaggg ccctttgtgc ggggggggagc ggctcggggg   1320
gtgcgtgcgt gtgtgtgtgc gtggggagcg ccgcgtgcgg cccgcgctgc ccggcggctg   1380
tgagcgctgc gggcgcggcg cggggctttg tgcgctccgc gtgtgcgcga ggggagcgcg   1440
gccgggggcg gtgccccgcg gtgcgggggg gctgcgaggg gaacaaaggc tgcgtgcggg   1500
gtgtgtgcgt gggggggtga gcagggggtg tgggcgcggc ggtcgggctg taaccccccc   1560
ctgcaccccc ctccccgagt tgctgagcac ggcccggctt cgggtgcggg gctccgtgcg   1620
gggcgtggcg cggggctcgc cgtgccgggc gggggggtggc ggcaggtggg ggtgccgggc   1680
ggggcggggc cgcctcgggc cggggagggc tcgggggagg ggcgcggcgg ccccggagcg   1740
ccggcggctg tcgaggcgcg gcgagccgca gccattgcct tttatggtaa tcgtgcgaga   1800
gggcgcaggg acttcctttg tcccaaatct ggcggagccg aaatctggga ggcgccgccg   1860
caccccctct agcgggcgcg ggcgaagcgg tgcggcgccg gcaggaagga aatgggcggg   1920
gagggccttc gtgcgtcgcc gcgccgccgt ccccttctcc atctccagcc tcggggctgc   1980
cgcaggggga cggctgcctt cggggggggac ggggcagggc ggggttcggc ttctggcgtg   2040
tgaccggcgg ctctagagcc tctgctaacc atgttcatgc cttcttcttt ttcctacaga   2100
tccttaatta attccaccat gggcgacggg tccggggagc agcttgggag cggcgggccc   2160
accagctctg aacagatcat gaagacaggg gccttttttgc tacagggttt catccaggat   2220
cgagcaggga ggatggctgg ggagacacct gagctgacct tggagcagcc gccccaggat   2280
gcgtccacca agaagctgag cgagtgtctc cggcgaattg gagatgaact ggacagcaat   2340
atggagctgc agaggatgat tgctgacgtg gacacggact ccccccgaga ggtcttcttc   2400
cgggtggcag ctgacatgtt tgctgatggc aacttcaact ggggccgcgt ggttgccctc   2460
ttctactttg ctagcaaact ggtgctcaag gccctgtgca ctaaagtgcc cgagctgatc   2520
agaaccatca tgggctggac actggacttc ctccgtgagc ggctgcttgt ctggatccaa   2580
gaccagggtg gctgggaagg cctcctctcc tacttcggga cccccacatg gcagacagtg   2640
accatctttg tggctggagt cctcaccgcc tcgctcacca tctggaagaa gatgggcctc   2700
gagccatctg ctggagacat gagagctgcc aacctttggc caagcccgct catgatcaaa   2760
cgctctaaga agaacagcct ggccttgtcc ctgacggccg accagatggt cagtgccttg   2820
ttggatgctg agccccccat actctattcc gagtatgatc ctaccagacc cttcagtgaa   2880
gcttcgatga tgggcttact gaccaacctg gcagacaggg agctggttca catgatcaac   2940
```

-continued

```
tgggcgaaga gggtgccagg ctttgtggat ttgaccctcc atgatcaggt ccaccttcta   3000
gaatgtgcct ggctagagat cctgatgatt ggtctcgtct ggcgctccat ggagcaccca   3060
gtgaagctac tgtttgctcc taacttgctc ttggacagga accagggaaa atgtgtagag   3120
ggcatggtgg agatcttcga catgctgctg gctacatcat ctcggttccg catgatgaat   3180
ctgcagggag aggagtttgt gtgcctcaaa tctattattt tgcttaattc tggagtgtac   3240
acatttctgt ccagcaccct gaagtctctg gaagagaagg accatatcca ccgagtcctg   3300
gacaagatca cagacacttt gatccacctg atggccaagg caggcctgac cctgcagcag   3360
cagcaccagc ggctggccca gctcctcctc atcctctccc acatcaggca catgagtaac   3420
aaaggcatgg agcatctgta cagcatgaag tgcaagaacg tggtgcccct ctatgacctg   3480
ctgctggagg cggcggacgc ccaccgccta catgcgccca ctagccgtgg aggggcatcc   3540
gtggaggaga cggaccaaag ccacttggcc actgcgggct ctacttcatc gcattccttg   3600
caaaagtatt acatcacggg ggaggcagag ggtttccctg ccacagcttg atgaagatct   3660
gagctccctg gcggaattgc gtaaatgatt gcagatccac tagttctaga gctcgctgat   3720
cagcctcgac tgtgccttct agttgccagc catctgttgt ttgcccctcc cccgtgcctt   3780
ccttgaccct ggaaggtgcc actcccactg tcctttccta ataaaatgag gaaattgcat   3840
cgcattgtct gagtaggtgt cattctattc tggggggtgg ggtggggcag gacagcaagg   3900
gggaggattg ggaagacaat agcaggcatg ctggggatgc ggtgggctct atggcttctg   3960
aggcggaaag aaccagaagc ttggcgtaat catggtcata gctgtttcct gtgtgaaatt   4020
gttatccgct cacaattcca cacaacatac gagccggaag cataaagtgt aaagcctggg   4080
gtgcctaatg agtgagctaa ctcacattaa ttgcgttgcg ctcactgccc gctttccagt   4140
cgggaaacct gtcgtgccag ctgcattaat gaatcggcca acgcgcgggg agaggcggtt   4200
tgcgtattgg gcgctcttcc gcttcctcgc tcactgactc gctgcgctcg gtcgttcggc   4260
tgcggcgagc ggtatcagct cactcaaagg cggtaatacg gttatccaca gaatcagggg   4320
ataacgcagg aaagaacatg tgagcaaaag gccagcaaaa ggccaggaac cgtaaaaagg   4380
ccgcgttgct ggcgtttttc cataggctcc gcccccctga cgagcatcac aaaaatcgac   4440
gctcaagtca gaggtggcga aacccgacag gactataaag ataccaggcg tttccccctg   4500
gaagctccct cgtgcgctct cctgttccga ccctgccgct taccggatac ctgtccgcct   4560
ttctcccttc gggaagcgtg gcgctttctc atagctcacg ctgtaggtat ctcagttcgg   4620
tgtaggtcgt tcgctccaag ctgggctgtg tgcacgaacc ccccgttcag cccgaccgct   4680
gcgccttatc cggtaactat cgtcttgagt ccaacccggt aagacacgac ttatcgccac   4740
tggcagcagc cactggtaac aggattagca gagcgaggta tgtaggcggt gctacagagt   4800
tcttgaagtg gtggcctaac tacggctaca ctagaaggac agtatttggt atctgcgctc   4860
tgctgaagcc agttaccttc ggaaaaagag ttggtagctc ttgatccggc aaacaaacca   4920
ccgctggtag cggtggtttt tttgtttgca agcagcagat tacgcgcaga aaaaaaggat   4980
ctcaagaaga tcctttgatc ttttctacgg ggtctgacgc tcagtggaac gaaaactcac   5040
gttaagggat tttggtcatg agattatcaa aaaggatctt cacctagatc cttttaaatt   5100
aaaaatgaag ttttaaatca atctaaagta tatatgagta aacttggtct gacagttacc   5160
aatgcttaat cagtgaggca cctatctcag cgatctgtct atttcgttca tccatagttg   5220
cctgactccc cgtcgtgtag ataactacga tacgggaggg cttaccatct ggccccagtg   5280
ctgcaatgat accgcgagac ccacgctcac cggctccaga tttatcagca ataaaccagc   5340
```

-continued

```
cagccggaag ggccgagcgc agaagtggtc ctgcaacttt atccgcctcc atccagtcta   5400
ttaattgttg ccgggaagct agagtaagta gttcgccagt taatagtttg cgcaacgttg   5460
ttgccattgc tacaggcatc gtggtgtcac gctcgtcgtt tggtatggct tcattcagct   5520
ccggttccca acgatcaagg cgagttacat gatcccccat gttgtgcaaa aaagcggtta   5580
gctccttcgg tcctccgatc gttgtcagaa gtaagttggc cgcagtgtta tcactcatgg   5640
ttatggcagc actgcataat tctcttactg tcatgccatc cgtaagatgc ttttctgtga   5700
ctggtgagta ctcaaccaag tcattctgag aatagtgtat gcggcgaccg agttgctctt   5760
gcccggcgtc aatacgggat aataccgcgc cacatagcag aactttaaaa gtgctcatca   5820
ttggaaaacg ttcttcgggg cgaaaactct caaggatctt accgctgttg agatccagtt   5880
cgatgtaacc cactcgtgca cccaactgat cttcagcatc ttttactttc accagcgttt   5940
ctgggtgagc aaaaacagga aggcaaaatg ccgcaaaaaa gggaataagg gcgacacgga   6000
aatgttgaat actcatactc ttcctttttc aatattattg aagcatttat cagggttatt   6060
gtctcatgag cggatacata tttgaatgta tttagaaaaa taaacaaata ggggttccgc   6120
gcacatttcc ccgaaaagtg ccacctgacg tctaagaaac cattattatc atgacattaa   6180
cctataaaaa taggcgtatc acgaggccct ttcgtc                              6216
```

<210> SEQ ID NO 47
<211> LENGTH: 1533
<212> TYPE: DNA
<213> ORGANISM: Artificial sequence
<220> FEATURE:
<223> OTHER INFORMATION: DNA sequence coding for fusion gene Bax-ER(T2)

<400> SEQUENCE: 47

```
atgggcgacg ggtccgggga gcagcttggg agcggcgggc ccaccagctc tgaacagatc     60
atgaagacag ggggcctttt gctacagggt ttcatccagg atcgagcagg gaggatggct    120
ggggagacac ctgagctgac cttggagcag ccgccccagg atgcgtccac caagaagctg    180
agcgagtgtc tccggcgaat tggagatgaa ctggacagca atatggagct gcagaggatg    240
attgctgacg tggacacgga ctcccccga gaggtcttct tccgggtggc agctgacatg    300
tttgctgatg gcaacttcaa ctggggccgc gtggttgccc tcttctactt tgctagcaaa    360
ctggtgctca aggccctgtg cactaaagtg cccgagctga tcagaaccat catgggctgg    420
acactggact tcctccgtga gcggctgctt gtctggatcc aagaccaggg tggctgggaa    480
ggcctcctct cctacttcgg gacccccaca tggcagacag tgaccatctt tgtggctgga    540
gtcctcaccg cctcgctcac catctggaag aagatgggcc tcgagccatc tgctggagac    600
atgagagctg ccaacctttg gccaagcccg ctcatgatca aacgctctaa gaagaacagc    660
ctggccttgt ccctgacggc cgaccagatg gtcagtgcct tgttggatgc tgagcccccc    720
atactctatt ccgagtatga tcctaccaga cccttcagtg aagcttcgat gatgggctta    780
ctgaccaacc tggcagacag ggagctggtt cacatgatca actgggcgaa gagggtgcca    840
ggctttgtgg atttgaccct ccatgatcag gtccaccttc tagaatgtgc ctggctagag    900
atcctgatga ttggtctcgt ctggcgctcc atggagcacc cagtgaagct actgtttgct    960
cctaacttgc tcttggacag gaaccaggga aaatgtgtag agggcatggt ggagatcttc   1020
gacatgctgc tggctacatc atctcggttc cgcatgatga atctgcaggg agaggagttt   1080
gtgtgcctca aatctattat tttgcttaat tctggagtgt acacatttct gtccagcacc   1140
ctgaagtctc tggaagagaa ggaccatatc caccgagtcc tggacaagat cacagacact   1200
```

```
ttgatccacc tgatggccaa ggcaggcctg accctgcagc agcagcacca gcggctggcc   1260

cagctcctcc tcatcctctc ccacatcagg cacatgagta acaaaggcat ggagcatctg   1320

tacagcatga agtgcaagaa cgtggtgccc ctctatgacc tgctgctgga ggcggcggac   1380

gcccaccgcc tacatgcgcc cactagccgt ggaggggcat ccgtggagga gacggaccaa   1440

agccacttgg ccactgcggg ctctacttca tcgcattcct tgcaaaagta ttacatcacg   1500

ggggaggcag agggtttccc tgccacagct tga                                1533
```

<210> SEQ ID NO 48
<211> LENGTH: 510
<212> TYPE: PRT
<213> ORGANISM: Artificial sequence
<220> FEATURE:
<223> OTHER INFORMATION: fusion gene Bax-ER(T2)

<400> SEQUENCE: 48

```
Met Gly Asp Gly Ser Gly Glu Gln Leu Gly Ser Gly Gly Pro Thr Ser
1               5                   10                  15

Ser Glu Gln Ile Met Lys Thr Gly Ala Phe Leu Leu Gln Gly Phe Ile
            20                  25                  30

Gln Asp Arg Ala Gly Arg Met Ala Gly Glu Thr Pro Glu Leu Thr Leu
        35                  40                  45

Glu Gln Pro Pro Gln Asp Ala Ser Thr Lys Lys Leu Ser Glu Cys Leu
    50                  55                  60

Arg Arg Ile Gly Asp Glu Leu Asp Ser Asn Met Glu Leu Gln Arg Met
65                  70                  75                  80

Ile Ala Asp Val Asp Thr Asp Ser Pro Arg Glu Val Phe Phe Arg Val
                85                  90                  95

Ala Ala Asp Met Phe Ala Asp Gly Asn Phe Asn Trp Gly Arg Val Val
            100                 105                 110

Ala Leu Phe Tyr Phe Ala Ser Lys Leu Val Leu Lys Ala Leu Cys Thr
        115                 120                 125

Lys Val Pro Glu Leu Ile Arg Thr Ile Met Gly Trp Thr Leu Asp Phe
    130                 135                 140

Leu Arg Glu Arg Leu Leu Val Trp Ile Gln Asp Gln Gly Gly Trp Glu
145                 150                 155                 160

Gly Leu Leu Ser Tyr Phe Gly Thr Pro Thr Trp Gln Thr Val Thr Ile
                165                 170                 175

Phe Val Ala Gly Val Leu Thr Ala Ser Leu Thr Ile Trp Lys Lys Met
            180                 185                 190

Gly Leu Glu Pro Ser Ala Gly Asp Met Arg Ala Ala Asn Leu Trp Pro
        195                 200                 205

Ser Pro Leu Met Ile Lys Arg Ser Lys Lys Asn Ser Leu Ala Leu Ser
    210                 215                 220

Leu Thr Ala Asp Gln Met Val Ser Ala Leu Leu Asp Ala Glu Pro Pro
225                 230                 235                 240

Ile Leu Tyr Ser Glu Tyr Asp Pro Thr Arg Pro Phe Ser Glu Ala Ser
                245                 250                 255

Met Met Gly Leu Leu Thr Asn Leu Ala Asp Arg Glu Leu Val His Met
            260                 265                 270

Ile Asn Trp Ala Lys Arg Val Pro Gly Phe Val Asp Leu Thr Leu His
        275                 280                 285

Asp Gln Val His Leu Leu Glu Cys Ala Trp Leu Glu Ile Leu Met Ile
    290                 295                 300
```

```
Gly Leu Val Trp Arg Ser Met Glu His Pro Val Lys Leu Leu Phe Ala
305                 310                 315                 320

Pro Asn Leu Leu Leu Asp Arg Asn Gln Gly Lys Cys Val Glu Gly Met
                325                 330                 335

Val Glu Ile Phe Asp Met Leu Leu Ala Thr Ser Ser Arg Phe Arg Met
            340                 345                 350

Met Asn Leu Gln Gly Glu Glu Phe Val Cys Leu Lys Ser Ile Ile Leu
        355                 360                 365

Leu Asn Ser Gly Val Tyr Thr Phe Leu Ser Ser Thr Leu Lys Ser Leu
    370                 375                 380

Glu Glu Lys Asp His Ile His Arg Val Leu Asp Lys Ile Thr Asp Thr
385                 390                 395                 400

Leu Ile His Leu Met Ala Lys Ala Gly Leu Thr Leu Gln Gln Gln His
                405                 410                 415

Gln Arg Leu Ala Gln Leu Leu Leu Ile Leu Ser His Ile Arg His Met
            420                 425                 430

Ser Asn Lys Gly Met Glu His Leu Tyr Ser Met Lys Cys Lys Asn Val
        435                 440                 445

Val Pro Leu Tyr Asp Leu Leu Leu Glu Ala Ala Asp Ala His Arg Leu
    450                 455                 460

His Ala Pro Thr Ser Arg Gly Gly Ala Ser Val Glu Glu Thr Asp Gln
465                 470                 475                 480

Ser His Leu Ala Thr Ala Gly Ser Thr Ser Ser His Ser Leu Gln Lys
                485                 490                 495

Tyr Tyr Ile Thr Gly Glu Ala Glu Gly Phe Pro Ala Thr Ala
            500                 505                 510
```

<210> SEQ ID NO 49
<211> LENGTH: 45
<212> TYPE: DNA
<213> ORGANISM: Artificial sequence
<220> FEATURE:
<223> OTHER INFORMATION: primer ERbax-1

<400> SEQUENCE: 49
ccttaattaa gtctagaccg atatgagcct ggccttgtcc ctgac 45

<210> SEQ ID NO 50
<211> LENGTH: 41
<212> TYPE: DNA
<213> ORGANISM: Artificial sequence
<220> FEATURE:
<223> OTHER INFORMATION: primer ERbax-2

<400> SEQUENCE: 50
aagctgctcc ccggacccgt cagctgtggc agggaaaccc t 41

<210> SEQ ID NO 51
<211> LENGTH: 21
<212> TYPE: DNA
<213> ORGANISM: Artificial sequence
<220> FEATURE:
<223> OTHER INFORMATION: primer ERbax-3

<400> SEQUENCE: 51
gacgggtccg gggagcagct t 21

<210> SEQ ID NO 52
<211> LENGTH: 34
<212> TYPE: DNA
<213> ORGANISM: Artificial sequence -continued
<220> FEATURE:
<223> OTHER INFORMATION: primer ERbax-4

<400> SEQUENCE: 52
cagtcgactc tagatcagcc catcttcttc caga 34

<210> SEQ ID NO 53
<211> LENGTH: 6165
<212> TYPE: DNA
<213> ORGANISM: Artificial sequence
<220> FEATURE:
<223> OTHER INFORMATION: vector pCAG-ER(T2)-Bax-bpA

<400> SEQUENCE: 53
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcaggcgcc 240
attcgccatt caggctgcgc aactgttggg aagggcgatc ggtgcgggcc tcttcgctat 300
tacgccagct ggcgaaaggg ggatgtgctg caaggcgatt aagttgggta acgccagggt 360
tttcccagtc acgacgttgt aaaacgacgg ccagtgaatt cgagctcggt acccggggc 420 gcgccggatc tcgacattga ttattgacta gttattaata gtaatcaatt acggggtcat 480
tagttcatag cccatatatg gagttccgcg ttacataact tacggtaaat ggcccgcctg 540
gctgaccgcc caacgacccc cgcccattga cgtcaataat gacgtatgtt cccatagtaa 600
cgccaatagg gactttccat tgacgtcaat gggtggacta tttacggtaa actgcccact 660
tggcagtaca tcaagtgtat catatgccaa gtacgccccc tattgacgtc aatgacggta 720
aatggcccgc ctggcattat gcccagtaca tgaccttatg ggactttcct acttggcagt 780
acatctacgt attagtcatc gctattacca tgggtcgagg tgagccccac gttctgcttc 840
actctcccca tctccccccc ctccccaccc ccaattttgt atttatttat tttttaatta 900
ttttgtgcag cgatgggggc gggggggggg ggggcgcgcg ccaggcgggg cggggcgggg 960
cgaggggcgg ggcggggcga ggcggagagg tgcggcggca gccaatcaga gcggcgcgct 1020
ccgaaagttt ccttttatgg cgaggcggcg gcggcggcgg ccctataaaa agcgaagcgc 1080
gcggcgggcg ggagtcgctg cgttgccttc gccccgtgcc ccgctccgcg ccgcctcgcg 1140
ccgcccgccc cggctctgac tgaccgcgtt actcccacag gtgagcgggc gggacggccc 1200
ttctcctccg ggctgtaatt agcgcttggt ttaatgacgg ctcgtttctt ttctgtggct 1260
gcgtgaaagc cttaaagggc tccgggaggg ccctttgtgc ggggggggagc ggctcggggg 1320 gtgcgtgcgt gtgtgtgtgc gtggggagcg ccgcgtgcgg cccgcgctgc ccggcggctg 1380
tgagcgctgc gggcgcggcg cggggctttg tgcgctccgc gtgtgcgcga ggggagcgcg 1440
gccgggggcg gtgccccgcg gtgcgggggg gctgcgaggg gaacaaaggc tgcgtgcggg 1500
gtgtgtgcgt gggggggtga gcagggggtg tgggcgcggc ggtcgggctg taaccccccc 1560
ctgcaccccc ctccccgagt tgctgagcac ggcccggctt cgggtgcggg gctccgtgcg 1620
gggcgtggcg cggggctcgc cgtgccgggc ggggggtggc ggcaggtggg ggtgccgggc 1680
ggggcggggc cgcctcgggc cggggagggc tcgggggagg ggcgcggcgg ccccggagcg 1740
ccggcggctg tcgaggcgcg gcgagccgca gccattgcct tttatggtaa tcgtgcgaga 1800
gggcgcaggg acttcctttg tcccaaatct ggcggagccg aaatctggga ggcgccgccg 1860
caccccctct agcgggcgcg ggcgaagcgg tgcggcgccg gcaggaagga aatgggcggg 1920

-continued

```
gagggccttc gtgcgtcgcc gcgccgccgt cccttctcc atctccagcc tcggggctgc   1980
cgcaggggga cggctgcctt cgggggggac ggggcagggc ggggttcggc ttctggcgtg   2040
tgaccggcgg ctctagagcc tctgctaacc atgttcatgc cttcttcttt ttcctacaga   2100
tccttaatta agtctagacc gatatgagcc tggccttgtc cctgacggcc gaccagatgg   2160
tcagtgcctt gttggatgct gagcccccca tactctattc cgagtatgat cctaccagac   2220
ccttcagtga agcttcgatg atgggcttac tgaccaacct ggcagacagg gagctggttc   2280
acatgatcaa ctgggcgaag agggtgccag gctttgtgga tttgaccctc catgatcagg   2340
tccaccttct agaatgtgcc tggctagaga tcctgatgat tggtctcgtc tggcgctcca   2400
tggagcaccc agtgaagcta ctgtttgctc ctaacttgct cttggacagg aaccagggaa   2460
aatgtgtaga gggcatggtg gagatcttcg acatgctgct ggctacatca tctcggttcc   2520
gcatgatgaa tctgcaggga gaggagtttg tgtgcctcaa atctattatt ttgcttaatt   2580
ctggagtgta cacatttctg tccagcaccc tgaagtctct ggaagagaag gaccatatcc   2640
accgagtcct ggacaagatc acagacactt tgatccacct gatggccaag gcaggcctga   2700
ccctgcagca gcagcaccag cggctggccc agctcctcct catcctctcc cacatcaggc   2760
acatgagtaa caaaggcatg gagcatctgt acagcatgaa gtgcaagaac gtggtgcccc   2820
tctatgacct gctgctggag gcggcggacg cccaccgcct acatgcgccc actagccgtg   2880
gaggggcatc cgtggaggag acggaccaaa gccacttggc cactgcgggc tctacttcat   2940
cgcattcctt gcaaaagtat tacatcacgg gggaggcaga gggtttccct gccacagctg   3000
acgggtccgg ggagcagctt gggagcggcg ggcccaccag ctctgaacag atcatgaaga   3060
caggggcctt tttgctacag ggtttcatcc aggatcgagc agggaggatg gctggggaga   3120
cacctgagct gaccttggag cagccgcccc aggatgcgtc caccaagaag ctgagcgagt   3180
gtctccggcg aattggagat gaactggaca gcaatatgga gctgcagagg atgattgctg   3240
acgtggacac ggactccccc cgagaggtct tcttccgggt ggcagctgac atgtttgctg   3300
atggcaactt caactggggc cgcgtggttg ccctcttcta ctttgctagc aaactggtgc   3360
tcaaggccct gtgcactaaa gtgcccgagc tgatcagaac catcatgggc tggacactgg   3420
acttcctccg tgagcggctg cttgtctgga tccaagacca gggtggctgg gaaggcctcc   3480
tctcctactt cgggaccccc acatggcaga cagtgaccat ctttgtggct ggagtcctca   3540
ccgcctcgct caccatctgg aagaagatgg gctgatctag agtcgactgt ttctagagct   3600
cgctgatcag cctcgactgt gccttctagt tgccagccat ctgttgtttg cccctccccc   3660
gtgccttcct tgaccctgga aggtgccact cccactgtcc tttcctaata aaatgaggaa   3720
attgcatcgc attgtctgag taggtgtcat tctattctgg ggggtggggt ggggcaggac   3780
agcaaggggg aggattggga agacaatagc aggcatgctg gggatgcggt gggctctatg   3840
gcttctgagg cggaaagaac cagctggggc tcgagatcca ctagttctag cctcgaggct   3900
agagcggcca aacctgcagg catgcaagct tggcgtaatc atggtcatag ctgtttcctg   3960
tgtgaaattg ttatccgctc acaattccac acaacatacg agccggaagc ataaagtgta   4020
aagcctgggg tgcctaatga gtgagctaac tcacattaat tgcgttgcgc tcactgcccg   4080
ctttccagtc gggaaacctg tcgtgccagc tgcattaatg aatcggccaa cgcgcgggga   4140
gaggcggttt gcgtattggg cgctcttccg cttcctcgct cactgactcg ctgcgctcgg   4200
tcgttcggct gcggcgagcg gtatcagctc actcaaaggc ggtaatacgg ttatccacag   4260
aatcagggga taacgcagga aagaacatgt gagcaaaagg ccagcaaaag gccaggaacc   4320
```

gtaaaaaggc cgcgttgctg gcgtttttcc ataggctccg cccccctgac gagcatcaca 4380
aaaatcgacg ctcaagtcag aggtggcgaa acccgacagg actataaaga taccaggcgt 4440
ttccccctgg aagctccctc gtgcgctctc ctgttccgac cctgccgctt accggatacc 4500
tgtccgcctt tctcccttcg ggaagcgtgg cgctttctca tagctcacgc tgtaggtatc 4560
tcagttcggt gtaggtcgtt cgctccaagc tgggctgtgt gcacgaaccc cccgttcagc 4620
ccgaccgctg cgccttatcc ggtaactatc gtcttgagtc caacccggta agacacgact 4680
tatcgccact ggcagcagcc actggtaaca ggattagcag agcgaggtat gtaggcggtg 4740
ctacagagtt cttgaagtgg tggcctaact acggctacac tagaaggaca gtatttggta 4800
tctgcgctct gctgaagcca gttaccttcg gaaaaagagt tggtagctct tgatccggca 4860
aacaaaccac cgctggtagc ggtggttttt ttgtttgcaa gcagcagatt acgcgcagaa 4920
aaaaaggatc tcaagaagat cctttgatct tttctacggg gtctgacgct cagtggaacg 4980
aaaactcacg ttaagggatt ttggtcatga gattatcaaa aaggatcttc acctagatcc 5040
ttttaaatta aaaatgaagt tttaaatcaa tctaaagtat atatgagtaa acttggtctg 5100
acagttacca atgcttaatc agtgaggcac ctatctcagc gatctgtcta tttcgttcat 5160
ccatagttgc ctgactcccc gtcgtgtaga taactacgat acgggagggc ttaccatctg 5220
gccccagtgc tgcaatgata ccgcgagacc cacgctcacc ggctccagat ttatcagcaa 5280
taaaccagcc agccggaagg gccgagcgca gaagtggtcc tgcaacttta tccgcctcca 5340
tccagtctat taattgttgc cgggaagcta gagtaagtag ttcgccagtt aatagtttgc 5400
gcaacgttgt tgccattgct acaggcatcg tggtgtcacg ctcgtcgttt ggtatggctt 5460
cattcagctc cggttcccaa cgatcaaggc gagttacatg atcccccatg ttgtgcaaaa 5520
aagcggttag ctccttcggt cctccgatcg ttgtcagaag taagttggcc gcagtgttat 5580
cactcatggt tatggcagca ctgcataatt ctcttactgt catgccatcc gtaagatgct 5640
tttctgtgac tggtgagtac tcaaccaagt cattctgaga atagtgtatg cggcgaccga 5700
gttgctcttg cccggcgtca atacgggata ataccgcgcc acatagcaga actttaaaag 5760
tgctcatcat tggaaaacgt tcttcggggc gaaaactctc aaggatctta ccgctgttga 5820
gatccagttc gatgtaaccc actcgtgcac ccaactgatc ttcagcatct tttactttca 5880
ccagcgtttc tgggtgagca aaaacaggaa ggcaaaatgc cgcaaaaaag ggaataaggg 5940
cgacacggaa atgttgaata ctcatactct tcctttttca atattattga agcatttatc 6000
agggttattg tctcatgagc ggatacatat ttgaatgtat ttagaaaaat aaacaaatag 6060
gggttccgcg cacatttccc cgaaaagtgc cacctgacgt ctaagaaacc attattatca 6120
tgacattaac ctataaaaat aggcgtatca cgaggccctt tcgtc 6165

<210> SEQ ID NO 54
<211> LENGTH: 1452
<212> TYPE: DNA
<213> ORGANISM: Artificial sequence
<220> FEATURE:
<223> OTHER INFORMATION: DNA sequence coding for fusion protein ER(T2)-Bax

<400> SEQUENCE: 54
atgagcctgg ccttgtccct gacggccgac cagatggtca gtgccttgtt ggatgctgag 60
ccccccatac tctattccga gtatgatcct accagaccct tcagtgaagc ttcgatgatg 120
ggcttactga ccaacctggc agacagggag ctggttcaca tgatcaactg ggcgaagagg 180

-continued

```
gtgccaggct ttgtggattt gaccctccat gatcaggtcc accttctaga atgtgcctgg    240
ctagagatcc tgatgattgg tctcgtctgg cgctccatgg agcacccagt gaagctactg    300
tttgctccta acttgctctt ggacaggaac cagggaaaat gtgtagaggg catggtggag    360
atcttcgaca tgctgctggc tacatcatct cggttccgca tgatgaatct gcagggagag    420
gagtttgtgt gcctcaaatc tattattttg cttaattctg gagtgtacac atttctgtcc    480
agcaccctga agtctctgga agagaaggac catatccacc gagtcctgga caagatcaca    540
gacactttga tccacctgat ggccaaggca ggcctgaccc tgcagcagca gcaccagcgg    600
ctggcccagc tcctcctcat cctctcccac atcaggcaca tgagtaacaa aggcatggag    660
catctgtaca gcatgaagtg caagaacgtg gtgcccctct atgacctgct gctggaggcg    720
gcggacgccc accgcctaca tgcgcccact agccgtggag gggcatccgt ggaggagacg    780
gaccaaagcc acttggccac tgcgggctct acttcatcgc attccttgca aaagtattac    840
atcacggggg aggcagaggg tttccctgcc acagctgacg ggtccgggga gcagcttggg    900
agcggcgggc ccaccagctc tgaacagatc atgaagacag gggccttttt gctacagggt    960
ttcatccagg atcgagcagg gaggatggct ggggagacac ctgagctgac cttggagcag   1020
ccgccccagg atgcgtccac caagaagctg agcgagtgtc tccggcgaat tggagatgaa   1080
ctggacagca atatggagct gcagaggatg attgctgacg tggacacgga ctcccccga    1140
gaggtcttct tccgggtggc agctgacatg tttgctgatg gcaacttcaa ctggggccgc   1200
gtggttgccc tcttctactt tgctagcaaa ctggtgctca aggccctgtg cactaaagtg   1260
cccgagctga tcagaaccat catgggctgg acactggact tcctccgtga gcggctgctt   1320
gtctggatcc aagaccaggg tggctgggaa ggcctcctct cctacttcgg gacccccaca   1380
tggcagacag tgaccatctt tgtggctgga gtcctcaccg cctcgctcac catctggaag   1440
aagatgggct ga                                                       1452
```

<210> SEQ ID NO 55
<211> LENGTH: 483
<212> TYPE: PRT
<213> ORGANISM: Artificial sequence
<220> FEATURE:
<223> OTHER INFORMATION: fusion protein ER(T2)-Bax

<400> SEQUENCE: 55

```
Met Ser Leu Ala Leu Ser Leu Thr Ala Asp Gln Met Val Ser Ala Leu
1               5                   10                  15

Leu Asp Ala Glu Pro Pro Ile Leu Tyr Ser Glu Tyr Asp Pro Thr Arg
            20                  25                  30

Pro Phe Ser Glu Ala Ser Met Met Gly Leu Leu Thr Asn Leu Ala Asp
        35                  40                  45

Arg Glu Leu Val His Met Ile Asn Trp Ala Lys Arg Val Pro Gly Phe
    50                  55                  60

Val Asp Leu Thr Leu His Asp Gln Val His Leu Leu Glu Cys Ala Trp
65                  70                  75                  80

Leu Glu Ile Leu Met Ile Gly Leu Val Trp Arg Ser Met Glu His Pro
                85                  90                  95

Val Lys Leu Leu Phe Ala Pro Asn Leu Leu Leu Asp Arg Asn Gln Gly
            100                 105                 110

Lys Cys Val Glu Gly Met Val Glu Ile Phe Asp Met Leu Leu Ala Thr
        115                 120                 125

Ser Ser Arg Phe Arg Met Met Asn Leu Gln Gly Glu Glu Phe Val Cys
    130                 135                 140
```

```
Leu Lys Ser Ile Ile Leu Leu Asn Ser Gly Val Tyr Thr Phe Leu Ser
145                 150                 155                 160

Ser Thr Leu Lys Ser Leu Glu Glu Lys Asp His Ile His Arg Val Leu
                165                 170                 175

Asp Lys Ile Thr Asp Thr Leu Ile His Leu Met Ala Lys Ala Gly Leu
            180                 185                 190

Thr Leu Gln Gln Gln His Gln Arg Leu Ala Gln Leu Leu Leu Ile Leu
        195                 200                 205

Ser His Ile Arg His Met Ser Asn Lys Gly Met Glu His Leu Tyr Ser
    210                 215                 220

Met Lys Cys Lys Asn Val Val Pro Leu Tyr Asp Leu Leu Leu Glu Ala
225                 230                 235                 240

Ala Asp Ala His Arg Leu His Ala Pro Thr Ser Arg Gly Gly Ala Ser
                245                 250                 255

Val Glu Glu Thr Asp Gln Ser His Leu Ala Thr Ala Gly Ser Thr Ser
            260                 265                 270

Ser His Ser Leu Gln Lys Tyr Tyr Ile Thr Gly Glu Ala Glu Gly Phe
        275                 280                 285

Pro Ala Thr Ala Asp Gly Ser Gly Glu Gln Leu Gly Ser Gly Gly Pro
    290                 295                 300

Thr Ser Ser Glu Gln Ile Met Lys Thr Gly Ala Phe Leu Leu Gln Gly
305                 310                 315                 320

Phe Ile Gln Asp Arg Ala Gly Arg Met Ala Gly Glu Thr Pro Glu Leu
                325                 330                 335

Thr Leu Glu Gln Pro Pro Gln Asp Ala Ser Thr Lys Lys Leu Ser Glu
            340                 345                 350

Cys Leu Arg Arg Ile Gly Asp Glu Leu Asp Ser Asn Met Glu Leu Gln
        355                 360                 365

Arg Met Ile Ala Asp Val Asp Thr Asp Ser Pro Arg Glu Val Phe Phe
    370                 375                 380

Arg Val Ala Ala Asp Met Phe Ala Asp Gly Asn Phe Asn Trp Gly Arg
385                 390                 395                 400

Val Val Ala Leu Phe Tyr Phe Ala Ser Lys Leu Val Leu Lys Ala Leu
                405                 410                 415

Cys Thr Lys Val Pro Glu Leu Ile Arg Thr Ile Met Gly Trp Thr Leu
            420                 425                 430

Asp Phe Leu Arg Glu Arg Leu Leu Val Trp Ile Gln Asp Gln Gly Gly
        435                 440                 445

Trp Glu Gly Leu Leu Ser Tyr Phe Gly Thr Pro Thr Trp Gln Thr Val
    450                 455                 460

Thr Ile Phe Val Ala Gly Val Leu Thr Ala Ser Leu Thr Ile Trp Lys
465                 470                 475                 480

Lys Met Gly
```

<210> SEQ ID NO 56
<211> LENGTH: 7164
<212> TYPE: DNA
<213> ORGANISM: Artificial sequence
<220> FEATURE:
<223> OTHER INFORMATION: vector pCMV--gal-pA

<400> SEQUENCE: 56

```
gaattcgagc ttgcatgcct gcaggtcgtt acataactta cggtaaatgg cccgcctggc      60

tgaccgccca acgacccccg cccattgacg tcaataatga cgtatgttcc catagtaacg     120
```

-continued

```
ccaataggga ctttccattg acgtcaatgg gtggagtatt tacggtaaac tgcccacttg    180
gcagtacatc aagtgtatca tatgccaagt acgcccccta ttgacgtcaa tgacggtaaa    240
tggcccgcct ggcattatgc ccagtacatg accttatggg actttcctac ttggcagtac    300
atctacgtat tagtcatcgc tattaccatg gtgatgcggt tttggcagta catcaatggg    360
cgtggatagc ggtttgactc acggggattt ccaagtctcc accccattga cgtcaatggg    420
agtttgtttt ggcaccaaaa tcaacgggac tttccaaaat gtcgtaacaa ctccgcccca    480
ttgacgcaaa tgggcggtag gcgtgtacgg tgggaggtct atataagcag agctcgttta    540
gtgaaccgtc agatcgcctg gagacgccat ccacgctgtt ttgacctcca tagaagacac    600
cgggaccgat ccagcctccg gactctagag gatccggtac tcgaggaact gaaaaaccag    660
aaagttaact ggtaagttta gtctttttgt cttttatttc aggtcccgga tccggtggtg    720
gtgcaaatca aagaactgct cctcagtgga tgttgccttt acttctaggc ctgtacggaa    780
gtgttacttc tgctctaaaa gctgcggaat tgtacccgcg gccgcaattc ccggggatcg    840
aaagagcctg ctaaagcaaa aaagaagtca ccatgtcgtt tactttgacc aacaagaacg    900
tgattttcgt tgccggtctg ggaggcattg gtctggacac cagcaaggag ctgctcaagc    960
gcgatcccgt cgttttacaa cgtcgtgact gggaaaaccc tggcgttacc caacttaatc   1020
gccttgcagc acatccccct ttcgccagct ggcgtaatag cgaagaggcc cgcaccgatc   1080
gcccttccca acagttgcgc agcctgaatg gcgaatggcg ctttgcctgg tttccggcac   1140
cagaagcggt gccggaaagc tggctggagt gcgatcttcc tgaggccgat actgtcgtcg   1200
tcccctcaaa ctggcagatg cacggttacg atgcgcccat ctacaccaac gtaacctatc   1260
ccattacggt caatccgccg tttgttccca cggagaatcc gacgggttgt tactcgctca   1320
catttaatgt tgatgaaagc tggctacagg aaggccagac gcgaattatt tttgatggcg   1380
ttaactcggc gtttcatctg tggtgcaacg ggcgctgggt cggttacggc caggacagtc   1440
gtttgccgtc tgaatttgac ctgagcgcat ttttacgcgc cggagaaaac cgcctcgcgg   1500
tgatggtgct gcgttggagt gacggcagtt atctggaaga tcaggatatg tggcggatga   1560
gcggcatttt ccgtgacgtc tcgttgctgc ataaaccgac tacacaaatc agcgatttcc   1620
atgttgccac tcgctttaat gatgatttca gccgcgctgt actggaggct gaagttcaga   1680
tgtgcggcga gttgcgtgac tacctacggg taacagtttc tttatggcag ggtgaaacgc   1740
aggtcgccag cggcaccgcg cctttcggcg gtgaaattat cgatgagcgt ggtggttatg   1800
ccgatcgcgt cacactacgt ctgaacgtcg aaaacccgaa actgtggagc gccgaaatcc   1860
cgaatctcta tcgtgcggtg gttgaactgc acaccgccga cggcacgctg attgaagcag   1920
aagcctgcga tgtcggtttc cgcgaggtgc ggattgaaaa tggtctgctg ctgctgaacg   1980
gcaagccgtt gctgattcga ggcgttaacc gtcacgagca tcatcctctg catggtcagg   2040
tcatggatga gcagacgatg gtgcaggata tcctgctgat gaagcagaac aactttaacg   2100
ccgtgcgctg ttcgcattat ccgaaccatc cgctgtggta cacgctgtgc gaccgctacg   2160
gcctgtatgt ggtggatgaa gccaatattg aaacccacgg catggtgcca atgaatcgtc   2220
tgaccgatga tccgcgctgg ctaccggcga tgagcgaacg cgtaacgcga atggtgcagc   2280
gcgatcgtaa tcacccgagt gtgatcatct ggtcgctggg gaatgaatca ggccacggcg   2340
ctaatcacga cgcgctgtat cgctggatca aatctgtcga tccttcccgc ccggtgcagt   2400
atgaaggcgg cggagccgac accacggcca ccgatattat ttgcccgatg tacgcgcgcg   2460
tggatgaaga ccagcccttc ccggctgtgc cgaaatggtc catcaaaaaa tggctttcgc   2520
```

-continued

```
tacctggaga gacgcgcccg ctgatccttt gcgaatacgc ccacgcgatg ggtaacagtc   2580
ttggcggttt cgctaaatac tggcaggcgt ttcgtcagta tccccgttta cagggcggct   2640
tcgtctggga ctgggtggat cagtcgctga ttaaatatga tgaaaacggc aacccgtggt   2700
cggcttacgg cggtgatttt ggcgatacgc cgaacgatcg ccagttctgt atgaacggtc   2760
tggtctttgc cgaccgcacg ccgcatccag cgctgacgga agcaaaacac cagcagcagt   2820
ttttccagtt ccgtttatcc gggcaaacca tcgaagtgac cagcgaatac ctgttccgtc   2880
atagcgataa cgagctcctg cactggatgg tggcgctgga tggtaagccg ctggcaagcg   2940
gtgaagtgcc tctggatgtc gctccacaag gtaaacagtt gattgaactg cctgaactac   3000
cgcagccgga gagcgccggg caactctggc tcacagtacg cgtagtgcaa ccgaacgcga   3060
ccgcatggtc agaagccggg cacatcagcg cctggcagca gtggcgtctg gcggaaaacc   3120
tcagtgtgac gctccccgcc gcgtcccacg ccatcccgca tctgaccacc agcgaaatgg   3180
atttttgcat cgagctgggt aataagcgtt ggcaatttaa ccgccagtca ggctttcttt   3240
cacagatgtg gattggcgat aaaaaacaac tgctgacgcc gctgcgcgat cagttcaccc   3300
gtgcaccgct ggataacgac attggcgtaa gtgaagcgac ccgcattgac cctaacgcct   3360
gggtcgaacg ctggaaggcg gcgggccatt accaggccga agcagcgttg ttgcagtgca   3420
cggcagatac acttgctgat gcggtgctga ttacgaccgc tcacgcgtgg cagcatcagg   3480
ggaaaacctt atttatcagc cggaaaacct accggattga tggtagtggt caaatggcga   3540
ttaccgttga tgttgaagtg gcgagcgata caccgcatcc ggcgcggatt ggcctgaact   3600
gccagctggc gcaggtagca gagcgggtaa actggctcgg attagggccg caagaaaact   3660
atcccgaccg ccttactgcc gcctgttttg accgctggga tctgccattg tcagacatgt   3720
ataccccgta cgtcttcccg agcgaaaacg gtctgcgctg cgggacgcgc gaattgaatt   3780
atggcccaca ccagtggcgc ggcgacttcc agttcaacat cagccgctac agtcaacagc   3840
aactgatgga aaccagccat cgccatctgc tgcacgcgga agaaggcaca tggctgaata   3900
tcgacggttt ccatatgggg attggtggcg acgactcctg gagcccgtca gtatcggcgg   3960
aattacagct gagcgccggt cgctaccatt accagttggt ctggtgtcaa aaataataat   4020
aaccgggcag gccatgtctg cccgtatttc gcgtaaggaa atccattatg tactatttaa   4080
aaaacacaaa cttttggatg ttcggtttat tctttttctt ttactttttt atcatgggag   4140
cctacttccc gtttttcccg atttggctac atgacatcaa ccatatcagc aaaagtgata   4200
cgggtattat ttttgccgct atttctctgt tctcgctatt attccaaccg ctgtttggtc   4260
tgctttctga caaactcggc ctcgactcta ggcggccgcg gggatccaga catgataaga   4320
tacattgatg agtttggaca aaccacaact agaatgcagt gaaaaaaatg ctttatttgt   4380
gaaatttgtg atgctattgc tttatttgta accattataa gctgcaataa acaagttaac   4440
aacaacaatt gcattcattt tatgtttcag gttcaggggg aggtgtggga ggttttttcg   4500
gatcctctag agtcgacctg caggcatgca agcttggcgt aatcatggtc atagctgttt   4560
cctgtgtgaa attgttatcc gctcacaatt ccacacaaca tacgagccgg aagcataaag   4620
tgtaaagcct ggggtgccta atgagtgagc taactcacat taattgcgtt gcgctcactg   4680
cccgctttcc agtcgggaaa cctgtcgtgc cagctgcatt aatgaatcgg ccaacgcgcg   4740
gggagaggcg gtttgcgtat tgggcgctct tccgcttcct cgctcactga ctcgctgcgc   4800
tcggtcgttc ggctgcggcg agcggtatca gctcactcaa aggcggtaat acggttatcc   4860
acagaatcag gggataacgc aggaaagaac atgtgagcaa aaggccagca aaaggccagg   4920
```

-continued

```
aaccgtaaaa aggccgcgtt gctggcgttt ttccataggc tccgcccccc tgacgagcat   4980
cacaaaaatc gacgctcaag tcagaggtgg cgaaacccga caggactata aagataccag   5040
gcgtttcccc ctggaagctc cctcgtgcgc tctcctgttc cgaccctgcc gcttaccgga   5100
tacctgtccg cctttctccc ttcgggaagc gtggcgcttt ctcatagctc acgctgtagg   5160
tatctcagtt cggtgtaggt cgttcgctcc aagctgggct gtgtgcacga accccccgtt   5220
cagcccgacc gctgcgcctt atccggtaac tatcgtcttg agtccaaccc ggtaagacac   5280
gacttatcgc cactggcagc agccactggt aacaggatta gcagagcgag gtatgtaggc   5340
ggtgctacag agttcttgaa gtggtggcct aactacggct acactagaag gacagtattt   5400
ggtatctgcg ctctgctgaa gccagttacc ttcggaaaaa gagttggtag ctcttgatcc   5460
ggcaaacaaa ccaccgctgg tagcggtggt ttttttgttt gcaagcagca gattacgcgc   5520
agaaaaaaag gatctcaaga agatcctttg atcttttcta cggggtctga cgctcagtgg   5580
aacgaaaact cacgttaagg gattttggtc atgagattat caaaaaggat cttcacctag   5640
atccttttaa attaaaaatg aagttttaaa tcaatctaaa gtatatatga gtaaacttgg   5700
tctgacagtt accaatgctt aatcagtgag gcacctatct cagcgatctg tctatttcgt   5760
tcatccatag ttgcctgact ccccgtcgtg tagataacta cgatacggga gggcttacca   5820
tctggcccca gtgctgcaat gataccgcga gacccacgct caccggctcc agatttatca   5880
gcaataaacc agccagccgg aagggccgag cgcagaagtg gtcctgcaac tttatccgcc   5940
tccatccagt ctattaattg ttgccgggaa gctagagtaa gtagttcgcc agttaatagt   6000
ttgcgcaacg ttgttgccat tgctacaggc atcgtggtgt cacgctcgtc gtttggtatg   6060
gcttcattca gctccggttc ccaacgatca aggcgagtta catgatcccc catgttgtgc   6120
aaaaaagcgg ttagctcctt cggtcctccg atcgttgtca gaagtaagtt ggccgcagtg   6180
ttatcactca tggttatggc agcactgcat aattctctta ctgtcatgcc atccgtaaga   6240
tgcttttctg tgactggtga gtactcaacc aagtcattct gagaatagtg tatgcggcga   6300
ccgagttgct cttgcccggc gtcaatacgg gataataccg cgccacatag cagaacttta   6360
aaagtgctca tcattggaaa acgttcttcg gggcgaaaac tctcaaggat cttaccgctg   6420
ttgagatcca gttcgatgta acccactcgt gcacccaact gatcttcagc atcttttact   6480
ttcaccagcg tttctgggtg agcaaaaaca ggaaggcaaa atgccgcaaa aaagggaata   6540
agggcgacac ggaaatgttg aatactcata ctcttccttt ttcaatatta ttgaagcatt   6600
tatcagggtt attgtctcat gagcggatac atatttgaat gtatttagaa aaataaacaa   6660
ataggggttc cgcgcacatt tccccgaaaa gtgccacctg acgtctaaga aaccattatt   6720
atcatgacat taacctataa aaataggcgt atcacgaggc cctttcgtct cgcgcgtttc   6780
ggtgatgacg gtgaaaacct ctgacacatg cagctcccgg agacggtcac agcttgtctg   6840
taagcggatg ccgggagcag acaagcccgt cagggcgcgt cagcgggtgt tggcgggtgt   6900
cggggctggc ttaactatgc ggcatcagag cagattgtac tgagagtgca ccatatgcgg   6960
tgtgaaatac cgcacagatg cgtaaggaga aaataccgca tcaggcgcca ttcgccattc   7020
aggctgcgca actgttggga agggcgatcg gtgcgggcct cttcgctatt acgccagctg   7080
gcgaaagggg gatgtgctgc aaggcgatta agttgggtaa cgccagggtt ttcccagtca   7140
cgacgttgta aaacgacggc cagt                                          7164
```

<210> SEQ ID NO 57
<211> LENGTH: 4416
<212> TYPE: DNA

<213> ORGANISM: Artificial sequence
<220> FEATURE:
<223> OTHER INFORMATION: vector pPgk-hygro-pA

<400> SEQUENCE: 57
agatctgata tcatcgatga attctaccgg gtaggggagg cgcttttccc aaggcagtct 60
ggagcatgcg ctttagcagc cccgctgggc acttggcgct acacaagtgg cctctggcct 120
cgcacacatt ccacatccac cggtaggcgc caaccggctc cgttctttgg tggccccttc 180
gcgccacctt ctactcctcc cctagtcagg aagttccccc ccgccccgca gctcgcgtcg 240
tgcaggacgt gacaaatgga agtagcacgt ctcactagtc tcgtgcagat ggacagcacc 300
gctgagcaat ggaagcgggt aggcctttgg ggcagcggcc aatagcagct ttgctccttc 360
gctttctggg ctcagaggct gggaaggggt gggtccgggg gcgggctcag gggcgggctc 420
aggggcgggg cgggcgcccg aaggtcctcc ggaggcccgg cattctgcac gcttcaaaag 480
cgcacgtctg ccgcgctgtt ctcctcttcc tcatctccgg gcctttcgac cgatccagcc 540
gccaccatga aaaagcctga actcaccgcg acgtctgtcg agaagtttct gatcgaaaag 600
ttcgacagcg tctccgacct gatgcagctc tcggagggcg aagaatctcg tgctttcagc 660
ttcgatgtag gagggcgtgg atatgtcctg cgggtaaata gctgcgccga tggtttctac 720
aaagatcgtt atgtttatcg gcactttgca tcggccgcgc tcccgattcc ggaagtgctt 780
gacattgggg aattcagcga gagcctgacc tattgcatct cccgccgtgc acagggtgtc 840
acgttgcaag acctgcctga aaccgaactg cccgctgttc tgcagccggt cgcggaggcc 900
atggatgcga tcgctgcggc cgatcttagc cagacgagcg ggttcggccc attcggaccg 960
caaggaatcg gtcaatacac tacatggcgt gatttcatat gcgcgattgc tgatccccat 1020
gtgtatcact ggcaaactgt gatggacgac accgtcagtg cgtccgtcgc gcaggctctc 1080
gatgagctga tgctttgggc cgaggactgc cccgaagtcc ggcacctcgt gcacgcggat 1140
ttcggctcca acaatgtcct gacggacaat ggccgcataa cagcggtcat tgactggagc 1200
gaggcgatgt tcggggattc ccaatacgag gtcgccaaca tcttcttctg gaggccgtgg 1260
ttggcttgta tggagcagca gacgcgctac ttcgagcgga ggcatccgga gcttgcagga 1320
tcgccgcggc tccgggcgta tatgctccgc attggtcttg accaactcta tcagagcttg 1380
gttgacggca atttcgatga tgcagcttgg gcgcagggtc gatgcgacgc aatcgtccga 1440
tccggagccg ggactgtcgg gcgtacacaa atcgcccgca gaagcgcggc cgtctggacc 1500
gatggctgtg tagaagtact cgccgatagt ggaaaccgac gccccagcac tcgtccgagg 1560
gcaaaggaat agtcgagaaa ttgatgatct attaaacaat aaagatgtcc actaaaatgg 1620
aagtttttcc tgtcatactt tgttaagaag ggtgagaaca gagtacctac attttgaatg 1680
gaaggattgg agctacgggg gtgggggtgg ggtgggatta gataaatgcc tgctctttac 1740
tgaaggctct ttactattgc tttatgataa tgtttcatag ttggatatca taatttaaac 1800
aagcaaaacc aaattaaggg ccagctcatt cctcccactc atgatctata gatctataga 1860
tctctcgtgg gatcattgtt tttctcttga ttcccacttt gtggttctaa gtactgtggt 1920
ttccaaatgt gtcagtttca tagcctgaag aacgagatca gcagcctctg ttccacatac 1980
acttcattct cagtattgtt ttgccaagtt ctaattccat cagaagcttc agctgctcga 2040
gttctatagt gtcacctaaa tcgtatgtgt atgatacata aggttatgta ttaattgtag 2100
ccgcgttcta acgacaatat gtccatatgg tgcactctca gtacaatctg ctctgatgcc 2160
gcatagttaa gccagccccg acacccgcca acacccgctg acgcgccctg acgggcttgt 2220

-continued

```
ctgctcccgg catccgctta cagacaagct gtgaccgtct ccgggagctg catgtgtcag   2280

aggttttcac cgtcatcacc gaaacgcgcg agacgaaagg gcctcgtgat acgcctattt   2340

ttataggtta atgtcatgat aataatggtt tcttagacgt caggtggcac ttttcgggga   2400

aatgtgcgcg gaacccctat ttgtttattt ttctaaatac attcaaatat gtatccgctc   2460

atgagacaat aaccctgata aatgcttcaa taatattgaa aaaggaagag tatgagtatt   2520

caacatttcc gtgtcgccct tattcccttt tttgcggcat tttgccttcc tgtttttgct   2580

cacccagaaa cgctggtgaa agtaaaagat gctgaagatc agttgggtgc acgagtgggt   2640

tacatcgaac tggatctcaa cagcggtaag atccttgaga gttttcgccc cgaagaacgt   2700

tttccaatga tgagcacttt taaagttctg ctatgtggcg cggtattatc ccgtattgac   2760

gccgggcaag agcaactcgg tcgccgcata cactattctc agaatgactt ggttgagtac   2820

tcaccagtca cagaaaagca tcttacggat ggcatgacag taagagaatt atgcagtgct   2880

gccataacca tgagtgataa cactgcggcc aacttacttc tgacaacgat cggaggaccg   2940

aaggagctaa ccgctttttt gcacaacatg ggggatcatg taactcgcct tgatcgttgg   3000

gaaccggagc tgaatgaagc cataccaaac gacgagcgtg acaccacgat gcctgtagca   3060

atggcaacaa cgttgcgcaa actattaact ggcgaactac ttactctagc ttcccggcaa   3120

caattaatag actggatgga ggcggataaa gttgcaggac cacttctgcg ctcggccctt   3180

ccggctggct ggtttattgc tgataaatct ggagccggtg agcgtgggtc tcgcggtatc   3240

attgcagcac tggggccaga tggtaagccc tcccgtatcg tagttatcta cacgacgggg   3300

agtcaggcaa ctatggatga acgaaataga cagatcgctg agataggtgc ctcactgatt   3360

aagcattggt aactgtcaga ccaagtttac tcatatatac tttagattga tttaaaactt   3420

catttttaat ttaaaaggat ctaggtgaag atcctttttg ataatctcat gaccaaaatc   3480

ccttaacgtg agttttcgtt ccactgagcg tcagaccccg tagaaaagat caaaggatct   3540

tcttgagatc ctttttttct gcgcgtaatc tgctgcttgc aaacaaaaaa accaccgcta   3600

ccagcggtgg tttgtttgcc ggatcaagag ctaccaactc tttttccgaa ggtaactggc   3660

ttcagcagag cgcagatacc aaatactgtt cttctagtgt agccgtagtt aggccaccac   3720

ttcaagaact ctgtagcacc gcctacatac ctcgctctgc taatcctgtt accagtggct   3780

gctgccagtg gcgataagtc gtgtcttacc gggttggact caagacgata gttaccggat   3840

aaggcgcagc ggtcgggctg aacggggggt tcgtgcacac agcccagctt ggagcgaacg   3900

acctacaccg aactgagata cctacagcgt gagctatgag aaagcgccac gcttcccgaa   3960

gggagaaagg cggacaggta tccggtaagc ggcagggtcg gaacaggaga gcgcacgagg   4020

gagcttccag ggggaaacgc ctggtatctt tatagtcctg tcgggtttcg ccacctctga   4080

cttgagcgtc gatttttgtg atgctcgtca ggggggcgga gcctatggaa aaacgccagc   4140

aacgcggcct ttttacggtt cctggccttt tgctggcctt ttgctcacat gttctttcct   4200

gcgttatccc ctgattctgt ggataaccgt attaccgcct ttgagtgagc tgataccgct   4260

cgccgcagcc gaacgaccga gcgcagcgag tcagtgagcg aggaagcgga agagcgccca   4320

atacgcaaac cgcctctccc cgcgcgttgg ccgattcatt aatgcaggtt aacctggctt   4380

atcgaaatta atacgactca ctatagggag accggc                             4416
```

<210> SEQ ID NO 58
<211> LENGTH: 277
<212> TYPE: PRT
<213> ORGANISM: Mus musculus

<400> SEQUENCE: 58

Met Glu Asn Asn Lys Thr Ser Val Asp Ser Lys Ser Ile Asn Asn Phe
1 5 10 15

Glu Val Lys Thr Ile His Gly Ser Lys Ser Val Asp Ser Gly Ile Tyr
20 25 30

Leu Asp Ser Ser Tyr Lys Met Asp Tyr Pro Glu Met Gly Ile Cys Ile
35 40 45

Ile Ile Asn Asn Lys Asn Phe His Lys Ser Thr Gly Met Ser Ser Arg
50 55 60

Ser Gly Thr Asp Val Asp Ala Ala Asn Leu Arg Glu Thr Phe Met Gly
65 70 75 80

Leu Lys Tyr Gln Val Arg Asn Lys Asn Asp Leu Thr Arg Glu Asp Ile
85 90 95

Leu Glu Leu Met Asp Ser Val Ser Lys Glu Asp His Ser Lys Arg Ser
100 105 110

Ser Phe Val Cys Val Ile Leu Ser His Gly Asp Glu Gly Val Ile Tyr
115 120 125

Gly Thr Asn Gly Pro Val Glu Leu Lys Lys Leu Thr Ser Phe Phe Arg
130 135 140

Gly Asp Tyr Cys Arg Ser Leu Thr Gly Lys Pro Lys Leu Phe Ile Ile
145 150 155 160

Gln Ala Cys Arg Gly Thr Glu Leu Asp Cys Gly Ile Glu Thr Asp Ser
165 170 175

Gly Thr Asp Glu Glu Met Ala Cys Gln Lys Ile Pro Val Glu Ala Asp
180 185 190

Phe Leu Tyr Ala Tyr Ser Thr Ala Pro Gly Tyr Tyr Ser Trp Arg Asn
195 200 205

Ser Lys Asp Gly Ser Trp Phe Ile Gln Ser Leu Cys Ser Met Leu Lys
210 215 220

Leu Tyr Ala His Lys Leu Glu Phe Met His Ile Leu Thr Arg Val Asn
225 230 235 240

Arg Lys Val Ala Thr Glu Phe Glu Ser Phe Ser Leu Asp Ser Thr Phe
245 250 255

His Ala Lys Lys Gln Ile Pro Cys Ile Val Ser Met Leu Thr Lys Glu
260 265 270

Leu Tyr Phe Tyr His
275

<210> SEQ ID NO 59
<211> LENGTH: 277
<212> TYPE: PRT
<213> ORGANISM: Homo sapiens

<400> SEQUENCE: 59

Met Glu Asn Thr Glu Asn Ser Val Asp Ser Lys Ser Ile Lys Asn Leu
1 5 10 15

Glu Pro Lys Ile Ile His Gly Ser Glu Ser Met Asp Ser Gly Ile Ser
20 25 30

Leu Asp Asn Ser Tyr Lys Met Asp Tyr Pro Glu Met Gly Leu Cys Ile
35 40 45

Ile Ile Asn Asn Lys Asn Phe His Lys Ser Thr Gly Met Thr Ser Arg
50 55 60

Ser Gly Thr Asp Val Asp Ala Ala Asn Leu Arg Glu Thr Phe Arg Asn
65 70 75 80

Leu Lys Tyr Glu Val Arg Asn Lys Asn Asp Leu Thr Arg Glu Glu Ile

```
                85                  90                  95

Val Glu Leu Met Arg Asp Val Ser Lys Glu Asp His Ser Lys Arg Ser
            100                 105                 110

Ser Phe Val Cys Val Leu Leu Ser His Gly Glu Glu Gly Ile Ile Phe
        115                 120                 125

Gly Thr Asn Gly Pro Val Asp Leu Lys Lys Ile Thr Asn Phe Phe Arg
    130                 135                 140

Gly Asp Arg Cys Arg Ser Leu Thr Gly Lys Pro Lys Leu Phe Ile Ile
145                 150                 155                 160

Gln Ala Cys Arg Gly Thr Glu Leu Asp Cys Gly Ile Glu Thr Asp Ser
                165                 170                 175

Gly Val Asp Asp Asp Met Ala Cys His Lys Ile Pro Val Glu Ala Asp
            180                 185                 190

Phe Leu Tyr Ala Tyr Ser Thr Ala Pro Gly Tyr Tyr Ser Trp Arg Asn
        195                 200                 205

Ser Lys Asp Gly Ser Trp Phe Ile Gln Ser Leu Cys Ala Met Leu Lys
    210                 215                 220

Gln Tyr Ala Asp Lys Leu Glu Phe Met His Ile Leu Thr Arg Val Asn
225                 230                 235                 240

Arg Lys Val Ala Thr Glu Phe Glu Ser Phe Ser Phe Asp Ala Thr Phe
                245                 250                 255

His Ala Lys Lys Gln Ile Pro Cys Ile Val Ser Met Leu Thr Lys Glu
            260                 265                 270

Leu Tyr Phe Tyr His
        275


<210> SEQ ID NO 60
<211> LENGTH: 303
<212> TYPE: PRT
<213> ORGANISM: Mus musculus

<400> SEQUENCE: 60

Met Thr Asp Asp Gln Asp Cys Ala Ala Glu Leu Glu Lys Val Asp Ser
1               5                   10                  15

Ser Ser Glu Asp Gly Val Asp Ala Lys Pro Asp Arg Ser Ser Ile Ile
            20                  25                  30

Ser Ser Ile Leu Leu Lys Lys Lys Arg Asn Ala Ser Ala Gly Pro Val
        35                  40                  45

Arg Thr Gly Arg Asp Arg Val Pro Thr Tyr Leu Tyr Arg Met Asp Phe
    50                  55                  60

Gln Lys Met Gly Lys Cys Ile Ile Ile Asn Asn Lys Asn Phe Asp Lys
65                  70                  75                  80

Ala Thr Gly Met Asp Val Arg Asn Gly Thr Asp Lys Asp Ala Gly Ala
                85                  90                  95

Leu Phe Lys Cys Phe Gln Asn Leu Gly Phe Glu Val Thr Val His Asn
            100                 105                 110

Asp Cys Ser Cys Ala Lys Met Gln Asp Leu Leu Arg Lys Ala Ser Glu
        115                 120                 125

Glu Asp His Ser Asn Ser Ala Cys Phe Ala Cys Val Leu Leu Ser His
    130                 135                 140

Gly Glu Glu Asp Leu Ile Tyr Gly Lys Asp Gly Val Thr Pro Ile Lys
145                 150                 155                 160

Asp Leu Thr Ala His Phe Arg Gly Asp Arg Cys Lys Thr Leu Leu Glu
                165                 170                 175

Lys Pro Lys Leu Phe Phe Ile Gln Ala Cys Arg Gly Thr Glu Leu Asp
```

```
            180                 185                 190

Asp Gly Ile Gln Ala Asp Ser Gly Pro Ile Asn Asp Ile Asp Ala Asn
        195                 200                 205

Pro Arg Asn Lys Ile Pro Val Glu Ala Asp Phe Leu Phe Ala Tyr Ser
    210                 215                 220

Thr Val Pro Gly Tyr Tyr Ser Trp Arg Asn Pro Gly Lys Gly Ser Trp
225                 230                 235                 240

Phe Val Gln Ala Leu Cys Ser Ile Leu Asn Glu His Gly Lys Asp Leu
                245                 250                 255

Glu Ile Met Gln Ile Leu Thr Arg Val Asn Asp Arg Val Ala Arg His
            260                 265                 270

Phe Glu Ser Gln Ser Asp Asp Pro Arg Phe Asn Glu Lys Lys Gln Ile
        275                 280                 285

Pro Cys Met Val Ser Met Leu Thr Lys Glu Leu Tyr Phe Ser Arg
    290                 295                 300


<210> SEQ ID NO 61
<211> LENGTH: 336
<212> TYPE: PRT
<213> ORGANISM: Homo sapiens

<400> SEQUENCE: 61

Met Asp Cys Val Gly Trp Pro Pro Gly Arg Lys Trp His Leu Glu Lys
1               5                   10                  15

Asn Thr Ser Cys Gly Gly Ser Ser Gly Ile Cys Ala Ser Tyr Val Thr
            20                  25                  30

Gln Met Ala Asp Asp Gln Gly Cys Ile Glu Glu Gln Gly Val Glu Asp
        35                  40                  45

Ser Ala Asn Glu Asp Ser Val Asp Ala Lys Pro Asp Arg Ser Ser Phe
    50                  55                  60

Val Pro Ser Leu Phe Ser Lys Lys Lys Lys Asn Val Thr Met Arg Ser
65                  70                  75                  80

Ile Lys Thr Thr Arg Asp Arg Val Pro Thr Tyr Gln Tyr Asn Met Asn
                85                  90                  95

Phe Glu Lys Leu Gly Lys Cys Ile Ile Ile Asn Asn Lys Asn Phe Asp
            100                 105                 110

Lys Val Thr Gly Met Gly Val Arg Asn Gly Thr Asp Lys Asp Ala Glu
        115                 120                 125

Ala Leu Phe Lys Cys Phe Arg Ser Leu Gly Phe Asp Val Ile Val Tyr
    130                 135                 140

Asn Asp Cys Ser Cys Ala Lys Met Gln Asp Leu Leu Lys Lys Ala Ser
145                 150                 155                 160

Glu Glu Asp His Thr Asn Ala Ala Cys Phe Ala Cys Ile Leu Leu Ser
                165                 170                 175

His Gly Glu Glu Asn Val Ile Tyr Gly Lys Asp Gly Val Thr Pro Ile
            180                 185                 190

Lys Asp Leu Thr Ala His Phe Arg Gly Asp Arg Cys Lys Thr Leu Leu
        195                 200                 205

Glu Lys Pro Lys Leu Phe Phe Ile Gln Ala Cys Arg Gly Thr Glu Leu
    210                 215                 220

Asp Asp Gly Ile Gln Ala Asp Ser Gly Pro Ile Asn Asp Thr Asp Ala
225                 230                 235                 240

Asn Pro Arg Tyr Lys Ile Pro Val Glu Ala Asp Phe Leu Phe Ala Tyr
                245                 250                 255

Ser Thr Val Pro Gly Tyr Tyr Ser Trp Arg Ser Pro Gly Arg Gly Ser
```

-continued

```
            260                 265                 270

Trp Phe Val Gln Ala Leu Cys Ser Ile Leu Glu Glu His Gly Lys Asp
        275                 280                 285

Leu Glu Ile Met Gln Ile Leu Thr Arg Val Asn Asp Arg Val Ala Arg
    290                 295                 300

His Phe Glu Ser Gln Ser Asp Asp Pro His Phe His Glu Lys Lys Gln
305                 310                 315                 320

Ile Pro Cys Val Val Ser Met Leu Thr Lys Glu Leu Tyr Phe Ser Gln
                325                 330                 335


<210> SEQ ID NO 62
<211> LENGTH: 276
<212> TYPE: PRT
<213> ORGANISM: Mus musculus

<400> SEQUENCE: 62

Met Thr Glu Thr Asp Gly Phe Tyr Lys Ser Arg Glu Val Phe Asp Pro
1               5                   10                  15

Ala Glu Gln Tyr Lys Met Asp His Lys Arg Arg Gly Val Ala Leu Ile
            20                  25                  30

Phe Asn His Glu Arg Phe Phe Trp His Leu Thr Leu Pro Glu Arg Arg
        35                  40                  45

Gly Thr Asn Ala Asp Arg Asp Asn Leu Thr Arg Arg Phe Ser Asp Leu
    50                  55                  60

Gly Phe Glu Val Lys Cys Phe Asn Asp Leu Arg Ala Glu Glu Leu Leu
65                  70                  75                  80

Leu Lys Ile His Glu Val Ser Thr Ser Ser His Ile Asp Ala Asp Cys
                85                  90                  95

Phe Ile Cys Val Phe Leu Ser His Gly Glu Gly Asn His Val Tyr Ala
            100                 105                 110

Tyr Asp Ala Lys Ile Glu Ile Gln Thr Leu Thr Gly Leu Phe Lys Gly
        115                 120                 125

Asp Lys Cys Gln Ser Leu Val Gly Lys Pro Lys Ile Phe Ile Ile Gln
    130                 135                 140

Ala Cys Arg Gly Ser Gln His Asp Val Pro Val Val Pro Leu Asp Val
145                 150                 155                 160

Val Asp His Gln Thr Asp Lys Leu Asp Asn Val Thr Gln Val Asp Ala
                165                 170                 175

Ala Ser Val Tyr Thr Leu Pro Ala Gly Ala Asp Phe Leu Met Cys Tyr
            180                 185                 190

Ser Val Ala Glu Gly Tyr Tyr Ser His Arg Glu Thr Val Asn Gly Ser
        195                 200                 205

Trp Tyr Ile Gln Asp Leu Cys Glu Met Leu Ala Arg Tyr Gly Ser Ser
    210                 215                 220

Leu Glu Phe Thr Glu Leu Leu Thr Leu Val Asn Arg Lys Val Ser Gln
225                 230                 235                 240

Arg Arg Val Asp Phe Cys Lys Asp Pro Asp Ala Ile Gly Lys Lys Gln
                245                 250                 255

Val Pro Cys Phe Ala Ser Met Leu Thr Lys Lys Leu His Phe Cys Pro
            260                 265                 270

Lys Pro Ser Lys
        275


<210> SEQ ID NO 63
<211> LENGTH: 293
<212> TYPE: PRT
```

<213> ORGANISM: Homo sapiens

<400> SEQUENCE: 63

```
Met Ser Ser Ala Ser Gly Leu Arg Arg Gly His Pro Ala Gly Gly Glu
1               5                   10                  15

Glu Asn Met Thr Glu Thr Asp Ala Phe Tyr Lys Arg Glu Met Phe Asp
            20                  25                  30

Pro Ala Glu Lys Tyr Lys Met Asp His Arg Arg Arg Gly Ile Ala Leu
        35                  40                  45

Ile Phe Asn His Glu Arg Phe Phe Trp His Leu Thr Leu Pro Glu Arg
    50                  55                  60

Arg Gly Thr Cys Ala Asp Arg Asp Asn Leu Thr Arg Arg Phe Ser Asp
65                  70                  75                  80

Leu Gly Phe Glu Val Lys Cys Phe Asn Asp Leu Lys Ala Glu Glu Leu
                85                  90                  95

Leu Leu Lys Ile His Glu Val Ser Thr Val Ser His Ala Asp Ala Asp
            100                 105                 110

Cys Phe Val Cys Val Phe Leu Ser His Gly Glu Gly Asn His Ile Tyr
        115                 120                 125

Ala Tyr Asp Ala Lys Ile Glu Ile Gln Thr Leu Thr Gly Leu Phe Lys
    130                 135                 140

Gly Asp Lys Cys His Ser Leu Val Gly Lys Pro Lys Ile Phe Ile Ile
145                 150                 155                 160

Gln Ala Cys Arg Gly Asn Gln His Asp Val Pro Val Ile Pro Leu Asp
                165                 170                 175

Val Val Asp Asn Gln Thr Glu Lys Leu Asp Thr Asn Ile Thr Glu Val
            180                 185                 190

Asp Ala Ala Ser Val Tyr Thr Leu Pro Ala Gly Ala Asp Phe Leu Met
        195                 200                 205

Cys Tyr Ser Val Ala Glu Gly Tyr Tyr Ser His Arg Glu Thr Val Asn
    210                 215                 220

Gly Ser Trp Tyr Ile Gln Asp Leu Cys Glu Met Leu Gly Lys Tyr Gly
225                 230                 235                 240

Ser Ser Leu Glu Phe Thr Glu Leu Leu Thr Leu Val Asn Arg Lys Val
                245                 250                 255

Ser Gln Arg Arg Val Asp Phe Cys Lys Asp Pro Ser Ala Ile Gly Lys
            260                 265                 270

Lys Gln Val Pro Cys Phe Ala Ser Met Leu Thr Lys Lys Leu His Phe
        275                 280                 285

Phe Pro Lys Ser Asn
    290
```

<210> SEQ ID NO 64
<211> LENGTH: 480
<212> TYPE: PRT
<213> ORGANISM: Mus musculus

<400> SEQUENCE: 64

```
Met Asp Phe Gln Ser Cys Leu Tyr Ala Ile Ala Glu Glu Leu Gly Ser
1               5                   10                  15

Glu Asp Leu Ala Ala Leu Lys Phe Leu Cys Leu Asp Tyr Ile Pro His
            20                  25                  30

Lys Lys Gln Glu Thr Ile Glu Asp Ala Gln Lys Leu Phe Leu Arg Leu
        35                  40                  45

Arg Glu Lys Gly Met Leu Glu Glu Gly Asn Leu Ser Phe Leu Lys Glu
    50                  55                  60
```

```
Leu Leu Phe His Ile Ser Arg Trp Asp Leu Leu Val Asn Phe Leu Asp
65                  70                  75                  80

Cys Asn Arg Glu Glu Met Val Arg Glu Leu Arg Asp Pro Asp Asn Ala
                85                  90                  95

Gln Ile Ser Pro Tyr Arg Val Met Leu Phe Lys Leu Ser Glu Glu Val
            100                 105                 110

Ser Glu Leu Glu Leu Arg Ser Phe Lys Phe Leu Leu Asn Asn Glu Ile
        115                 120                 125

Pro Lys Cys Lys Leu Glu Asp Asp Leu Ser Leu Leu Glu Ile Phe Val
    130                 135                 140

Glu Met Glu Lys Arg Thr Met Leu Ala Glu Asn Asn Leu Glu Thr Leu
145                 150                 155                 160

Lys Ser Ile Cys Asp Gln Val Asn Lys Ser Leu Leu Gly Lys Ile Glu
                165                 170                 175

Asp Tyr Glu Arg Ser Ser Thr Glu Arg Arg Met Ser Leu Glu Gly Arg
            180                 185                 190

Glu Glu Leu Pro Pro Ser Val Leu Asp Glu Met Ser Leu Lys Met Ala
        195                 200                 205

Glu Leu Cys Asp Ser Pro Arg Glu Gln Asp Ser Glu Ser Arg Thr Ser
    210                 215                 220

Asp Lys Val Tyr Gln Met Lys Asn Lys Pro Arg Gly Tyr Cys Leu Ile
225                 230                 235                 240

Ile Asn Asn His Asp Phe Ser Lys Ala Arg Glu Asp Ile Thr Gln Leu
                245                 250                 255

Arg Lys Met Lys Asp Arg Lys Gly Thr Asp Cys Asp Lys Glu Ala Leu
            260                 265                 270

Ser Lys Thr Phe Lys Glu Leu His Phe Glu Ile Val Ser Tyr Asp Asp
        275                 280                 285

Cys Thr Ala Asn Glu Ile His Glu Ile Leu Glu Gly Tyr Gln Ser Ala
    290                 295                 300

Asp His Lys Asn Lys Asp Cys Phe Ile Cys Cys Ile Leu Ser His Gly
305                 310                 315                 320

Asp Lys Gly Val Val Tyr Gly Thr Asp Gly Lys Glu Ala Ser Ile Tyr
                325                 330                 335

Asp Leu Thr Ser Tyr Phe Thr Gly Ser Lys Cys Pro Ser Leu Ser Gly
            340                 345                 350

Lys Pro Lys Ile Phe Phe Ile Gln Ala Cys Gln Gly Ser Asn Phe Gln
        355                 360                 365

Lys Gly Val Pro Asp Glu Ala Gly Phe Glu Gln Gln Asn His Thr Leu
    370                 375                 380

Glu Val Asp Ser Ser Ser His Lys Asn Tyr Ile Pro Asp Glu Ala Asp
385                 390                 395                 400

Phe Leu Leu Gly Met Ala Thr Val Lys Asn Cys Val Ser Tyr Arg Asp
                405                 410                 415

Pro Val Asn Gly Thr Trp Tyr Ile Gln Ser Leu Cys Gln Ser Leu Arg
            420                 425                 430

Glu Arg Cys Pro Gln Gly Asp Asp Ile Leu Ser Ile Leu Thr Gly Val
        435                 440                 445

Asn Tyr Asp Val Ser Asn Lys Asp Asp Arg Arg Asn Lys Gly Lys Gln
    450                 455                 460

Met Pro Gln Pro Thr Phe Thr Leu Arg Lys Lys Leu Phe Phe Pro Pro
465                 470                 475                 480
```

<210> SEQ ID NO 65
<211> LENGTH: 479
<212> TYPE: PRT
<213> ORGANISM: Homo sapiens

<400> SEQUENCE: 65

```
Met Asp Phe Ser Arg Asn Leu Tyr Asp Ile Gly Glu Gln Leu Asp Ser
1               5                   10                  15

Glu Asp Leu Ala Ser Leu Lys Phe Leu Ser Leu Asp Tyr Ile Pro Gln
            20                  25                  30

Arg Lys Gln Glu Pro Ile Lys Asp Ala Leu Met Leu Phe Gln Arg Leu
        35                  40                  45

Gln Glu Lys Arg Met Leu Glu Glu Ser Asn Leu Ser Phe Leu Lys Glu
    50                  55                  60

Leu Leu Phe Arg Ile Asn Arg Leu Asp Leu Leu Ile Thr Tyr Leu Asn
65                  70                  75                  80

Thr Arg Lys Glu Glu Met Glu Arg Glu Leu Gln Thr Pro Gly Arg Ala
                85                  90                  95

Gln Ile Ser Ala Tyr Arg Val Met Leu Tyr Gln Ile Ser Glu Glu Val
            100                 105                 110

Ser Arg Ser Glu Leu Arg Ser Phe Lys Phe Leu Leu Gln Glu Glu Ile
        115                 120                 125

Ser Lys Cys Lys Leu Asp Asp Asp Met Asn Leu Leu Asp Ile Phe Ile
    130                 135                 140

Glu Met Glu Lys Arg Val Ile Leu Gly Glu Gly Lys Leu Asp Ile Leu
145                 150                 155                 160

Lys Arg Val Cys Ala Gln Ile Asn Lys Ser Leu Leu Lys Ile Ile Asn
                165                 170                 175

Asp Tyr Glu Glu Phe Ser Lys Glu Arg Ser Ser Ser Leu Glu Gly Ser
            180                 185                 190

Pro Asp Glu Phe Ser Asn Gly Glu Glu Leu Cys Gly Val Met Thr Ile
        195                 200                 205

Ser Asp Ser Pro Arg Glu Gln Asp Ser Glu Ser Gln Thr Leu Asp Lys
    210                 215                 220

Val Tyr Gln Met Lys Ser Lys Pro Arg Gly Tyr Cys Leu Ile Ile Asn
225                 230                 235                 240

Asn His Asn Phe Ala Lys Ala Arg Glu Lys Val Pro Lys Leu His Ser
                245                 250                 255

Ile Arg Asp Arg Asn Gly Thr His Leu Asp Ala Gly Ala Leu Thr Thr
            260                 265                 270

Thr Phe Glu Glu Leu His Phe Glu Ile Lys Pro His Asp Asp Cys Thr
        275                 280                 285

Val Glu Gln Ile Tyr Glu Ile Leu Lys Ile Tyr Gln Leu Met Asp His
    290                 295                 300

Ser Asn Met Asp Cys Phe Ile Cys Cys Ile Leu Ser His Gly Asp Lys
305                 310                 315                 320

Gly Ile Ile Tyr Gly Thr Asp Gly Gln Glu Ala Pro Ile Tyr Glu Leu
                325                 330                 335

Thr Ser Gln Phe Thr Gly Leu Lys Cys Pro Ser Leu Ala Gly Lys Pro
            340                 345                 350

Lys Val Phe Phe Ile Gln Ala Cys Gln Gly Asp Asn Tyr Gln Lys Gly
        355                 360                 365

Ile Pro Val Glu Thr Asp Ser Glu Glu Gln Pro Tyr Leu Glu Met Asp
    370                 375                 380

Leu Ser Ser Pro Gln Thr Arg Tyr Ile Pro Asp Glu Ala Asp Phe Leu
```

```
385                 390                 395                 400

Leu Gly Met Ala Thr Val Asn Asn Cys Val Ser Tyr Arg Asn Pro Ala
                405                 410                 415

Glu Gly Thr Trp Tyr Ile Gln Ser Leu Cys Gln Ser Leu Arg Glu Arg
            420                 425                 430

Cys Pro Arg Gly Asp Asp Ile Leu Thr Ile Leu Thr Glu Val Asn Tyr
        435                 440                 445

Glu Val Ser Asn Lys Asp Asp Lys Lys Asn Met Gly Lys Gln Met Pro
    450                 455                 460

Gln Pro Thr Phe Thr Leu Arg Lys Lys Leu Val Phe Pro Ser Asp
465                 470                 475


<210> SEQ ID NO 66
<211> LENGTH: 522
<212> TYPE: PRT
<213> ORGANISM: Homo sapiens

<400> SEQUENCE: 66

Met Lys Ser Gln Gly Gln His Trp Tyr Ser Ser Ser Asp Lys Asn Cys
1               5                   10                  15

Lys Val Ser Phe Arg Glu Lys Leu Leu Ile Ile Asp Ser Asn Leu Gly
            20                  25                  30

Val Gln Asp Val Glu Asn Leu Lys Phe Leu Cys Ile Gly Leu Val Pro
        35                  40                  45

Asn Lys Lys Leu Glu Lys Ser Ser Ser Ala Ser Asp Val Phe Glu His
    50                  55                  60

Leu Leu Ala Glu Asp Leu Leu Ser Glu Glu Asp Pro Phe Phe Leu Ala
65                  70                  75                  80

Glu Leu Leu Tyr Ile Ile Arg Gln Lys Lys Leu Leu Gln His Leu Asn
                85                  90                  95

Cys Thr Lys Glu Glu Val Glu Arg Leu Leu Pro Thr Arg Gln Arg Val
            100                 105                 110

Ser Leu Phe Arg Asn Leu Leu Tyr Glu Leu Ser Glu Gly Ile Asp Ser
        115                 120                 125

Glu Asn Leu Lys Asp Met Ile Phe Leu Leu Lys Asp Ser Leu Pro Lys
    130                 135                 140

Thr Glu Met Thr Ser Leu Ser Phe Leu Ala Phe Leu Glu Lys Gln Gly
145                 150                 155                 160

Lys Ile Asp Glu Asp Asn Leu Thr Cys Leu Glu Asp Leu Cys Lys Thr
                165                 170                 175

Val Val Pro Lys Leu Leu Arg Asn Ile Glu Lys Tyr Lys Arg Glu Lys
            180                 185                 190

Ala Ile Gln Ile Val Thr Pro Pro Val Asp Lys Glu Ala Glu Ser Tyr
        195                 200                 205

Gln Gly Glu Glu Glu Leu Val Ser Gln Thr Asp Val Lys Thr Phe Leu
    210                 215                 220

Glu Ala Leu Pro Gln Glu Ser Trp Gln Asn Lys His Ala Gly Ser Asn
225                 230                 235                 240

Gly Asn Arg Ala Thr Asn Gly Ala Pro Ser Leu Val Ser Arg Gly Met
                245                 250                 255

Gln Gly Ala Ser Ala Asn Thr Leu Asn Ser Glu Thr Ser Thr Lys Arg
            260                 265                 270

Ala Ala Val Tyr Arg Met Asn Arg Asn His Arg Gly Leu Cys Val Ile
        275                 280                 285

Val Asn Asn His Ser Phe Thr Ser Leu Lys Asp Arg Gln Gly Thr His
```

```
    290                 295                 300

Lys Asp Ala Glu Ile Leu Ser His Val Phe Gln Trp Leu Gly Phe Thr
305                 310                 315                 320

Val His Ile His Asn Asn Val Thr Lys Val Glu Met Glu Met Val Leu
                325                 330                 335

Gln Lys Gln Lys Cys Asn Pro Ala His Ala Asp Gly Asp Cys Phe Val
            340                 345                 350

Phe Cys Ile Leu Thr His Gly Arg Phe Gly Ala Val Tyr Ser Ser Asp
        355                 360                 365

Glu Ala Leu Ile Pro Ile Arg Glu Ile Met Ser His Phe Thr Ala Leu
    370                 375                 380

Gln Cys Pro Arg Leu Ala Glu Lys Pro Lys Leu Phe Phe Ile Gln Ala
385                 390                 395                 400

Cys Gln Gly Glu Glu Ile Gln Pro Ser Val Ser Ile Glu Ala Asp Ala
                405                 410                 415

Leu Asn Pro Glu Gln Ala Pro Thr Ser Leu Gln Asp Ser Ile Pro Ala
            420                 425                 430

Glu Ala Asp Phe Leu Leu Gly Leu Ala Thr Val Pro Gly Tyr Val Ser
        435                 440                 445

Phe Arg His Val Glu Glu Gly Ser Trp Tyr Ile Gln Ser Leu Cys Asn
    450                 455                 460

His Leu Lys Lys Leu Val Pro Arg His Glu Asp Ile Leu Ser Ile Leu
465                 470                 475                 480

Thr Ala Val Asn Asp Asp Val Ser Arg Arg Val Asp Lys Gln Gly Thr
                485                 490                 495

Lys Lys Gln Met Pro Gln Pro Ala Phe Thr Leu Arg Lys Lys Leu Val
            500                 505                 510

Phe Pro Val Pro Leu Asp Ala Leu Ser Leu
        515                 520


<210> SEQ ID NO 67
<211> LENGTH: 454
<212> TYPE: PRT
<213> ORGANISM: Mus musculus

<400> SEQUENCE: 67

Met Asp Glu Ala Asp Arg Gln Leu Leu Arg Arg Cys Arg Val Arg Leu
1               5                   10                  15

Val Ser Glu Leu Gln Val Ala Glu Leu Trp Asp Ala Leu Leu Ser Arg
            20                  25                  30

Glu Leu Phe Thr Arg Asp Met Ile Glu Asp Ile Gln Gln Ala Gly Ser
        35                  40                  45

Gly Ser Arg Arg Asp Gln Ala Arg Gln Leu Val Thr Asp Leu Glu Thr
    50                  55                  60

Arg Gly Arg Gln Ala Leu Pro Leu Phe Ile Ser Cys Leu Glu Asp Thr
65                  70                  75                  80

Gly Gln Gly Thr Leu Ala Ser Leu Leu Gln Ser Gly Arg Gln Ala Ala
                85                  90                  95

Lys Gln Asp Pro Glu Ala Val Lys Pro Leu Asp His Leu Val Pro Val
            100                 105                 110

Val Leu Gly Pro Met Gly Leu Thr Ala Lys Glu Gln Arg Val Val Lys
        115                 120                 125

Leu Asp Pro Ser Gln Pro Ala Val Gly Asn Leu Thr Pro Val Val Leu
    130                 135                 140

Gly Pro Glu Glu Leu Trp Pro Ala Arg Leu Lys Pro Glu Val Leu Arg
```

```
145                 150                 155                 160

Pro Glu Thr Pro Arg Pro Val Asp Ile Gly Ser Gly Gly Ala His Asp
                165                 170                 175

Val Cys Val Pro Gly Lys Ile Arg Gly His Ala Asp Met Ala Tyr Thr
            180                 185                 190

Leu Asp Ser Asp Pro Cys Gly His Cys Leu Ile Ile Asn Asn Val Asn
        195                 200                 205

Phe Cys Pro Ser Ser Gly Leu Gly Thr Arg Thr Gly Ser Asn Leu Asp
    210                 215                 220

Arg Asp Lys Leu Glu His Arg Phe Arg Trp Leu Arg Phe Met Val Glu
225                 230                 235                 240

Val Lys Asn Asp Leu Thr Ala Lys Lys Met Val Thr Ala Leu Met Glu
                245                 250                 255

Met Ala His Arg Asn His Arg Ala Leu Asp Cys Phe Val Val Val Ile
            260                 265                 270

Leu Ser His Gly Cys Gln Ala Ser His Leu Gln Phe Pro Gly Ala Val
        275                 280                 285

Tyr Gly Thr Asp Gly Cys Ser Val Ser Ile Glu Lys Ile Val Asn Ile
    290                 295                 300

Phe Asn Gly Ser Gly Cys Pro Ser Leu Gly Gly Lys Pro Lys Leu Phe
305                 310                 315                 320

Phe Ile Gln Ala Cys Gly Gly Glu Gln Lys Asp His Gly Phe Glu Val
                325                 330                 335

Ala Cys Thr Ser Ser Gln Gly Arg Thr Leu Asp Ser Asp Ser Glu Pro
            340                 345                 350

Asp Ala Val Pro Tyr Gln Glu Gly Pro Arg Pro Leu Asp Gln Leu Asp
        355                 360                 365

Ala Val Ser Ser Leu Pro Thr Pro Ser Asp Ile Leu Val Ser Tyr Ser
    370                 375                 380

Thr Phe Pro Gly Phe Val Ser Trp Arg Asp Lys Lys Ser Gly Ser Trp
385                 390                 395                 400

Tyr Ile Glu Thr Leu Asp Gly Ile Leu Glu Gln Trp Ala Arg Ser Glu
                405                 410                 415

Asp Leu Gln Ser Leu Leu Leu Arg Val Ala Asn Ala Val Ser Ala Lys
            420                 425                 430

Gly Thr Tyr Lys Gln Ile Pro Gly Cys Phe Asn Phe Leu Arg Lys Lys
        435                 440                 445

Leu Phe Phe Lys Thr Ser
    450


<210> SEQ ID NO 68
<211> LENGTH: 416
<212> TYPE: PRT
<213> ORGANISM: Homo sapiens

<400> SEQUENCE: 68

Met Asp Glu Ala Asp Arg Arg Leu Leu Arg Arg Cys Arg Leu Arg Leu
1               5                   10                  15

Val Glu Glu Leu Gln Val Asp Gln Leu Trp Asp Ala Leu Leu Ser Arg
            20                  25                  30

Glu Leu Phe Arg Pro His Met Ile Glu Asp Ile Gln Arg Ala Gly Ser
        35                  40                  45

Gly Ser Arg Arg Asp Gln Ala Arg Gln Leu Ile Ile Asp Leu Glu Thr
    50                  55                  60

Arg Gly Ser Gln Ala Leu Pro Leu Phe Ile Ser Cys Leu Glu Asp Thr
```

-continued

```
65                  70                  75                  80

Gly Gln Asp Met Leu Ala Ser Phe Leu Arg Thr Asn Arg Gln Ala Ala
                85                  90                  95

Lys Leu Ser Lys Pro Thr Leu Glu Asn Leu Thr Pro Val Val Leu Arg
            100                 105                 110

Pro Glu Ile Arg Lys Pro Glu Val Leu Arg Pro Glu Thr Pro Arg Pro
        115                 120                 125

Val Asp Ile Gly Ser Gly Gly Phe Gly Asp Val Gly Ala Leu Glu Ser
    130                 135                 140

Leu Arg Gly Asn Ala Asp Leu Ala Tyr Ile Leu Ser Met Glu Pro Cys
145                 150                 155                 160

Gly His Cys Leu Ile Ile Asn Asn Val Asn Phe Cys Arg Glu Ser Gly
                165                 170                 175

Leu Arg Thr Arg Thr Gly Ser Asn Ile Asp Cys Glu Lys Leu Arg Arg
            180                 185                 190

Arg Phe Ser Ser Leu His Phe Met Val Glu Val Lys Gly Asp Leu Thr
        195                 200                 205

Ala Lys Lys Met Val Leu Ala Leu Leu Glu Leu Ala Gln Gln Asp His
    210                 215                 220

Gly Ala Leu Asp Cys Cys Val Val Val Ile Leu Ser His Gly Cys Gln
225                 230                 235                 240

Ala Ser His Leu Gln Phe Pro Gly Ala Val Tyr Gly Thr Asp Gly Cys
                245                 250                 255

Pro Val Ser Val Glu Lys Ile Val Asn Ile Phe Asn Gly Thr Ser Cys
            260                 265                 270

Pro Ser Leu Gly Gly Lys Pro Lys Leu Phe Phe Ile Gln Ala Cys Gly
        275                 280                 285

Gly Glu Gln Lys Asp His Gly Phe Glu Val Ala Ser Thr Ser Pro Glu
    290                 295                 300

Asp Glu Ser Pro Gly Ser Asn Pro Glu Pro Asp Ala Thr Pro Phe Gln
305                 310                 315                 320

Glu Gly Leu Arg Thr Phe Asp Gln Leu Asp Ala Ile Ser Ser Leu Pro
                325                 330                 335

Thr Pro Ser Asp Ile Phe Val Ser Tyr Ser Thr Phe Pro Gly Phe Val
            340                 345                 350

Ser Trp Arg Asp Pro Lys Ser Gly Ser Trp Tyr Val Glu Thr Leu Asp
        355                 360                 365

Asp Ile Phe Glu Gln Trp Ala His Ser Glu Asp Leu Gln Ser Leu Leu
    370                 375                 380

Leu Arg Val Ala Asn Ala Val Ser Val Lys Gly Ile Tyr Lys Gln Met
385                 390                 395                 400

Pro Gly Cys Phe Asn Phe Leu Arg Lys Lys Leu Phe Phe Lys Thr Ser
                405                 410                 415


<210> SEQ ID NO 69
<211> LENGTH: 452
<212> TYPE: PRT
<213> ORGANISM: Mus musculus

<400> SEQUENCE: 69

Met Ala Ala Pro Ser Gly Arg Ser Gln Ser Ser Leu His Arg Lys Gly
1               5                   10                  15

Leu Met Ala Ala Asp Arg Arg Ser Arg Ile Leu Ala Val Cys Gly Met
            20                  25                  30

His Pro Asp His Gln Glu Thr Leu Lys Lys Asn Arg Val Val Leu Ala
```

```
        35                  40                  45

Lys Gln Leu Leu Leu Ser Glu Leu Leu Glu His Leu Leu Glu Lys Asp
    50                  55                  60

Ile Ile Thr Leu Glu Met Arg Glu Leu Ile Gln Ala Lys Gly Gly Ser
65                  70                  75                  80

Phe Ser Gln Asn Val Glu Leu Leu Asn Leu Leu Pro Lys Arg Gly Pro
                85                  90                  95

Gln Ala Phe Asp Ala Phe Cys Glu Ala Leu Arg Glu Thr Arg Gln Gly
            100                 105                 110

His Leu Glu Asp Leu Leu Leu Thr Thr Leu Ser Asp Ile Gln His Val
        115                 120                 125

Leu Pro Pro Leu Ser Cys Asp Tyr Asp Thr Ser Leu Pro Phe Ser Val
    130                 135                 140

Cys Glu Ser Cys Pro Pro His Lys Gln Leu Arg Leu Ser Thr Asp Ala
145                 150                 155                 160

Thr Glu His Ser Leu Asp Asn Gly Asp Gly Pro Pro Cys Leu Leu Val
                165                 170                 175

Lys Pro Cys Thr Pro Glu Phe Tyr Gln Ala His Tyr Gln Leu Ala Tyr
            180                 185                 190

Arg Leu Gln Ser Gln Pro Arg Gly Leu Ala Leu Val Leu Ser Asn Val
        195                 200                 205

His Phe Thr Gly Glu Lys Asp Leu Glu Phe Arg Ser Gly Gly Asp Val
    210                 215                 220

Asp His Thr Thr Leu Val Thr Leu Phe Lys Leu Leu Gly Tyr Asn Val
225                 230                 235                 240

His Val Leu His Asp Gln Thr Ala Gln Glu Met Gln Glu Lys Leu Gln
                245                 250                 255

Asn Phe Ala Gln Leu Pro Ala His Arg Val Thr Asp Ser Cys Val Val
            260                 265                 270

Ala Leu Leu Ser His Gly Val Glu Gly Gly Ile Tyr Gly Val Asp Gly
        275                 280                 285

Lys Leu Leu Gln Leu Gln Glu Val Phe Arg Leu Phe Asp Asn Ala Asn
    290                 295                 300

Cys Pro Ser Leu Gln Asn Lys Pro Lys Met Phe Phe Ile Gln Ala Cys
305                 310                 315                 320

Arg Gly Asp Glu Thr Asp Arg Gly Val Asp Gln Gln Asp Gly Lys Asn
                325                 330                 335

His Thr Gln Ser Pro Gly Cys Glu Glu Ser Asp Ala Gly Lys Glu Glu
            340                 345                 350

Leu Met Lys Met Arg Leu Pro Thr Arg Ser Asp Met Ile Cys Gly Tyr
        355                 360                 365

Ala Cys Leu Lys Gly Asn Ala Ala Met Arg Asn Thr Lys Arg Gly Ser
    370                 375                 380

Trp Tyr Ile Glu Ala Leu Thr Gln Val Phe Ser Glu Arg Ala Cys Asp
385                 390                 395                 400

Met His Val Ala Asp Met Leu Val Lys Val Asn Ala Leu Ile Lys Glu
                405                 410                 415

Arg Glu Gly Tyr Ala Pro Gly Thr Glu Phe His Arg Cys Lys Glu Met
            420                 425                 430

Ser Glu Tyr Cys Ser Thr Leu Cys Gln Gln Leu Tyr Leu Phe Pro Gly
        435                 440                 445

Tyr Pro Pro Thr
    450
```

<210> SEQ ID NO 70
<211> LENGTH: 452
<212> TYPE: PRT
<213> ORGANISM: Homo sapiens

<400> SEQUENCE: 70

```
Met Ala Ala Pro Ser Ala Gly Ser Trp Ser Thr Phe Gln His Lys Glu
1               5                   10                  15

Leu Met Ala Ala Asp Arg Gly Arg Arg Ile Leu Gly Val Cys Gly Met
            20                  25                  30

His Pro His His Gln Glu Thr Leu Lys Lys Asn Arg Val Val Leu Ala
        35                  40                  45

Lys Gln Leu Leu Leu Ser Glu Leu Leu Glu His Leu Leu Glu Lys Asp
    50                  55                  60

Ile Ile Thr Leu Glu Met Arg Glu Leu Ile Gln Ala Lys Val Gly Ser
65                  70                  75                  80

Phe Ser Gln Asn Val Glu Leu Leu Asn Leu Leu Pro Lys Arg Gly Pro
                85                  90                  95

Gln Ala Phe Asp Ala Phe Cys Glu Ala Leu Arg Glu Thr Lys Gln Gly
            100                 105                 110

His Leu Glu Asp Met Leu Leu Thr Thr Leu Ser Gly Leu Gln His Val
        115                 120                 125

Leu Pro Pro Leu Ser Cys Asp Tyr Asp Leu Ser Leu Pro Phe Pro Val
    130                 135                 140

Cys Glu Ser Cys Pro Leu Tyr Lys Lys Leu Arg Leu Ser Thr Asp Thr
145                 150                 155                 160

Val Glu His Ser Leu Asp Asn Lys Asp Gly Pro Val Cys Leu Gln Val
                165                 170                 175

Lys Pro Cys Thr Pro Glu Phe Tyr Gln Thr His Phe Gln Leu Ala Tyr
            180                 185                 190

Arg Leu Gln Ser Arg Pro Arg Gly Leu Ala Leu Val Leu Ser Asn Val
        195                 200                 205

His Phe Thr Gly Glu Lys Glu Leu Glu Phe Arg Ser Gly Gly Asp Val
    210                 215                 220

Asp His Ser Thr Leu Val Thr Leu Phe Lys Leu Leu Gly Tyr Asp Val
225                 230                 235                 240

His Val Leu Cys Asp Gln Thr Ala Gln Glu Met Gln Glu Lys Leu Gln
                245                 250                 255

Asn Phe Ala Gln Leu Pro Ala His Arg Val Thr Asp Ser Cys Ile Val
            260                 265                 270

Ala Leu Leu Ser His Gly Val Glu Gly Ala Ile Tyr Gly Val Asp Gly
        275                 280                 285

Lys Leu Leu Gln Leu Gln Glu Val Phe Gln Leu Phe Asp Asn Ala Asn
    290                 295                 300

Cys Pro Ser Leu Gln Asn Lys Pro Lys Met Phe Phe Ile Gln Ala Cys
305                 310                 315                 320

Arg Gly Asp Glu Thr Asp Arg Gly Val Asp Gln Gln Asp Gly Lys Asn
                325                 330                 335

His Ala Gly Ser Pro Gly Cys Glu Glu Ser Asp Ala Gly Lys Glu Lys
            340                 345                 350

Leu Pro Lys Met Arg Leu Pro Thr Arg Ser Asp Met Ile Cys Gly Tyr
        355                 360                 365

Ala Cys Leu Lys Gly Thr Ala Ala Met Arg Asn Thr Lys Arg Gly Ser
    370                 375                 380
```

Trp Tyr Ile Glu Ala Leu Ala Gln Val Phe Ser Glu Arg Ala Cys Asp
385 390 395 400

Met His Val Ala Asp Met Leu Val Lys Val Asn Ala Leu Ile Lys Asp
405 410 415

Arg Glu Gly Tyr Ala Pro Gly Thr Glu Phe His Arg Cys Lys Glu Met
420 425 430

Ser Glu Tyr Cys Ser Thr Leu Cys Arg His Leu Tyr Leu Phe Pro Gly
435 440 445

His Pro Pro Thr
450

<210> SEQ ID NO 71
<211> LENGTH: 419
<212> TYPE: PRT
<213> ORGANISM: Mus musculus

<400> SEQUENCE: 71

Met Ala Ala Arg Arg Thr His Glu Arg Asp Pro Ile Tyr Lys Ile Lys
1 5 10 15

Gly Leu Ala Lys Asp Met Leu Asp Gly Val Phe Asp Asp Leu Val Glu
20 25 30

Lys Asn Val Leu Asn Gly Asp Glu Leu Leu Lys Ile Gly Glu Ser Ala
35 40 45

Ser Phe Ile Leu Asn Lys Ala Glu Asn Leu Val Glu Asn Phe Leu Glu
50 55 60

Lys Thr Asp Met Ala Gly Lys Ile Phe Ala Gly His Ile Ala Asn Ser
65 70 75 80

Gln Glu Gln Leu Ser Leu Gln Phe Ser Asn Asp Glu Asp Asp Gly Pro
85 90 95

Gln Lys Ile Cys Thr Pro Ser Ser Pro Ser Glu Ser Lys Arg Lys Val
100 105 110

Glu Asp Asp Glu Met Glu Val Asn Ala Gly Leu Ala His Glu Ser His
115 120 125

Leu Met Leu Thr Ala Pro His Gly Leu Gln Ser Ser Glu Val Gln Asp
130 135 140

Thr Leu Lys Leu Cys Pro Arg Asp Gln Phe Cys Lys Ile Lys Thr Glu
145 150 155 160

Arg Ala Lys Glu Ile Tyr Pro Val Met Glu Lys Glu Gly Arg Thr Arg
165 170 175

Leu Ala Leu Ile Ile Cys Asn Lys Lys Phe Asp Tyr Leu Phe Asp Arg
180 185 190

Asp Asn Ala Asp Thr Asp Ile Leu Asn Met Gln Glu Leu Leu Glu Asn
195 200 205

Leu Gly Tyr Ser Val Val Leu Lys Glu Asn Leu Thr Ala Gln Glu Met
210 215 220

Glu Thr Glu Leu Met Gln Phe Ala Gly Arg Pro Glu His Gln Ser Ser
225 230 235 240

Asp Ser Thr Phe Leu Val Phe Met Ser His Gly Ile Leu Glu Gly Ile
245 250 255

Cys Gly Val Lys His Arg Asn Lys Lys Pro Asp Val Leu His Asp Asp
260 265 270

Thr Ile Phe Lys Ile Phe Asn Asn Ser Asn Cys Arg Ser Leu Arg Asn
275 280 285

Lys Pro Lys Ile Leu Ile Met Gln Ala Cys Arg Gly Arg Tyr Asn Gly
290 295 300

```
Thr Ile Trp Val Ser Thr Asn Lys Gly Ile Ala Thr Ala Asp Thr Asp
305                 310                 315                 320

Glu Glu Arg Val Leu Ser Cys Lys Trp Asn Asn Ser Ile Thr Lys Ala
                325                 330                 335

His Val Glu Thr Asp Phe Ile Ala Phe Lys Ser Ser Thr Pro His Asn
            340                 345                 350

Ile Ser Trp Lys Val Gly Lys Thr Gly Ser Leu Phe Ile Ser Lys Leu
        355                 360                 365

Val Asp Cys Phe Lys Lys Tyr Cys Trp Cys Tyr His Leu Glu Glu Ile
    370                 375                 380

Phe Arg Lys Val Gln His Ser Phe Glu Val Pro Gly Glu Leu Thr Gln
385                 390                 395                 400

Met Pro Thr Ile Glu Arg Val Ser Met Thr Arg Tyr Phe Tyr Leu Phe
                405                 410                 415

Pro Gly Asn


<210> SEQ ID NO 72
<211> LENGTH: 599
<212> TYPE: PRT
<213> ORGANISM: Mus musculus

<400> SEQUENCE: 72

Met Thr Met Thr Leu His Thr Lys Ala Ser Gly Met Ala Leu Leu His
1               5                   10                  15

Gln Ile Gln Gly Asn Glu Leu Glu Pro Leu Asn Arg Pro Gln Leu Lys
            20                  25                  30

Met Pro Met Glu Arg Ala Leu Gly Glu Val Tyr Val Asp Asn Ser Lys
        35                  40                  45

Pro Thr Val Phe Asn Tyr Pro Glu Gly Ala Ala Tyr Glu Phe Asn Ala
    50                  55                  60

Ala Ala Ala Ala Ala Ala Ala Ala Ser Ala Pro Val Tyr Gly Gln Ser
65                  70                  75                  80

Gly Ile Ala Tyr Gly Pro Gly Ser Glu Ala Ala Ala Phe Ser Ala Asn
                85                  90                  95

Ser Leu Gly Ala Phe Pro Gln Leu Asn Ser Val Ser Pro Ser Pro Leu
            100                 105                 110

Met Leu Leu His Pro Pro Pro Gln Leu Ser Pro Phe Leu His Pro His
        115                 120                 125

Gly Gln Gln Val Pro Tyr Tyr Leu Glu Asn Glu Pro Ser Ala Tyr Ala
    130                 135                 140

Val Arg Asp Thr Gly Pro Pro Ala Phe Tyr Arg Ser Asn Ser Asp Asn
145                 150                 155                 160

Arg Arg Gln Asn Gly Arg Glu Arg Leu Ser Ser Ser Asn Glu Lys Gly
                165                 170                 175

Asn Met Ile Met Glu Ser Ala Lys Glu Thr Arg Tyr Cys Ala Val Cys
            180                 185                 190

Asn Asp Tyr Ala Ser Gly Tyr His Tyr Gly Val Trp Ser Cys Glu Gly
        195                 200                 205

Cys Lys Ala Phe Phe Lys Arg Ser Ile Gln Gly His Asn Asp Tyr Met
    210                 215                 220

Cys Pro Ala Thr Asn Gln Cys Thr Ile Asp Lys Asn Arg Arg Lys Ser
225                 230                 235                 240

Cys Gln Ala Cys Arg Leu Arg Lys Cys Tyr Glu Val Gly Met Met Lys
                245                 250                 255

Gly Gly Ile Arg Lys Asp Arg Arg Gly Gly Arg Met Leu Lys His Lys
```

```
            260                 265                 270

Arg Gln Arg Asp Asp Leu Glu Gly Arg Asn Glu Met Gly Ala Ser Gly
        275                 280                 285

Asp Met Arg Ala Ala Asn Leu Trp Pro Ser Pro Leu Val Ile Lys His
    290                 295                 300

Thr Lys Lys Asn Ser Pro Ala Leu Ser Leu Thr Ala Asp Gln Met Val
305                 310                 315                 320

Ser Ala Leu Leu Asp Ala Glu Pro Pro Met Ile Tyr Ser Glu Tyr Asp
                325                 330                 335

Pro Ser Arg Pro Phe Ser Glu Ala Ser Met Met Gly Leu Leu Thr Asn
            340                 345                 350

Leu Ala Asp Arg Glu Leu Val His Met Ile Asn Trp Ala Lys Arg Val
        355                 360                 365

Pro Gly Phe Gly Asp Leu Asn Leu His Asp Gln Val His Leu Leu Glu
    370                 375                 380

Cys Ala Trp Leu Glu Ile Leu Met Ile Gly Leu Val Trp Arg Ser Met
385                 390                 395                 400

Glu His Pro Gly Lys Leu Leu Phe Ala Pro Asn Leu Leu Leu Asp Arg
                405                 410                 415

Asn Gln Gly Lys Cys Val Glu Gly Met Val Glu Ile Phe Asp Met Leu
            420                 425                 430

Leu Ala Thr Ser Ser Arg Phe Arg Met Met Asn Leu Gln Gly Glu Glu
        435                 440                 445

Phe Val Cys Leu Lys Ser Ile Ile Leu Leu Asn Ser Gly Val Tyr Thr
    450                 455                 460

Phe Leu Ser Ser Thr Leu Lys Ser Leu Glu Glu Lys Asp His Ile His
465                 470                 475                 480

Arg Val Leu Asp Lys Ile Thr Asp Thr Leu Ile His Leu Met Ala Lys
                485                 490                 495

Ala Gly Leu Thr Leu Gln Gln Gln His Arg Arg Leu Ala Gln Leu Leu
            500                 505                 510

Leu Ile Leu Ser His Ile Arg His Met Ser Asn Lys Gly Met Glu His
        515                 520                 525

Leu Tyr Asn Met Lys Cys Lys Asn Val Val Pro Leu Tyr Asp Leu Leu
    530                 535                 540

Leu Glu Met Leu Asp Ala His Arg Leu His Ala Pro Ala Ser Arg Met
545                 550                 555                 560

Gly Val Pro Pro Glu Glu Pro Ser Gln Thr Gln Leu Ala Thr Thr Ser
                565                 570                 575

Ser Thr Ser Ala His Ser Leu Gln Thr Tyr Tyr Ile Pro Pro Glu Ala
            580                 585                 590

Glu Gly Phe Pro Asn Thr Ile
        595


<210> SEQ ID NO 73
<211> LENGTH: 595
<212> TYPE: PRT
<213> ORGANISM: Homo sapiens

<400> SEQUENCE: 73

Met Thr Met Thr Leu His Thr Lys Ala Ser Gly Met Ala Leu Leu His
1               5                   10                  15

Gln Ile Gln Gly Asn Glu Leu Glu Pro Leu Asn Arg Pro Gln Leu Lys
            20                  25                  30

Ile Pro Leu Glu Arg Pro Leu Gly Glu Val Tyr Leu Asp Ser Ser Lys
```

```
        35                  40                  45

Pro Ala Val Tyr Asn Tyr Pro Glu Gly Ala Ala Tyr Glu Phe Asn Ala
    50                  55                  60

Ala Ala Ala Ala Asn Ala Gln Val Tyr Gly Gln Thr Gly Leu Pro Tyr
65                  70                  75                  80

Gly Pro Gly Ser Glu Ala Ala Ala Phe Gly Ser Asn Gly Leu Gly Gly
                85                  90                  95

Phe Pro Pro Leu Asn Ser Val Ser Pro Ser Pro Leu Met Leu Leu His
            100                 105                 110

Pro Pro Pro Gln Leu Ser Pro Phe Leu Gln Pro His Gly Gln Gln Val
        115                 120                 125

Pro Tyr Tyr Leu Glu Asn Glu Pro Ser Gly Tyr Thr Val Arg Glu Ala
    130                 135                 140

Gly Pro Pro Ala Phe Tyr Arg Pro Asn Ser Asp Asn Arg Arg Gln Gly
145                 150                 155                 160

Gly Arg Glu Arg Leu Ala Ser Thr Asn Asp Lys Gly Ser Met Ala Met
                165                 170                 175

Glu Ser Ala Lys Glu Thr Arg Tyr Cys Ala Val Cys Asn Asp Tyr Ala
            180                 185                 190

Ser Gly Tyr His Tyr Gly Val Trp Ser Cys Glu Gly Cys Lys Ala Phe
        195                 200                 205

Phe Lys Arg Ser Ile Gln Gly His Asn Asp Tyr Met Cys Pro Ala Thr
    210                 215                 220

Asn Gln Cys Thr Ile Asp Lys Asn Arg Arg Lys Ser Cys Gln Ala Cys
225                 230                 235                 240

Arg Leu Arg Lys Cys Tyr Glu Val Gly Met Met Lys Gly Gly Ile Arg
                245                 250                 255

Lys Asp Arg Arg Gly Gly Arg Met Leu Lys His Lys Arg Gln Arg Asp
            260                 265                 270

Asp Gly Glu Gly Arg Gly Glu Val Gly Ser Ala Gly Asp Met Arg Ala
        275                 280                 285

Ala Asn Leu Trp Pro Ser Pro Leu Met Ile Lys Arg Ser Lys Lys Asn
    290                 295                 300

Ser Leu Ala Leu Ser Leu Thr Ala Asp Gln Met Val Ser Ala Leu Leu
305                 310                 315                 320

Asp Ala Glu Pro Pro Ile Leu Tyr Ser Glu Tyr Asp Pro Thr Arg Pro
                325                 330                 335

Phe Ser Glu Ala Ser Met Met Gly Leu Leu Thr Asn Leu Ala Asp Arg
            340                 345                 350

Glu Leu Val His Met Ile Asn Trp Ala Lys Arg Val Pro Gly Phe Val
        355                 360                 365

Asp Leu Thr Leu His Asp Gln Val His Leu Leu Glu Cys Ala Trp Leu
    370                 375                 380

Glu Ile Leu Met Ile Gly Leu Val Trp Arg Ser Met Glu His Pro Gly
385                 390                 395                 400

Lys Leu Leu Phe Ala Pro Asn Leu Leu Leu Asp Arg Asn Gln Gly Lys
                405                 410                 415

Cys Val Glu Gly Met Val Glu Ile Phe Asp Met Leu Leu Ala Thr Ser
            420                 425                 430

Ser Arg Phe Arg Met Met Asn Leu Gln Gly Glu Glu Phe Val Cys Leu
        435                 440                 445

Lys Ser Ile Ile Leu Leu Asn Ser Gly Val Tyr Thr Phe Leu Ser Ser
    450                 455                 460
```

```
Thr Leu Lys Ser Leu Glu Glu Lys Asp His Ile His Arg Val Leu Asp
465                 470                 475                 480

Lys Ile Thr Asp Thr Leu Ile His Leu Met Ala Lys Ala Gly Leu Thr
                485                 490                 495

Leu Gln Gln Gln His Gln Arg Leu Ala Gln Leu Leu Leu Ile Leu Ser
            500                 505                 510

His Ile Arg His Met Ser Asn Lys Gly Met Glu His Leu Tyr Ser Met
        515                 520                 525

Lys Cys Lys Asn Val Val Pro Leu Tyr Asp Leu Leu Leu Glu Met Leu
    530                 535                 540

Asp Ala His Arg Leu His Ala Pro Thr Ser Arg Gly Gly Ala Ser Val
545                 550                 555                 560

Glu Glu Thr Asp Gln Ser His Leu Ala Thr Ala Gly Ser Thr Ser Ser
                565                 570                 575

His Ser Leu Gln Lys Tyr Tyr Ile Thr Gly Glu Ala Glu Gly Phe Pro
            580                 585                 590

Ala Thr Val
        595


<210> SEQ ID NO 74
<211> LENGTH: 923
<212> TYPE: PRT
<213> ORGANISM: Mus musculus

<400> SEQUENCE: 74

Met Thr Glu Leu Gln Ala Lys Asp Pro Gln Val Leu His Thr Ser Gly
1               5                   10                  15

Ala Ser Pro Ser Pro Pro His Ile Gly Ser Pro Leu Leu Ala Arg Leu
            20                  25                  30

Asp Ser Gly Pro Phe Gln Gly Ser Gln His Ser Asp Val Ser Ser Val
        35                  40                  45

Val Ser Pro Ile Pro Ile Ser Leu Asp Gly Leu Leu Phe Pro Arg Ser
    50                  55                  60

Cys Arg Gly Pro Glu Leu Pro Asp Gly Lys Thr Gly Asp Gln Gln Ser
65                  70                  75                  80

Leu Ser Asp Val Glu Gly Ala Phe Ser Gly Val Glu Ala Thr His Arg
                85                  90                  95

Glu Gly Gly Arg Asn Ser Arg Pro Pro Glu Lys Asp Ser Arg Leu Leu
            100                 105                 110

Asp Ser Val Leu Asp Ser Leu Leu Thr Pro Ser Gly Pro Glu Gln Ser
        115                 120                 125

His Ala Ser Pro Pro Ala Cys Glu Ala Ile Thr Ser Trp Cys Leu Phe
    130                 135                 140

Gly Pro Glu Leu Pro Glu Asp Pro Arg Ser Val Pro Ala Thr Lys Gly
145                 150                 155                 160

Leu Leu Ser Pro Leu Met Ser Arg Pro Glu Ile Lys Val Gly Asp Gln
                165                 170                 175

Ser Gly Thr Gly Arg Gly Gln Lys Val Leu Pro Lys Gly Leu Ser Pro
            180                 185                 190

Pro Arg Gln Leu Leu Leu Pro Thr Ser Gly Ser Ala His Trp Pro Gly
        195                 200                 205

Ala Gly Val Lys Pro Ser Pro Gln Pro Ala Ala Gly Glu Val Glu Glu
    210                 215                 220

Asp Ser Gly Leu Glu Thr Glu Gly Ser Ala Ser Pro Leu Leu Lys Ser
225                 230                 235                 240
```

-continued

```
Lys Pro Arg Ala Leu Glu Gly Thr Gly Gln Gly Gly Gly Val Ala Ala
            245                 250                 255

Asn Ala Pro Ser Ala Ala Pro Gly Gly Val Thr Leu Val Pro Lys Glu
            260                 265                 270

Asp Ser Arg Phe Ser Ala Pro Arg Val Ser Leu Glu Gln Asp Ser Pro
        275                 280                 285

Ile Ala Pro Gly Arg Ser Pro Leu Ala Thr Thr Val Val Asp Phe Ile
    290                 295                 300

His Val Pro Ile Leu Pro Leu Asn His Ala Leu Leu Ala Ala Arg Thr
305                 310                 315                 320

Arg Gln Leu Leu Glu Gly Glu Ser Tyr Asp Gly Gly Ala Thr Ala Gly
                325                 330                 335

Pro Phe Cys Pro Pro Arg Ser Pro Ser Ala Pro Ser Thr Pro Val Pro
            340                 345                 350

Arg Gly Asp Phe Pro Asp Cys Thr Tyr Pro Leu Glu Gly Asp Pro Lys
        355                 360                 365

Glu Asp Val Phe Pro Leu Tyr Gly Asp Phe Gln Thr Pro Gly Leu Lys
    370                 375                 380

Ile Lys Glu Glu Glu Glu Gly Ala Asp Ala Ala Val Arg Ser Pro Arg
385                 390                 395                 400

Pro Tyr Leu Ser Ala Gly Ala Ser Ser Ser Thr Phe Pro Asp Phe Pro
                405                 410                 415

Leu Ala Pro Ala Pro Gln Ala Ala Pro Ser Ser Arg Pro Gly Glu Ala
            420                 425                 430

Ala Val Ala Gly Gly Pro Ser Ser Ala Ala Val Ser Pro Ala Ser Ser
        435                 440                 445

Ser Gly Ser Ala Leu Glu Cys Ile Leu Tyr Lys Ala Glu Ala Pro Pro
    450                 455                 460

Thr Gln Gly Ser Phe Ala Pro Leu Pro Cys Lys Pro Pro Ala Ala Ala
465                 470                 475                 480

Ser Cys Leu Leu Pro Arg Asp Ser Leu Pro Ala Ala Pro Gly Thr Ala
                485                 490                 495

Ala Ala Pro Ala Ile Tyr Gln Pro Leu Gly Leu Asn Gly Leu Pro Gln
            500                 505                 510

Leu Gly Tyr Gln Ala Ala Val Leu Lys Asp Ser Leu Pro Gln Val Tyr
        515                 520                 525

Pro Pro Tyr Leu Asn Tyr Leu Arg Pro Asp Ser Glu Ala Ser Gln Ser
    530                 535                 540

Pro Gln Tyr Gly Phe Asp Ser Leu Pro Gln Lys Ile Cys Leu Ile Cys
545                 550                 555                 560

Gly Asp Glu Ala Ser Gly Cys His Tyr Gly Val Leu Thr Cys Gly Ser
                565                 570                 575

Cys Lys Val Phe Phe Lys Arg Ala Met Glu Gly Gln His Asn Tyr Leu
            580                 585                 590

Cys Ala Gly Arg Asn Asp Cys Ile Val Asp Lys Ile Arg Arg Lys Asn
        595                 600                 605

Cys Pro Ala Cys Arg Leu Arg Lys Cys Cys Gln Ala Gly Met Val Leu
    610                 615                 620

Gly Gly Arg Lys Phe Lys Lys Phe Asn Lys Val Arg Val Met Arg Thr
625                 630                 635                 640

Leu Asp Gly Val Ala Leu Pro Gln Ser Val Gly Leu Pro Asn Glu Ser
                645                 650                 655

Gln Ala Leu Ser Gln Arg Ile Thr Phe Ser Pro Asn Gln Glu Ile Gln
            660                 665                 670
```

```
Leu Val Pro Pro Leu Ile Asn Leu Leu Met Ser Ile Glu Pro Asp Val
        675                 680                 685

Ile Tyr Ala Gly His Asp Asn Thr Lys Pro Asp Thr Ser Ser Ser Leu
    690                 695                 700

Leu Thr Ser Leu Asn Gln Leu Gly Glu Arg Gln Leu Leu Ser Val Val
705                 710                 715                 720

Lys Trp Ser Lys Ser Leu Pro Gly Phe Arg Asn Leu His Ile Asp Asp
                725                 730                 735

Gln Ile Thr Leu Ile Gln Tyr Ser Trp Met Ser Leu Met Val Phe Gly
            740                 745                 750

Leu Gly Trp Arg Ser Tyr Lys His Val Ser Gly Gln Met Leu Tyr Phe
        755                 760                 765

Ala Pro Asp Leu Ile Leu Asn Glu Gln Arg Met Lys Glu Leu Ser Phe
    770                 775                 780

Tyr Ser Leu Cys Leu Thr Met Trp Gln Ile Pro Gln Glu Phe Val Lys
785                 790                 795                 800

Leu Gln Val Thr His Glu Glu Phe Leu Cys Met Lys Val Leu Leu Leu
                805                 810                 815

Leu Asn Thr Ile Pro Leu Glu Gly Leu Arg Ser Gln Ser Gln Phe Glu
            820                 825                 830

Glu Met Arg Ser Ser Tyr Ile Arg Glu Leu Ile Lys Ala Ile Gly Leu
        835                 840                 845

Arg Gln Lys Gly Val Val Pro Thr Ser Gln Arg Phe Tyr Gln Leu Thr
    850                 855                 860

Lys Leu Leu Asp Ser Leu His Asp Leu Val Lys Gln Leu His Leu Tyr
865                 870                 875                 880

Cys Leu Asn Thr Phe Ile Gln Ser Arg Thr Leu Ala Val Glu Phe Pro
                885                 890                 895

Glu Met Met Ser Glu Val Ile Ala Ala Gln Leu Pro Lys Ile Leu Ala
            900                 905                 910

Gly Met Val Lys Pro Leu Leu Phe His Lys Lys
        915                 920


<210> SEQ ID NO 75
<211> LENGTH: 933
<212> TYPE: PRT
<213> ORGANISM: Homo sapiens

<400> SEQUENCE: 75

Met Thr Glu Leu Lys Ala Lys Gly Pro Arg Ala Pro His Val Ala Gly
1               5                   10                  15

Gly Pro Pro Ser Pro Glu Val Gly Ser Pro Leu Leu Cys Arg Pro Ala
            20                  25                  30

Ala Gly Pro Phe Pro Gly Ser Gln Thr Ser Asp Thr Leu Pro Glu Val
        35                  40                  45

Ser Ala Ile Pro Ile Ser Leu Asp Gly Leu Leu Phe Pro Arg Pro Cys
    50                  55                  60

Gln Gly Gln Asp Pro Ser Asp Glu Lys Thr Gln Asp Gln Gln Ser Leu
65                  70                  75                  80

Ser Asp Val Glu Gly Ala Tyr Ser Arg Ala Glu Ala Thr Arg Gly Ala
                85                  90                  95

Gly Gly Ser Ser Ser Ser Pro Pro Glu Lys Asp Ser Gly Leu Leu Asp
            100                 105                 110

Ser Val Leu Asp Thr Leu Leu Ala Pro Ser Gly Pro Gly Gln Ser Gln
        115                 120                 125
```

```
Pro Ser Pro Pro Ala Cys Glu Val Thr Ser Ser Trp Cys Leu Phe Gly
    130                 135                 140

Pro Glu Leu Pro Glu Asp Pro Pro Ala Ala Pro Ala Thr Gln Arg Val
145                 150                 155                 160

Leu Ser Pro Leu Met Ser Arg Ser Gly Cys Lys Val Gly Asp Ser Ser
                165                 170                 175

Gly Thr Ala Ala Ala His Lys Val Leu Pro Arg Gly Leu Ser Pro Ala
            180                 185                 190

Arg Gln Leu Leu Leu Pro Ala Ser Glu Ser Pro His Trp Ser Gly Ala
        195                 200                 205

Pro Val Lys Pro Ser Pro Gln Ala Ala Ala Val Glu Val Glu Glu Glu
    210                 215                 220

Asp Ser Ser Glu Ser Glu Glu Ser Ala Gly Pro Leu Leu Lys Gly Lys
225                 230                 235                 240

Pro Arg Ala Leu Gly Gly Ala Ala Ala Gly Gly Gly Ala Ala Ala Cys
                245                 250                 255

Pro Pro Gly Ala Ala Ala Gly Gly Val Ala Leu Val Pro Lys Glu Asp
            260                 265                 270

Ser Arg Phe Ser Ala Pro Arg Val Ala Leu Val Glu Gln Asp Ala Pro
        275                 280                 285

Met Ala Pro Gly Arg Ser Pro Leu Ala Thr Thr Val Met Asp Phe Ile
    290                 295                 300

His Val Pro Ile Leu Pro Leu Asn His Ala Leu Leu Ala Ala Arg Thr
305                 310                 315                 320

Arg Gln Leu Leu Glu Asp Glu Ser Tyr Asp Gly Gly Ala Gly Ala Ala
                325                 330                 335

Ser Ala Phe Ala Pro Pro Arg Ser Ser Pro Cys Ala Ser Ser Thr Pro
            340                 345                 350

Val Ala Val Gly Asp Phe Pro Asp Cys Ala Tyr Pro Pro Asp Ala Glu
        355                 360                 365

Pro Lys Asp Asp Ala Tyr Pro Leu Tyr Ser Asp Phe Gln Pro Pro Ala
    370                 375                 380

Leu Lys Ile Lys Glu Glu Glu Glu Gly Ala Glu Ala Ser Ala Arg Ser
385                 390                 395                 400

Pro Arg Ser Tyr Leu Val Ala Gly Ala Asn Pro Ala Ala Phe Pro Asp
                405                 410                 415

Phe Pro Leu Gly Pro Pro Pro Pro Leu Pro Pro Arg Ala Thr Pro Ser
            420                 425                 430

Arg Pro Gly Glu Ala Ala Val Thr Ala Ala Pro Ala Ser Ala Ser Val
        435                 440                 445

Ser Ser Ala Ser Ser Ser Gly Ser Thr Leu Glu Cys Ile Leu Tyr Lys
    450                 455                 460

Ala Glu Gly Ala Pro Pro Gln Gln Gly Pro Phe Ala Pro Pro Pro Cys
465                 470                 475                 480

Lys Ala Pro Gly Ala Ser Gly Cys Leu Leu Pro Arg Asp Gly Leu Pro
                485                 490                 495

Ser Thr Ser Ala Ser Ala Ala Ala Ala Gly Ala Ala Pro Ala Leu Tyr
            500                 505                 510

Pro Ala Leu Gly Leu Asn Gly Leu Pro Gln Leu Gly Tyr Gln Ala Ala
        515                 520                 525

Val Leu Lys Glu Gly Leu Pro Gln Val Tyr Pro Pro Tyr Leu Asn Tyr
    530                 535                 540

Leu Arg Pro Asp Ser Glu Ala Ser Gln Ser Pro Gln Tyr Ser Phe Glu
```

```
545                 550                 555                 560

Ser Leu Pro Gln Lys Ile Cys Leu Ile Cys Gly Asp Glu Ala Ser Gly
                565                 570                 575

Cys His Tyr Gly Val Leu Thr Cys Gly Ser Cys Lys Val Phe Phe Lys
            580                 585                 590

Arg Ala Met Glu Gly Gln His Asn Tyr Leu Cys Ala Gly Arg Asn Asp
        595                 600                 605

Cys Ile Val Asp Lys Ile Arg Arg Lys Asn Cys Pro Ala Cys Arg Leu
    610                 615                 620

Arg Lys Cys Cys Gln Ala Gly Met Val Leu Gly Gly Arg Lys Phe Lys
625                 630                 635                 640

Lys Phe Asn Lys Val Arg Val Val Arg Ala Leu Asp Ala Val Ala Leu
                645                 650                 655

Pro Gln Pro Leu Gly Val Pro Asn Glu Ser Gln Ala Leu Ser Gln Arg
            660                 665                 670

Phe Thr Phe Ser Pro Gly Gln Asp Ile Gln Leu Ile Pro Pro Leu Ile
        675                 680                 685

Asn Leu Leu Met Ser Ile Glu Pro Asp Val Ile Tyr Ala Gly His Asp
    690                 695                 700

Asn Thr Lys Pro Asp Thr Ser Ser Ser Leu Leu Thr Ser Leu Asn Gln
705                 710                 715                 720

Leu Gly Glu Arg Gln Leu Leu Ser Val Val Lys Trp Ser Lys Ser Leu
                725                 730                 735

Pro Gly Phe Arg Asn Leu His Ile Asp Asp Gln Ile Thr Leu Ile Gln
            740                 745                 750

Tyr Ser Trp Met Ser Leu Met Val Phe Gly Leu Gly Trp Arg Ser Tyr
        755                 760                 765

Lys His Val Ser Gly Gln Met Leu Tyr Phe Ala Pro Asp Leu Ile Leu
    770                 775                 780

Asn Glu Gln Arg Met Lys Glu Ser Ser Phe Tyr Ser Leu Cys Leu Thr
785                 790                 795                 800

Met Trp Gln Ile Pro Gln Glu Phe Val Lys Leu Gln Val Ser Gln Glu
                805                 810                 815

Glu Phe Leu Cys Met Lys Val Leu Leu Leu Leu Asn Thr Ile Pro Leu
            820                 825                 830

Glu Gly Leu Arg Ser Gln Thr Gln Phe Glu Glu Met Arg Ser Ser Tyr
        835                 840                 845

Ile Arg Glu Leu Ile Lys Ala Ile Gly Leu Arg Gln Lys Gly Val Val
    850                 855                 860

Ser Ser Ser Gln Arg Phe Tyr Gln Leu Thr Lys Leu Leu Asp Asn Leu
865                 870                 875                 880

His Asp Leu Val Lys Gln Leu His Leu Tyr Cys Leu Asn Thr Phe Ile
                885                 890                 895

Gln Ser Arg Ala Leu Ser Val Glu Phe Pro Glu Met Met Ser Glu Val
            900                 905                 910

Ile Ala Ala Gln Leu Pro Lys Ile Leu Ala Gly Met Val Lys Pro Leu
        915                 920                 925

Leu Phe His Lys Lys
    930
```

<210> SEQ ID NO 76
<211> LENGTH: 783
<212> TYPE: PRT
<213> ORGANISM: Mus musculus -continued

<400> SEQUENCE: 76

Met Asp Ser Lys Glu Ser Leu Ala Pro Pro Gly Arg Asp Glu Val Pro
1 5 10 15

Ser Ser Leu Leu Gly Arg Gly Arg Gly Ser Val Met Asp Leu Tyr Lys
20 25 30

Thr Leu Arg Gly Gly Ala Thr Val Lys Val Ser Ala Ser Ser Pro Ser
35 40 45

Val Ala Ala Ala Ser Gln Ala Asp Ser Lys Gln Gln Arg Ile Leu Leu
50 55 60

Asp Phe Ser Lys Gly Ser Ala Ser Asn Ala Gln Gln Gln Gln Gln Gln
65 70 75 80

Gln Gln Pro Gln Pro Asp Leu Ser Lys Ala Val Ser Leu Ser Met Gly
85 90 95

Leu Tyr Met Gly Glu Thr Glu Thr Lys Val Met Gly Asn Asp Leu Gly
100 105 110

Tyr Pro Gln Gln Gly Gln Leu Gly Leu Ser Ser Gly Glu Thr Asp Phe
115 120 125

Arg Leu Leu Glu Glu Ser Ile Ala Asn Leu Asn Arg Ser Thr Ser Arg
130 135 140

Pro Glu Asn Pro Lys Ser Ser Thr Pro Ala Ala Gly Cys Ala Thr Pro
145 150 155 160

Thr Glu Lys Glu Phe Pro Gln Thr His Ser Asp Pro Ser Ser Glu Gln
165 170 175

Gln Asn Arg Lys Ser Gln Pro Gly Thr Asn Gly Gly Ser Val Lys Leu
180 185 190

Tyr Thr Thr Asp Gln Ser Thr Phe Asp Ile Leu Gln Asp Leu Glu Phe
195 200 205

Ser Ala Gly Ser Pro Gly Lys Glu Thr Asn Glu Ser Pro Trp Arg Ser
210 215 220

Asp Leu Leu Ile Asp Glu Asn Leu Leu Ser Pro Leu Ala Gly Glu Asp
225 230 235 240

Asp Pro Phe Leu Leu Glu Gly Asp Val Asn Glu Asp Cys Lys Pro Leu
245 250 255

Ile Leu Pro Asp Thr Lys Pro Lys Ile Gln Asp Thr Gly Asp Thr Ile
260 265 270

Leu Ser Ser Pro Ser Ser Val Ala Leu Pro Gln Val Lys Thr Glu Lys
275 280 285

Asp Asp Phe Ile Glu Leu Cys Thr Pro Gly Val Ile Lys Gln Glu Lys
290 295 300

Leu Gly Pro Val Tyr Cys Gln Ala Ser Phe Ser Gly Thr Asn Ile Ile
305 310 315 320

Gly Asn Lys Met Ser Ala Ile Ser Val His Gly Val Ser Thr Ser Gly
325 330 335

Gly Gln Met Tyr His Tyr Asp Met Asn Thr Ala Ser Leu Ser Gln Gln
340 345 350

Gln Asp Gln Lys Pro Val Phe Asn Val Ile Pro Pro Ile Pro Val Gly
355 360 365

Ser Glu Asn Trp Asn Arg Cys Gln Gly Ser Gly Glu Asp Asn Leu Thr
370 375 380

Ser Leu Gly Ala Met Asn Phe Ala Gly Arg Ser Val Phe Ser Asn Gly
385 390 395 400

Tyr Ser Ser Pro Gly Met Arg Pro Asp Val Ser Ser Pro Pro Ser Ser
405 410 415

-continued

Ser Ser Thr Ala Thr Gly Pro Pro Pro Lys Leu Cys Leu Val Cys Ser
420 425 430

Asp Glu Ala Ser Val Cys His Tyr Gly Val Leu Thr Cys Gly Ser Cys
435 440 445

Lys Val Phe Phe Lys Arg Ala Val Glu Gly Gln His Asn Tyr Leu Cys
450 455 460

Ala Gly Arg Asn Asp Cys Ile Ile Asp Lys Ile Arg Arg Lys Asn Cys
465 470 475 480

Pro Ala Cys Arg Tyr Arg Lys Cys Leu Gln Ala Gly Met Asn Leu Glu
485 490 495

Ala Arg Lys Thr Lys Lys Lys Ile Lys Gly Ile Gln Gln Ala Thr Ala
500 505 510

Gly Val Ser Gln Asp Thr Ser Glu Asn Ala Asn Lys Thr Ile Val Pro
515 520 525

Ala Ala Leu Pro Gln Leu Thr Pro Thr Leu Val Ser Leu Leu Glu Val
530 535 540

Ile Glu Pro Glu Val Leu Tyr Ala Gly Tyr Asp Ser Ser Val Pro Asp
545 550 555 560

Ser Ala Trp Arg Ile Met Thr Thr Leu Asn Met Leu Gly Gly Arg Gln
565 570 575

Val Ile Ala Ala Val Lys Trp Ala Lys Ala Ile Pro Gly Phe Arg Asn
580 585 590

Leu His Leu Asp Asp Gln Met Thr Leu Leu Gln Tyr Ser Trp Met Phe
595 600 605

Leu Met Ala Phe Ala Leu Gly Trp Arg Ser Tyr Arg Gln Ala Ser Gly
610 615 620

Asn Leu Leu Cys Phe Ala Pro Asp Leu Ile Ile Asn Glu Gln Arg Met
625 630 635 640

Thr Leu Pro Cys Met Tyr Asp Gln Cys Lys His Met Leu Phe Ile Ser
645 650 655

Thr Glu Leu Gln Arg Leu Gln Val Ser Tyr Glu Glu Tyr Leu Cys Met
660 665 670

Lys Thr Leu Leu Leu Leu Ser Ser Val Pro Lys Glu Gly Leu Lys Ser
675 680 685

Gln Glu Leu Phe Asp Glu Ile Arg Met Thr Tyr Ile Lys Glu Leu Gly
690 695 700

Lys Ala Ile Val Lys Arg Glu Gly Asn Ser Ser Gln Asn Trp Gln Arg
705 710 715 720

Phe Tyr Gln Leu Thr Lys Leu Leu Asp Ser Met His Asp Val Val Glu
725 730 735

Asn Leu Leu Ser Tyr Cys Phe Gln Thr Phe Leu Asp Lys Ser Met Ser
740 745 750

Ile Glu Phe Pro Glu Met Leu Ala Glu Ile Ile Thr Asn Gln Ile Pro
755 760 765

Lys Tyr Ser Asn Gly Asn Ile Lys Lys Leu Leu Phe His Gln Lys
770 775 780

<210> SEQ ID NO 77
<211> LENGTH: 777
<212> TYPE: PRT
<213> ORGANISM: Homo sapiens

<400> SEQUENCE: 77

Met Asp Ser Lys Glu Ser Leu Thr Pro Gly Arg Glu Glu Asn Pro Ser
1 5 10 15

-continued

```
Ser Val Leu Ala Gln Glu Arg Gly Asp Val Met Asp Phe Tyr Lys Thr
            20                  25                  30

Leu Arg Gly Gly Ala Thr Val Lys Val Ser Ala Ser Ser Pro Ser Leu
        35                  40                  45

Ala Val Ala Ser Gln Ser Asp Ser Lys Gln Arg Arg Leu Leu Val Asp
    50                  55                  60

Phe Pro Lys Gly Ser Val Ser Asn Ala Gln Gln Pro Asp Leu Ser Lys
65                  70                  75                  80

Ala Val Ser Leu Ser Met Gly Leu Tyr Met Gly Glu Thr Glu Thr Lys
                85                  90                  95

Val Met Gly Asn Asp Leu Gly Phe Pro Gln Gln Gly Gln Ile Ser Leu
            100                 105                 110

Ser Ser Gly Glu Thr Asp Leu Lys Leu Leu Glu Glu Ser Ile Ala Asn
        115                 120                 125

Leu Asn Arg Ser Thr Ser Val Pro Glu Asn Pro Lys Ser Ser Ala Ser
    130                 135                 140

Thr Ala Val Ser Ala Ala Pro Thr Glu Lys Glu Phe Pro Lys Thr His
145                 150                 155                 160

Ser Asp Val Ser Ser Glu Gln Gln His Leu Lys Gly Gln Thr Gly Thr
                165                 170                 175

Asn Gly Gly Asn Val Lys Leu Tyr Thr Thr Asp Gln Ser Thr Phe Asp
            180                 185                 190

Ile Leu Gln Asp Leu Glu Phe Ser Ser Gly Ser Pro Gly Lys Glu Thr
        195                 200                 205

Asn Glu Ser Pro Trp Arg Ser Asp Leu Leu Ile Asp Glu Asn Cys Leu
    210                 215                 220

Leu Ser Pro Leu Ala Gly Glu Asp Asp Ser Phe Leu Leu Glu Gly Asn
225                 230                 235                 240

Ser Asn Glu Asp Cys Lys Pro Leu Ile Leu Pro Asp Thr Lys Pro Lys
                245                 250                 255

Ile Lys Asp Asn Gly Asp Leu Val Leu Ser Ser Pro Ser Asn Val Thr
            260                 265                 270

Leu Pro Gln Val Lys Thr Glu Lys Glu Asp Phe Ile Glu Leu Cys Thr
        275                 280                 285

Pro Gly Val Ile Lys Gln Glu Lys Leu Gly Thr Val Tyr Cys Gln Ala
    290                 295                 300

Ser Phe Pro Gly Ala Asn Ile Ile Gly Asn Lys Met Ser Ala Ile Ser
305                 310                 315                 320

Val His Gly Val Ser Thr Ser Gly Gly Gln Met Tyr His Tyr Asp Met
                325                 330                 335

Asn Thr Ala Ser Leu Ser Gln Gln Gln Asp Gln Lys Pro Ile Phe Asn
            340                 345                 350

Val Ile Pro Pro Ile Pro Val Gly Ser Glu Asn Trp Asn Arg Cys Gln
        355                 360                 365

Gly Ser Gly Asp Asp Asn Leu Thr Ser Leu Gly Thr Leu Asn Phe Pro
    370                 375                 380

Gly Arg Thr Val Phe Ser Asn Gly Tyr Ser Ser Pro Ser Met Arg Pro
385                 390                 395                 400

Asp Val Ser Ser Pro Pro Ser Ser Ser Ser Thr Ala Thr Thr Gly Pro
                405                 410                 415

Pro Pro Lys Leu Cys Leu Val Cys Ser Asp Glu Ala Ser Gly Cys His
            420                 425                 430

Tyr Gly Val Leu Thr Cys Gly Ser Cys Lys Val Phe Phe Lys Arg Ala
        435                 440                 445
```

```
Val Glu Gly Gln His Asn Tyr Leu Cys Ala Gly Arg Asn Asp Cys Ile
    450                 455                 460

Ile Asp Lys Ile Arg Arg Lys Asn Cys Pro Ala Cys Arg Tyr Arg Lys
465                 470                 475                 480

Cys Leu Gln Ala Gly Met Asn Leu Glu Ala Arg Lys Thr Lys Lys Lys
                485                 490                 495

Ile Lys Gly Ile Gln Gln Ala Thr Thr Gly Val Ser Gln Glu Thr Ser
            500                 505                 510

Glu Asn Pro Gly Asn Lys Thr Ile Val Pro Ala Thr Leu Pro Gln Leu
        515                 520                 525

Thr Pro Thr Leu Val Ser Leu Leu Glu Val Ile Glu Pro Glu Val Leu
    530                 535                 540

Tyr Ala Gly Tyr Asp Ser Ser Val Pro Asp Ser Thr Trp Arg Ile Met
545                 550                 555                 560

Thr Thr Leu Asn Met Leu Gly Gly Arg Gln Val Ile Ala Ala Val Lys
                565                 570                 575

Trp Ala Lys Ala Ile Pro Gly Phe Arg Asn Leu His Leu Asp Asp Gln
            580                 585                 590

Met Thr Leu Leu Gln Tyr Ser Trp Met Phe Leu Met Ala Phe Ala Leu
        595                 600                 605

Gly Trp Arg Ser Tyr Arg Gln Ser Ser Ala Asn Leu Leu Cys Phe Ala
    610                 615                 620

Pro Asp Leu Ile Ile Asn Glu Gln Arg Met Thr Leu Pro Cys Met Tyr
625                 630                 635                 640

Asp Gln Cys Lys His Met Leu Tyr Val Ser Ser Glu Leu His Arg Leu
                645                 650                 655

Gln Val Ser Tyr Glu Glu Tyr Leu Cys Met Lys Thr Leu Leu Leu Leu
            660                 665                 670

Ser Ser Val Pro Lys Asp Gly Leu Lys Ser Gln Glu Leu Phe Asp Glu
        675                 680                 685

Ile Arg Met Thr Tyr Ile Lys Glu Leu Gly Lys Ala Ile Val Lys Arg
    690                 695                 700

Glu Gly Asn Ser Ser Gln Asn Trp Gln Arg Phe Tyr Gln Leu Thr Lys
705                 710                 715                 720

Leu Leu Asp Ser Met His Glu Val Val Glu Asn Leu Leu Asn Tyr Cys
                725                 730                 735

Phe Gln Thr Phe Leu Asp Lys Thr Met Ser Ile Glu Phe Pro Glu Met
            740                 745                 750

Leu Ala Glu Ile Ile Thr Asn Gln Ile Pro Lys Tyr Ser Asn Gly Asn
        755                 760                 765

Ile Lys Lys Leu Leu Phe His Gln Lys
    770                 775


<210> SEQ ID NO 78
<211> LENGTH: 899
<212> TYPE: PRT
<213> ORGANISM: Mus musculus

<400> SEQUENCE: 78

Met Glu Val Gln Leu Gly Leu Gly Arg Val Tyr Pro Arg Pro Pro Ser
1               5                   10                  15

Lys Thr Tyr Arg Gly Ala Phe Gln Asn Leu Phe Gln Ser Val Arg Glu
            20                  25                  30

Ala Ile Gln Asn Pro Gly Pro Arg His Pro Glu Ala Ala Asn Ile Ala
        35                  40                  45
```

-continued

```
Pro Pro Gly Ala Cys Leu Gln Gln Arg Gln Glu Thr Ser Pro Arg Arg
    50                  55                  60

Arg Arg Arg Gln Gln His Thr Glu Asp Gly Ser Pro Gln Ala His Ile
65                  70                  75                  80

Arg Gly Pro Thr Gly Tyr Leu Ala Leu Glu Glu Glu Gln Gln Pro Ser
                85                  90                  95

Gln Gln Gln Ala Ala Ser Glu Gly His Pro Glu Ser Ser Cys Leu Pro
            100                 105                 110

Glu Pro Gly Ala Ala Thr Ala Pro Gly Lys Gly Leu Pro Gln Gln Pro
        115                 120                 125

Pro Ala Pro Pro Asp Gln Asp Asp Ser Ala Ala Pro Ser Thr Leu Ser
    130                 135                 140

Leu Leu Gly Pro Thr Phe Pro Gly Leu Ser Ser Cys Ser Ala Asp Ile
145                 150                 155                 160

Lys Asp Ile Leu Asn Glu Ala Gly Thr Met Gln Leu Leu Gln Gln Gln
                165                 170                 175

Gln Gln Gln Gln Gln His Gln Gln Gln His Gln Gln His Gln Gln Gln
            180                 185                 190

Gln Glu Val Ile Ser Glu Gly Ser Ser Ala Arg Ala Arg Glu Ala Thr
        195                 200                 205

Gly Ala Pro Ser Ser Ser Lys Asp Ser Tyr Leu Gly Gly Asn Ser Thr
    210                 215                 220

Ile Ser Asp Ser Ala Lys Glu Leu Cys Lys Ala Val Ser Val Ser Met
225                 230                 235                 240

Gly Leu Gly Val Glu Ala Leu Glu His Leu Ser Pro Gly Glu Gln Leu
                245                 250                 255

Arg Gly Asp Cys Met Tyr Ala Ser Leu Leu Gly Gly Pro Pro Ala Val
            260                 265                 270

Arg Pro Thr Pro Cys Ala Pro Leu Pro Glu Cys Lys Gly Leu Pro Leu
        275                 280                 285

Asp Glu Gly Pro Gly Lys Ser Thr Glu Glu Thr Ala Glu Tyr Ser Ser
    290                 295                 300

Phe Lys Gly Gly Tyr Ala Lys Gly Leu Glu Gly Glu Ser Leu Gly Cys
305                 310                 315                 320

Ser Gly Ser Ser Glu Ala Gly Ser Ser Gly Thr Leu Glu Ile Pro Ser
                325                 330                 335

Ser Leu Ser Leu Tyr Lys Ser Gly Ala Leu Asp Glu Ala Ala Ala Tyr
            340                 345                 350

Gln Asn Arg Asp Tyr Tyr Asn Phe Pro Leu Ala Leu Ser Gly Pro Pro
        355                 360                 365

His Pro Pro Pro Pro Thr His Pro His Ala Arg Ile Lys Leu Glu Asn
    370                 375                 380

Pro Leu Asp Tyr Gly Ser Ala Trp Ala Ala Ala Ala Ala Gln Cys Arg
385                 390                 395                 400

Tyr Gly Asp Leu Gly Ser Leu His Gly Gly Ser Val Ala Gly Pro Ser
                405                 410                 415

Thr Gly Ser Pro Pro Ala Thr Thr Ser Ser Ser Trp His Thr Leu Phe
            420                 425                 430

Thr Ala Glu Glu Gly Gln Leu Tyr Gly Pro Gly Gly Gly Gly Gly Ser
        435                 440                 445

Ser Ser Pro Ser Asp Ala Gly Pro Val Ala Pro Tyr Gly Tyr Thr Arg
    450                 455                 460

Pro Pro Gln Gly Leu Thr Ser Gln Glu Ser Asp Tyr Ser Ala Ser Glu
```

-continued

```
465                 470                 475                 480

Val Trp Tyr Pro Gly Gly Val Val Asn Arg Val Pro Tyr Pro Ser Pro
                485                 490                 495

Asn Cys Val Lys Ser Glu Met Gly Pro Trp Met Glu Asn Tyr Ser Gly
            500                 505                 510

Pro Tyr Gly Asp Met Arg Leu Asp Ser Thr Arg Asp His Val Leu Pro
        515                 520                 525

Ile Asp Tyr Tyr Phe Pro Pro Gln Lys Thr Cys Leu Ile Cys Gly Asp
    530                 535                 540

Glu Ala Ser Gly Cys His Tyr Gly Ala Leu Thr Cys Gly Ser Cys Lys
545                 550                 555                 560

Val Phe Phe Lys Arg Ala Ala Glu Gly Lys Gln Lys Tyr Leu Cys Ala
                565                 570                 575

Ser Arg Asn Asp Cys Thr Ile Asp Lys Phe Arg Arg Lys Asn Cys Pro
            580                 585                 590

Ser Cys Arg Leu Arg Lys Cys Tyr Glu Ala Gly Met Thr Leu Gly Ala
        595                 600                 605

Arg Lys Leu Lys Lys Leu Gly Asn Leu Lys Leu Gln Glu Glu Gly Glu
    610                 615                 620

Asn Ser Asn Ala Gly Ser Pro Thr Glu Asp Pro Ser Gln Lys Met Thr
625                 630                 635                 640

Val Ser His Ile Glu Gly Tyr Glu Cys Gln Pro Ile Phe Leu Asn Val
                645                 650                 655

Leu Glu Ala Ile Glu Pro Gly Val Val Cys Ala Gly His Asp Asn Asn
            660                 665                 670

Gln Pro Asp Ser Phe Ala Ala Leu Leu Ser Ser Leu Asn Glu Leu Gly
        675                 680                 685

Glu Arg Gln Leu Val His Val Val Lys Trp Ala Lys Ala Leu Pro Gly
    690                 695                 700

Phe Arg Asn Leu His Val Asp Asp Gln Met Ala Val Ile Gln Tyr Ser
705                 710                 715                 720

Trp Met Gly Leu Met Val Phe Ala Met Gly Trp Arg Ser Phe Thr Asn
                725                 730                 735

Val Asn Ser Arg Met Leu Tyr Phe Ala Pro Asp Leu Val Phe Asn Glu
            740                 745                 750

Tyr Arg Met His Lys Ser Arg Met Tyr Ser Gln Cys Val Arg Met Arg
        755                 760                 765

His Leu Ser Gln Glu Phe Gly Trp Leu Gln Ile Thr Pro Gln Glu Phe
    770                 775                 780

Leu Cys Met Lys Ala Leu Leu Leu Phe Ser Ile Ile Pro Val Asp Gly
785                 790                 795                 800

Leu Lys Asn Gln Lys Phe Phe Asp Glu Leu Arg Met Asn Tyr Ile Lys
                805                 810                 815

Glu Leu Asp Arg Ile Ile Ala Cys Lys Arg Lys Asn Pro Thr Ser Cys
            820                 825                 830

Ser Arg Arg Phe Tyr Gln Leu Thr Lys Leu Leu Asp Ser Val Gln Pro
        835                 840                 845

Ile Ala Arg Glu Leu His Gln Phe Thr Phe Asp Leu Leu Ile Lys Ser
    850                 855                 860

His Met Val Ser Val Asp Phe Pro Glu Met Met Ala Glu Ile Ile Ser
865                 870                 875                 880

Val Gln Val Pro Lys Ile Leu Ser Gly Lys Val Lys Pro Ile Tyr Phe
                885                 890                 895
```

His Thr Gln

<210> SEQ ID NO 79
<211> LENGTH: 919
<212> TYPE: PRT
<213> ORGANISM: Homo sapiens

<400> SEQUENCE: 79

Met Glu Val Gln Leu Gly Leu Gly Arg Val Tyr Pro Arg Pro Pro Ser
1 5 10 15

Lys Thr Tyr Arg Gly Ala Phe Gln Asn Leu Phe Gln Ser Val Arg Glu
20 25 30

Val Ile Gln Asn Pro Gly Pro Arg His Pro Glu Ala Ala Ser Ala Ala
35 40 45

Pro Pro Gly Ala Ser Leu Leu Leu Leu Gln Gln Gln Gln Gln Gln Gln
50 55 60

Gln Gln Gln Gln Gln Gln Gln Gln Gln Gln Gln Gln Gln Gln Glu Thr
65 70 75 80

Ser Pro Arg Gln Gln Gln Gln Gln Gln Gly Glu Asp Gly Ser Pro Gln
85 90 95

Ala His Arg Arg Gly Pro Thr Gly Tyr Leu Val Leu Asp Glu Glu Gln
100 105 110

Gln Pro Ser Gln Pro Gln Ser Ala Leu Glu Cys His Pro Glu Arg Gly
115 120 125

Cys Val Pro Glu Pro Gly Ala Ala Val Ala Ala Ser Lys Gly Leu Pro
130 135 140

Gln Gln Leu Pro Ala Pro Pro Asp Glu Asp Asp Ser Ala Ala Pro Ser
145 150 155 160

Thr Leu Ser Leu Leu Gly Pro Thr Phe Pro Gly Leu Ser Ser Cys Ser
165 170 175

Ala Asp Leu Lys Asp Ile Leu Ser Glu Ala Ser Thr Met Gln Leu Leu
180 185 190

Gln Gln Gln Gln Gln Glu Ala Val Ser Glu Gly Ser Ser Ser Gly Arg
195 200 205

Ala Arg Glu Ala Ser Gly Ala Pro Thr Ser Ser Lys Asp Asn Tyr Leu
210 215 220

Gly Gly Thr Ser Thr Ile Ser Asp Asn Ala Lys Glu Leu Cys Lys Ala
225 230 235 240

Val Ser Val Ser Met Gly Leu Gly Val Glu Ala Leu Glu His Leu Ser
245 250 255

Pro Gly Glu Gln Leu Arg Gly Asp Cys Met Tyr Ala Pro Leu Leu Gly
260 265 270

Val Pro Pro Ala Val Arg Pro Thr Pro Cys Ala Pro Leu Ala Glu Cys
275 280 285

Lys Gly Ser Leu Leu Asp Asp Ser Ala Gly Lys Ser Thr Glu Asp Thr
290 295 300

Ala Glu Tyr Ser Pro Phe Lys Gly Gly Tyr Thr Lys Gly Leu Glu Gly
305 310 315 320

Glu Ser Leu Gly Cys Ser Gly Ser Ala Ala Ala Gly Ser Ser Gly Thr
325 330 335

Leu Glu Leu Pro Ser Thr Leu Ser Leu Tyr Lys Ser Gly Ala Leu Asp
340 345 350

Glu Ala Ala Ala Tyr Gln Ser Arg Asp Tyr Tyr Asn Phe Pro Leu Ala
355 360 365

Leu Ala Gly Pro Pro Pro Pro Pro Pro Pro Pro His Pro His Ala Arg

-continued

```
    370                 375                 380

Ile Lys Leu Glu Asn Pro Leu Asp Tyr Gly Ser Ala Trp Ala Ala Ala
385                 390                 395                 400

Ala Ala Gln Cys Arg Tyr Gly Asp Leu Ala Ser Leu His Gly Ala Gly
                405                 410                 415

Ala Ala Gly Pro Gly Ser Gly Ser Pro Ser Ala Ala Ala Ser Ser Ser
            420                 425                 430

Trp His Thr Leu Phe Thr Ala Glu Glu Gly Gln Leu Tyr Gly Pro Cys
        435                 440                 445

Gly Gly Gly Gly Gly Gly Gly Gly Gly Gly Gly Gly Gly Gly Gly Gly
    450                 455                 460

Gly Gly Gly Gly Gly Gly Gly Gly Glu Ala Gly Ala Val Ala Pro Tyr
465                 470                 475                 480

Gly Tyr Thr Arg Pro Pro Gln Gly Leu Ala Gly Gln Glu Ser Asp Phe
                485                 490                 495

Thr Ala Pro Asp Val Trp Tyr Pro Gly Gly Met Val Ser Arg Val Pro
            500                 505                 510

Tyr Pro Ser Pro Thr Cys Val Lys Ser Glu Met Gly Pro Trp Met Asp
        515                 520                 525

Ser Tyr Ser Gly Pro Tyr Gly Asp Met Arg Leu Glu Thr Ala Arg Asp
    530                 535                 540

His Val Leu Pro Ile Asp Tyr Tyr Phe Pro Pro Gln Lys Thr Cys Leu
545                 550                 555                 560

Ile Cys Gly Asp Glu Ala Ser Gly Cys His Tyr Gly Ala Leu Thr Cys
                565                 570                 575

Gly Ser Cys Lys Val Phe Phe Lys Arg Ala Ala Glu Gly Lys Gln Lys
            580                 585                 590

Tyr Leu Cys Ala Ser Arg Asn Asp Cys Thr Ile Asp Lys Phe Arg Arg
        595                 600                 605

Lys Asn Cys Pro Ser Cys Arg Leu Arg Lys Cys Tyr Glu Ala Gly Met
    610                 615                 620

Thr Leu Gly Ala Arg Lys Leu Lys Lys Leu Gly Asn Leu Lys Leu Gln
625                 630                 635                 640

Glu Glu Gly Glu Ala Ser Ser Thr Thr Ser Pro Thr Glu Glu Thr Thr
                645                 650                 655

Gln Lys Leu Thr Val Ser His Ile Glu Gly Tyr Glu Cys Gln Pro Ile
            660                 665                 670

Phe Leu Asn Val Leu Glu Ala Ile Glu Pro Gly Val Val Cys Ala Gly
        675                 680                 685

His Asp Asn Asn Gln Pro Asp Ser Phe Ala Ala Leu Leu Ser Ser Leu
    690                 695                 700

Asn Glu Leu Gly Glu Arg Gln Leu Val His Val Val Lys Trp Ala Lys
705                 710                 715                 720

Ala Leu Pro Gly Phe Arg Asn Leu His Val Asp Asp Gln Met Ala Val
                725                 730                 735

Ile Gln Tyr Ser Trp Met Gly Leu Met Val Phe Ala Met Gly Trp Arg
            740                 745                 750

Ser Phe Thr Asn Val Asn Ser Arg Met Leu Tyr Phe Ala Pro Asp Leu
        755                 760                 765

Val Phe Asn Glu Tyr Arg Met His Lys Ser Arg Met Tyr Ser Gln Cys
    770                 775                 780

Val Arg Met Arg His Leu Ser Gln Glu Phe Gly Trp Leu Gln Ile Thr
785                 790                 795                 800
```

Pro Gln Glu Phe Leu Cys Met Lys Ala Leu Leu Leu Phe Ser Ile Ile
805 810 815

Pro Val Asp Gly Leu Lys Asn Gln Lys Phe Phe Asp Glu Leu Arg Met
820 825 830

Asn Tyr Ile Lys Glu Leu Asp Arg Ile Ile Ala Cys Lys Arg Lys Asn
835 840 845

Pro Thr Ser Cys Ser Arg Arg Phe Tyr Gln Leu Thr Lys Leu Leu Asp
850 855 860

Ser Val Gln Pro Ile Ala Arg Glu Leu His Gln Phe Thr Phe Asp Leu
865 870 875 880

Leu Ile Lys Ser His Met Val Ser Val Asp Phe Pro Glu Met Met Ala
885 890 895

Glu Ile Ile Ser Val Gln Val Pro Lys Ile Leu Ser Gly Lys Val Lys
900 905 910

Pro Ile Tyr Phe His Thr Gln
915

<210> SEQ ID NO 80
<211> LENGTH: 314
<212> TYPE: PRT
<213> ORGANISM: Homo sapiens

<400> SEQUENCE: 80

Ser Ala Gly Asp Met Arg Ala Ala Asn Leu Trp Pro Ser Pro Leu Met
1 5 10 15

Ile Lys Arg Ser Lys Lys Asn Ser Leu Ala Leu Ser Leu Thr Ala Asp
20 25 30

Gln Met Val Ser Ala Leu Leu Asp Ala Glu Pro Pro Ile Leu Tyr Ser
35 40 45

Glu Tyr Asp Pro Thr Arg Pro Phe Ser Glu Ala Ser Met Met Gly Leu
50 55 60

Leu Thr Asn Leu Ala Asp Arg Glu Leu Val His Met Ile Asn Trp Ala
65 70 75 80

Lys Arg Val Pro Gly Phe Val Asp Leu Thr Leu His Asp Gln Val His
85 90 95

Leu Leu Glu Cys Ala Trp Leu Glu Ile Leu Met Ile Gly Leu Val Trp
100 105 110

Arg Ser Met Glu His Pro Val Lys Leu Leu Phe Ala Pro Asn Leu Leu
115 120 125

Leu Asp Arg Asn Gln Gly Lys Cys Val Glu Gly Met Val Glu Ile Phe
130 135 140

Asp Met Leu Leu Ala Thr Ser Ser Arg Phe Arg Met Met Asn Leu Gln
145 150 155 160

Gly Glu Glu Phe Val Cys Leu Lys Ser Ile Ile Leu Leu Asn Ser Gly
165 170 175

Val Tyr Thr Phe Leu Ser Ser Thr Leu Lys Ser Leu Glu Glu Lys Asp
180 185 190

His Ile His Arg Val Leu Asp Lys Ile Thr Asp Thr Leu Ile His Leu
195 200 205

Met Ala Lys Ala Gly Leu Thr Leu Gln Gln Gln His Gln Arg Leu Ala
210 215 220

Gln Leu Leu Leu Ile Leu Ser His Ile Arg His Met Ser Asn Lys Gly
225 230 235 240

Met Glu His Leu Tyr Ser Met Lys Cys Lys Asn Val Val Pro Leu Tyr
245 250 255

-continued

```
Asp Leu Leu Leu Glu Ala Ala Asp Ala His Arg Leu His Ala Pro Thr
            260                 265                 270

Ser Arg Gly Gly Ala Ser Val Glu Glu Thr Asp Gln Ser His Leu Ala
        275                 280                 285

Thr Ala Gly Ser Thr Ser Ser His Ser Leu Gln Lys Tyr Tyr Ile Thr
    290                 295                 300

Gly Glu Ala Glu Gly Phe Pro Ala Thr Ala
305                 310


<210> SEQ ID NO 81
<211> LENGTH: 9
<212> TYPE: PRT
<213> ORGANISM: Artificial sequence
<220> FEATURE:
<223> OTHER INFORMATION: influenza virus hemagglutinin epitope

<400> SEQUENCE: 81

Tyr Pro Tyr Asp Val Pro Asp Tyr Ala
1               5


<210> SEQ ID NO 82
<211> LENGTH: 13
<212> TYPE: PRT
<213> ORGANISM: Artificial sequence
<220> FEATURE:
<223> OTHER INFORMATION: myristoylation signal sequence, 13 aa

<400> SEQUENCE: 82

Gly Ser Ser Lys Ser Lys Pro Lys Asp Pro Ser Gln Arg
1               5                   10
```